(12) United States Patent
Ransom et al.

(10) Patent No.: US 6,280,967 B1
(45) Date of Patent: *Aug. 28, 2001

(54) CELL FLOW APPARATUS AND METHOD FOR REAL-TIME OF CELLULAR RESPONSES

(75) Inventors: John Ransom, Encinitas; Ilya Okun; Alex Okun, both of San Diego, all of CA (US)

(73) Assignee: Axiom Biotechnologies, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 69 days.

(21) Appl. No.: 09/370,786

(22) Filed: Aug. 5, 1999

Related U.S. Application Data

(63) Continuation-in-part of application No. 09/317,793, filed on May 24, 1999, which is a continuation-in-part of application No. 08/904,904, filed on Aug. 1, 1997, now Pat. No. 5,919,646, which is a continuation-in-part of application No. 08/691,356, filed on Aug. 2, 1996, now Pat. No. 5,804,436.

(51) Int. Cl.[7] ............................. C12Q 1/02; C12Q 1/04
(52) U.S. Cl. ........................ 435/29; 435/34; 435/283.1; 435/968; 435/286.1
(58) Field of Search ..................... 435/29, 34, 283.1, 435/968, 286.1

(56) References Cited

U.S. PATENT DOCUMENTS

| | | | |
|---|---|---|---|
| 3,772,154 | 11/1973 | Isenberg et al. | 435/29 |
| 3,826,899 | 7/1974 | Ehrlich et al. | 435/29 |
| 4,271,123 | 6/1981 | Curry et al. | 435/29 |
| 4,343,782 | 8/1982 | Shapiro | 435/29 |
| 4,632,808 | 12/1986 | Yamamoto et al. | 435/29 |
| 4,676,951 | 6/1987 | Armes et al. | 435/29 |
| 4,678,752 | 7/1987 | Thorne et al. | 435/29 |
| 4,766,078 | 8/1988 | Gang | 435/29 |
| 5,278,048 | 1/1994 | Parce et al. | 435/29 |
| 5,320,808 | 6/1994 | Holen et al. | 435/29 |
| 5,401,629 | 3/1995 | Harpold et al. | 435/29 |
| 5,436,128 | 7/1995 | Harpold et al. | 435/29 |
| 5,463,564 | 10/1995 | Agrafiotis et al. | 435/29 |
| 5,541,061 | 7/1996 | Fodor et al. | 435/29 |
| 5,556,762 | 9/1996 | Pinilla et al. | 435/29 |

(List continued on next page.)

FOREIGN PATENT DOCUMENTS

| | | |
|---|---|---|
| WO 90 04645 | 5/1990 | (WO). |
| WO 93 13423 | 7/1993 | (WO). |
| WO 96 30760 | 10/1996 | (WO). |

OTHER PUBLICATIONS

Dunne, Time Window Analysis and Sorting, (1991), Cytometry 12:597–601.*

(List continued on next page.)

Primary Examiner—Louise N. Leary
(74) Attorney, Agent, or Firm—Knobbe, Martens, Olson & Bear LLP

(57) ABSTRACT

An apparatus and method for real-time measurement of a cellular response of a test compound or series of test compounds (303) on a flowing suspension of cells (349), in which a homogeneous suspension of each member of a series of cell types (349) is combined with a concentration of a test compound (303), directed through a detection zone (355), and a cellular response of the living cells is measured in real time as the cells in the test mixture are flowing through the detection zone (355). The apparatus may be used in automated screening of libraries of compounds, and is capable of real-time variation of concentrations of test and standard compounds and generation of dose/response profiles within a short time span.

84 Claims, 63 Drawing Sheets

U.S. PATENT DOCUMENTS

| | | | |
|---|---|---|---|
| 5,559,002 | 9/1996 | Uzan et al. | 435/29 |
| 5,569,588 | 10/1996 | Ashby et al. | 435/29 |
| 5,573,909 | 11/1996 | Singer et al. | 435/29 |
| 5,574,656 | 11/1996 | Agrafiotis et al. | 435/29 |
| 5,585,275 | 12/1996 | Hudson et al. | 435/29 |
| 5,601,992 | 2/1997 | Lerner et al. | 435/29 |
| 5,620,894 | 4/1997 | Barger et al. | 435/29 |
| 5,630,706 | 5/1997 | Yang | 435/29 |
| 5,648,219 | 7/1997 | MacKay et al. | 435/29 |
| 5,804,436 | 9/1998 | Okun et al. | 435/286.1 |
| 5,919,646 | 7/1999 | Okun et al. | 435/286.1 |
| 5,942,443 | 8/1999 | Parce et al. | 435/29 |

OTHER PUBLICATIONS

Ransom et al., $AT_1$ Angiotensin Receptors Mobilize Intracellular Calcium in a Subclone of NG108–15 Neuroblastoma Cells, (1992) Journal of Neurochemistry 58:1883:1888.*

Ransom et al., Flow Cytometric Analysis of Internal Calcium Mobilization via a $B_2$–Bradykinin Receptor on a Subclone of PC–12 Cells, (1991) Journal of Neurochemistry 56:983:989.*

Ransom et al., Flow Cytometric Selection of Responsive Subclones and Fluorimetric Analysis of Intracellular $Ca^{2+}$ Mobilization (1994) Molecular Imaging in Neuroscience: A Practical oach pp. 209–233.*

Ransom et al., Flow Cytometric Systems for Drug Discovery and Development (2000), Optical Diagnostics of Living Cells III, D.L. Farkas and R.C. Lief eds. Proceedings of SPIE, vol. 3921, pp 90–100.*

Ransom et al., Isolation of Sublones With Enhanced $Ca^{2+}$ Response Homogeneity by Flow Cytometric Selection of Single Cells During a Ligand–Activated $Ca^{2+}$ Response, (1991) Methods A Companion to Methods in Enzymology vol. 2 No. 3 Jun. pp. 227–233.*

Arunlakshana, O. & Schild, H.O., Brit. J. Pharmacol., vol. 14, pp. 48–58, 1959, "Some Quantitative Uses of Drug Antagonist."

Berridge, et al., Nature, vol. 341, pp. 197–205, 1989, "Inositol Phosphate and Cell Signaling."

Berridge, M.J., Nature, vol. 361, pp. 315–325, 1993, "Inositol Triphosphate and Calcium Signaling."

Cheng, et al., Biochem. Pharmacol., vol. 22, pp. 3099–3108, 1973, "Relationship Between the Inhibition Constant ($K_i$) and the Concentration of the Inhibitor Which Causes 50 Percent Inhibition ($IC_{50}$) of an Enzymatic Reaction."

Clapham, D.E., Cell, vol. 80, pp. 259–268, 1995, "Calcium Signaling."

Claudio, et al., Science, vol. 239, pp. 1688–1694, 1987, "Genetic Reconstitution of Functional Acetylcholine Receptor Channels in Mouse Fibroblasts."

Divecha, et al., Cell, vol. 80, pp. 269–278, 1995, "Phospholipid Signaling."

Fagerstam, et al., Journal of Chromatography, vol. 597, pp. 397–410, 1992, "Biospecific Interaction Analysis Using Surface Plasmon Resonance Detection Applied to Kinetic, Binding Site and Concentration Analysis."

Gaddum, J.H., Pharmacol. Rev., vol. 9, pp. 211–218, 1957, "Theories of Drug Antagonism."

Grynkiewicz, et al., J. Biol. Chem., vol. 260, pp. 3440–3450, 1985, "A new generation of $Ca^{2+}$ Indicators With Greatly Improved Fluorescent Properties."

Herskowtiz, I., Cell, vol. 80, pp. 187–197, 1995, "MAP Kinase Pathways in Yeast For Mating and More."

Hill, et al., Cell, vol. 80, pp. 199–211, 1995, "Transcriptional Regulation by Extracellular Signals: Mechanisms and Specificity."

Lazareno, et al., TIPS, vol. 14, pp. 237–239, 1993, "Estimation of Antagonist $K_b$ From Inhibition Curves in Functional Experiments: Alternatives to the Cheng–Prusoff Equation."

Marshall, C.J., Cell, vol. 80, pp. 179–185, 1995, "Specificity of Receptor Tyrosine Kinase Signaling: Transient Versus Sustained Extracellular Signal Regulated Kinase Activation."

McConnell, et al., Science, vol. 257, pp. 1906–1912, 1992, "The Cytosensor Microphysiometer: Biological Applications of Silicon Technology."

Means, A.R., FEBS Lett., vol. 347, pp. 1–4, 1994, "Calcium, Calmodulin and Cell Cycle Regulation."

Molecular Devices Corporation (1994) "Cytosensor Microphysiometer at Work Reference Guide."

Molecular Device Corporation (1996) "Cytosensor Microphysiometer."ad.

Molecular Devices (1996) "Evaluating Receptor Desensitization using the Cytosensor Microphysiometer System."

Nicotera, et al., Cell Calcium, vol. 16 pp. 279–288, 1994, "Nuclear Calcium Transport and the Role of Calcium in Apoptosis."

Sakamoto, et al., Biochem. Biophys. Res. Comm., vol. 200, pp. 679–686, 1994, "Psuedo–Noncompetitive Anatagonism by BQ–123 of Intracellular Calcium Transients Mediated by Human $ET_A$ Endothelin Receptor."

Salon, et al., Method of Neurosciences, vol. 25, pp. 201–224, 1995, "Real–Time Measurements of Receptor Activity: Applications of Microphysipmetric Techniques to Receptor Biology."

Sheng, et al., Science, vol. 252, pp. 1427–1430, 1991, "CREB a $Ca^{2+}$–Regulated Transcription Factor Phosphorylated by Calmodulin–Dependent Kinases."

Sternweis, et al., Trends Biol. Sci., vol. 17, pp. 502–506, 1992, "Regulation of Phospholipase C by G Proteins."

Swillens, et al., TIPS, vol. 16, pp. 151–155, 1995, "Does a Radiolabled Ligand Bind to a Homogenous Population of Non–Interacting Receptor Sites?".

Weiland, et al., Life Sciences, vol. 29, pp. 313–330, 1981, "Quantitative Analysis of Drug–receptor Interactions: 1. Determination of Kinetic and Equilibrium Properties."

* cited by examiner

| | PRIMING VALVES | | | | DIVERTING VALVES | | | PROPORTIONING VALVES | |
|---|---|---|---|---|---|---|---|---|---|
| STEP | 345 | 341 | 313 | 329 | 335 | 333 | 347 | 327 | 311 |
| START | − | − | − | − | − | − | − | − | − |
| 608 | + | | + | | | | | | |
| 612 | | | | | | | | + | |
| 614 | | | | | | | | − | |
| 616 | | | − | | | | | | |
| 618 | | | | + | | | | | |
| 620 | | | | | | | | | + |
| 622 | | | | | | | | | − |
| 624 | | | | − | | | | | |
| 626 | | | | | + | + | | | |
| 628 | | | | | − | | | | |
| 630 | | | | | | − | | | |
| 632 | − | + | | | | | | | |
| 636 | | | | | | | + | | |
| 638 | | − | | | | | − | | |
| STOP | − | − | − | − | − | − | − | − | − |

*FIG. 7d*

| FIG. 8a |
|---|
| FIG. 8b |
| FIG. 8c |
| FIG. 8d |
| FIG. 8e |
| FIG. 8f |
| FIG. 8g |

FIG. 8

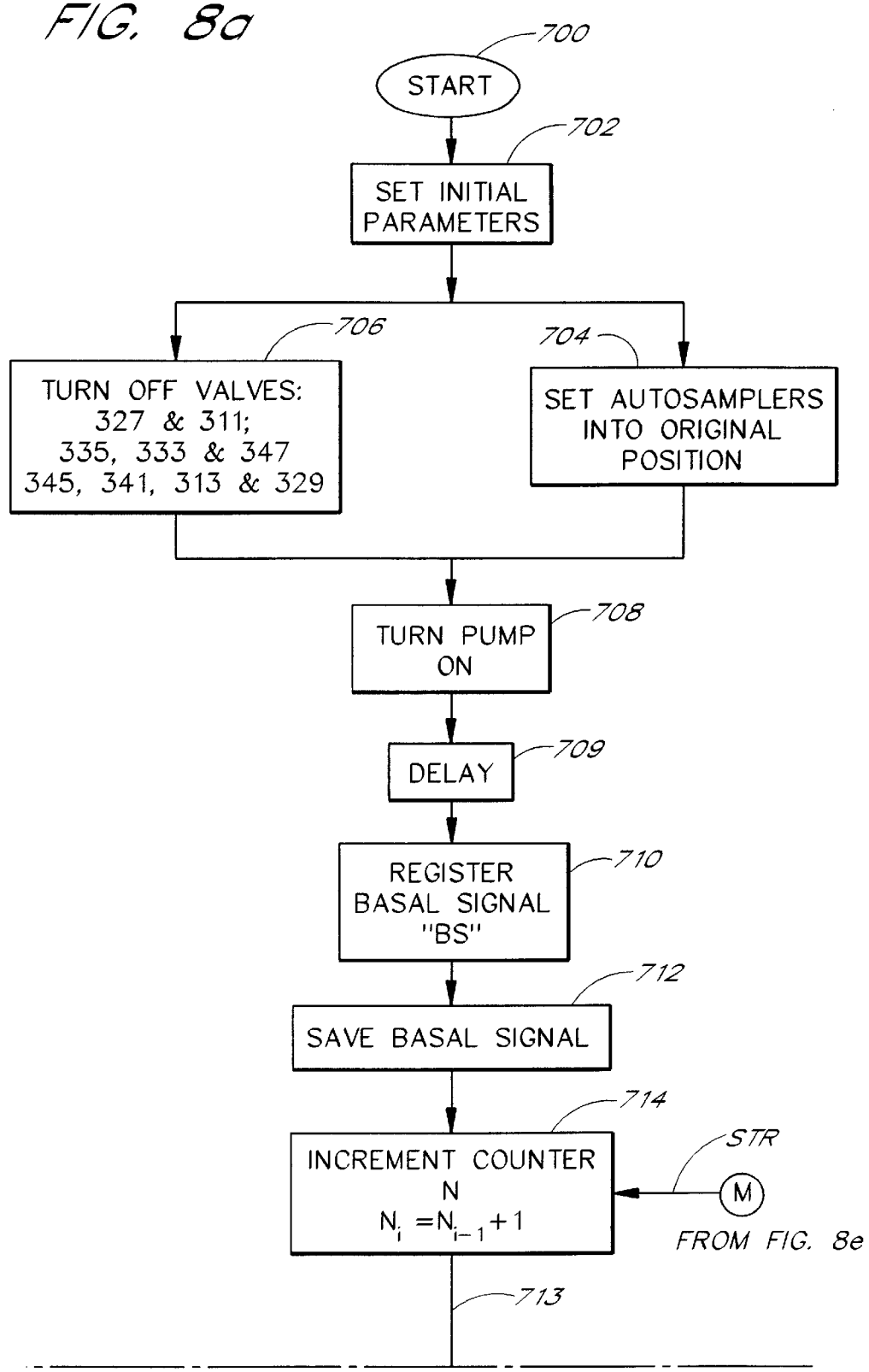

| FIG. 17a |
|---|
| FIG. 17b |
| FIG. 17c |
| FIG. 17d |
| FIG. 17e |
| FIG. 17f |
| FIG. 17g |

FIG. 17

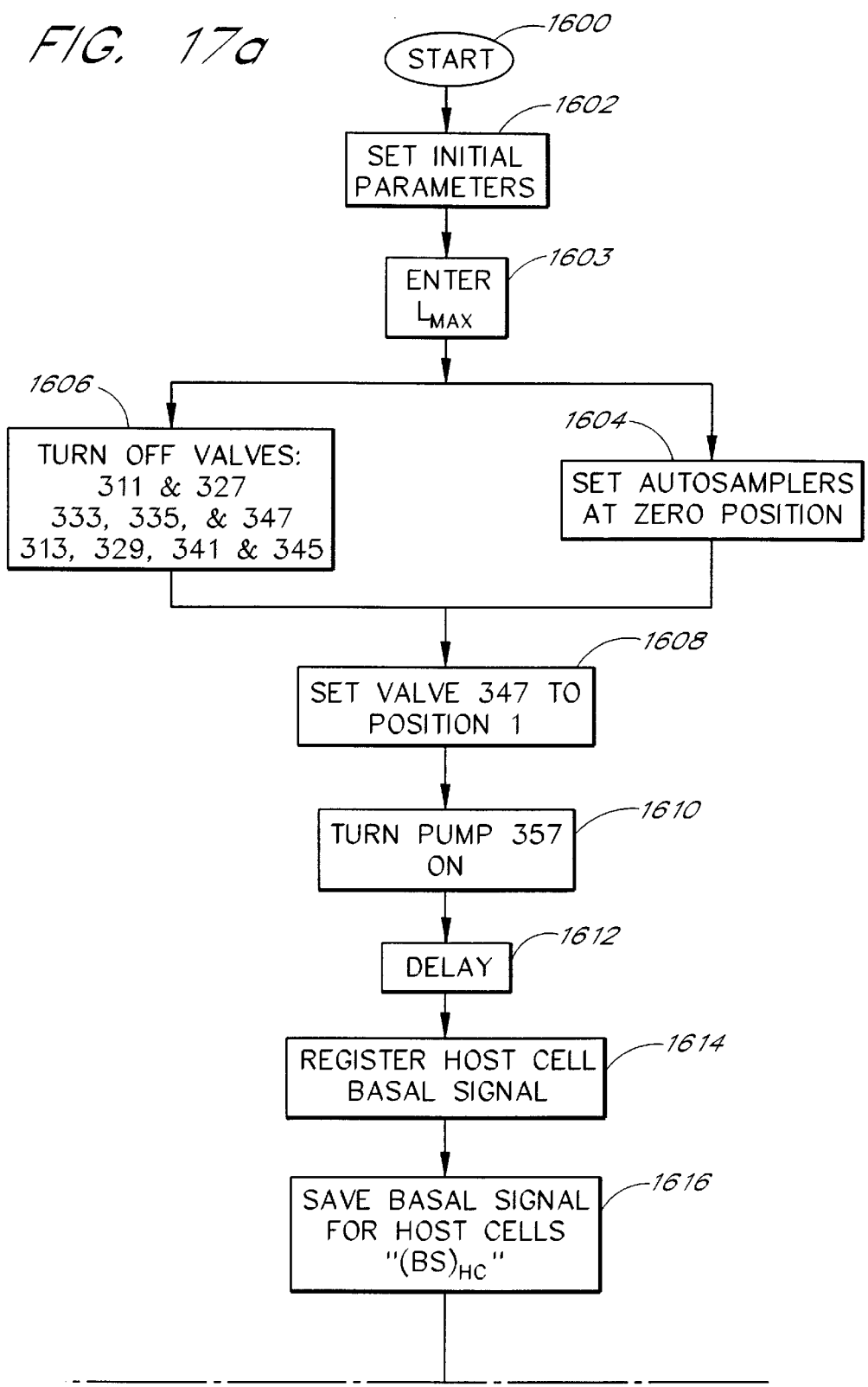

CELL FLOW APPARATUS AND METHOD FOR REAL-TIME OF CELLULAR RESPONSES

RELATED APPLICATIONS

The present application is a continuation-in-part of U.S. patent application Ser. No. 09/317,793, filed May 24, 1999 which is a continuation of U.S. patent application Ser. No. 08/904,904, filed Aug. 1, 1997, (now U.S. Pat. No. 5,919,646, issued Jul. 6, 1999), which was a continuation-in-part of U.S. patent application Ser. No. 08/691,356 filed Aug. 2, 1996 (now U.S. Pat. No. 5,804,436, issued Sep. 8, 1998), the disclosures of which are incorporated herein by reference in their entireties.

FIELD OF THE INVENTION

This invention relates generally to an apparatus for screening and the pharmacological profiling of compounds modulating a cellular physiological response. This invention also relates to devices for rapid assessment of the properties of compounds that modulate the activities of cells. The compounds investigated may be involved in regulating the activity of signal transduction pathways, cellular responses, cell surface receptors, ion channels, non-selective pores, second messenger pathways, downstream signal transduction pathways, apoptosis, cellular necrosis or any other cellular responses. The devices and methods of the present invention may also be used to perform biochemical analyses, such as Western analyses, Northern analyses, detection of single nucleotide polymorphisms (SNPs), detection of enzymatic activities, or molecular assembly assays.

In some embodiments, this invention relates to methods and apparatus for detecting, evaluating and characterizing the ability and potency of substances to act as agonists or antagonists against receptors and ion channels localized on a cell surface membrane.

BACKGROUND INFORMATION

Biological cells contain receptor molecules located on their external membrane. The function of these receptors is to "sense" the cell environment and supply the cell with an input signal about any changes in the environment. In eukaryotic organisms such cell environment is comprised of the neighboring cells and the function of the receptor is to allow cells to communicate with each other directly (the paracrine regulatory system) or indirectly (the endocrine regulatory system) thus achieving harmonized response of a tissue, organ or a whole organism. In prokaryotic cells, the surface localized receptors provide a means for detecting extracellular environment.

Having received such a signal, neurotransmitters, hormones, chemoattractant or chemorepellant substances for example, the surface localized receptors transmit this information about extracellular environment into the cell through specific intracellular pathways in such a way that the cell responds in the specific fashion to accommodate these changes. When there is an altered supply of the external signal molecules or an altered activity of the cell surface molecules, the cell response would be abnormal causing malfunctioning of a tissue or an organ.

In eukaryotic cells, receptor molecules determine the selective response of the cell. Each type of receptor can interact only with a specific set of ligand molecules. For example, adrenergic receptors interact with adrenaline and noradrenaline, cholinergic receptors interact with acetylcholine, serotoninergic receptors interact with 5-hydroxytryptamine, dopamineergic with DOPA and so on. The cells derived from the different tissues invariably express specific sets of tissue receptors. Different types of receptors are connected to different signal transduction pathways. For example, nicotinic cholinergic receptor, upon binding acetylcholine molecule, directly activates sodium channel (Claudio et al., 1987, is incorporated herein by reference). G-protein coupled receptors activate enzymes of second messenger pathways, for example, adenylate cyclase or phospholipase C with subsequent activation of cAMP or phosphoinositide cascades (Divecha and Itvine, 1995, is incorporated herein by reference). Receptor tyrosine kinases activate cascade of MEK/MAPK kinases leading to cell differentiation and proliferation (Marshall, 1995 and Herskowitz, 1995, are incorporated herein by reference)]. Cytokine receptors activate JAK/STAT cascade which in turn can regulate other pathways as well as activate gene transcription (Hill & Treisman, 1995, is incorporated herein by reference).

Together with the receptors, the cell surface membrane carries ion pumps, ion transporters and ion channels. These molecular assemblies work in concert to maintain intracellular ion homeostasis. Any changes in the activity of these systems would cause a shift in the intracellular concentrations of ions and consequently to the cell metabolic response.

Ion pumps act to maintain transmembrane ion gradients utilizing ATP as a source of energy. The examples of the ion pumps are: $Na^+/K^+$-ATPase maintaining transmembrane gradient of sodium and potassium ions, $Ca^{2+}$-ATPase maintaining transmembrane gradient of calcium ions and $H^+$-ATPase maintaining transmembrane gradient of protons.

Ion transporters use the electrochemical energy of transmembrane gradients of one ion species to maintain gradients of other ion counterpart. For example, the $Na^+/Ca^{2+}$-exchanger uses the chemical potential of the sodium gradient directed inward to pump out calcium ions against their chemical potential.

Ion channels, upon activation, allow for the ions to move across the cell membrane in accordance with their electrochemical potential. There are two main types of ion channels: voltage operated and ligand-gated. Voltage operated channels are activated to the open state upon changes in transmembrane electric potential. Sodium channels in the neuronal axon or L-type calcium channels in neuromuscular junctions exemplify this kind of channel. Ligand-gated channels are activated to the open state upon binding a certain ligand with the chemoreceptor part of their molecules. The classical example of ligand-gated channels is nicotinic cholinergic receptor which, at the same time, is the sodium channel.

There are numerous methods for detecting ligand/receptor interaction. The most conventional are methods where the affinity of a receptor to a substance of interest is measured in radioligand binding assays. In these assays, one measures specific binding of a reference radiolabeled ligand molecule in the presence and in the absence of different concentrations of the compound of interest. The characteristic inhibition parameter of the specific binding of the reference radiolabeled ligand with the compound of interest, $IC_{50}$, is taken as a measure of the affinity of the receptor to this compound (Weiland & Molinoff, 1981 and Swillens et all., 1995, are incorporated herein by reference). Recent advances in microchip sensor technology made it possible to measure direct interactions of a receptor molecule with a compound of interest in real time. This method allows for determination of both association and dissociation rate constants with subsequent calculation of the affinity parameter (F_gerstam et al., 1992, is incorporated herein by reference). While being very precise and convenient, these methods do not allow to distinguish between agonist and antagonist activity of the compound.

The type of biological activity of the compounds, agonist or antagonist, may be determined in the cell based assays. In the methods described in Harpold & Brust, 1995, which is incorporated herein by reference, cells cotransfected with a receptor gene and reporter gene construct, are used to provide means for identification of agonist and antagonist potential pharmaceutical compounds. These methods are inconvenient because they require very laborious manipulations with gene transfection procedures, are highly time consuming and use artificially modified cells. Besides, to prove that the agonistic effect of a particular compound is connected to the stimulation of a transfected receptor, several control experiments with a positive and negative control cell lines should be performed as well.

Most closely related to the methods of this invention are the methods described in Parce et al., 1994, which is incorporated herein by reference. These prior art methods use natural cells and are based on registering the natural cell responses, such as the rate of metabolic acidification, to the biologically active compounds. The disadvantage of the prior art is low throughput speed, each measurement point taking about three minutes. Another disadvantage of the prior art is the use of cells immobilized on the internal surface of the measuring microflow chamber. This leads to the necessity of using separate silicon sensors, or cover slips, with the cells adherent to them for each concentration point of the agonist or antagonist, for the receptors that undergo desensitization upon binding to the agonist molecule. This results in high variability of the experimental results.

Ionized calcium, unlike other intracellular ion events, e.g. changes in the intracellular concentrations of protons, sodium, magnesium, or potassium, serves as the most common element in different signal transduction pathways of the cells ranging from bacteria to specialized neurons (Clapham, 1995, is incorporated herein by reference). There are two major pools which supply signal transduction pathways in the cell with the calcium ions, extracellular space and the endoplasmic reticulum. There are several mechanisms to introduce small bursts of calcium into cytosol for signal transduction.

Both excitable and nonexcitable cells have on their plasma membrane predominantly two receptor classes, G-protein coupled serpentine receptors (GPCSR) and the receptor tyrosine kinases (RTK), that control calcium entry into cell cytoplasm. Both GPCSR and RTK receptors activate phospholipase C to convert phosphatidylinositol into inositol(1,4,5)-trisphosphate ($InsP_3$) and diacylglicerol. $InsP_3$ acts as an intracellular second messenger and activates specialized receptor that spans the endoplasmic reticular membrane. The activation of this receptor triggers release of calcium ions from the endoplasmic reticulum (Berridge, 1993, is incorporated herein by reference). The calcium ions can also enter the cytoplasm of excitable and nonexcitable cell from extracellular environment through specialized voltage-independent $Ca^{2+}$-selective channels triggered by specific ligands. In nonexcitable cells, hyperpolarization of the plasma cell membrane also enhances entry of calcium ions through passive transmembrane diffusion along the electric potential. For example, opening of potassium channels brings the membrane potential to more negative values inside the cell, thus facilitating $Ca^{2+}$ entry across the plasma membrane. Excitable cells contain voltage-dependent $Ca^{2+}$ channels on their plasma membrane, which, upon membrane depolarization, open for a short period of time and allow inflow of $Ca^{2+}$ from external media into cytoplasm. The endoplasmic reticulum membrane as well as plasma membrane of the excitable cells contains $InsP_3$ receptors and $Ca^{2+}$-sensitive ryanodine receptors (RyR) releasing $Ca^{2+}$ from intracellular stores upon membrane receptor triggered phospholipase C activation or depolarization-induced short burst of $Ca^{2+}$ entry into cell cytoplasm from extracellular media respectively.

It is well established that G-protein coupled serpentine receptors initiate $Ca^{2+}$ mobilization through the activation of phospholipase $C_\beta$ (Sternweis and Smrcka, 1992, is incorporated herein by reference) whereas tyrosine kinase receptors activate phospholipase $C\gamma$ with subsequent intracellular $Ca^{2+}$ mobilization (Berridge & Irvine, 1989, is incorporated herein by reference).

There are many plasma membrane G-protein coupled serpentine receptors, tyrosine kinase growth factor receptors and voltage- and ligand-regulated channels known to initiate intracellular $Ca^{2+}$ mobilization.

$Ca^{2+}$ plays an essential role in many functional processes of a cell. For example, $Ca^{2+}$ affects the cell cycle (Means, 1994, is incorporated herein by reference) and activates specific transcription factors (Sheng et al., 1991, is incorporated herein by reference). Scores of receptors and ion channels use the $Ca^{2+}$ signal to initiate events as basic as cell motility, contraction, secretion, division etc.

Increases in cytosolic and, consequently, in nuclear concentration of the $Ca^{2+}$ can also be a cell death promoting signal. For example, prolonged increase in free $Ca^{2+}$ activates degradation processes in programmed cell death, apoptosis, activates nucleases that cleave DNA and degrade cell chromatin, promotes DNA digestion by direct stimulation of endonucleases, or indirectly by activation of $Ca^{2+}$-dependent proteases, phosphatases and phospholipases, resulting in a loss of chromatin structural integrity (Nicoteraet all., 1994, is incorporated herein by reference).

A development of intracellular fluorescent calcium indicators (Grynkiewicz et all., 1985, is incorporated herein by reference) made it possible for intracellular concentration of free calcium to be measured directly in the living cell. Thus the ability to register changes in intracellular calcium concentration provide the means for monitoring effects of different compounds useful in treating various diseases, whose action is thought to be a result of an interaction with membrane receptors and ion channels.

With the advent of combinatorial chemistry approaches to identify pharmacologically useful compounds, it is increasingly evident that there is a need for methods and apparatuses capable of performing automated characterization of pharmacological profiles and corresponding potencies of the compounds in synthesized combinatorial libraries. This would enable the rapid screening of a large number of compounds in the combinatorial library the identification of those compounds which have biological activity, and the characterization of those compounds in terms of potency, affinity and selectivity.

It is an object of this invention to provide methods for screening and the quantitative characterization of potentially pharmacologically effective compounds that specifically interact with and modulate the activity of cell membrane receptors, ion pumps and ion channels using living cells.

It is an additional object of this invention to provide methods capable of characterizing an affinity of the active compounds to the binding sites of the cell.

It is another additional object of this invention to provide methods to distinguish between agonistic and antagonistic activity of the compounds.

It is yet another additional object of this invention to provide methods to determine the nature of the receptor, ion channel or ion pump entity which is sensitive to the active compounds discovered during the screening process.

It is yet another additional object of this invention to provide methods to characterize cell receptor pattern for particular cell source tissue.

It is yet another additional object of this invention to perform each of the above methods on each member of a series of cell types.

It is yet another additional object of the invention to determine the pattern of cell surface receptors expressed in one or more cell types.

It is yet another additional object of the invention to confirm that a test compound influences the activity of a particular receptor.

It is yet an additional object of the invention to determine the activity of a given receptor in a variety of cell types in which it is expressed.

It is a specific object of this invention to provide an apparatus for fulfillment of the objectives above.

It is yet another additional object of this invention to provide an apparatus for fulfillment of each of the objectives above for each member of a series of cell types.

At least some of these and other objectives are addressed by the various embodiments of the invention disclosed herein.

SUMMARY OF THE INVENTION

The present invention addresses the above and other needs by providing a method and corresponding apparatuses which allows the automated characterization of pharmacological profiles and corresponding potencies of compounds in synthesized combinatorial libraries. This enables the rapid screening of a large number of compounds in the combinatorial library, the identification of those compounds which have biological activity, and the characterization of those compounds in terms of potency, affinity and selectivity.

A variety of effects caused by the compounds to be screened may be detected and quantitatively characterized according to the present invention. Preferably, these effects include but are not limited to changes in intracellular concentration of ionized calcium, cAMP or pH, transmembrane potential and other physiological and biochemical characteristics of living cell which can be measured by a variety of conventional means, for example using specific fluorescent, luminescent or color developing dyes.

The present invention also includes methods of screening for agonist or antagonist activity of drugs, methods of characterizing their potency profiles, methods of identifying the receptor expression pattern of cell membrane ("receptor fingerprinting") and methods of determining toxicity profiles for the compounds. In these methods, a steady flow of cells is mixed with flows of the compound and a standard substance. The effects of the compound alone and in mixture with the standard substance are measured and provide the means for pharmacological profiling of the compounds, drug screening and cell receptor pattern characterizing.

In a preferred embodiment of the invention, the compounds to be screened and standard agonist and antagonist substances are organized in a 96-well plate format, or other regular two dimensional array, such as a 48-well and 24-well plate format or an array of test tubes. In another preferred embodiment of the invention, the non-adherent cells are grown in a suspension of freely flowing cells by growing them in an appropriate cell cultivating system.

In another preferred embodiment of the invention, the naturally adherent cells which need attachment to a surface for their growth, are grown in the appropriate cell cultivating system containing commercially available micro spherical beads to which the cells adhere during the growth.

In yet another preferred embodiment of the invention, the naturally adherent cells which need attachment to a surface for their growth, are grown in the cell culture flasks with a subsequent detachment of the cells from the flask bottom with an appropriate detaching reagent.

In accordance with the present invention, either eukaryotic or prokaryotic cells can be used. The cells can be transfected with a gene coding to express a receptor of interest, for example, an orphaned receptor. In addition, the variety of compounds having biologically relevant activity may be used including but not limited to neurotransmitters, hormones, toxins, receptor activators and inhibitors, ion channels and ion pump modulators, irritants and/or drugs.

The cells grown in accordance with the preferred embodiments described above, are mixed with an appropriate fluorescent dye, for example FURA-2AM for measurements of concentrations of intracellular calcium or BCECF-AM for measurements of intracellular pH, and are incubated in the appropriate conditions to allow the dye to penetrate into the cell. The cells loaded with a dye are supplied to the apparatus. In the apparatus, the cells are successively mixed with a solutions of the compounds to be tested.

The methods of the present invention may be performed automatically using the apparatti disclosed herein. In particular, the cells or particles may be automatically mixed with test compound(s) and or standard compound(s). The cells or particles may be automatically delivered to the detector. The detector may automatically analyze the cells for particular characteristics, automatically identify test compounds having the desired cellular effects, or automatically identify the presence of a particular molecule in a sample. In some embodiments, a coupling device may automatically deliver the cells or particles to the detector. Calibration solutions may be input automatically. In addition, gradients of test compounds or standard compounds may be automatically provided. The automation of the present methods increases the number of samples which can be evaluated over a given time period.

A first embodiment of the present invention is a method for identifying compounds which produce a cellular response comprising:

(a) using an apparatus to combine a suspension of cells with one or more test compounds to form test mixtures;

(b) directing the test mixtures through a detection zone, the detection zone being capable of detecting a plurality of cellular responses simultaneously; and (c) simultaneously measuring a plurality of cellular responses to the one or more test compounds in the suspended cells as the test mixtures are flowing through the detection zone.

In one aspect of the first embodiment, the plurality of cellular responses includes a cellular response selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, and activation or inhibition of cellular necrosis, and cellular toxicity.

In another aspect of the first embodiment, the plurality of cellular responses are measured by contacting the cells with one or more response indicating reagents which generate signals indicative of particular cellular responses. For example, the signal generated by the response indicating reagents may be fluorescence.

In another aspect of the first embodiment, the step of directing the test mixtures through a detection zone comprises directing the text mixtures through a detection zone which is capable of detecting the cellular responses in individual cells.

In another aspect of the first embodiment, the step of directing the test mixtures through a detection zone comprises directing the test mixtures through a flow cytometer.

In another aspect of the first embodiment, the step of simultaneously measuring a plurality of cellular responses comprises measuring the plurality of cellular responses in the suspended cells as a slug is flowing through the detection zone.

In another aspect of the first embodiment, the suspension of cells comprises more than one type of cell.

A second embodiment of the present invention is a method for identifying compounds which produce a cellular response comprising:
  (a) using an apparatus to combine a suspension of cells with one or more test compounds to form test mixtures;
  (b) directing the test mixtures through a detection zone, the detection zone being capable of detecting cellular responses in individual cells; and
  (c) measuring one or more cellular responses to the one or more test compounds in individual suspended cells as the test mixtures are flowing through the detection zone.

In one aspect of the second embodiment, the one or more cellular responses is selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, and activation or inhibition of cellular necrosis, and cellular toxicity.

In another aspect of the second embodiment, wherein the one or more cellular responses is measured by contacting the cells with one or more response indicating reagents which generate signals indicative of particular cellular responses. For example, the signal generated by the response indicating reagents may be fluorescence.

In another aspect of the second embodiment, the step of directing the test mixtures through a detection zone comprises directing the test mixtures through a flow cytometer.

In another aspect of the second embodiment, the suspension of cells comprises more than one type of cell.

In another aspect of the second embodiment, the step of simultaneously measuring a plurality of cellular responses comprises measuring the plurality of cellular responses in the suspended cells as a slug is flowing through the detection zone.

A third embodiment of the present invention is a method of determining whether a sample contains one or more molecules comprising:
  using an apparatus to combine one or more agents capable of binding one or more molecules with the sample to form test mixtures;
  directing the test mixtures through a detection zone; and
  determining whether the one or more agents are bound to the one or more molecules as the one or more agents are flowing through the detection zone.

In one aspect of the third embodiment, the one or more agents are fixed to a solid support. For example, a plurality of agents capable of binding a plurality of molecules may be fixed to uniquely identifiable solid supports. The determining step may comprise detecting a signal from an individual solid support wherein the signal indicates that the agent on the solid support has bound to the molecule.

In another aspect of the third embodiment, the one or more agents are selected from the group consisting of antibodies, nucleic acids, polypeptides, enzymatic substrates, and receptors.

In another aspect of the third embodiment, the one or more molecules are selected from the group consisting of polypeptides, nucleic acids, receptor ligands, enzymatic agonists and enzymatic antagonists.

A fourth embodiment of the present invention is a method of determining whether a sample contains one or more polypeptides comprising:
  attaching one or more antibodies which specifically bind the one or more polypeptides to solid supports;
  using an apparatus to combine the one or more antibodies attached to solid supports with samples to form test mixtures;
  directing the test mixtures through a detection zone; and
  determining whether the one or more antibodies are bound to the one or more polypeptides as the solid supports are flowing through the detection zone.

In one aspect of the fourth embodiment, a plurality of antibodies which specifically bind to a plurality of polypeptides are fixed to uniquely identifiable solid supports. The determining step may comprise detecting a signal from an individual solid support wherein the signal indicates that the antibodies have bound to the molecules. The signal may be generated by detectably labeled secondary antibodies which bind the molecules.

A fifth embodiment of the present invention is a method of determining whether a sample contains one or more nucleic acids comprising:
  attaching one or more nucleic acid probes which specifically bind the nucleic acids to solid supports;
  using an apparatus to combine the one or more probes attached to the solid supports with samples to form test mixtures;
  directing the test mixtures through a detection zone; and
  determining whether the one or more probes are bound to the one or more nucleic acids as the solid supports are flowing through the detection zone.

In one aspect of the fifth embodiment, a plurality of nucleic acid probes are fixed to uniquely addressable solid supports. The determining step may comprise detecting a signal from an individual solid support wherein the signal indicates that the probes have bound to the nucleic acids. The signal may be generated by detectable nucleic acid probes which bind the nucleic acids.

A sixth embodiment of the present invention is a method of determining whether a sample contains one or more single nucleotide polymorphisms comprising:
  performing an extension reaction on a nucleic acid sample using one or more nucleic acid primers having a 3' end immediately adjacent to the polymorphic base of one or more single nucleotide polymorphisms, thereby incorporating one base into the nucleic acid primers;

attaching the extended primers to solid supports;

directing the solid supports having primers attached thereto through a detection zone in an apparatus; and determining the identities of the bases incorporated in the extension reaction.

In one aspect of the sixth embodiment, a plurality of primers are fixed to uniquely identifiable solid supports. The determining step comprises detecting a signal from an individual solid support wherein the signal is indicative of the identity of the polymorphic base in a SNP. The signal may be generated by detectably labeled nucleotides incorporated in the extension reaction.

In another aspect, the first embodiment further comprises the steps of:

(d) combining a suspension of the cells with one or more standard compounds having a known effect on the cellular response of the cells to form standard mixtures;

(e) directing the standard mixtures through the detection zone; and (f) measuring the cellular response of the cells to the one or more standard compounds.

In the above aspect of the first embodiment, the one or more standard compounds and the one or more test compounds may be simultaneously mixed with the cells in the combining steps, and the measuring step detects the known effect or an alteration of the known effect. The one or more standard compounds is an antagonist of the cellular response. The one or more standard compounds is an agonist of the cellular response. The suspension of cells may comprise more than one cell type. The step of directing the test mixtures through a detection zone may comprise directing the test mixtures through a flow cytometer.

A seventh embodiment of the present invention is a method of obtaining cells having a desired phenotype or cellular response profile comprising the steps of:

(a) using an apparatus to combine a suspension of cells with one or more compounds which produce a cellular response to form test mixtures;

(b) directing the test mixtures through a detection zone, the detection zone being capable of detecting a plurality of cellular parameters simultaneously;

(c) simultaneously measuring a plurality of cellular parameters in the suspended cells as the test mixtures are flowing through the detection zone; and (d) delivering cells having a desired phenotype or cellular response profile into a receptacle.

An eighth embodiment of the present invention is a method of obtaining cells having a desired phenotype or cellular response profile comprising the steps of:

(a) using an apparatus to combine a suspension of cells with one or more compounds which produce a cellular response to form test mixtures;

(b) directing the test mixtures through a detection zone, the detection zone being capable of detecting cellular responses in individual cells;

(c) simultaneously measuring a plurality of cellular parameters in the suspended cells as the test mixtures are flowing through the detection zone; and (d) delivering cells having a desired phenotype or cellular response profile into a receptacle.

A ninth embodiment of the present invention is an apparatus comprising:

one or more sample inputs for sequentially providing multiple samples, the samples comprising one or more test compounds to be evaluated for the ability to produce a cellular response or a solution to be evaluated for the presence of molecules;

one or more cell or particle inputs for providing a cell suspension or particles;

a mixing zone, coupled to the sample input, for receiving the samples, receiving the cell suspension or particles from the cell or particle input and mixing each sample with the cell suspension or particles; and a detector capable of detecting a plurality of signals simultaneously, the detector being coupled to the mixing zone and being capable of simultaneously measuring a plurality of cellular responses in the suspended cells or simultaneously determining whether a plurality of molecules are present in the samples.

In one aspect of the ninth embodiment, the detector detects a signal from a single cell in the cell suspension or from a single particle.

In another aspect of the ninth embodiment, the detector is a flow cytometer.

In another aspect of the ninth embodiment, the apparatus further comprises a coupler disposed between the mixing zone and the detector. The coupler may deliver slugs comprising the samples and the cell suspension or particles to the detector. In some embodiments the coupler delivers substantially undiluted slugs to the detector. In another aspect of the ninth embodiment, the detector delivers cells having a desired phenotype or cellular response to a receptacle.

In another aspect of the ninth embodiment, the sample input is an automated robotic sampler capable of selecting a specified test compound from a library of test compounds. The device may further comprise a controller, coupled to the sample input, for controlling the operation of the test compound sampler; and a computer, coupled to the controller, for sending command signals to the controller in accordance with a software program implemented by the computer, thereby controlling the selection and retrieval of test compounds by the sample input from the test compound library. The apparatus may further comprise a gradient pump having an input and an output, coupled to the sample input, for adjusting the concentration level of the test compound transferred to the mixing zone from the sample input, wherein:

the sample input comprises:

a first intake nozzle for receiving the specified test compound;

a second intake nozzle for receiving a buffer solution; and wherein the gradient pump is coupled to the first and second intake nozzles and receives specified concentrations of the test compound by adjusting the amount of test compound and buffer solution received by the first and second intake nozzles, respectively, wherein the buffer solution is a diluting agent of the test compound. The apparatus may further comprise a second pump, coupled to an input of the mixing zone, for pumping the suspension of cells or the particles from the cell or particle input into the mixing zone. The apparatus may further comprise a reaction developing line, having an input coupled to an output of the mixing zone and an output in fluid communication with the detector wherein the reaction developing line provides a reaction time delay for a mixture received from the mixing zone. The apparatus may further comprise:

a pump, coupled to the output of the detector, for providing negative pressure to the apparatus;

a proportionating valve, coupled to the sample input, for adjusting the concentration level of the test compound transferred to the mixing zone from the sample input, wherein the sample input further comprises:

a first intake nozzle for receiving the specified test compound;

a second intake nozzle for receiving a buffer solution; and the proportionating valve receives specified concentrations of the test compound by adjusting the amount of test compound and buffer solution received by the first and second intake nozzles, respectively, wherein the buffer solution is a diluting agent of the test compound.

In another aspect of the ninth embodiment, the apparatus further comprises a plurality of cell suspension reservoirs.

In another aspect of the ninth embodiment, the apparatus further comprises a standard compound sampler, coupled to the mixing zone, for providing one or more standard compounds having a known effect on the cellular response of the suspended cells or a known interaction with the particles, wherein the mixing zone receives the one or more standard compounds from the standard compound sampler and mixes the one or more standard compounds with the suspended cells or particles and the detector measures the cellular response of the suspended cells to the one or more standard compounds or the interaction between the one or more standard compounds and the particles. The mixing zone may simultaneously mix the sample and the one or more standard compounds with the suspended cells or the particles and the detector detects the known effect or an alteration of the known effect on the cellular responses of the suspended cells or the known interaction between the standard compound and the particles or an alteration of the known interaction between the standard compound and the particles. The standard compound sampler may be an automated robotic sampler capable of selecting a specified standard compound from a library of standard compounds.

A tenth embodiment of the present invention is an apparatus comprising:

a sample input for sequentially providing multiple samples, the samples comprising one or more test compounds to be evaluated for the ability to produce a cellular response or a solution to be evaluated for the presence of molecules;

a cell or particle input for providing a cell suspension or particles;

a mixing zone, coupled to the sample input, for receiving the samples, receiving the cell suspension or particles from the cell or particle input and mixing each sample with the cell suspension or particles; and a detector which detects one or more signals from a single cell or particle, the detector being coupled to the mixing zone and being capable of measuring one or more cellular responses in the suspended cells or determining whether one or more molecules are present in the samples.

In one aspect of the tenth embodiment, the apparatus further comprises a coupler disposed between the mixing zone and the detector. The coupler may deliver slugs comprising the samples and the cell suspension or particles to the detector. The coupler may deliver substantially undiluted slugs to the detector. The apparatus may further comprise an input system for inputting solutions into the mixing zone. The detector may deliver cells having a desired phenotype or cellular response to a receptacle.

An eleventh embodiment of the present invention is an apparatus comprising:

a sample input for sequentially providing multiple samples, the samples comprising one or more test compounds to be evaluated for the ability to produce a cellular response or a solution to be evaluated for the presence of molecules;

a cell or particle input for providing a cell suspension or particles;

a mixing zone, coupled to the sample input, for receiving the samples, receiving the cell suspension or particles from the cell or particle input and mixing each sample with the cell suspension or particles; and a detector capable of detecting a plurality of signals simultaneously, the detector being coupled to the mixing zone and being capable of simultaneously measuring a plurality of cellular responses in the suspended cells or simultaneously determining whether a plurality of molecules are present in the samples.

In one aspect of the eleventh embodiment, the detector detects a signal from a single cell in the cell suspension or from a single particle.

In another aspect of the eleventh embodiment, the detector is a flow cytometer. In another aspect of the eleventh embodiment, the apparatus further comprises a coupler disposed between the mixing zone and the detector. The coupler may deliver slugs comprising the samples and the cell suspension or particles to the detector.

The coupler may deliver substantially undiluted slugs to the detector.

In another aspect of the eleventh embodiment, the apparatus further comprises an input system for inputting solutions into the mixing zone.

In another aspect of the eleventh embodiment, the detector delivers cells having a desired phenotype or cellular response to a receptacle.

In another aspect of the eleventh embodiment, the apparatus further comprises a standard compound sampler, coupled to the mixing zone, for providing one or more standard compounds having a known effect on the cellular response of the suspended cells or a known interaction with the particles, wherein the mixing zone receives the one or more standard compounds from the standard compound sampler and mixes the one or more standard compounds with the suspended cells or particles and the detector measures the cellular response of the suspended cells to the one or more standard compounds or the interaction between the one or more standard compounds and the particles. The mixing zone may simultaneously mix the sample and the one or more standard compounds with the suspended cells or the particles and the detector detects the known effect or an alteration of the known effect on the cellular responses of the suspended cells or the known interaction between the standard compound and the particles or an alteration of the known interaction between the standard compound and the particles.

The apparatus may further comprise:

a first gradient device, coupled to the sample input, for automatically adjusting the concentration level of the one or more test compounds transferred to the mixing zone from the sample input; and a second gradient device, coupled to the standard compound sampler, for automatically adjusting the concentration level of the one or more standard compounds transferred to the mixing zone from the standard compound sampler. The apparatus may further comprise a switching valve, coupled to the first and second gradient devices at an input of the switching valve and coupled to the mixing zone at an output of the switching valve, for selectively switching the flow of a concentration of the one or more test compounds or a concentration of the one or more standard compounds or both to the mixing zone where the one or more test compounds and/or the one or more standard compounds are then mixed with the suspension of cells or the particles. The apparatus may further comprise a calibration unit, coupled to the switching valve, wherein the switching valve also selectively switches the flow of a calibration solution provided by the calibration unit into the mixing zone where the calibration solution is mixed with the suspension of cells or the particles. The apparatus may further comprise reaction developing lines coupled to the output of the mixing zone, for receiving a mixture of the cell suspension or the particles mixed with either the one or more test compounds, the one or more standard compounds or the calibration solution, and providing a flow path for the mixture such that there is adequate time for the suspended cells or particles to react with the one or more test compounds, the one or more standard compounds or the calibration solution, wherein the reaction developing lines are further coupled to the input of the detector which receives the mixture from the reaction developing lines.

In another aspect of the eleventh embodiment, the detector simultaneously detects a plurality of cellular responses including a cellular response selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, activation or inhibition of cellular necrosis, and cellular toxicity The apparatus may further comprise:
  a controller, coupled to the first and second gradient devices, the sample input, the standard compound sampler, the switching valve, and the coupler for controlling their operation; and
  a computer, coupled to the controller, for sending command signals to the controller in accordance with a software program implemented by the computer, wherein the computer is also coupled to the detector in order to send and receive signals indicative of a cellular response or the presence of a molecule in the sample to and from the detector.

In another aspect of the eleventh embodiment, the sample input is an automated robotic sampler capable of selecting a specified test compound from a library of test compounds. The apparatus may further comprise:
  a controller, coupled to the sample input, for controlling the operation of the test compound sampler; and
  a computer, coupled to the controller, for sending command signals to the controller in accordance with a software program implemented by the computer, thereby controlling the selection and retrieval of test compounds by the sample input from the test compound library.

The apparatus may further comprise a gradient pump having an input and an output, coupled to the sample input, for adjusting the concentration level of the test compound transferred to the mixing zone from the sample input, wherein:
  the sample input comprises:
    a first intake nozzle for receiving the specified test compound;
    a second intake nozzle for receiving a buffer solution; and
  wherein the gradient pump is coupled to the first and second intake nozzles and receives specified concentrations of the test compound by adjusting the amount of test compound and buffer solution received by the first and second intake nozzles, respectively, wherein the buffer solution is a diluting agent of the test compound. The apparatus may further comprise a standard compound sampler for providing a sample of a standard compound to the mixing zone. The standard compound sampler may be an automated robotic sampler capable of selecting a specified standard compound from a library of standard compounds. The apparatus may further comprise a second gradient pump having an input and an output, coupled to the standard compound sampler, for adjusting the concentration level of the standard compound provided to the mixing zone from the standard compound sampler, wherein:
  the standard compound sampler comprises:
    a third intake nozzle for receiving the specified standard compound;
    a fourth intake nozzle for receiving a buffer solution; and
  wherein the second gradient pump is coupled to the third and fourth intake nozzles and receives specified concentrations of the standard compound by adjusting the amount of standard compound and buffer solution received by the third and fourth intake nozzles, respectively, wherein the buffer solution is a diluting agent of the standard compound. The apparatus may further comprise a second mixing zone coupled to the outputs of the first and second gradient pumps, for receiving and mixing the specified concentrations of the specified test compound and the specified standard compound, such that the output of the second mixing zone is provided to the first mixing zone. The apparatus may further comprise:
a calibration unit for providing a calibration solution; and
a switching valve, having a first input coupled to the second mixing zone, a second input coupled to the calibration unit, and an output coupled to the first mixing zone, for switching between the flow of either a compound mixture from the second mixing zone or the calibration solution from the calibration unit and then providing the flow to the first mixing zone where it may be mixed with the cell suspension or particles. The calibration unit may comprise:
a calibration maximum solution which provides for maximal cell response or maximum interaction of particles with a molecule when mixed with the cell suspension or particles;
a calibration minimum solution which provides for minimal cell response or minimal interaction of a particle with a molecule when mixed with the cell suspension or particles;
a diverting valve having a first input coupled to the calibration maximum solution and a second input coupled to the calibration minimum solution, for switching between the flow of either the calibration maximum solution or calibration minimum solution; and
a pump, coupled to the output of the diverting valve and an input of the switching valve, for pumping either the calibration maximum or calibration minimum solution from the diverting valve into the switching valve. The apparatus may further comprise a second pump, coupled to an input of the first mixing zone, for pumping the suspension of cells or the particles from the cell or particle input into the first mixing zone. The apparatus may further comprise a reaction developing line, having an input coupled to an output of the first mixing zone and an output coupled to an input of the detector, for providing a flow path and a reaction time delay for a mixture received from the first mixing zone and for providing the mixture to the detector. The apparatus may further comprise:

a controller, coupled to the first and second gradient pumps, the sample input, the standard compound sampler and the switching valve, the first and second mixing zones, the first and second pumps and the diverting valve for controlling their operation; and a computer, coupled to the controller, for sending command signals to the controller in accordance with a software program implemented by the computer, wherein the computer is also coupled to the detector in order to send and receive signals indicative of a cellular response or the presence of a molecule in a sample to and from the detector. The detector may detect a plurality of cellular responses including a cellular response selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, activation or inhibition of cellular necrosis, and cellular toxicity.

The apparatus may further comprise:

a pump, coupled to the output of the detector, for providing negative pressure to the apparatus;

a proportionating valve, coupled to the sample input, for adjusting the concentration level of the test compound transferred to the mixing zone from the sample input, wherein the sample input further comprises:

a first intake nozzle for receiving the specified test compound;

a second intake nozzle for receiving a buffer solution; and the proportionating valve receives specified concentrations of the test compound by adjusting the amount of test compound and buffer solution received by the first and second intake nozzles, respectively, wherein the buffer solution is a diluting agent of the test compound.

The apparatus may further comprise:

an automated standard compound sampler capable of selecting a specified standard compound from a library of standard compounds, the standard compound sampler including a third intake nozzle for receiving the specified standard compound and a fourth intake nozzle for receiving a buffer solution; and a second proportionating valve, coupled to the third and fourth intake nozzles, for receiving specified concentrations of the standard compound by adjusting the amount of standard compound and buffer solution received by the third and fourth intake nozzles, respectively, wherein the buffer solution is a diluting agent of the standard compound. The apparatus may further comprise:

a first priming valve, coupled to the output of the first proportionating valve, for receiving the specified concentration of the test compound and providing the test compound to the mixing zone;

a second priming valve, coupled to the output of the second proportionating valve, for receiving the specified concentration of the standard compound and providing the standard compound to the mixing zone. The apparatus may further comprise:

a calibration unit including a calibration maximum solution which provides for maximal cell response or maximum interaction with particles when mixed with the cell suspension or particles and a calibration minimum solution which provides for minimal cell response or minimal interaction with particles when mixed with the cell suspension;

a first diverting valve, having a first input coupled to the calibration maximum solution and a second input coupled to the calibration minimum solution, for switching between the flow of either the calibration maximum solution or calibration minimum solution;

a second diverting valve, having a first input coupled to the output of the mixing zone and a second input coupled to the output of the first diverting valve, for switching between the flow of either a calibration solution from the first diverting valve or a mixture from the mixing zone;

a third priming valve, coupled to the output of the second diverting valve, for receiving a mixture from the second diverting valve; and a second mixing zone, coupled to the output of the third priming valve, for mixing a mixture provided by the third priming valve with the cell suspension or particles, wherein the cell or particle input and the detector are coupled to the second mixing zone instead of the first mixing zone. The apparatus may further comprise a reaction developing line, having an input coupled to the output of the second mixing zone and an output coupled to an input of the detector, for providing a flow path and a reaction time delay for a mixture received from the second mixing zone before the mixture reaches the detector. The cell or particle input may comprise:

a cell suspension or particle reservoir;

a buffer reservoir;

a third diverting valve, having a first input coupled to the cell suspension or particle reservoir and a second input coupled to the buffer reservoir, for adjusting the concentration of the cell suspension or the particles, wherein the buffer is a diluting agent of the cell suspension or particles; and a fourth priming valve, coupled to the output of the third diverting valve, for receiving the cell suspension or particle mixture from the third diverting valve and providing this mixture to the second mixing zone. The detector may detect a plurality of cellular responses including a cellular response selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, activation or inhibition of cellular necrosis, and cellular toxicity. The apparatus may further comprise a plurality of cell suspension reservoirs.

A twelfth embodiment of the present invention is an apparatus comprising:

a sample input for sequentially providing multiple samples, the samples comprising one or more test compounds to be evaluated for the ability to produce a cellular response or a solution to be evaluated for the presence of molecules;

a cell or particle input for providing a cell suspension or particles;

a mixing zone, coupled to the sample input, for receiving the samples, receiving the cell suspension or particles from the cell or particle input and mixing each sample with the cell suspension or particles; and a detector which detects one or more signals from a single cell or particle, the detector being coupled to the mixing zone and being capable of measuring one or more cellular responses in the suspended cells or determining whether one or more molecules are present in the samples.

In one aspect of the twelfth embodiment, the detector is a flow cytometer.

In another aspect of the twelfth embodiment, the detector delivers cells having a desired phenotype or cellular response to a receptacle.

In another aspect of the twelfth embodiment, further comprising a coupler disposed between the mixing zone and the detector. The coupler may deliver slugs comprising the samples and the cell suspension or particles to the detector. The coupler may deliver substantially undiluted slugs to the detector.

In another aspect of the twelfth embodiment, the apparatus further comprises a standard compound sampler, coupled to the mixing zone, for providing a sample of one or more standard compounds having a known effect on the cellular response of the suspended cells or a known interaction with the particles, wherein the mixing zone receives the sample of the one or more standard compounds from the standard compound sampler and mixes the one or more standard compounds with the suspended cells or particles and the detector measures the cellular response of the suspended cells to the one or more standard compounds or the interaction between the one or more standard compounds and the particles. The mixing zone may simultaneously mix the one or more test compounds and the one or more standard compounds with the suspended cells or the particles and the detector detects the known effect or an alteration of the known effect on the cellular responses of the suspended cells or the known interaction between the one or more standard compounds and the particles or an alteration of the known interaction between the one or more standard compounds and the particles. The apparatus may further comprise:

a first gradient device, coupled to the sample input, for automatically adjusting the concentration level of the one or more test compounds transferred to the mixing zone from the sample input; and a second gradient device, coupled to the standard compound sampler, for automatically adjusting the concentration level of the one or more standard compounds transferred to the mixing zone from the standard compound sampler. The apparatus may further comprise a switching valve, coupled to the first and second gradient devices at an input of the switching valve and coupled to the mixing zone at an output of the switching valve, for selectively switching the flow of a concentration of the one or more test compounds or a concentration of the standard compound or both to the mixing zone where the one or more test compounds and/or the one or more standard compounds are then mixed with the suspension of cells or the particles. The apparatus may further comprise a calibration unit, coupled to the switching valve, wherein the switching valve also selectively switches the flow of a calibration solution provided by the calibration unit into the mixing zone where the calibration solution is mixed with the suspension of cells or the particles. The apparatus may further comprise reaction developing lines coupled to the output of the mixing zone, for receiving a mixture of the cell suspension or the particles mixed with either the one or more test compounds, the one or more standard compounds or the calibration solution, and providing a flow path for the mixture such that there is adequate time for the suspended cells or particles to react with the one or more test compounds, the standard compound or the calibration solution, wherein the reaction developing lines is further coupled to the input of the detector which receives the mixture from the reaction developing lines. The detector may detect one or more cellular responses selected from the group consisting of are selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, activation or inhibition of cellular necrosis, and cellular toxicity. The apparatus may further comprise:

a controller, coupled to the first and second gradient devices, the sample input, the standard compound sampler, the switching valve, and the coupler for controlling their operation; and a computer, coupled to the controller, for sending command signals to the controller in accordance with a software program implemented by the computer, wherein the computer is also coupled to the detector in order to send and receive signals indicative of a cellular response or the presence of a molecule in the sample to and from the detector.

In another aspect of the twelfth embodiment, the sample input is an automated robotic sampler capable of selecting a specified test compound from a library of test compounds. The apparatus may further comprise:

a controller, coupled to the sample input, for controlling the operation of the test compound sampler; and a computer, coupled to the controller, for sending command signals to the controller in accordance with a software program implemented by the computer, thereby controlling the selection and retrieval of test compounds by the sample input from the test compound library. The apparatus may further comprise a gradient pump having an input and an output, coupled to the sample input, for adjusting the concentration level of the test compound transferred to the mixing zone from the sample input, wherein:

the sample input comprises:

a first intake nozzle for receiving the specified test compound;

a second intake nozzle for receiving a buffer solution; and wherein the gradient pump is coupled to the first and second intake nozzles and receives specified concentrations of the test compound by adjusting the amount of test compound and buffer solution received by the first and second intake nozzles, respectively, wherein the buffer solution is a diluting agent of the test compound.

The apparatus may further comprise:

a pump, coupled to the output of the detector, for providing negative pressure to the apparatus;

a proportionating valve, coupled to the sample input, for adjusting the concentration level of the test compound transferred to the mixing zone from the sample input, wherein the sample input further comprises:

a first intake nozzle for receiving the specified test compound;

a second intake nozzle for receiving a buffer solution; and the proportionating valve receives specified concentrations of the test compound by adjusting the amount of test compound and buffer solution received by the first and second intake nozzles, respectively, wherein the buffer solution is a diluting agent of the test compound. The apparatus may further comprise:

an automated standard compound sampler capable of selecting a specified standard compound from a library of standard compounds, the standard compound sampler including a third intake nozzle for receiving the specified standard compound and a fourth intake nozzle for receiving a buffer solution; and a second proportionating valve, coupled to the third and fourth intake nozzles, for receiving specified concentrations of the standard compound by adjusting the amount of standard compound and buffer solution received by the third and fourth intake nozzles, respectively, wherein the buffer solution is a diluting agent of the standard compound. The apparatus may further comprise:

a first priming valve, coupled to the output of the first proportionating valve, for receiving the specified concentration of the test compound and providing the test compound to the mixing zone;

a second priming valve, coupled to the output of the second proportionating valve, for receiving the specified concentration of the standard compound and providing the standard compound to the mixing zone. The apparatus may further comprise:

a calibration unit including a calibration maximum solution which provides for maximal cell response or maximum interaction with particles when mixed with the cell suspension or particles and a calibration minimum solution which provides for minimal cell response or minimal interaction with particles when mixed with the cell suspension;

a first diverting valve, having a first input coupled to the calibration maximum solution and a second input coupled to the calibration minimum solution, for switching between the flow of either the calibration maximum solution or calibration minimum solution;

a second diverting valve, having a first input coupled to the output of the mixing zone and a second input coupled to the output of the first diverting valve, for switching between the flow of either a calibration solution from the first diverting valve or a mixture from the mixing zone;

a third priming valve, coupled to the output of the second diverting valve, for receiving a mixture from the second diverting valve; and a second mixing zone, coupled to the output of the third priming valve, for mixing a mixture provided by the third priming valve with the cell suspension or particles, wherein the cell or particle input and the detector are coupled to the second mixing zone instead of the first mixing zone. The apparatus may further comprise a reaction developing line, having an input coupled to the output of the second mixing zone and an output coupled to an input of the detector, for providing a flow path and a reaction time delay for a mixture received from the second mixing zone before the mixture reaches the detector. The cell or particle input may comprise:

a cell suspension or particle reservoir;

a buffer reservoir;

a third diverting valve, having a first input coupled to the cell suspension or particle reservoir and a second input coupled to the buffer reservoir, for adjusting the concentration of the cell suspension or the particles, wherein the buffer is a diluting agent of the cell suspension or particles; and a fourth priming valve, coupled to the output of the third diverting valve, for receiving the cell suspension or particle mixture from the third diverting valve and providing this mixture to the second mixing zone. The detector may detect a plurality of cellular responses including a cellular response selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, activation or inhibition of cellular necrosis, and cellular toxicity. The apparatus may further comprise a plurality of cell suspension reservoirs.

BRIEF DESCRIPTION OF THE DRAWINGS

FIG. 7 comprises the combination of FIGS. 7a–7d.

FIG. 8 comprises the combination of FIGS. 8a–8g.

FIG. 9 comprises the combination of FIGS. 9a–9e.

FIG. 16 comprises the combination of FIGS. 16a–16f.

FIG. 17 comprises the combination of FIGS. 17a–17g.

DESCRIPTION OF THE PREFERRED EMBODIMENTS

Figure 1A:
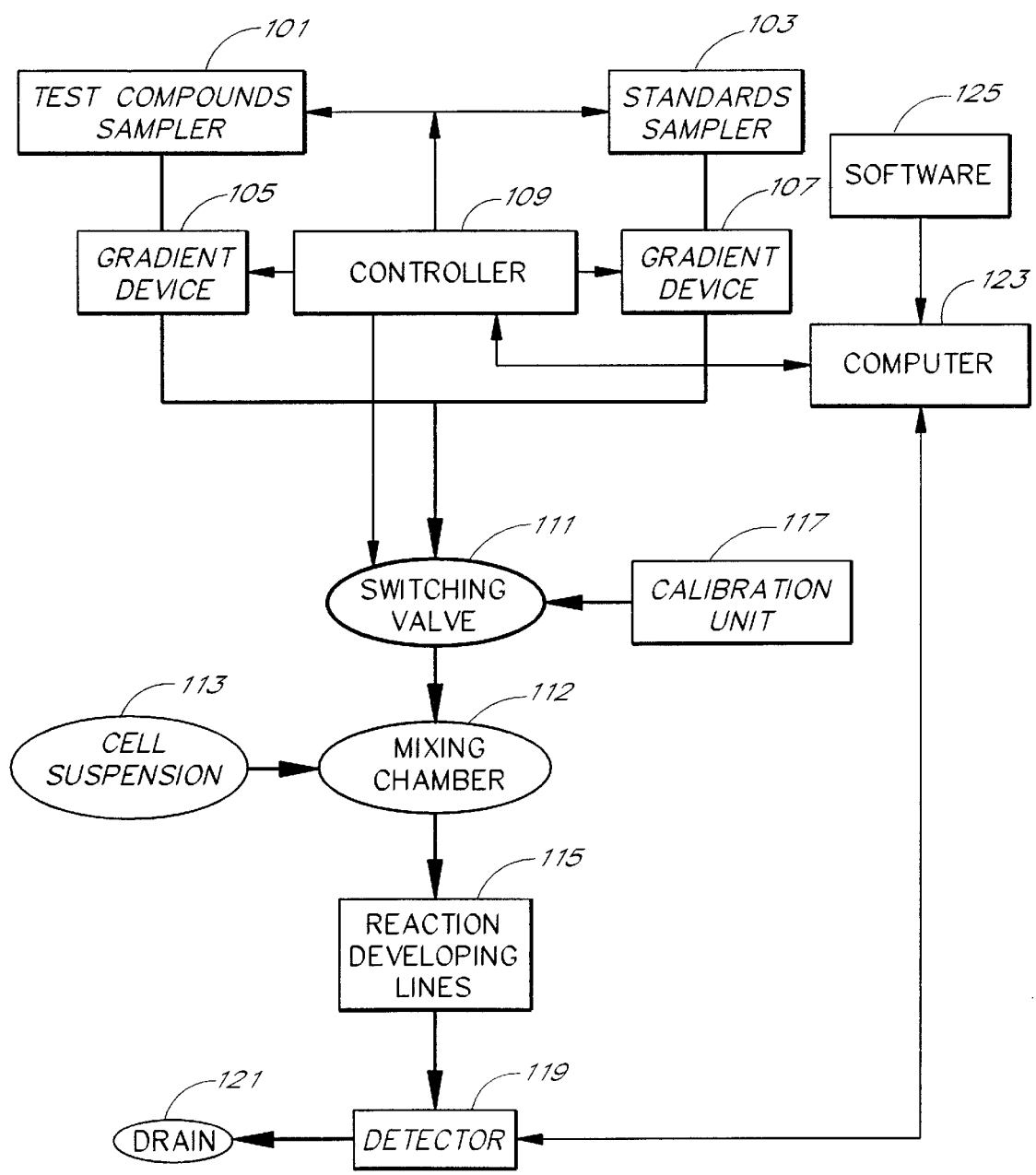
FIGS. 1A and 1B are block-diagrams of one embodiment of the combinatorial screening apparatus of the present invention which do not include or do include a coupling system.

The present invention provides for real-time, continuous monitoring and detection of the physiological or pharmacological effect of a test compound on a series of cell types or on a single cell type. In its simplest embodiment, the present invention comprises a method and apparatus for continuously contacting a single cell suspension, a series of cell suspensions, each of which contains a single cell type included in the series of cell types to be tested, a single cell suspension containing more than one cell type, or a series of cell suspensions containing more than one cell type with a predetermined concentration of at least one potentially active compound, preferably with predetermined concentrations of at least two active compounds. Then, intracellular changes that occur in response to contact between the cells and the active compounds are continuously measured as the suspensions pass a detector. In some embodiments, a plurality of cellular responses can be simultaneously evaluated. In some embodiments, one or more cellular responses are evaluated in a single cell.

In other embodiments, the present invention comprises a method and apparatus for continuously contacting particles, or a series of particles, each of which contains a particle type included in the series of particles to be tested, a single particle preparation containing more than one type of particle, or a series of particle preparations containing more than one type of particle with a predetermined concentration of at least one molecule to be tested for interaction with the particles. In some embodiments, the particles are contacted with predetermined concentrations of at least two molecules. Then, interactions between the particles and the molecules are continuously measured as the particles and the test molecules pass a detector. In some embodiments, a plurality of interactions can be simultaneously evaluated. In some embodiments, one or more interactions are evaluated in a particle.

In other embodiments, the present invention allows the monitoring of the physiological effects of test compounds, the pharmacological effects of test compounds, or the biochemical properties of cells to be measured at the level of individual cells or in each of the cell types in a heterogeneous population of cells. In further embodiments, the present invention allows the simultaneous examination of multiple characteristics of each cell or cell type or the examination of heterogeneous or mixed cell populations.

It is contemplated that the present invention will be of major value in high-throughput screening; e.g., in screening a large number of candidate compounds for activity against one or more cell types. It has particular value, for example, in screening synthetic or natural product libraries for active compounds or biochemical characterization.

It is also contemplated that the present invention will be of major value in high-throughput screening of a sample for a plurality of molecules, such as biological molecules. The present invention can be used to screen a sample for the presence of a large number of biological molecules such as polypeptides, receptor ligands, enzymatic substrates, agonists or antagonists of enzymatic or receptor activity, or nucleic acids.

In one preferred embodiment, a test compound, a standard compound, and a cell suspension containing the cell type to be tested or particle preparation, or a member of the series of cell types or series of particles to be tested are continuously mixed together and, after an incubation period, are passed by a detector that measures one or more cellular responses, one or more interactions between the molecules and the particles, or the concentration in the cells or in the intracellular medium of at least one analyte. In a preferred embodiment, the detector comprises a device capable of analyzing individual cells, individual cell types in a cell suspension, individual particles in a sample, individual particle types in a sample, individual components in a sample, or individual types of components in a sample. In some embodiments, the detector is capable of evaluating a plurality of cellular responses or a plurality of interactions between particles and molecules simultaneously. Preferably, the detector is a flow cytometer (FCM) which permits the analysis or characterization of individual cells, individual cell types in a cell suspension, individual particles in a sample, individual particle types in a sample, individual components in a sample, or individual types of components in a sample. In some embodiments, the detector may be capable of delivering cells exhibiting a desired set of parameters to a receptacle, thereby separating desired cells from undesired cells. For example, the detector may be a fluorescence activated cell sorter. Alternatively, the detector may comprise a microscope based imaging system such as those available from Bio-Rad (Eugene, OR) or Zeiss (Germany). In one embodiment, the concentration of the test compound and/or the standard compound is varied over time to generate dose/response curves as output from the detector.

It is preferred that the apparatus of the present invention is under the control of a computer or other programmable controller. The controller can continuously monitor the results of each step of the process, and can automatically alter the testing paradigm in response to those results.

The incubation period after mixing of the compound or compounds and the cells can advantageously be controlled by passing that mixture through a length of tubing connecting the mixing zone with the detector. After mixing with the test compound or compounds, the cell suspension or particles may be delivered to the detector, such as a flow cytometer, directly through the tubing. Alternatively, after mixing with the test compound or compounds, the cell suspension or particles may be delivered to the detector, such as a flow cytometer, via a coupling system.

Figure 1B:
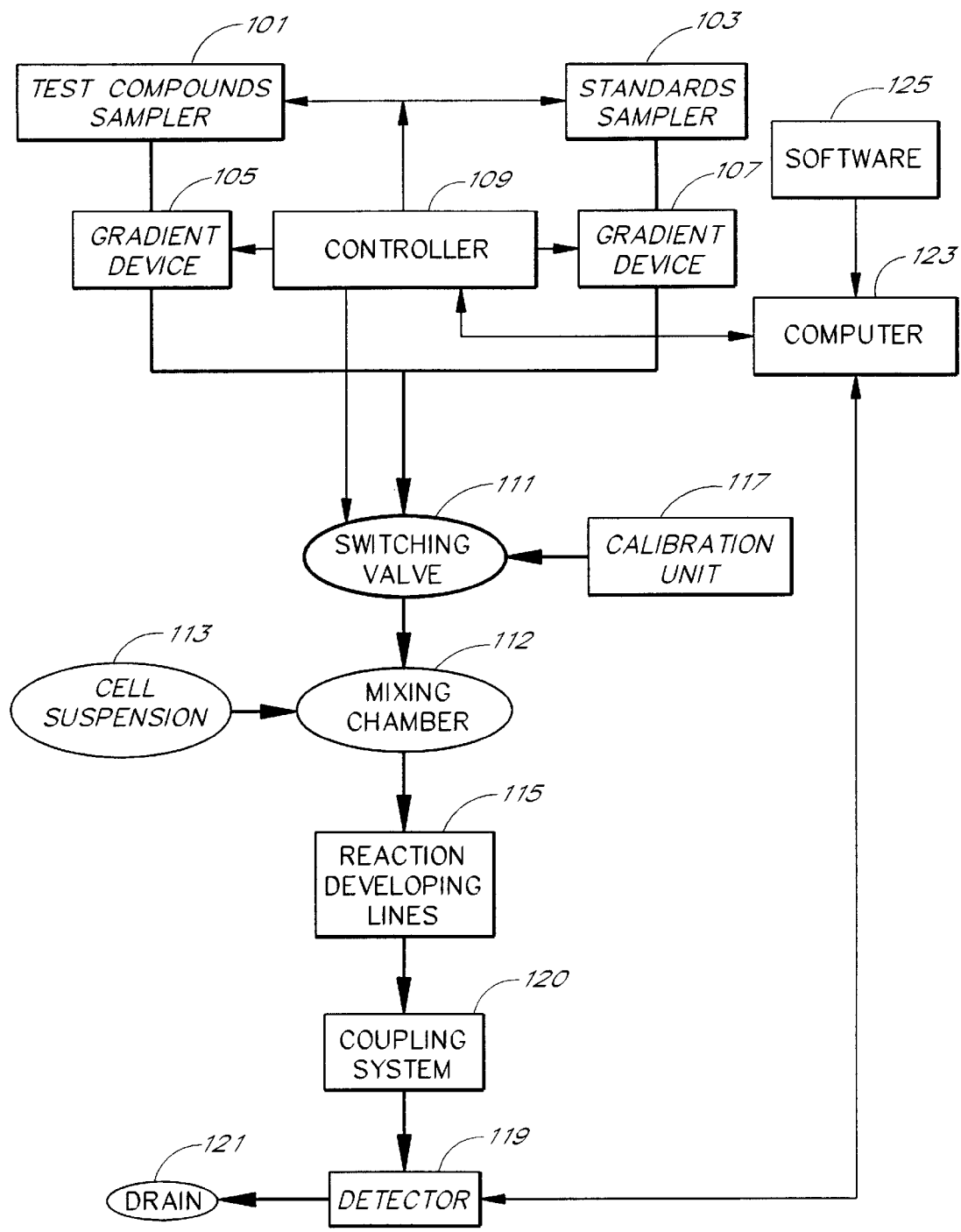
Figure 3A:
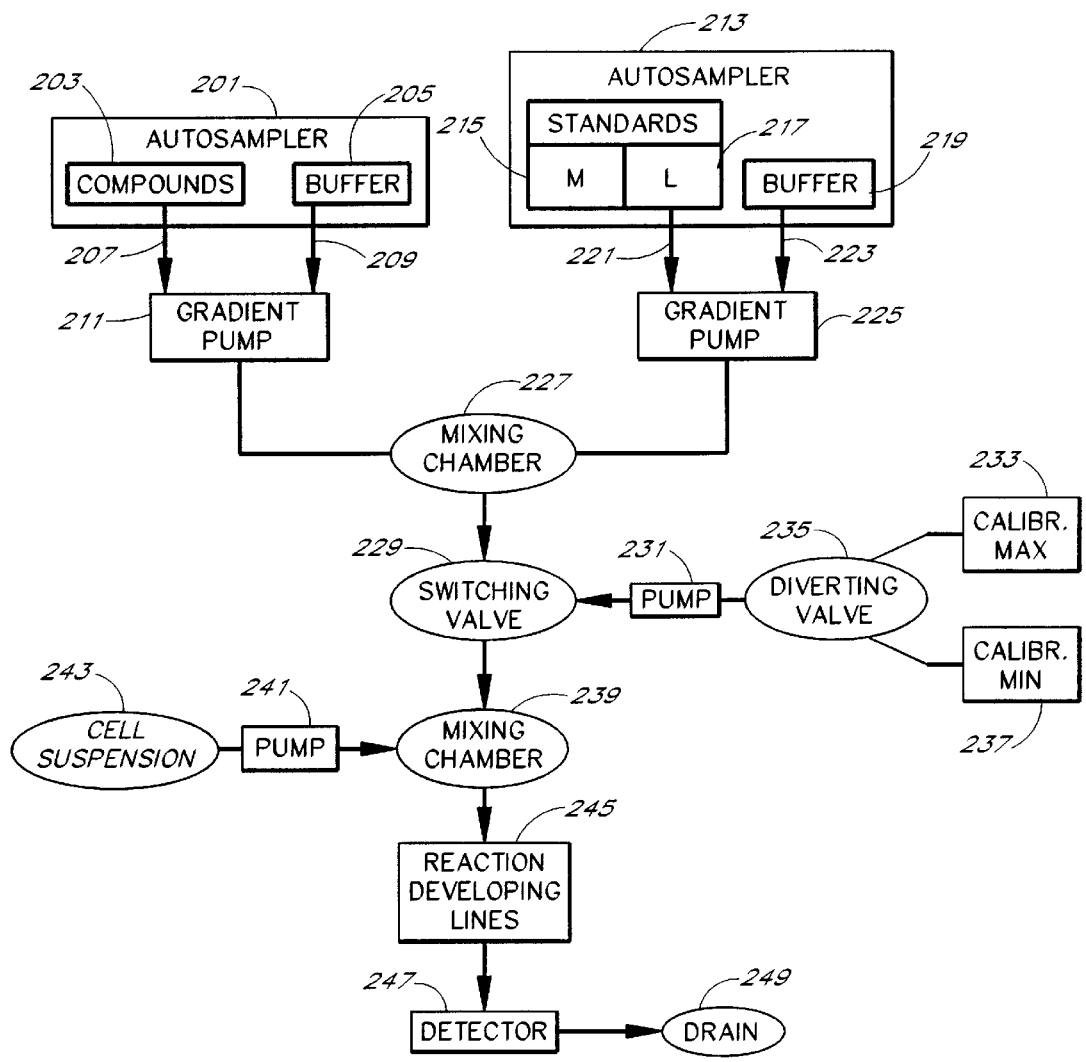
FIGS. 3A and 3B are block-diagrams of a positive pressure fluidic system which do not include or do include a coupling system and which may be used in a combinatorial screening apparatus of the present invention.
Figure 3B:
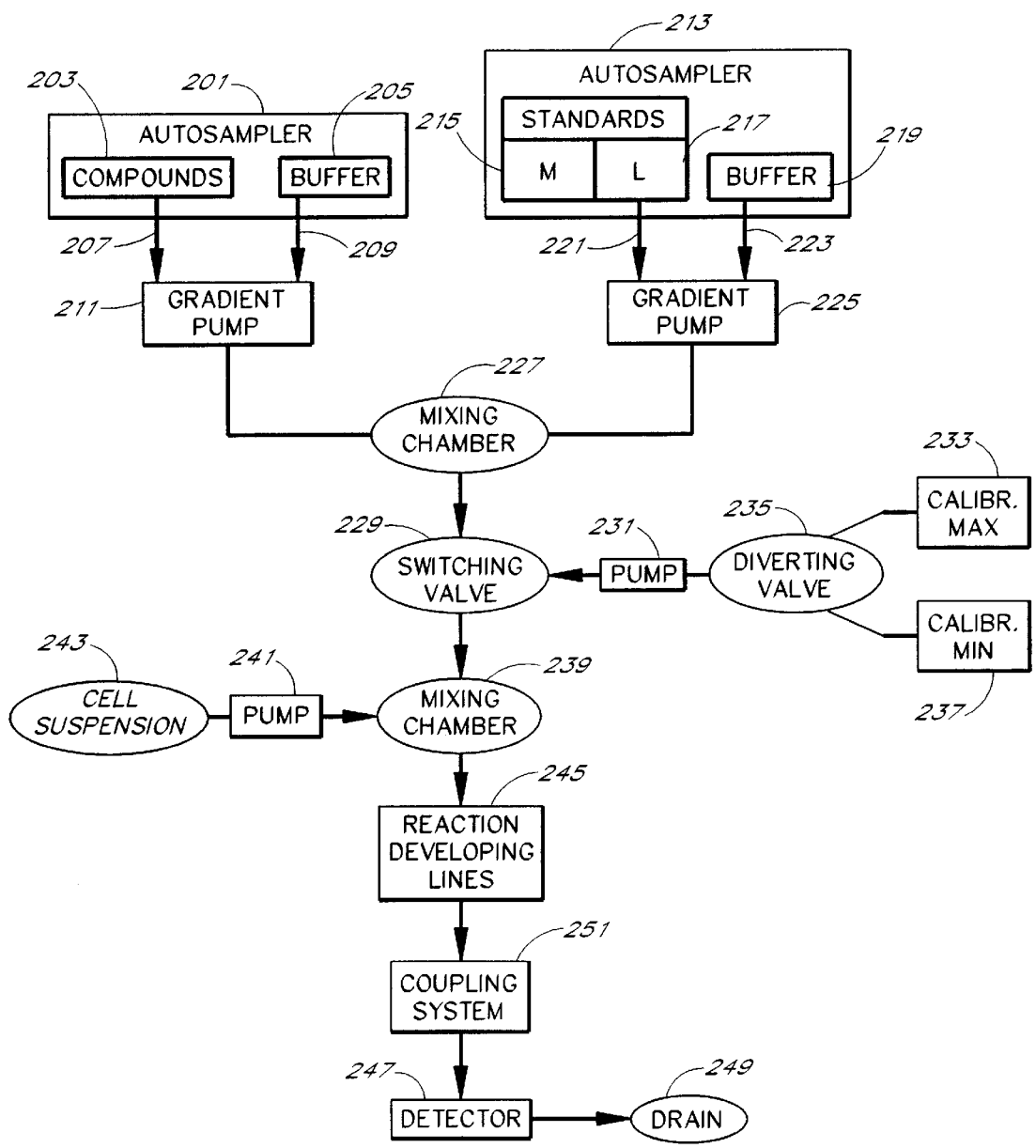
Figure 4A:
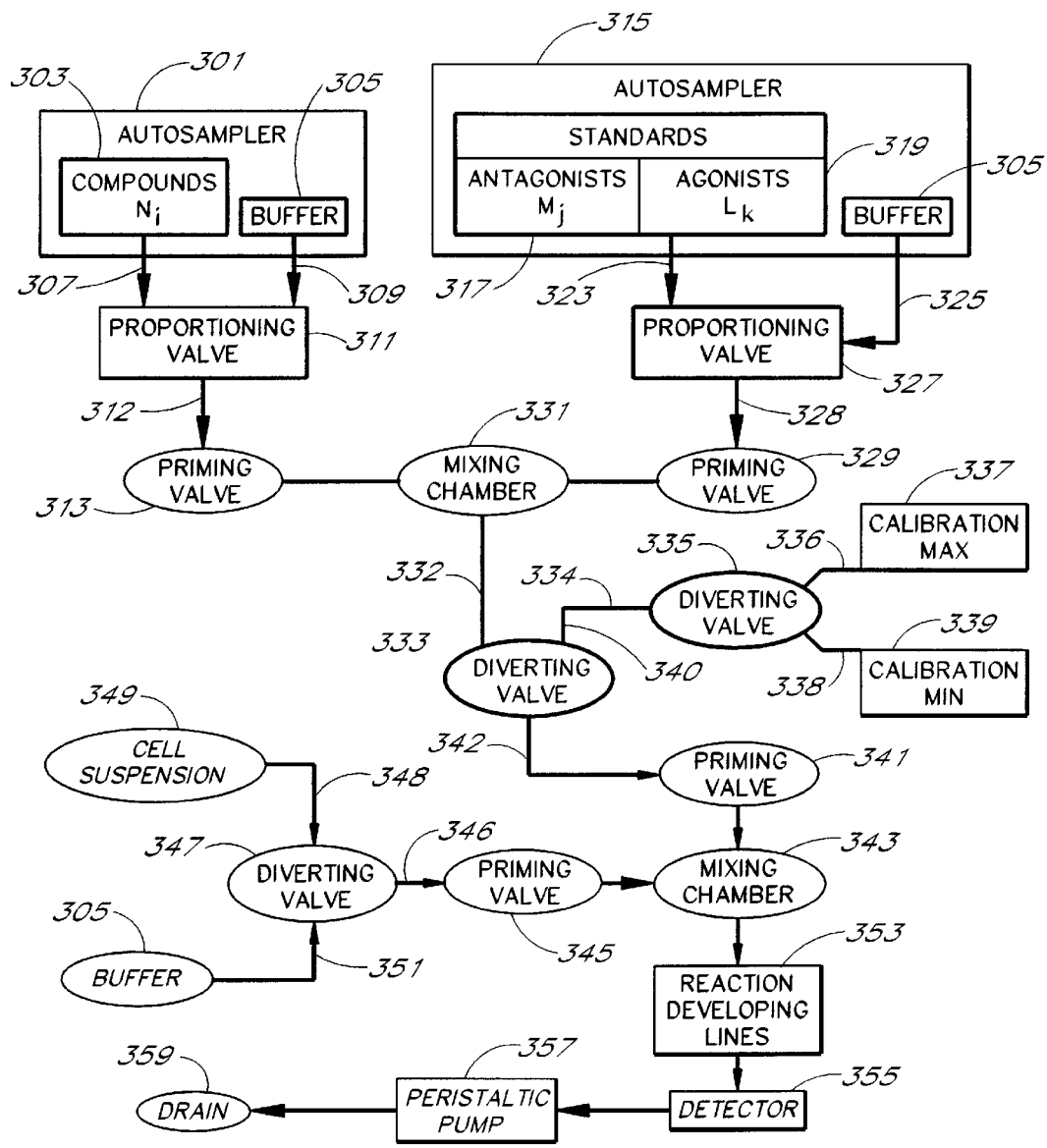
FIGS. 4A and 4B are block-diagrams of one embodiment of a preferred system which do not include or do include a coupling system and which may be used in a combinatorial screening apparatus of the present invention.
Figure 4B:
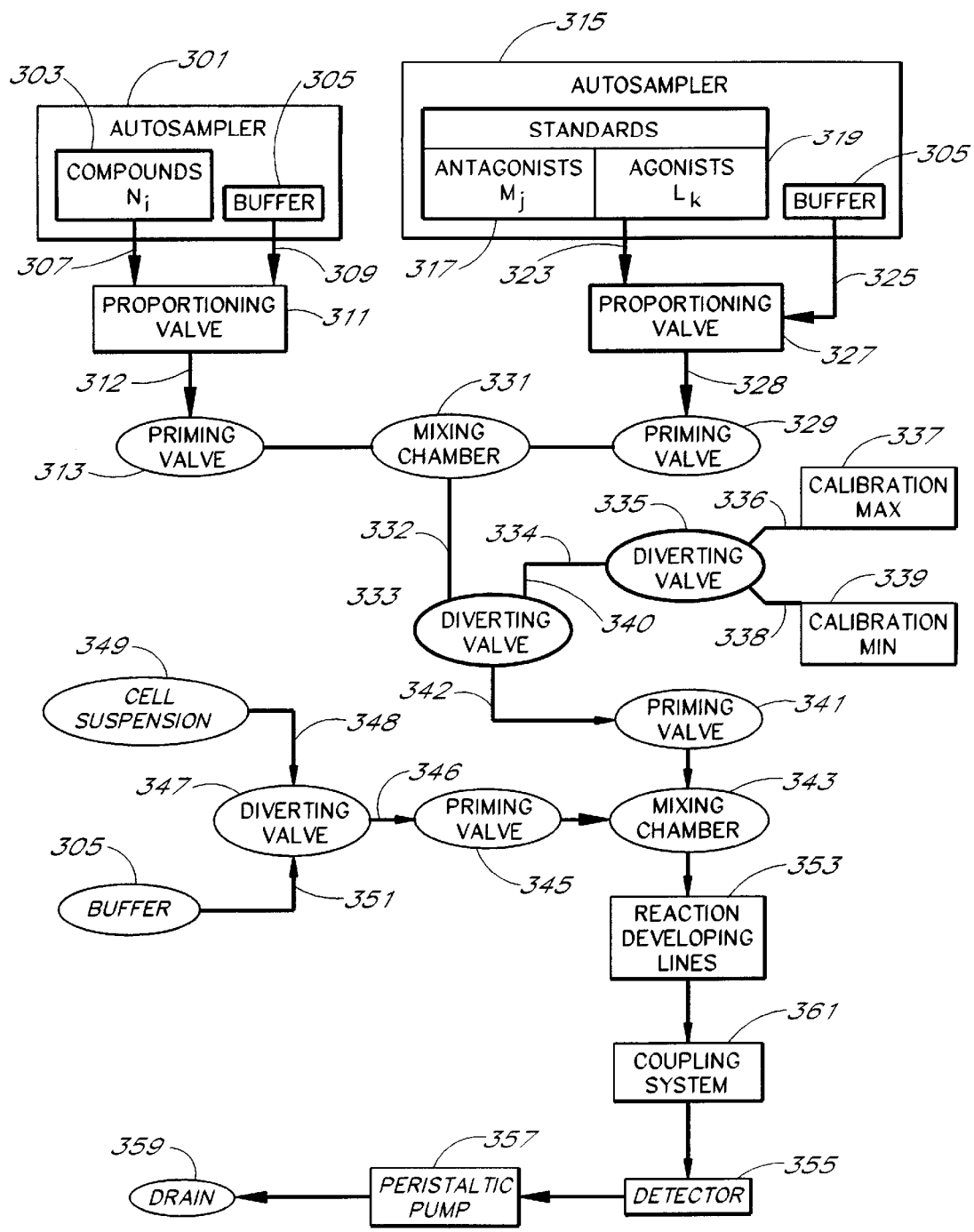

The coupling system is disposed between the mixing chamber and the detector as illustrated in FIGS. 1B, 3B, and 4B. Preferably, the coupling system rapidly provides the samples to the detector to optimize the number of samples which can be analyzed in a given time period. A variety of coupling systems are known to those skilled in the art.

More preferably, the coupler is a device which captures a slug comprising the cell and test compound(s) mixture from the output tubing connected to the mixing chamber and delivers the slug to the detector under conditions which minimize oscillations. Such a device will be referred to hereinafter as a Plug Flow Coupler (PFC). Preferably, the slug is isolated from the output tubing from the mixing chamber to a separate piece of tubing and rapidly delivered to the detector, such as a flow cytometer. Isolating the sample slug from the output tubing connected to the mixing chamber helps to reduce the effects of the oscillatory hydrodynamics of the peristaltic pump-driven output tubing, thereby enhancing the quality of the data. For example, the PFC may deliver the sample under positive air pressure.

Preferably, the PFC selects a substantially undiluted portion of the sample slug for analysis instead of analyzing the entire slug. During transit through the tubing from the mixing point, diffusion of the cells and test compound(s) occurs resulting in dilution of the test compound(s) contacted by the cells. Thus, in this preferred embodiment, diluted portions of the slug are not analyzed. Timing and other activities of the PFC may be controlled through a special section of software that will be incorporated within the software that controls the overall system.

Preferably, the PFC is the PFC described in the U.S. Patent Application entitled "Plug-Flow Cytometry for High Throughput Screening and Drug Discovery", filed Jun. 10, 1999, the corresponding PCT application of which is published as WO00/208. However, it will be appreciated that any device which provides a sample slug may be used.

In embodiments in which the detector is directly coupled to the mixing chamber via the reaction lines, the incubation period will thus be determined by the flow rate and the length of the tubing. In embodiments where a coupling system is used, the incubation period is determined by the amount of time it takes for the cell suspension or particles to pass from the mixing chamber, through the coupling system, and into the detector. Incubation periods can vary by several orders of magnitude, depending on the particular analyte and the resultant reaction time. For example, the incubation period could be as little as one second or a fraction of a second for rapid or short-lived physiological responses, or as long as several minutes or even hours.

The analyte can be any analyte that is readily detectable by detectors, such as flow cytometers, and/or detector/chemistry combinations. Thus, various ion or electrolyte concentrations, colorimetric changes, optical density changes, fluorescence, luminescence, pH, gas production, and the like are all readily adaptable for use in the present method and apparatus.

In detecting ion or electrolyte changes, calorimetric or fluorescent dyes are one particularly preferred embodiment. For example, calcium ion is detectable by such probes as Fura-2, Indo-1, Fura Red or Quin-2, sodium ions by SBFL, proton ions by BCECF, SNAFL, DM-NERF, magnesium ions by Mag-Fura-2 or Mag-Fura-5, chloride ions by SPO, SPA or MOAE. All these dyes are commercially available, for example, from Molecular Probes, Inc., Oregon.

In some embodiments, it may be desirable to correlate the parameter of transit time from the final mixing point with compound concentration in order to conduct compound concentration-cell response measurements. In such embodiments, the device may include a calibration unit between the mixing point and the detector to determine the amount of signal generated by different concentrations of compounds. For example, the calibration unit may determine the amount of fluorescence generated by different concentrations of fluorescent materials. In embodiments which include a PFC, the calibration unit may be inserted in the output tubing from the mixing point just upstream of the PFC.

In one embodiment, the calibration unit may comprise a light emitting diode (LED), a glass cuvette and a fluorescence detector in line immediately before the PFC. The glass cuvette is inserted into the output line from the mixing point just upstream of the PFC. The LED provides light to the cuvette. A light sensing device, such as a fiber optic based microfluorimeter, is aligned at right angles to the LED source to collect fluorescence emissions from the cuvette. The single step and gradient forming systems of the mixing apparatus are used to form a pre-gradient slug and a concentration gradient of a solution of fluorescent material such as fluorescein. As the gradient of fluorescent material passes through the cuvette, its fluorescent signature is registered by the microfluorimeter. The fluorescence intensity is an index of the concentration of the fluorescent material. The concentration of the fluorescent material is correlated with its time of transit to 'calibrate' the gradient formed by the mixing apparatus.

FIGS. 1A and 1B illustrate schematic configurations of some embodiments of the apparatus of the present invention.

The embodiments shown in FIGS. 1A and 1B consist of a test compound sampler 101, for receiving and holding a sample of a compound to be tested; a standards sampler 103, for receiving and holding a sample of a standard solution (e.g., a buffer and/or a known agonist or antagonist) to be mixed with the compound to be tested; a concentration gradient device 105 connected to compound sampler 101 for controlling the flow volume of the compound to be tested; a concentration gradient device 107, connected to standards sampler 103, for controlling the flow volume of the standard solution; a switching valve 111 for receiving a compound/standard solution mixture or a calibration solution and for directing them to the mixing zone 112 for mixing one of these solutions with cell suspensions containing one or more cell types to be tested, a member of a series of one or more cell types to be tested, or one or more types of particles to be tested; at least one cell suspension or particle reservoir 113 (and, where a series of cell types or particles is to be examined, a plurality of cell suspension or particle reservoirs each of which contains a cell suspension of one of the cell types in the series to be examined or a preparation of one or more particle types to be tested); a calibration unit 117, for supplying calibration solutions to the switching valve 111 so that the calibration solutions may be mixed with the cell suspension or particles in predetermined ratios; a reaction developing lines unit 115, for receiving the cell suspensions or particles mixed with either the compound/standard solution mixture or the calibration solution and for transferring this mixture to a detector 119; and a drain 121 for receiving and draining the mixture from detector 119 after the cell response or particle interaction has been detected and measured by detector 119. A controller 109 is coupled to the test compound sampler 101, the standards sampler 103, gradient devices 105 and 107 and switching valve 111. The controller controls the above devices by receiving command signals from a computer 123 which in turn generates, sends and receives signals in accordance with a software program 125. The mixing zone 112 can constitute a chamber, a tube, a series of baffles, or any other structure in which mixing can occur. In some embodiments, the computer 123 may also control the operation of the coupling system 120. In further embodiments, the computer 123 may synchronize the coupling system 120 with the test compound sampler 101 such that the next sample slug is delivered to the detector shortly after the analysis of the current sample slug is completed, thereby optimizing the number of samples which may be analyzed in a given time period. In further embodiments, the computer 123 may also control the operation of the standards sampler 103. It will also be appreciated that the operation of the preceding devices may be controlled by more than one computer.

While the embodiments shown in FIGS. 1A and 1B include a standards sampler 103, gradient device 107, switching valve 111, and calibration unit 117, it will be appreciated that these aspects of the device need not be present if the analysis being performed does not require the use of a standard compound(s) or calibration solution(s). Likewise, when the analysis being performed does not require a concentration gradient of the test compound(s), the device need not include a gradient device 105 connected to the test compound sampler 101.

After a compound and/or standard is mixed with cells or particles in mixing zone 112, which is readily commercially available and in the preferred embodiment is the static mixer 125–1345 (Bio Rad), this mixture is then sent through reaction developing lines 115 so that it may be mixed more thoroughly and provided with enough time for its reagents to thoroughly react with one another. The detector 119, is connected to the reaction developing lines unit 115, and receives the cell or particle/compound/standard mixture from the reaction developing lines 115.

In a preferred embodiment, each of the samplers 101 and 103 include a sipper nozzle which may be positioned into a vial containing a respective compound or standard solution. These samplers are well-known in the art and are readily available commercial products, e.g. A/S 300 Autosampler, Catalog # 15006330, Scientific Measurement Systems, Inc., Colorado. For handling multiple samples, conventional automated or robotic equipment (not shown) may be used to supply the apparatus with the samples. Banks of different samples, arranged in 48 or 96 well plate format for example, can easily be accommodated by such automated sampling equipment.

The gradient devices 105 and 107 are also readily available commercial devices, e.g., GP40 Gradient Pump (Dionex). Depending on the mode of action, the corresponding concentration gradient devices 105 and 107 can prepare either discrete concentrations or continuous gradients of concentrations of the compound to be tested or the standard substance (agonist or antagonist) by diluting them with buffer. For example, if a continuous curve of cell response or particle interactions versus compound concentration in the presence of a standard substance is desired, the computer 123 will instruct the controller 109 to control the gradient devices 105 and 107 in such a way that continuous gradients of respective compound and a predetermined constant concentration of standard solution are provided to switching valve 111. Alternatively, if a continuous curve of cell response or particle interaction versus standard solution concentration in the presence of a compound is desired, the computer 123 will instruct the controller 109 to control the gradient devices 105 and 107 such a way that continuous gradients of the respective standard solution and a predetermined constant concentration of the respective compound are provided to switching valve 111.

The calibration unit 117, connected to the switching valve 111, supplies calibration solutions needed to calibrate the output signal, MAX and MIN, of the apparatus. In a preferred embodiment, this calibration unit consists of a diverting valve which is a readily available commercial device, e.g., the SV3–2 Diverter Valve, (Bio-Rad). The diverter valve alternates supply of two calibration solutions to the switching valve 111. The switching valve 111 combines outflows from the gradient devices 105 and 107 or, alternatively, from the calibration unit 117 with a cell flow or particle flow from a cell suspension or particle reservoir 113 (or from one of a plurality of cell suspension or particle reservoirs 113 each of which contains one or more cell types or particle preparations each of which contains one or more particle types in a series of cell types or particle preparations to be examined) and directs the mixed flow into one of the reaction developing lines 115. The switching valve 111 is of a type which is well-known in the industry and in a preferred embodiment is the 3-way microvalve 4-8-900 manufactured by General Valve Corp. The cell suspension or particle reservoir(s) 113 are also of a type which is well known in the art and in a preferred embodiment is a regular glass beaker. Cells or particles are maintained in suspension pending introduction into the device by simple low shear stirring.

The reaction developing lines 115 are typically tubes made from a non-corrosive material, having a specified diameter, through which the above mentioned mixture of cell suspension or particle preparation, compound and standard solution may flow. For example, polyethylene, polypropylene, or polytetrafluoroethylene tubing can be used. Tubing to which cells or particles and other reagents will not stick is particularly preferred. The diameter of the tubing is a matter of choice. Capillary tubing having an inner diameter of from about 0.2 mm to about 2 mm is particularly advantageous, because it allows the use of very small sample sizes.

This tubing is typically set in a winding configuration so that as the mixture flows through it, the mixture is thoroughly agitated and mixed. Even if the mixture is well mixed before introduction into the tubing, a spiral or wound configuration allows long tubing lengths in a compact area. These reaction developing lines 115 are commercially available and in one embodiment may be formed by Teflon tubing.

The mixture of a cell suspension containing one or more cell types to be tested, one or more cell types included in a series of cell types to be tested, particle preparations containing one or more particle types, or particle preparations containing one or more particle types included in a series of particle preparations to be tested and compound/standard solution, also referred to as "reaction suspension," enters the detector's flow-through optical cell or other detection zone with a time delay or incubation period determined by the length of the reaction developing line 115. Once the reaction suspension reaches detector 119, the detector 119 can measure the cell suspension response to the specified concentration of the test compound or the presence of a particular molecule in the sample.

In a preferred embodiment, the detector 119 measures a fluorescence signal from the calcium sensitive dye, FURA 2, spectral characteristics of which depend on a concentration of the intracellular ionized calcium, in order to determine the level of cell activity. In order to make this measurement, the detector 119 alternately irradiates the reaction suspension passing through a flow-through optical quvette, with the light of the wavelengths 340 nm and 380 nm and measures fluorescence intensity at 540 nm. The ratio (R) of the fluorescence intensities registered at 540 nm upon excitation at 340 nm and 380 nm, respectively, is transmitted to the computer 123. The computer 123 calculates the concentration of the intracellular ionized calcium in accordance with the following equation which is well-known in the art:

$$[Ca^{2+}] = K_d(R-R_{min})/R_{max}-R)(I_f/I_b)$$

where $K_d$ is the dissociation constant of calcium/FURA 2 complex and $R_{min}$ and $R_{max}$ are the ratios obtained in the presence of the calibration solutions MIN and MAX, respectively, and $I_f$ and $I_b$ are the fluorescence intensities measured at 540 nm upon excitation at 380 nm in the presence of calibration solutions MIN and MAX respectively.

In another preferred embodiment, the detector irradiates the mixture of cells or particles with test compound(s) with laser light of one or more wavelengths. The irradiation and emission wavelengths may be any wavelengths suitable for the particular cellular responses or particle interactions to be measured. It will be appreciated that the detector may detect any type of signal suitable for detecting the cellular responses or particle interactions and is not limited to detectors based on light.

A computer 123, connected to the detector 119, dictates its operation. The computer 123 is also connected to or is a part of the controller 109 which controls the first and second gradient devices 105 and 107, switching valve 111 as well as test compound sampler 101 and standard sampler 103 in accordance with a software 125 implemented within the computer 123. The detector 119 is capable of measuring the particular desired signal, whatever its origin. An optical detector 119, may be a spectrophotometer, spectrofluorometer, or a luminometer, each of which have a flow-through optical cell. These devices are well-known in the art and are commercially available. For example, one embodiment of the apparatus of the present invention may use an AMINCO-Bowman Series 2 Luminescence Spectrofluorometer (Fa-256, Spectronic Instruments, Inc.). If the detector is a direct ion measuring device, it can, for example, comprise a pH sensor or an ion selective electrode. Sodium, calcium, and potassium detectors are examples of such devices. Detectors of this type are commercially available.

In the embodiment of FIG. 1B, the apparatus further includes a coupling system 120, such as the plug flow coupling systems described above. The coupling system 120 is disposed between the mixing chamber 112 and the detector 119.

In a preferred embodiment, the detector 119 comprises a device capable of analyzing individual cells, individual cell types in a cell suspension, individual particles in a sample, individual particle types in a sample, individual components in a sample, or individual types of components in a sample. Preferably, the detector has the ability to simultaneously resolve multiple characteristics or properties derived from each particle or cell. For example, in one embodiment, the detector is a flow cytometer (FCM). The FCM may be any current or future system, such as the Epics Elite from Beckman-Coulter or the FACSCalibur from Becton-Dickinson. The single particle/single cell, multiparametric properties permit resolution of subsets of particles or cells within a heterogeneous population. For example, subsets of cells from within heterogeneous cell populations or mixed cell populations which respond to a particular test compound or test compounds may be resolved from the entire population by this technique. Alternatively, subsets of particles in heterogeneous or mixed populations which possess particular properties may be resolved from the population.

Figure 2:
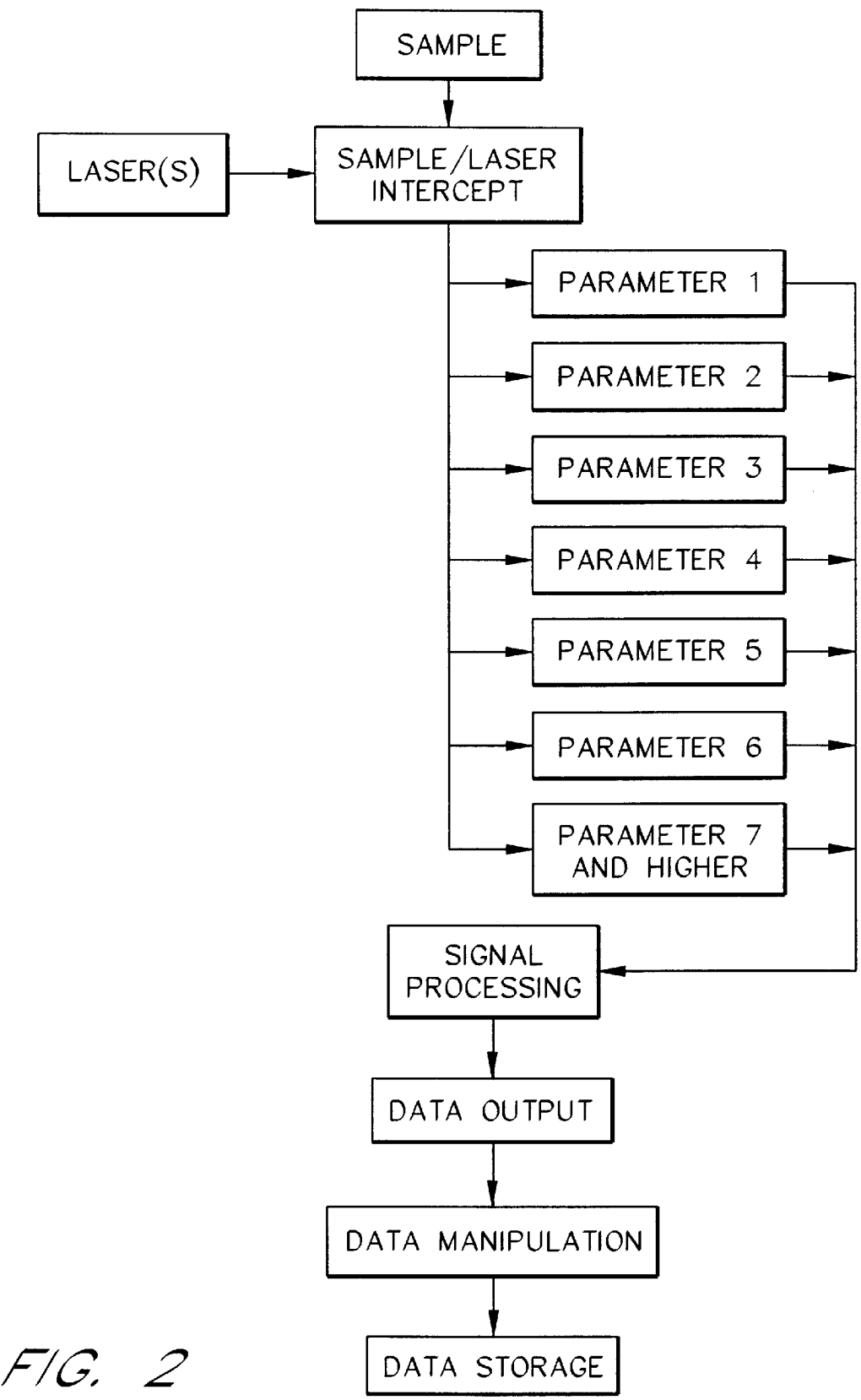
FIG. 2 illustrates the multiparametric capacity of the FCM, and indicates the flow of information obtained from the FCM

Preferably, the detector also has the ability to measure properties that can not be resolved using standard fluorimetric techniques. FIG. 2 illustrates the multiparametric capacity of the FCM, and indicates the flow of information obtained from the FCM.

For the simultaneous analysis of multiple parameters, a sample, such as an individual cell, particle, or components, or individual cell types, particle types, or component types, is exposed to an agent which produces a signal detectable by the detector. The signal may be a fluorescent signal or a non-fluorexcent signal. After the cell or particle samples are delivered from the mixing system, they are interrogated by one or more detection agents, such as lasers, and, if the sample possesses one or more of the parameters being evaluated, a signal indicative of the presence of that parameter is generated and processed to provide a data output which may be manipulated or stored using conventional procedures.

All of the detectors described above can be controlled by means of a computer 123 during the data acquisition process.

The apparatus of the present invention is contemplated in two different specific embodiments. A positive pressure system may be created with piston pumps or other suitable pumps supplying reagents under positive pressure. Alternatively, a negative pressure system may be created with a peristaltic pump or other suitable pump drawing reagents through the system. The negative pressure system is the simplest embodiment, because a large number of input sources can be driven by a single downstream pump.

FIGS. 3A and 3B illustrate schematic configurations of some embodiments of a positive pressure fluidic system. In a preferred embodiment, this system operates automatically under the control of a programmable controller, as will be explained in more detail below. This embodiment includes an autosampler 201 which holds one or more compounds to be tested 203 and buffer 205 which may be mixed with the compound 203 in order to provide various concentrations of the compound 203; intake nozzles, or ports, 207 and 209 for receiving a compound and buffer, respectively and delivering the same to a gradient pump 211 which controls the concentration level and flow of a test compound 203 into a mixing zone 227; an autosampler 213 which holds one or more standards (i.e., antagonists 215 and/or agonists 217) and a buffer 219 which may be mixed with the standard 215 or 217, in order to provide various concentrations of the standard; intake nozzles, or ports, 221 and 223, for receiving a standard and buffer, respectively, and providing the same to a gradient pump 225 which controls the concentration level and flow of a standard solution (agonist or antagonist) into the mixing zone 227. Each of the gradient pumps, 211 and 225, respectively, may advantageously have two inlet tubing lines and one outlet tubing line, the outlet tubes being connected to each other through the mixing zone 227. A controller (109 of FIGS. 1A and 1B) which is not shown in FIGS. 3A and 3B controls the operation of autosamplers 201 and 213 and gradient pumps 211 and 225 by supplying remote signals to start/stop the pumping. In a preferred embodiment, gradient pumps 211 and 225 may be the GP 40 Gradient Pump manufactured by Dionex.

The mixing zone 227 receives the compound solution flowing through gradient pump 211 and, optionally, a standard solution flowing through the gradient pump 225, and mixes the compound and standard substances together. A diverting valve 235 alternates the supply of either the calibration solution for maximal response 233 or the calibration solution for minimal response 237. The diverting valve 235 preferably includes two inlet tubes, one tube for each of the two different calibration solutions 233, 237, and one outlet tube connected to a pump 231. The diverting valve 235 is well-known in the art and can be implemented by the SV-3 Diverter Valve (BioRad). The controller (109 of FIGS. 1A and 1B) which is not shown in FIGS. 3A and 3B, sends signals to the diverter valve 235 which switches intake ports to connect one calibration solution 233 or another, 237, to the intake of the pump 231. The pump 231 for supplying calibration solutions to the fluidic system is also shown in FIGS. 3A and 3B. The pump 231 receives either the calibration max. solution 233 or the calibration min. solution 237 from diverting valve 235 and then pumps the received calibration solution to switching valve 229. The outlet tube of pump 231 is connected to an input of the switching valve 229. The pump 231 is advantageously a standard piston pump which is well-known in the art. In a preferred embodiment, the pump 231 is the series 1350 Soft-Start Pump (BioRad). The switching valve 229 alternates the supply of either the compound/standard mixture or one of the calibration solutions to a mixing zone 239. A pump 241 supplies cells or particles from a cell suspension or particle reservoir 243 containing one or more cell types or one or more particle types to be tested (or from one of a plurality of cell suspension or particle reservoirs 243 each containing one or more cell types or one or more particle types included in a series of cell types or particle types to be examined) to the mixing zone 239. The pump 241 receives cells or particles from the cell suspension or particle reservoir 243 from an inlet tube and pumps the received cells or particles through an outlet tube to one intake of the mixing zone 239. The compound/standard solutions or calibration solutions come through another intake of mixing zone 239. Both mixing zones 227 and 239, are well known in the art and in a preferred embodiment may be implemented by the Static Mixer, 125–1345 (BioRad). The pump 241 can be a standard piston pump which is well-known in the art. In a preferred embodiment, the pump 241 is the series 1350 Soft-Start Pump (BioRad). The mixture of cells or particles and compound/standard solution or cells and a calibration solution is then fed from mixing zone 239 to reaction developing lines 245. The length of these lines, combined with the flow rate, determines the incubation period; i.e., the time elapsed from the point where the cells or particles are mixed with the compound/standard mixture or the calibration mixture to the point of reaching detector 247. The detector 247 then measures the amount of cell response or particle interaction due to the compound/standard mixture or the calibration solution. After the cell response or particle interaction has been measured by detector 247, the mixture is then drained from the detector via drain 249.

In the embodiment of FIG. 3B, the apparatus further includes a coupling system 251, such as the plug flow coupling systems described above. The coupling system 251 is disposed between the mixing chamber 239 and the detector 247.

As discussed above, while the embodiments shown in FIGS. 3A and 3B include an autosampler 213, antagonists 215 and/or agonists 217, buffer 219, intake nozzles or ports 221 and 223, gradient pump 225, pump 231, diverting valve 235, calibration solutions 233 and 237, and switching valve 229, it will be appreciated that these aspects of the device need not be present if the analysis being performed does not require the use of a standard compound(s) or calibration solution(s). Likewise, when the analysis being performed does not require a concentration gradient of the test compound(s), the device need not include a gradient pump 211, buffer 205 or port 209, but instead may include a pump for delivering the test compound(s) to the mixing chamber.

FIGS. 4A and 4B illustrate schematic configurations of some embodiments of the negative pressure fluidic system. As shown in FIGS. 4A and 4B, one preferred embodiment includes an autosampler 301 which holds one or more compounds ($N_i$) 303 and a buffer 305, the autosampler 301 further including two intake nozzles, or ports, 307 and 309, for receiving the compound ($N_i$) 303 and buffer 305, respectively; a proportionating valve 311 for preparing dilutions of the compound 303 with the buffer 305 in predetermined or specified proportions and delivering this mixture to a priming valve 313; an autosampler 315 which holds standard antagonists ($M_j$) 317 agonists ($L_k$) 319 and the buffer 305, the autosampler 315 further including two intake nozzles 323 and 325 for receiving the standard and the buffer, respectively; a proportionating valve 327 for preparing dilutions of the standard substance 317 or 319 with buffer 305 in predetermined or specified proportions and delivering this mixture to a priming valve 329. The proportionating valves 311 and 327 may be of any type which is well-known in the art. In a preferred embodiment these valves 311 and 327 are the series 4 miniature solenoid type valves (4-8-900 General Valve Corp.) working in a proportioning frequency mode. Similarly, priming valves 313 and 329 may be of any "normally opened" type which is well-known in the art and, in a preferred embodiment, are the series 4 miniature solenoid type valves (4-39-900) manufactured by General Valve Corp.

A mixing zone 331 mixes a compound solution received from priming valve 313 and a standard solution received from priming valve 329. The first mixing zone 331, as with the other mixing zones discussed herein, can constitute a simple "Y" connector; a chamber having a diameter several times that of the tubing; a length of tubing; a serpentine, baffled chamber; a chamber containing a mechanical rotating mixer; or any other suitable structure. Typically, the method will involve very small quantities of liquid (e.g., a full concentration gradient run can be accomplished with as little as 0.3 ml of sample). Thus, the volumes to be mixed are small and the mixing zone should have small internal volume and high mixing efficacy. These types of mixers are well known in the art and in a preferred embodiment may be implemented by the Visco Jet® Micro-Mixer (#TCMA0120113T) manufactured by The Lee Company.

A diverting valve 335 alternates the supply of either a calibration solution for maximal response 337 or a calibration solution for minimal response 339. The diverting valve 335 includes two inlet tubes for receiving the two different calibration solutions and one outlet tube connected to another diverting valve 333. The diverting valve 333 can have two inlet tubes, one for receiving a compound/standard solution mixture and the other for receiving one of the calibration solutions 337 or 339. The diverting valve 333 then alternates the supply of either the compound/standard mixture or one of the calibration solutions through an outlet tube to a priming valve 341 which then delivers the received fluid to a mixing zone 343. A third diverting valve 347 alternates the supply of either cells or particles from a cell suspension or particle reservoir 349 containing one or more cell types or one or more particle types to be tested (or from one of a plurality of cell suspension or particle reservoirs each containing one or more cell types or one or more particle types included in a series of cell types or particle types to be tested) or the buffer solution 305 through an outlet tubing 346 to a priming valve 345 which then delivers either the cells or particles or buffer to the mixing zone 343 where it is mixed with either a compound/standard mixture or one of the calibration solutions received from priming valve 341. The diverting valves 333, 335 and 347 may be of any type which is well known in the art, for example, a SV-3 Diverter Valve (BioRad). This mixture is then sent to reaction developing lines 353 which determine the time elapsed from the point where the cells or particles are mixed with the compound/standard mixture or one of the calibration solutions to the point where the mixture reaches the detector optical cell 355. As explained above, the reaction developing lines 353 and the detector 355 may be of any type which are well-known in the art.

A peristaltic pump 357, used as a negative pressure pump, can advantageously supply the necessary pressure required to make the various solutions and mixtures described above flow through the various valves (311, 313, 327, 329, 333, 335, 341, 345 and 347) mixing zones (331 and 343), the reaction developing lines 353, the detector 355, and finally to the drain 359. Suitable peristaltic pumps 357 are well-known in the industry and in a preferred embodiment may be implemented by a EP-1 Econo Pump (BioRad). The pumps, valves, detectors, and other active components of the system are preferably under the automated control of a programmable controller, as explained in more detail below.

In the embodiment of FIG. 4B, the apparatus further includes a coupling system 361, such as the plug flow coupling systems described above. The coupling system 361 is disposed between the mixing chamber 343 and the detector 355.

As discussed above, while the embodiments shown in FIGS. 4A and 4B include components for supplying a standard(s) and a calibration solution(s), it will be appreciated that these aspects of the device need not be present if the analysis being performed does not require the use of a standard compound(s) or calibration solution(s). Likewise, when the analysis being performed does not require a concentration gradient of the test compound(s), the device need not include components which provide a gradient, but instead may include a pump for delivering the test compound(s) to the mixing chamber.

The apparatus in the present invention preferably has two primary modes of action, a screening mode and a potency mode.

Figure 5:
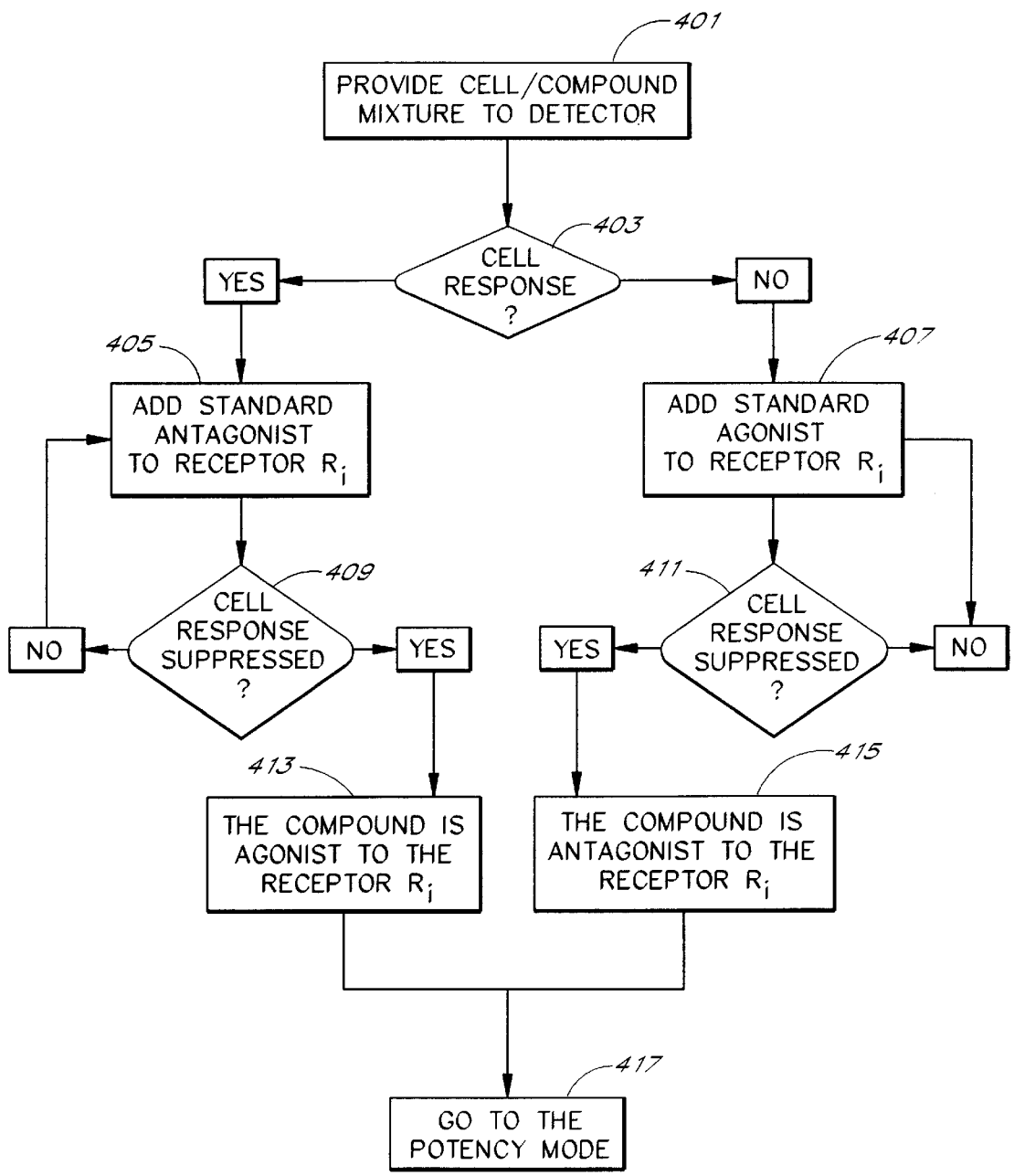
FIG. 5 represents a simplified algorithm of a screening mode which may be utilized in a combinatorial screening apparatus of the present invention.

FIG. 5 shows an algorithm that may be used in the invention to detect one or more cell responses or the presence of one or more molecules during the screening mode. First, a cell or particle/compound mixture or a sample is provided to a detector (step 401). Next, the apparatus determines if the compound, upon contact with the cells, triggers any cell response or whether the sample contains a molecule (step 403). There are two possibilities: either the compound does not produce any of the responses being analyzed or the sample does not contain any of the molecules being analyzed (NO), or it induces one or more of the cell responses or does contain one or more of the molecules (YES). Cell response is determined by monitoring the signal from the detector for the particular analyte or analytes being detected. Similarly, the presence of one or more molecules in the sample is determined by monitoring the signal from the detector for the presence of signal which will be produced if the particular molecule or molecules being analyzed is present. The control system first calibrates to establish a baseline and a maximal response, and any signal from the detector falling between those values is considered to be a positive response.

If the compound causes no cell response or no particle binding, (NO), as measured by the monitoring part of the apparatus, the cells or particles are successively and automatically brought into contact with a mixture of the compound and the standard substances from a predetermined set of agonist solutions (step 407). Each solution in the set contains one or more ingredients that initiates cell response or that binds to particles in the absence of the test compound, e.g., through the stimulation of a known cell receptor, ion pump or ion channel molecules or through a known molecular interaction. Next, a determination is made as to whether a cell response or particle interaction normally triggered with a particular agonist is suppressed by the particular compound (step 411). The apparatus will keep repeating an admixture of different standard agonist substances with the compound until it detects that the cell response or particle interactions triggered with a particular standard agonist is suppressed in the presence of the compound, or until all agonists available to the machine have been tested. If in step 411, it is determined that a cell response or particle interaction normally triggered with a particular agonist is suppressed by the particular compound (YES), that compound is categorized as an antagonist to the receptor Ri (step 415). After this happens, the instrument is switched over to the potency mode of action if instructed by the software managing the apparatus' performance (step 417).

If the contact of the cells or particles with the compound does initiate the cell response or particle interaction, (YES), as measured by the monitoring part of the apparatus, the cells or particles are automatically brought into contact with successive mixtures of the compound and the standard substance from a predetermined set of antagonist solutions (step 405). Each solution in the antagonist set contains one or more ingredients that block the cell response or particle interaction initiated by at least one known agonist, for example through the stimulation of a known cell receptor, ion pump or ion channel molecules. Next, a determination is made as to whether a cell response or particle interaction triggered with the compound is suppressed in the presence of a particular standard antagonist (step 409). The apparatus will keep repeating an admixture of different standard antagonist substances with the compound until it detects that the cell response or particle interaction triggered with the compound is suppressed in the presence of particular standard antagonist, or until all the antagonists have been tested. If it is determined in step 409, that a cell response or particle interaction triggered with the compound is suppressed by the particular antagonist (YES), that compound will be characterized as an agonist to the receptor Ri or other molecule on the cell or particle (step 413). After this happens, the instrument is switched over to the potency mode of action if instructed by the software managing the apparatus' performance (step 417).

By using known sets of standard agonist and antagonist substances to different receptors, it is possible to screen the compounds against several receptor types and subtypes for specificity and selectivity. When a series of cell types or particle types is to be tested, the process can be repeated for each of the cell types or particle types included in the series of cell types or particle types to be tested in order to evaluate the compounds' activities in a number of cell types or interactions with a number of particle types.

For example, for the endothelin receptor, stimulation of which is indicated by an increase in intracellular concentration of ionized calcium, the following receptor subtype specific antagonists may be used: BQ-123, BQ-788, BQ-153, BQ-485, BMS-182874 PD 151, 242, and the following receptor subtype specific agonists may be used: endothelin-1, endothelin-2, and endothelin-3. Sarafotoxin S6c, IRL 1620, BQ-3020.

For calcium channels, there are sets of channel type specific agonists and antagonists which can be used in a preferred embodiment. For example, agonists of intracellular calcium channels are: Ins $(1,4,5)P_3$, Ryanodine, Caffeine, Heparine, Perchlorate, and their antagonists are: Decavanadte, Ruthenium Red and high concentrations of Ryanodine.

As discussed above, while the embodiments shown in FIG. 5 include steps for supplying a standard(s), it will be appreciated that these steps need not be present if the analysis being performed does not require the use of a standard compound(s). Instead, the algorithm simply determines whether the cells responded to the test compound(s) or whether the sample contains a molecule.

In another embodiment, the screening mode is used for the characterization of the cell receptor pattern, commonly known as "receptor fingerprinting". In accordance with this embodiment, a cell type to be tested or a series of cell types are screened against standard substances from a predetermined set of agonist solutions. Each solution in the set contains one or more ingredients that initiates cell response through the stimulation of a known cell receptor. In this way, the patterns of receptor expression in two or more cell types may be evaluated. When one or more of the cell types respond to the particular agonist substance, the instrument is switched over to the potency mode of action if instructed by the software managing the apparatus' performance.

Figure 6:
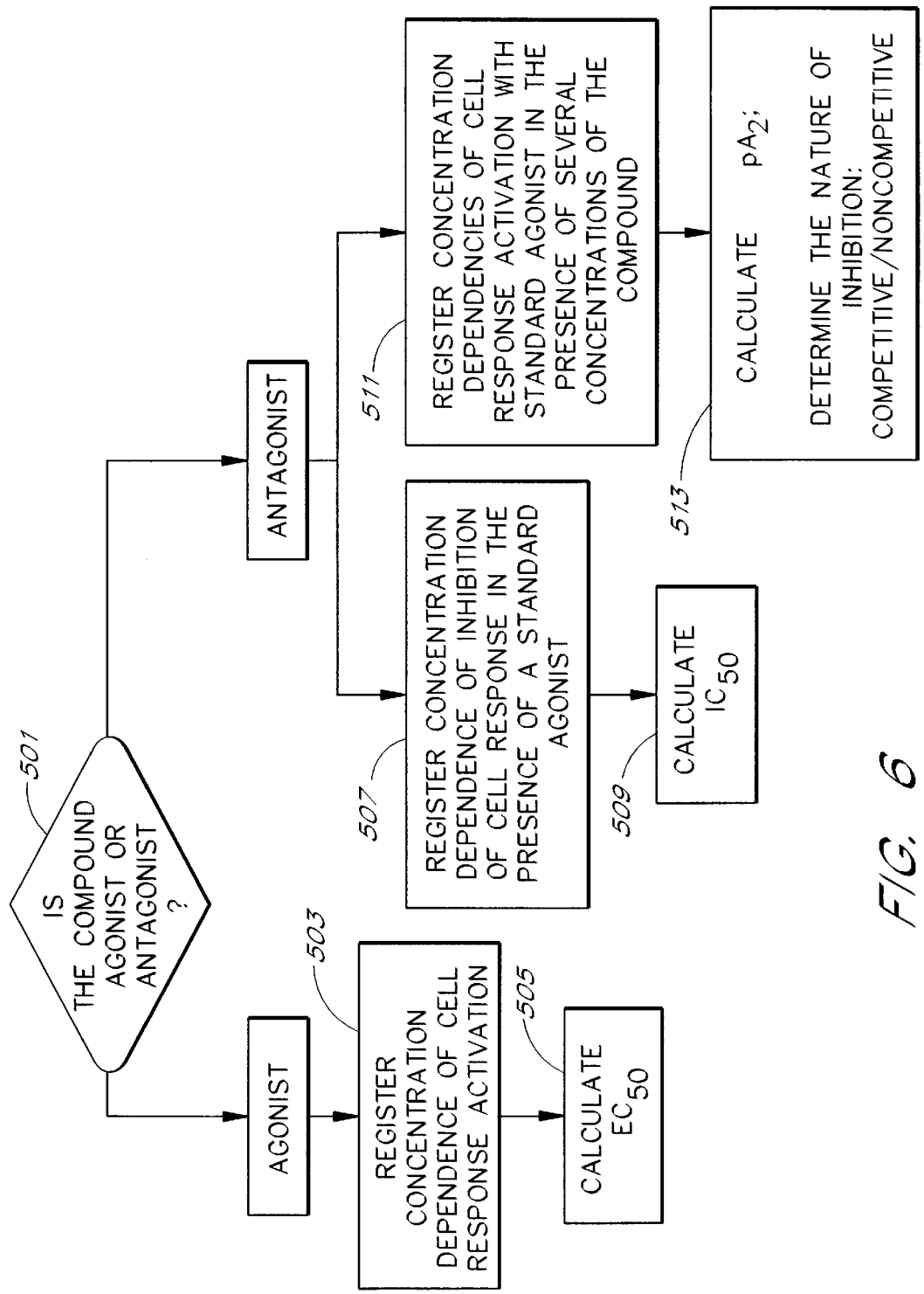
FIG. 6 represents a simplified algorithm for a potency mode which may be utilized in a combinatorial screening apparatus of the present invention.

FIG. 6 shows one algorithm that may be used in the invention in the preferred potency mode. The first step in the potency mode is to determine whether a particular compound has been categorized as an agonist or antagonist (step 501). The apparatus then prepares continuous concentration gradients of either the standard substance or the compound being tested.

If the compound has been categorized as an agonist for one or more of the cell types or particle interactions to be tested during the screening mode, the apparatus will measure and register the concentration dependence of the cell response in the responding cells or the particle interaction (step 503). During step 503, the apparatus will generate continuous experimental activation curves for the activatory compound. From these curves, one can calculate the potency of the compound in terms, for example, of $EC_{50}$ (the effective concentration of an activator which causes 50% of the maximal stimulatory response of the cells)(step 505). This calculation can be performed using well known in the art curve fitting software. In a preferred embodiment this software may be implemented by the graphical software PRISM, manufactured by GraphPad, Inc.

If the compound is determined to be an antagonist for one or more of the cell types or particle interactions to be tested during the screening mode, the apparatus will measure and register the concentration dependence of cell response or particle interaction inhibition in these cell types or particle types in the presence of a standard agonist (step 507). During step 507, the apparatus will generate continuous experimental inhibition curves for the antagonist compound taken at constant concentrations of the standard agonist substance. From these curves, one can calculate the potency of the compound in terms, for example, of $IC_{50}$ (the effective concentration of a blocker which causes 50% of the maximal inhibitory response cells or 50% of the maximal level of particle interaction) (step 509). The calculation of the $IC_{50}$ valves can also be implemented in a preferred embodiment with the PRISM software package.

If the compound is determined to be an antagonist for one or more of the cell types or particle types to be tested, the apparatus will also measure and register the concentration dependence of the cell response or particle interaction in these cell types or particle types to a standard agonist substance in the presence of several concentrations of the antagonist compound (step 511). During step 511, the apparatus will generate a series of continuous experimental activation curves for the standard agonist substance taken at different discrete concentrations of the antagonist compound. The apparatus will then calculate the affinity and the potency of the compound in terms, for example, of $pA_2$ values and determine whether the antagonist is competitive or non-competitive (step 513). The $pA_2$ value is proportional to a negative logarithm of the binding constant of a ligand/receptor complex and is a measure of the affinity of the ligand to the receptor: the bigger $pA_2$ value, the higher the compound's affinity to the receptor. Practically, $pA_2$ value can be calculated from the shift of the activation curves in the presence of different concentrations of the antagonist compound and can be implemented by the formula:

$$pA_2 = \text{Log}(R-1) - \text{Log } B,$$

where R is a ratio of equipotent concentrations of the standard agonist substance measured both in the presence of discrete concentration (B) of the antagonist compound and without the antagonist. In a preferred embodiment the equipotent concentrations of the standard agonist substance can be found from the PRISM software activation curves. With the above sets of experimental curves, one can evaluate the potency and the pharmacological profile for the compound under investigation in accordance with Cheng-Prusoff(Cheng & Prusoff, 1973, incorporated herein by reference), Gaddum (Gaddum, 1957, incorporated herein by reference) or Schild (Arunlakshana & Schild, 1959, incorporated herein by reference) analyses.

A detailed description of the operation of the negative pressure fluidics system of FIGS. 4A and 4B is given below.

The process is started when a computer prompts an operator to chose a mode of operation from a choice of three modes: system priming mode, screening mode and potency profiling mode. In the presently preferred top-level process, the first choice is to perform system priming. Referring to FIGS. 4A and 4B, before the priming process starts, the operator is prompted to place the nozzles of intake ports 309, 325 and 351 into a reservoir 305 filled with a buffer, the nozzles of the intake ports 336 and 338 into reservoirs 337 and 339, respectively, filled with corresponding calibration solutions, and the nozzle of the intake port 348 into one of the cell suspension or particle reservoirs 349 filled with one or more cell types or one or more particle types to be tested.

Figure 7:
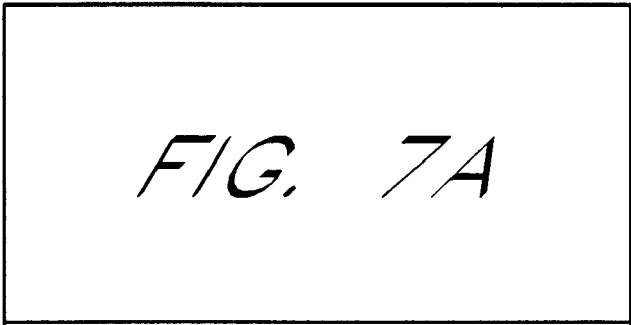
FIG. 7 is a flow diagram of a preferred primary mode operation which may be implemented by a combinatorial screening apparatus of the present invention.
Figure 7:
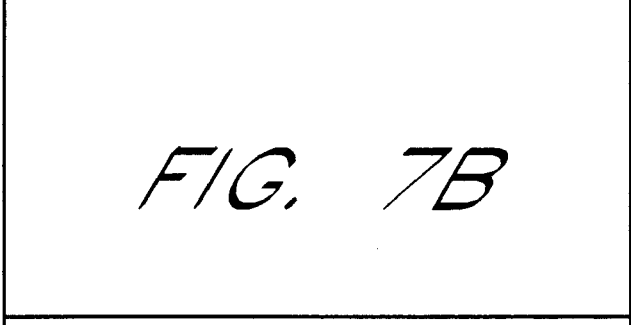
Figure 7:
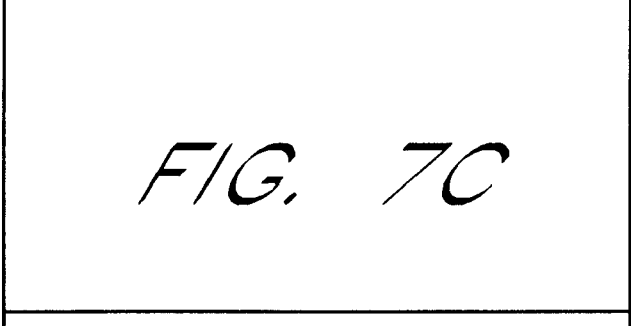
Figure 7:
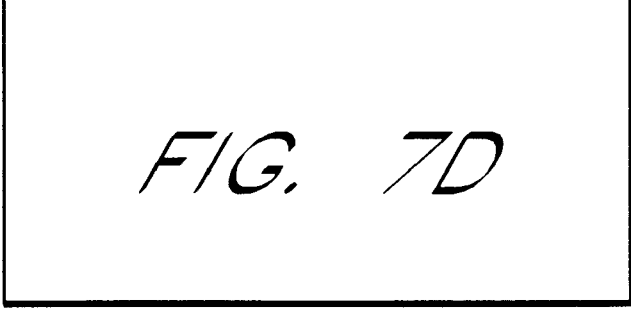
Figure 7A:
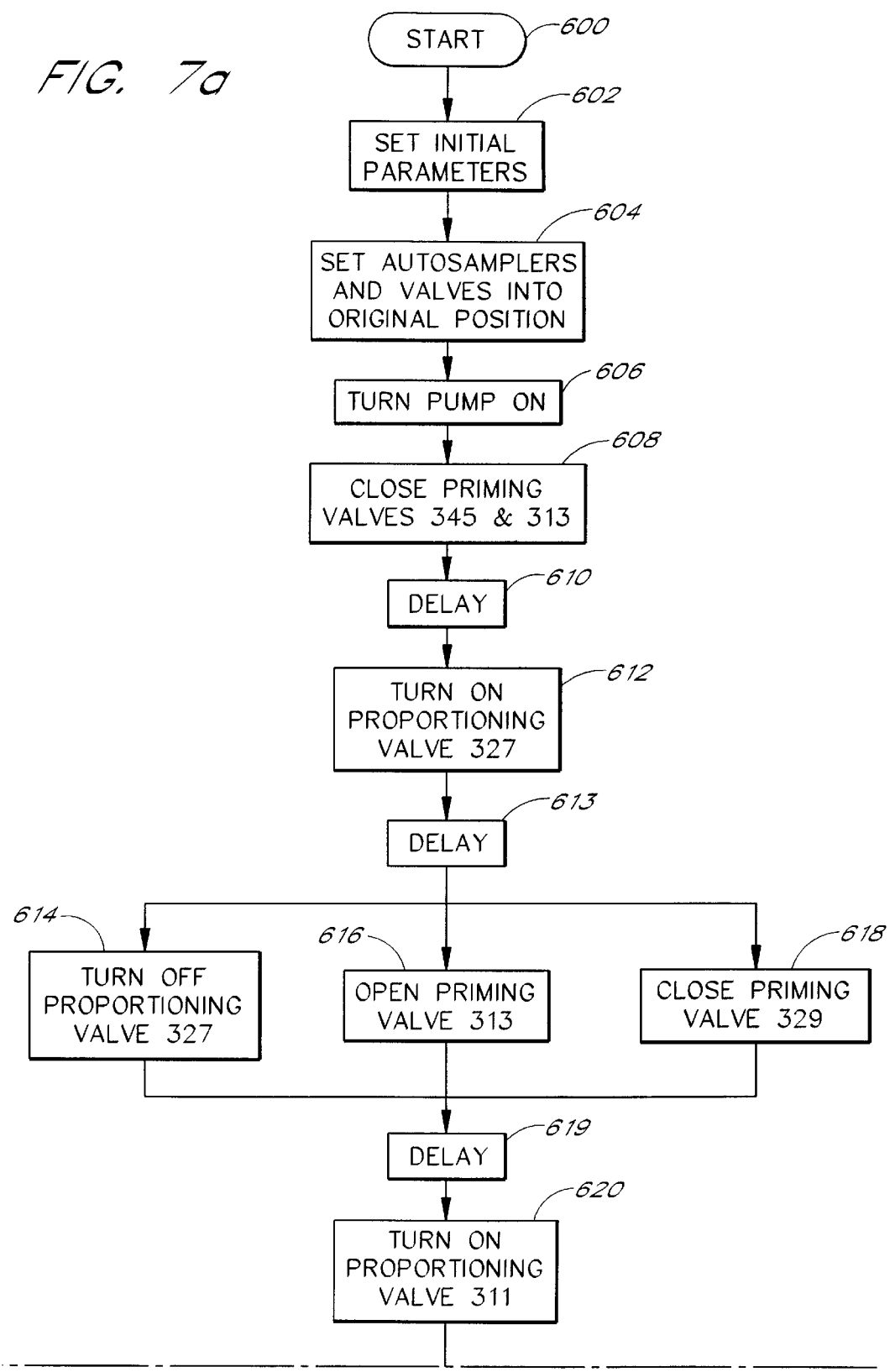
Figure 7B:
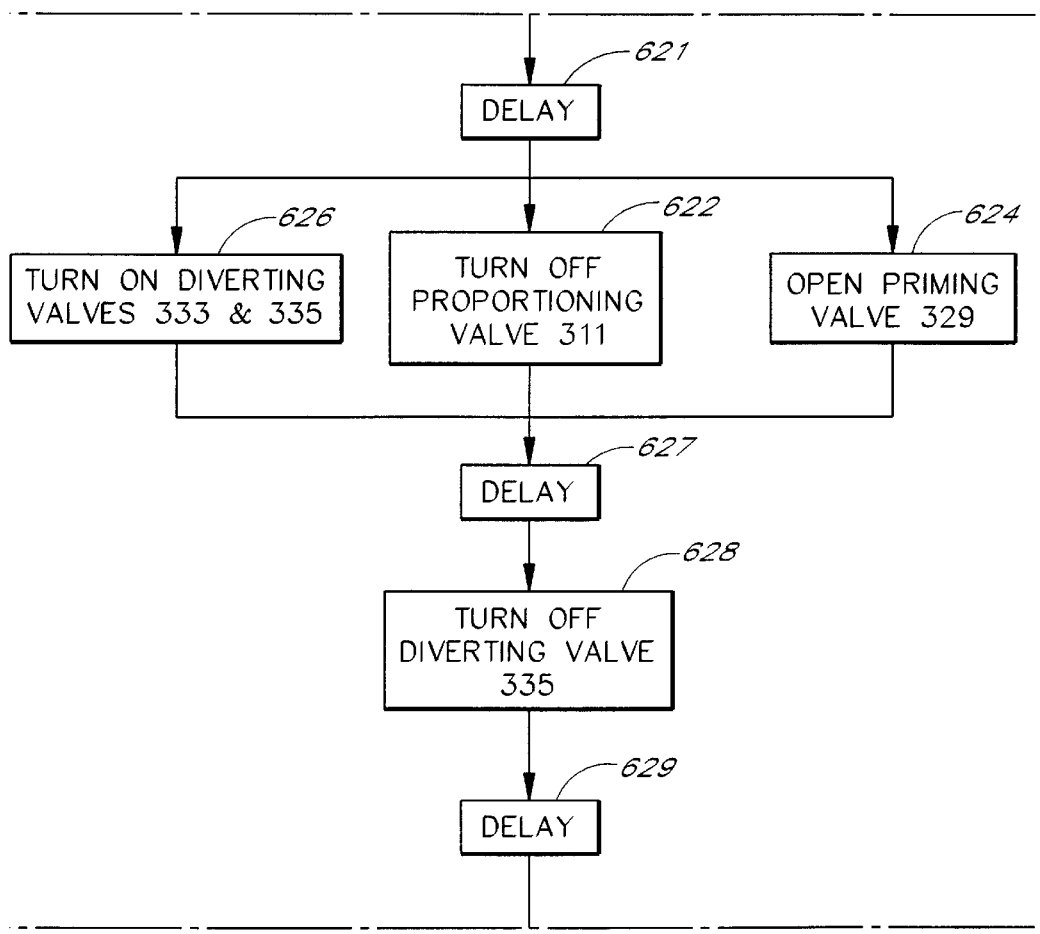
Figure 7C:
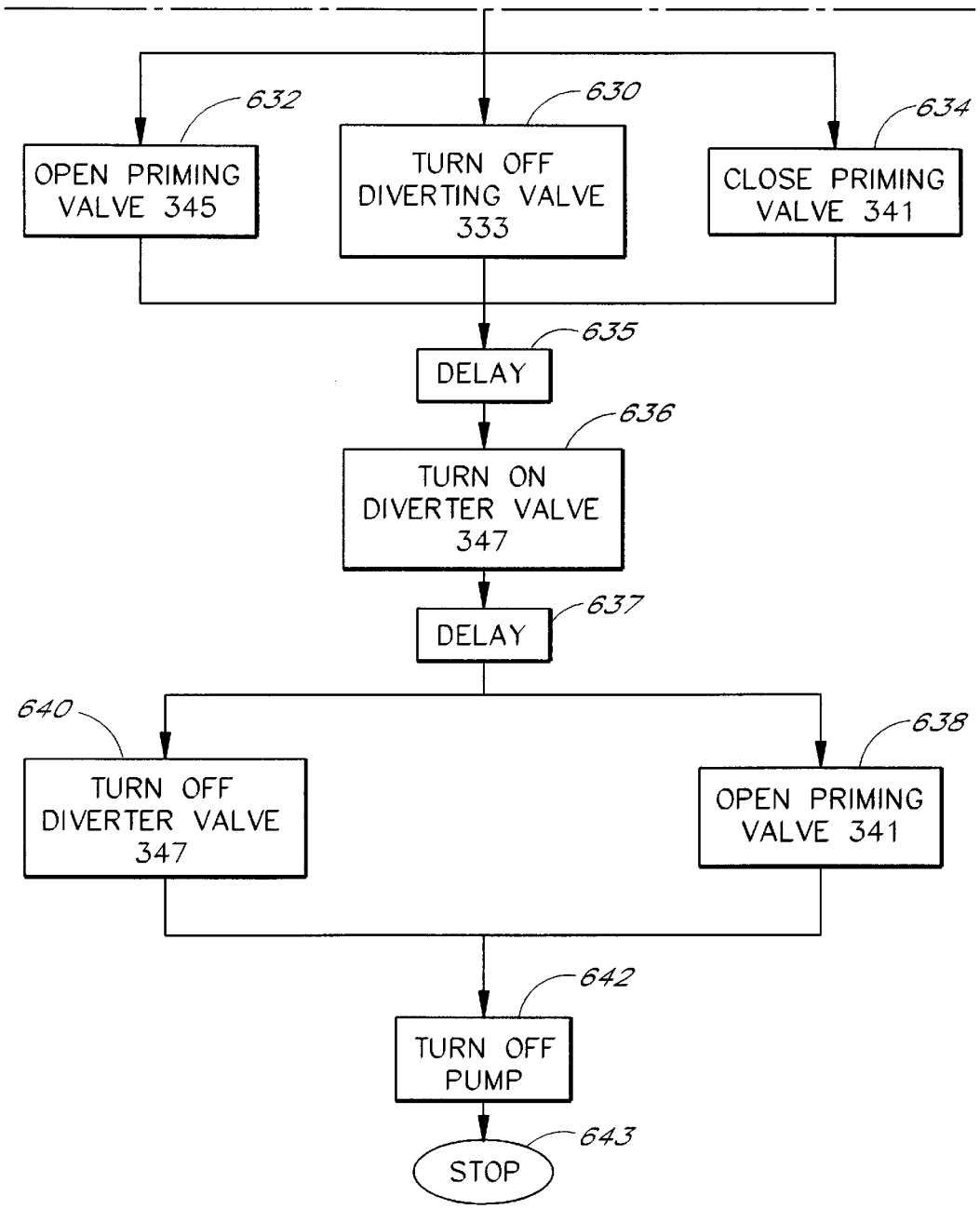
Figure 8B:
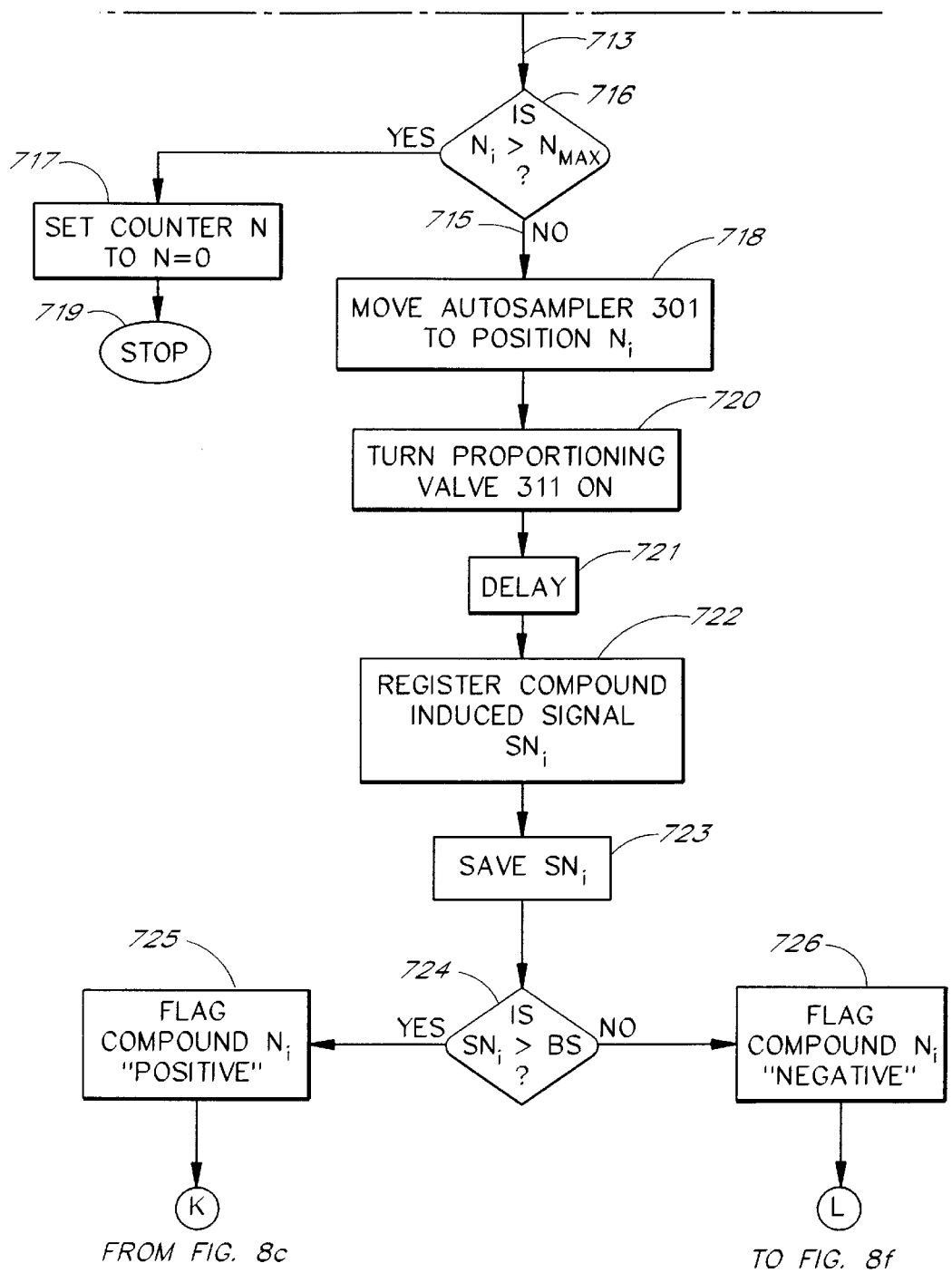
FIG. 8 is a flow diagram of a preferred screening mode operation which may be implemented by a combinatorial screening apparatus of the present invention.
Figure 8C:
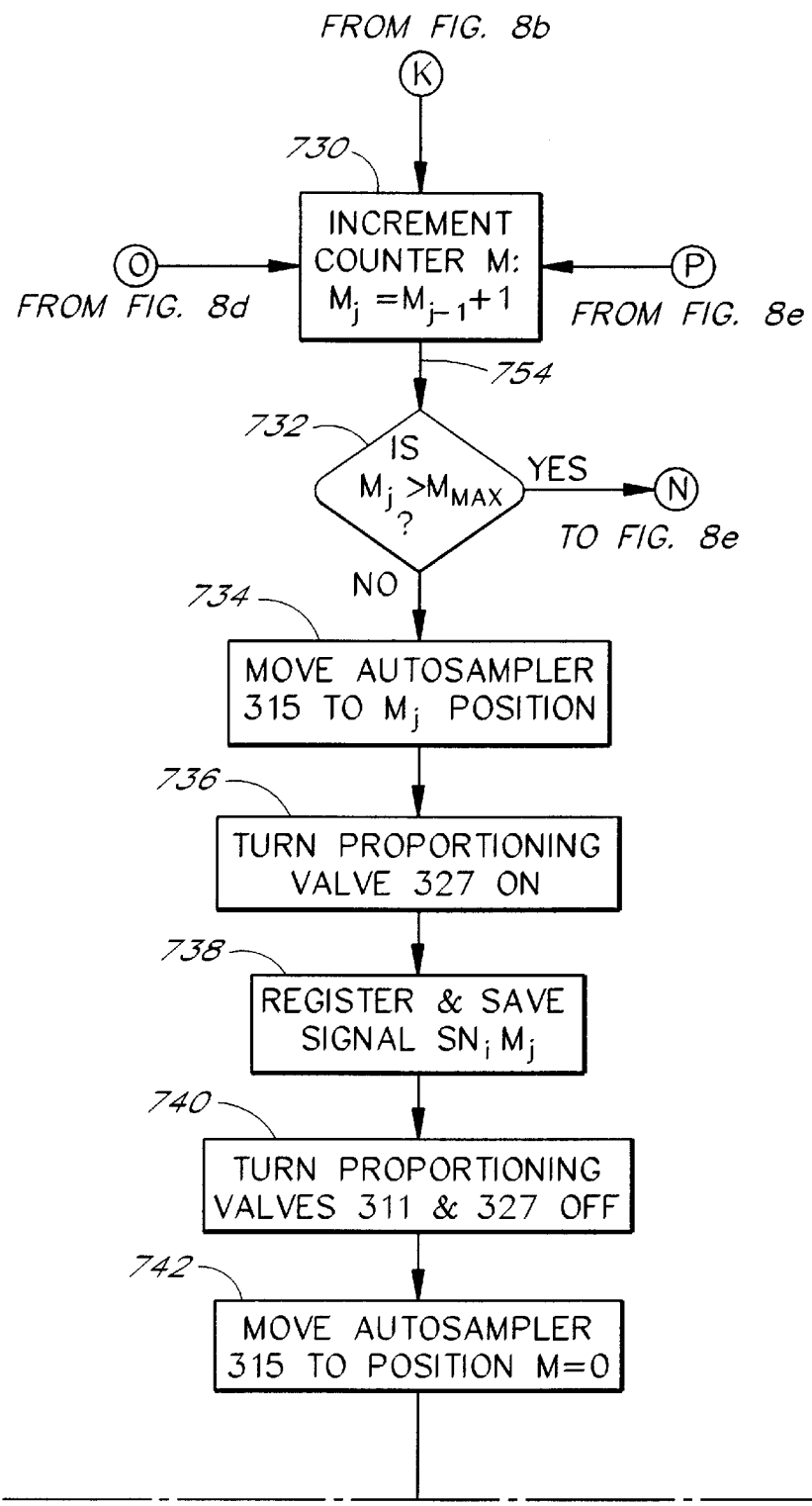
Figure 8D:
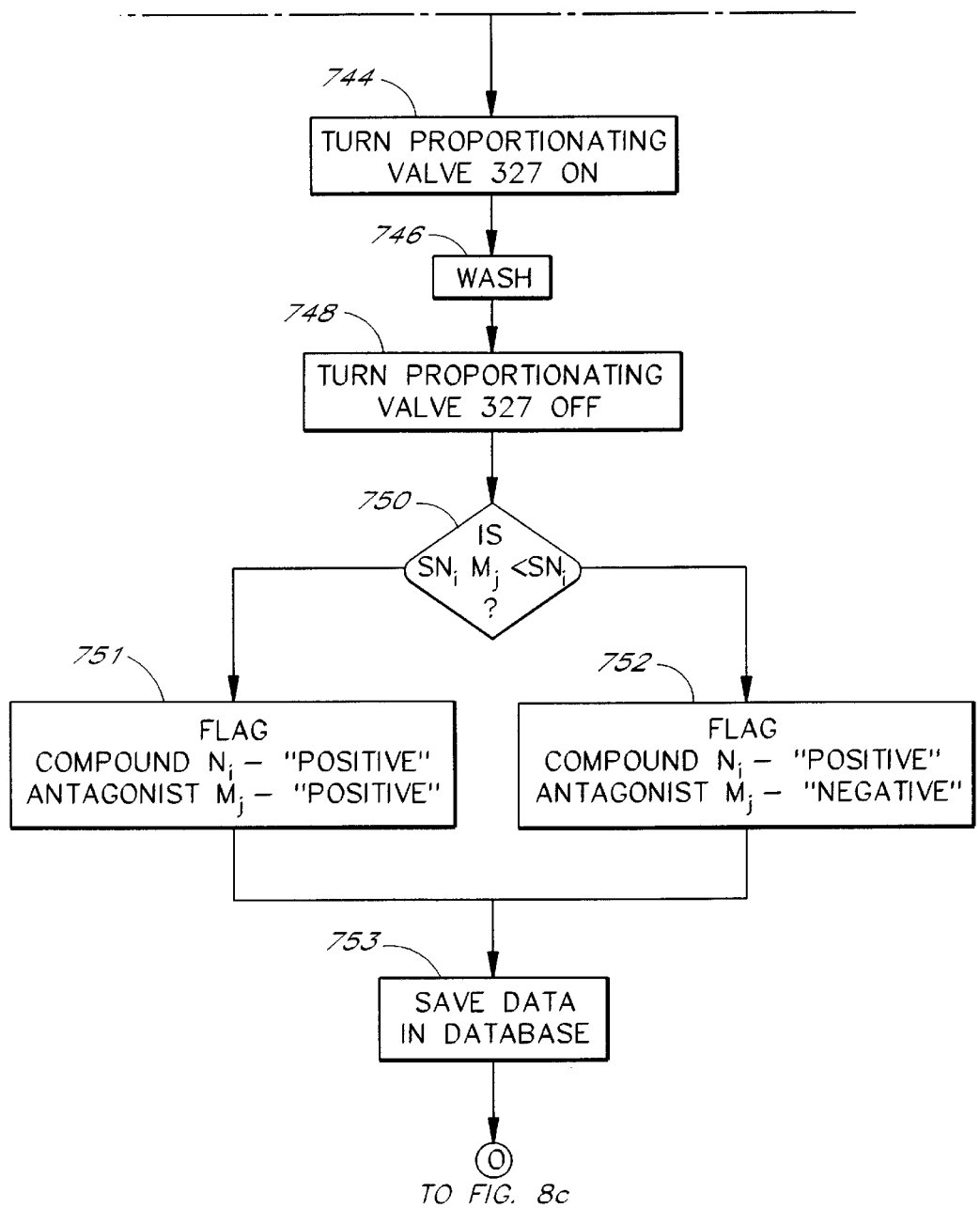
Figure 8E:
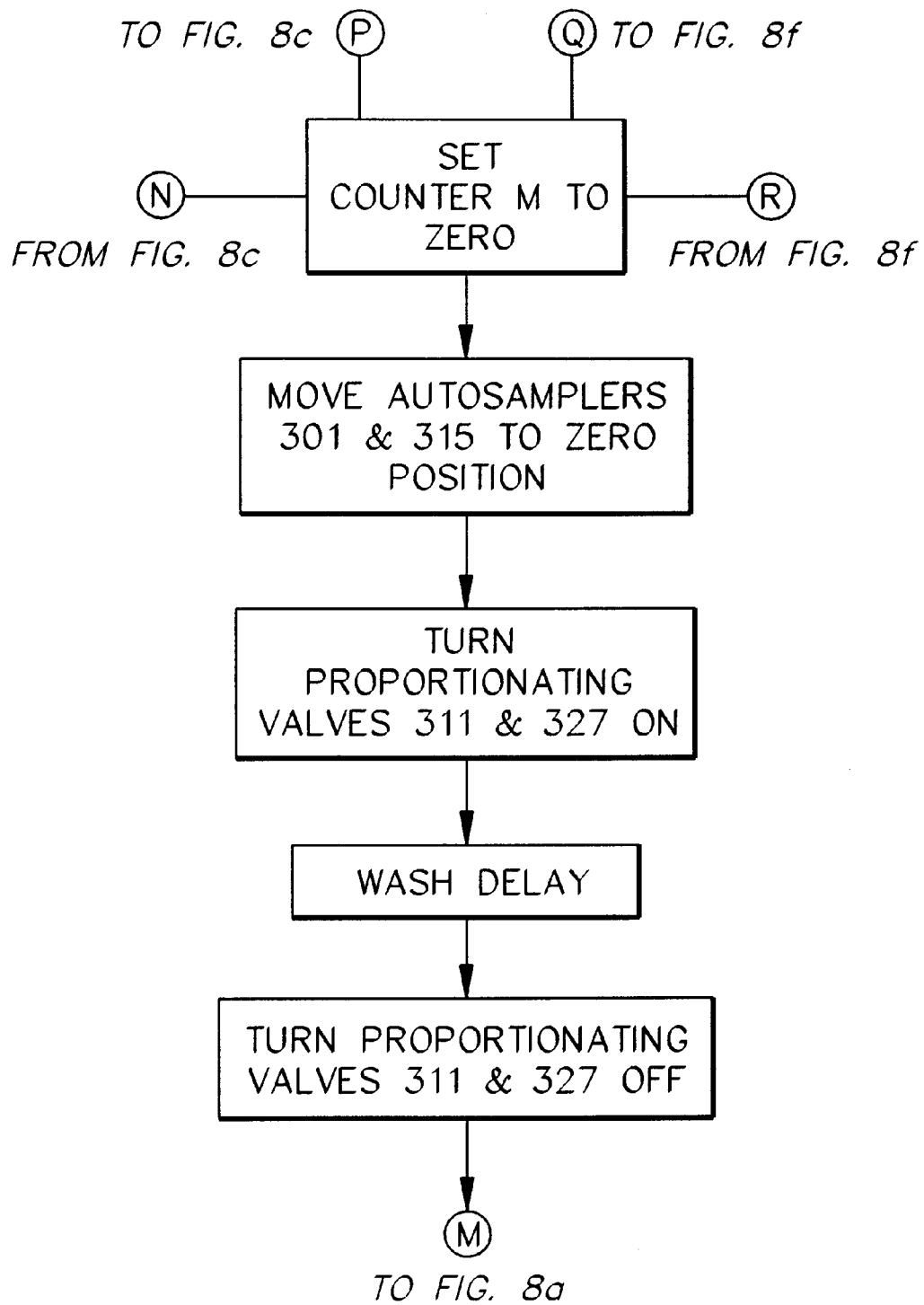
Figure 8F:
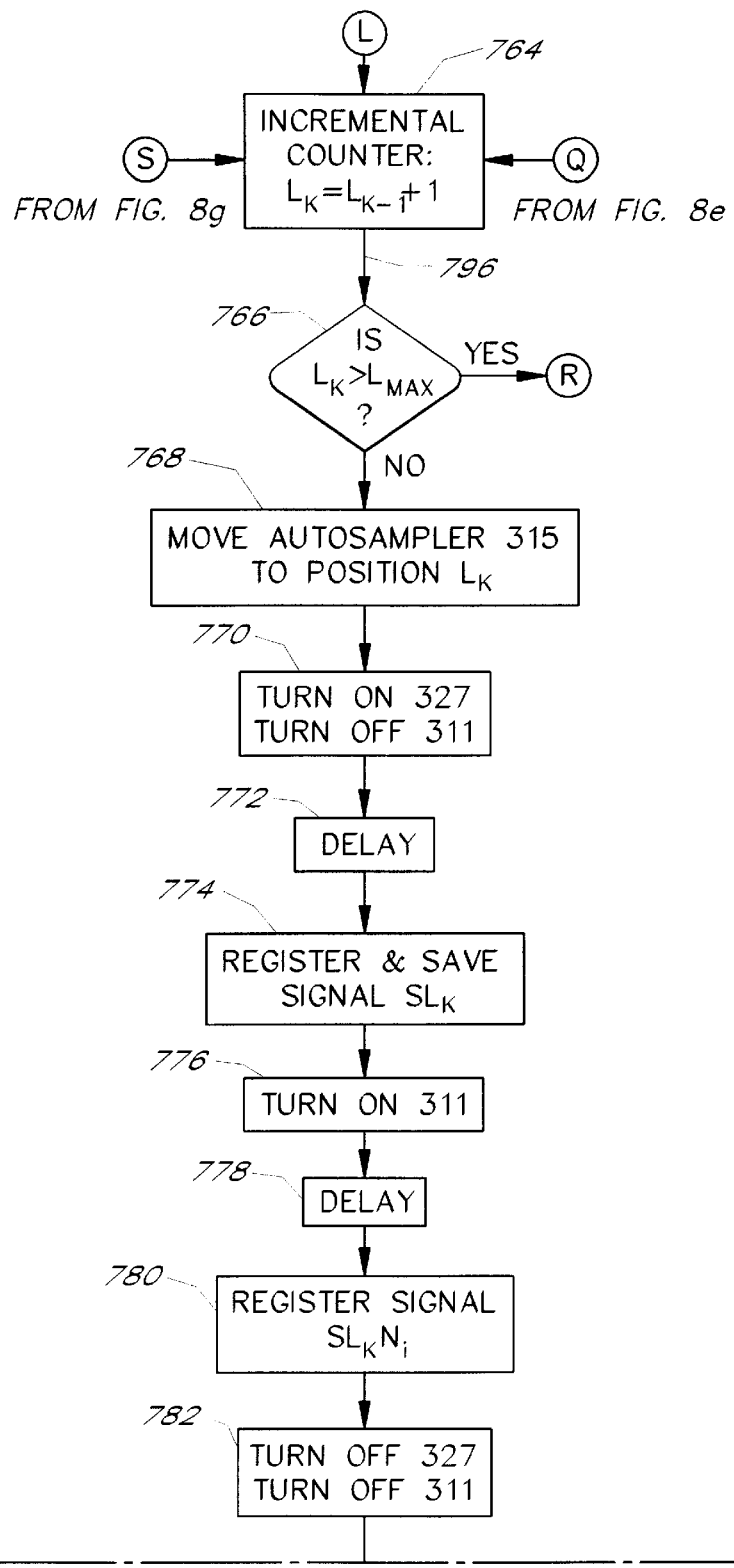
Figure 8G:
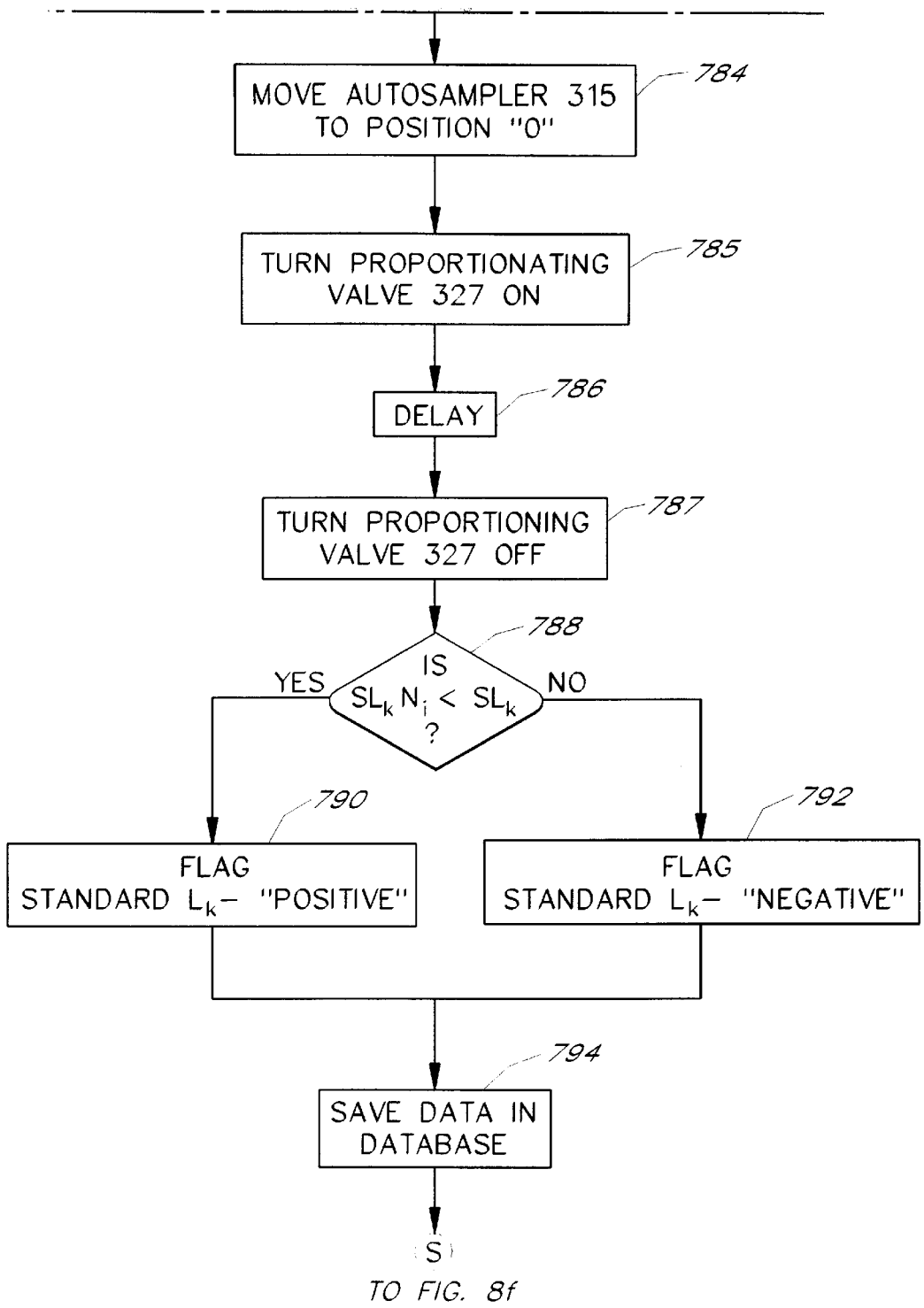

A continuous flow diagram of a preferred system priming process is shown in FIGS. 7a–7d for the preferred negative pressure fluidics system presented in FIGS. 3A and 3B. Referring to FIG. 7a, the system priming program begins from a start state 600 and enters state 602 where it sets all parameters to their initial values. These initial parameters include, but are not limited to, the internal initialization of software variables and subroutines.

Once the initial parameters are determined, autosamplers 301 and 302 (FIGS. 4A and 4B), position their corresponding intake nozzles 307 and 323 at "zero" position (Step 604). Each autosampler, in its "zero" position, contains a reservoir 305 filled with a washing buffer. During step 604, the power supply which supplies power to proportioning valves 311 and 327 (FIGS. 4A and 4B), to diverting valves 333, 335 and 347 (FIGS. 4A and 4B), and to priming valves 313, 329, 341 and 345 (FIGS. 4A and 4b) is turned off. In the preferred embodiment, the priming valves, 313, 329, 341 and 345, are normally opened in a non-powered state (off); the proportioning valves, 311 and 327, in the non-powered (off) state, connect their outlets 312 and 328 with respective "normally opened" intake ports, 309 and 325; and in the non-powered (off) state, the diverting valve 335 connects its common outlet 334 with the "normally opened" intake port 336, diverting valve 333 connects its common outlet 342 with the "normally opened" intake port 332 and diverting valve 347 connects its common outlet 346 with the "normally opened" intake port 348.

After the system has been initialized, peristaltic pump 357 is started (Step 606) and priming valves 313 and 345 are turned on (Step 608). In the powered state, the priming valves 313 and 345 are closed. This forces the buffer flow through tubing 325, outlet tubing 328 of proportioning valve 327, priming valve 329, mixing zone 331, intake tubing 332 and outlet tubing 342 of the diverting valve 333, priming valve 341, mixing zone 343, a reaction developing line 353, detector 355, pump 357 and then into a drain container 359.

Referring again to FIGS. 1A and 1B, computer 123 implements software code 125 to provide control signals to a controller 109 which controls the various valves, chambers etc. of the system. This control signal is delayed in order to provide adequate time for liquid to fill the fluidic lines (Step 610). Next, the proportioning valve 327 is turned on (Step 612). While proportioning valve 327 is in the powered state, the buffer located at "zero" position of the autosampler 315 will flow through tubing 323, outlet tubing 328 of proportioning valve 327, priming valve 329, mixing zone 331, intake tubing 332 and outlet tubing 342 of diverting valve 333, priming valve 341, mixing zone 343, a reaction developing line 353, detector 355, pump 357 and then into a drain container 359.

After energizing the proportioning valve 327, the control signal is delayed again (Step 613) in order to provide the time needed for the buffer to fill out the fluidics system. After the delay in Step 613, the control signal will set the proportioning valve 327 to its off position (Step 614), turn off (open) priming valve 313 (Step 616) and turn on (close) the priming valve 329 (Step 618). This will fill out fluidic lines 309, 312, 332, 342, priming valve 341, mixing zone 343, a reaction developing line 353, detector 355 and pump 357 during a delay (Step 619) which is needed for the lines to be filled with buffer 305.

Next, the proportioning valve 311 is powered (Step 620) for a time duration controlled by Step 621. During this delay period, the same fluidic lines are being fed with the buffer located at "zero" position of the autosampler 301, coming through the nozzle 307.

After the delay period (Step 621) the control signal simultaneously turns off both proportioning valve 311 (Step 622) and priming valve 329 (Step 624) and turns on both diverting valve 335 and diverting valve 333 (Step 626). During a delay period, determined by Step 627, the liquid flow will be directed from intake tubing 338 and outlet tubing 334 of the diverting valve 335 through the intake tubing 340 and the outlet tubing 342 of the diverting valve 333 through the priming valve 341, the mixing zone 343 and further through the reaction developing line 353, the detector 355, the pump 357 and then to the drain container 359. Then the control signal turns off diverting valve 335 (Step 628), which allows the same fluidic lines to be fed from intake tubing 336. The length of time required is a function of the length of the different lines involved and the rate of fluid flow through the system, which for any particular system can be readily determined.

After the delay provided by Step 629, the control signal turns off diverting valve 333 (Step 630), turns off (opens) priming valve 345 (Step 632) and turns on (closes) priming valve 341 (Step 634). Under these conditions, the liquid flow will be directed from the intake tubing 348 to outlet tubing 346 of diverting valve 347, through the priming valve 345, the mixing zone 343, the reaction developing line 353, the detector 355, the pump 357 and then to the drain container 359. The time required for the above liquid flow to occur is provided by a delay period in Step 635. After this delay, the control signal turns on diverting valve 347 (Step 636), which allows the same fluidic lines to be filled with the buffer 305 coming from tubing 351, during a delay period provided in Step 637.

After the delay provided by Step 637, the control signal turns off (opens) priming valve 341 (Step 638), and turns off the diverting valve 347 (Step 640). The control signal then turns off pump 357 (Step 642). Finally, the priming program ends the system priming mode and all components of the fluidics system are filled with liquids (Step 643).

The state of the valves at each step of the program is shown in FIG. 7d. Priming valves 345, 341, 313 and 329 are of a two-way normally opened type. Diverting valves 335, 333 and 347 are of a three-way type with one common outlet port and one each normally opened and normally closed intake ports. Proportionating valves 311 and 327 are also of the three-way type similar to diverting valves 335, 333 and 347. The symbols "−" and "+" indicate turned off and turned on state of the valves. The state of all the valves after the priming mode is finished is the same as at the initial state.

After the priming of the system is done, the operator is prompted to start either the screening or potency profiling mode. If screening mode is chosen, the operator is prompted to specify how many compounds are located in the set of compounds to be tested, $N_{max}$, and how many antagonists, $M_{max}$, and agonists, $L_{max}$, solutions are located in the respective sets of the standards. If potency profiling mode is chosen, the operator is prompted to specify which compounds in a set should be measured.

A continuous flow diagram of the presently preferred screening mode with the negative pressure fluidics system of FIGS. 4A and 4B is shown on FIGS. 8a–8g.

The screening program begins from a start state 700 and enters state 702 where it sets all parameters to their initial values. These initial parameters include, but are not limited to, the internal initialization of software variables and subroutines.

Once the initial parameters are determined, the autosamplers 301 and 315 (FIGS. 4A and 4B) position the intake nozzles 307 and 323 at the corresponding "zero" position occupied by a wash buffer reservoir 305 (Step 704), and turns off proportioning valves 311 and 327, diverting valves 333, 335 and 347, and priming valves 313, 329, 341 and 345 (Step 706). In a turned off state, priming valves 313, 329, 341 and 345, are normally opened, proportioning valves 311 and 327 connect, respectively, their outlets 312 and 328 with corresponding "normally opened" intake ports 309 and 325, diverting valve 335 connects its common outlet 334 with "normally opened" intake port 336, diverting valve 333 connects its common outlet 342 with the "normally opened" intake port 332, and diverting valve 347 connects its common outlet 346 with the "normally opened" intake port 348.

After the system has been initialized, pump 357 is started (Step 708). This will force the wash buffer from the "zero" positioned reservoirs of both autosamplers 301 and 315 to run through nozzles 309 and 325 and outlet ports 312 and 328 of proportioning valves 311 and 327, respectively, priming valves 313 and 329, mixing zone 331, intake port 332 and outlet port 342 of diverting valve 333, priming valve 341, mixing zone 343, a reaction developing line 353, detector 355, pump 357 and then into a drain container 359. In mixing zone 343 this flow is mixed with cell suspensions or particle preparations, which contain one or more cell types or one or more particle types to be tested, from cell suspension or particle reservoir(s) 349 coming from intake tubing 348 and an outlet port 346 of diverting valve 347 through priming valve 345. Thus, the total flow passing mixing zone 343 is a sum of three flows, one of each coming from the proportioning valves 311 and 327 and one coming from diverting valve 347. During this step, both proportioning valves supply wash buffer 305 from the reservoirs located at "zero" position of each autosampler in such a way that the final mixture consists of one part cell suspension or particle preparation and two parts wash buffer 305.

After the delay determined in step 709, which is needed for the flow of the mixture of the cell suspension or particle types containing one or more cell types or particle types to be tested (or a member of a series of cell types or particle types to be tested) and wash buffer 305 to stabilize, detector 355 registers a basal signal produced by the cells or particles alone, BS (Step 710). After the BS signal is registered, it is saved as a reference (Step 712) and computer 123 (FIGS. 1A and 1B) triggers incremental counter N (Step 714).

The numerical content of the incremental counter N is increased by unity each time it is triggered thus determining the position of the nozzle of intake port 307 of autosampler 301 which samples the sets of compounds 303 to be tested.

Next, the numerical content, $N_i$, of the incremental counter is checked against an entered maximum number of the compounds to be tested, $N_{max}$ (Step 716). If $N_i$ does not exceed $N_{max}$, autosampler 301 positions nozzle 307 into the compound reservoir located at the $N_i$ position of a rack of compounds 303. Next, proportioning valve 311 is switched on to open its "normally closed" intake port 307 to the common output port 312 (Step 720). During Step 720, the combined flow in mixing zone 343 and afterwards in detector 355, is composed of one portion of buffer 305 coming through nozzle 325 of proportioning valve 327, one portion of the compound 303 to be tested coming from nozzle 307 of proportioning valve 311 and one portion of the cell suspension or particle preparation containing one or more cell types or one or more particle types to be tested coming from the intake tubing 348 which is "normally opened" to the output port 346 of diverting valve 347. After a delay provided by Step 721, which is needed for the mixing process to stabilize, detector 355 registers a signal, $SN_i$, produced by the cells or particles in the presence of the given compound, $N_i$ (Step 722). After the $SN_i$ signal is registered, its value is saved as a reference value (Step 723). The value of the $SN_i$ signal is then compared with the value of the reference basal signal, BS (Step 724). If the $SN_i$ signal is greater than the BS signal, the computer 123 (FIGS. 1A and 1B) will "flag" the corresponding compound as "positive" (Step 725), which means that the compound stimulates the cell signal or interacts with the particle. If $SN_i$ is greater than BS, the computer 123 controls a set of antagonists and calculates corresponding coordinates for positioning the nozzle 323 of autosampler 315 over the antagonist containing reservoirs located in rack 317. If $SN_i$ is less than BS, computer 123 will "flag" the corresponding compound as "negative" (Step 726). In this case, the computer 123 controls a set of agonists and calculates corresponding coordinates for positioning the nozzle 323 of autosampler 315 over the agonist containing reservoirs located in rack 319.

Each time the condition, "$SN_i$>BS", is satisfied, the program flow will go through loop K-O of the incremental counter M (Step 730). The incremental counter, M, increases the count number by one each time it is triggered and thus determines the successive positions of nozzle 323 of autosampler 315 which serves the set of standard antagonists located on rack 317. Next, computer 123 checks if the numerical content of the incremental counter ($M_j$) exceeds the maximum number of standards to be tested ($M_{max}$) entered by the operator (Step 732).

If $M_j$ is less than or equal to $M_{max}$, autosampler will position nozzle 323 into the standard antagonist reservoir, located on rack 317 corresponding to the numerical content of the incremental counter, $M_j$(Step 734). Next, proportioning valve 327 is switched over to connect its "normally closed" intake port 323 with the outlet port 328 (Step 736). During Step 736, the combined flow through mixing zone 343, reaction developing lines 353 and detector 355 is composed of one portion of standard antagonist coming from proportioning valve 327, one portion of the compound to be tested, coming from proportioning valve 311 and one portion of the cell suspension or particle preparation containing one or more cell types or one or more particle types to be tested coming from diverting valve 347.

Next, detector 355 registers and saves (Step 738) for further comparison, a signal, $SN_iM_j$, produced by a given compound, $N_i$, in the presence of a given standard antagonist, $M_j$. Then, both proportioning valves 311 and 327 are turned off (step 740). This closes intake ports 307 and 323 and opens intake ports 309 and 325 to the corresponding outlet ports 312 and 328. Autosampler 315 then positions nozzle 323 into "zero" position occupied by wash buffer reservoir 305. The proportioning valve 327 is then turned on again to open its "normally closed" intake port 323 into the outlet port 328 (Step 744) and the content of nozzle 323 is washed out (Step 746). Next, proportioning valve 327 is turned off to close intake port 323 and to open "normally opened" intake port 325. During this process, the fluidic lines are washed with buffer coming from nozzle 325 of autosampler 315. Next, Computer 123 (FIGS. 1A and 1B) compares signal, $SN_i$, measured in the presence of a compound $N_i$ alone, with the signal, $SN_iM_j$, measured in the presence of both a compound $N_i$ and a standard antagonist, $M_j$ (Step 750). If the signal in the presence of a standard antagonist, $M_j$, is lower than the signal generated by a compound $N_i$ alone, $SN_iM_j<SN_i$, then both the compound $N_i$ and the standard antagonist, $M_j$, is flagged as "positive" (Step 751). If both signals are equal to each other, then the compound $N_i$ is flagged as "positive" and the standard antagonist $M_j$ is flagged as "negative" (Step 752). After the data is flagged, the data, containing the ID number of the compound $N_i$ with its flag value and ID number of the standard antagonist $M_j$ with its flag value is transferred into a database (Step 753). After the data is saved the program loops back to trigger the incremental counter M (Step 730), to increase its count by one and Step 754 is repeated until the condition 732 is achieved.

When the condition determined in the decision step 732 is met, that is the compound has been tested against all standard antagonists in a given set, the program resets the content of incremental counter M to zero (Step 755), and both autosampler 301 and autosampler 315 position their respective nozzles 307 and 323 to "zero" position, where the reservoirs with a washing buffer 305 are located (Step 756). Next, both proportioning valves 311 and 327 are turned on (Step 758). This opens "normally closed" intake ports 307 and 323 to the corresponding outlet ports 312 and 328. During this washing delay period determined by Step 760, the contents of both nozzle 312 and nozzle 328 are washed out with buffer 305. After Step 760 is finished, both proportioning valves 311 and 327 are turned off (Step 762). After the washing delay period (Step 760), the program loops back to the incremental counter N content of which is incremented by one (Step 714) by triggering signal $S_{tr}$ from the computer 123 (FIGS. 1A and 1B). Then, the numerical content $N_i$ of counter N is compared with the maximum number, $N_{max}$, of the compounds to be tested. If $N_i$ exceeds $N_{max}$, the content of incremental counter N is zeroed (Step 717) and the screening mode is stopped (Step 719). Otherwise, Step 715 will be repeated with the next compound.

If the condition of the decision process 724, $SN_i>BS$, is not satisfied, the $N_i$ compound is flagged as "negative" (Step 726) and the incremental counter L is triggered (Step 764). The incremental counter L is increased by one (Step 764) each time it is triggered and thus determines the successive positions of nozzle 323 of autosampler 315 relative to the set of standard agonists located on rack 319. Next, the numerical content, $L_k$, of incremental counter L is compared with the maximum number, $L_{max}$, of standard agonists to be used (step 766).

If $L_k$ is less than or equal to the $L_{max}$, autosampler 315 positions nozzle 323 into the standard agonist reservoir in rack 319, which corresponds to the numerical content, $L_k$, of incremental counter L. Next, proportioning valve 327 is turned on to open its "normally closed" intake port 323 to outlet port 328 and proportioning valve 311 is turned off to close its intake port 307 and open intake port 309 to outlet port 312 (Step 770). During step 770, the combined flow coming through mixing zone 343, reaction developing lines 353 and detector 355 is composed of one portion of standard agonist 319 coming from inlet port 323 of proportioning valve 327, one portion of buffer 305, coming from inlet port 309 of proportioning valve 311 and one portion of the cell suspension or particle preparation containing one or more cell types or one or more particle types to be tested coming from the diverting valve 347.

After a delay period provided by Step 772, which is needed for the mixing process to stabilize, a signal, $SL_k$, produced by a given standard agonist, $L_k$ is registered and saved (Step 774). Next, proportioning valve 311 is turned on to open its "normally closed" intake port 307 to outlet port 312 (Step 776). A delay period needed for the mixing process to stabilize is provided in Step 778, after which a signal, $SL_kN_i$, is stimulated by a given standard agonist, $L_k$, in the presence of a given compound, $N_i$ is registered and saved in (Step 780).

After the signal $SL_kN_i$, is registered (Step 780), both proportioning valves 311 and 327 are turned off to close their respective "normally closed" intake ports 307 and 323 and to open intake ports 309 and 325 to the corresponding outlet ports 312 and 328 (Step 782). Next, autosampler 315 positions the nozzle of intake port 323 to its "zero" position which corresponds to washing buffer reservoir 305 (Step 784). Then, the proportioning valve 327 is turned on (Step 785). This opens the "normally closed" intake port 323 to the outflow port 328, and after some delay provided by step 786, which is needed for washing out the content of nozzle 323, the proportioning valve 327 is turned off (Step 787), and the two signals, $SL_kN_i$ and $SL_k$, are compared (Step 788).

If $SL_kN_i$ is less than $SL_k$, then the corresponding standard agonist, $L_k$, is flagged as "positive" (Step 790). If both signals are equal to each other, then the standard agonist, $L_k$, is flagged as "negative" (Step 792). After the data is flagged, the data, containing the ID number of the compound $N_i$ with its flag value and the ID number of the standard agonist $L_k$ with its flag value is transferred into a database (Step 794). After the data is saved the program triggers the incremental counter L (Step 764) to increase its count by one and Step 796 is repeated until condition 766 is achieved.

When the condition determined in Step 766 is met, that is the compound has been tested against all standard agonists in a given set, the content of incremental counter L is reset to zero (Step 755) and both autosampler 301 and autosampler 315 position their respective nozzles 307 and 323 to "zero" position where the reservoirs with washing buffer 305 are located (Step 756). The system then turns on both proportioning valve 311 and proportioning valve 327 to open "normally closed" intake ports 307 and 323 to the corresponding outlet ports 312 and 328 respectively (Step 758). During a washing period provided by Step 760, the contents of both nozzle 307 and nozzle 323 are washed out with the buffer 305. Next, both proportioning valves 311 and 327 are turned off (Step 762) and incremental counter N is incremented by one (Step 714). Next, the new triggered numerical content $N_i$ of the incremental counter N is compared with the maximum number, $N_{max}$, of compounds to be tested (Step 716). If $N_i$, exceeds $N_{max}$, the counter N is set to zero in step 717 and the screening mode is stopped (Step 719). Otherwise, the whole cycle will be repeated with a subsequent compound.

After the screening mode is stopped (Step 719), the operator is prompted by the computer to choose either potency profiling mode or to repeat screening mode with a new set of compounds.

As discussed above, while the methods described in FIGS. 8a–8g include steps for supplying a standard(s) and a calibration solution(s), it will be appreciated that these steps need not be present if the analysis being performed does not require the use of a standard compound(s) or a calibration solution(s).

Figure 9A:
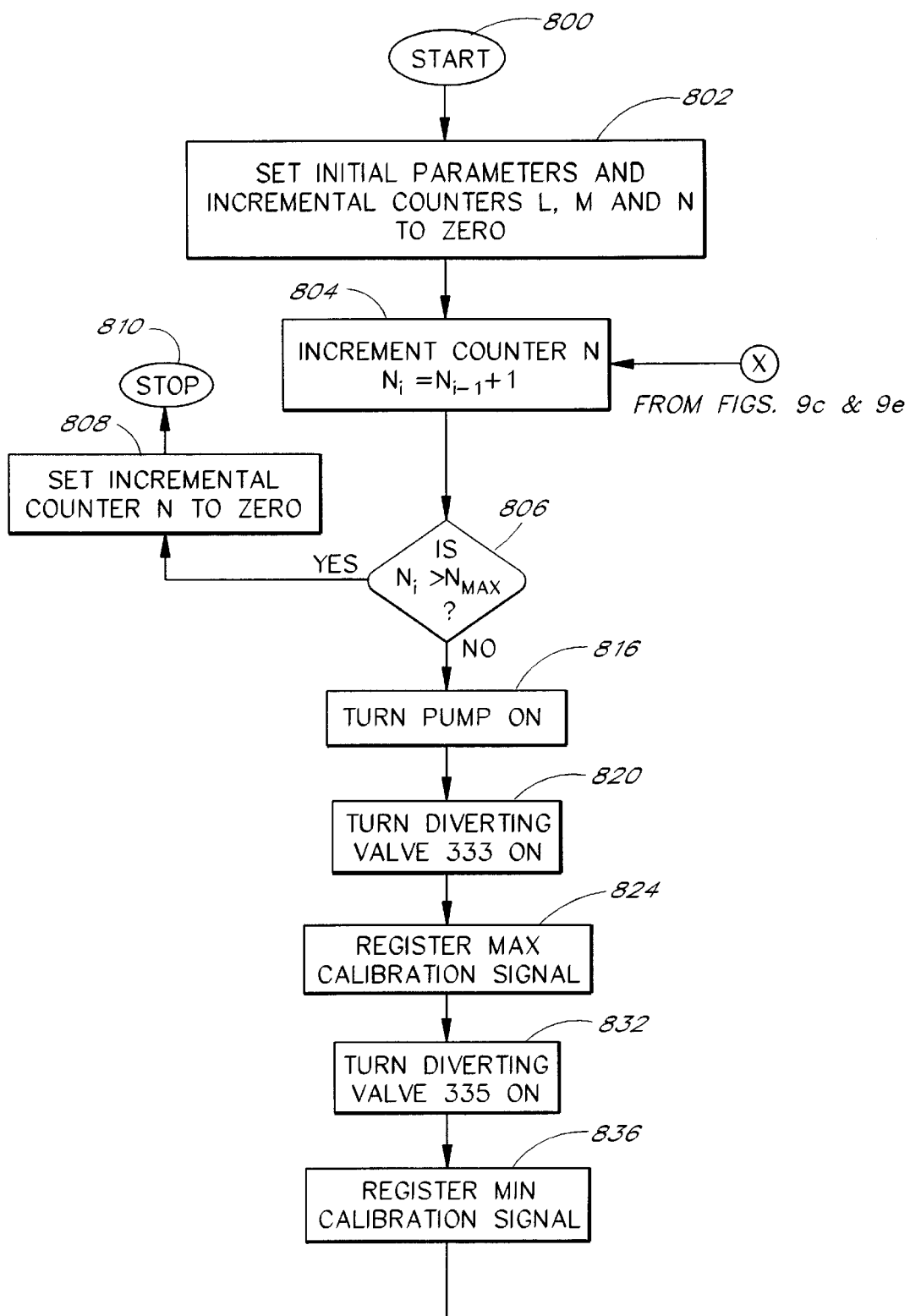
FIG. 9 is a flow diagram of a preferred potency mode operation which may be implemented by a combinatorial screening apparatus of the present invention.
Figure 9B:
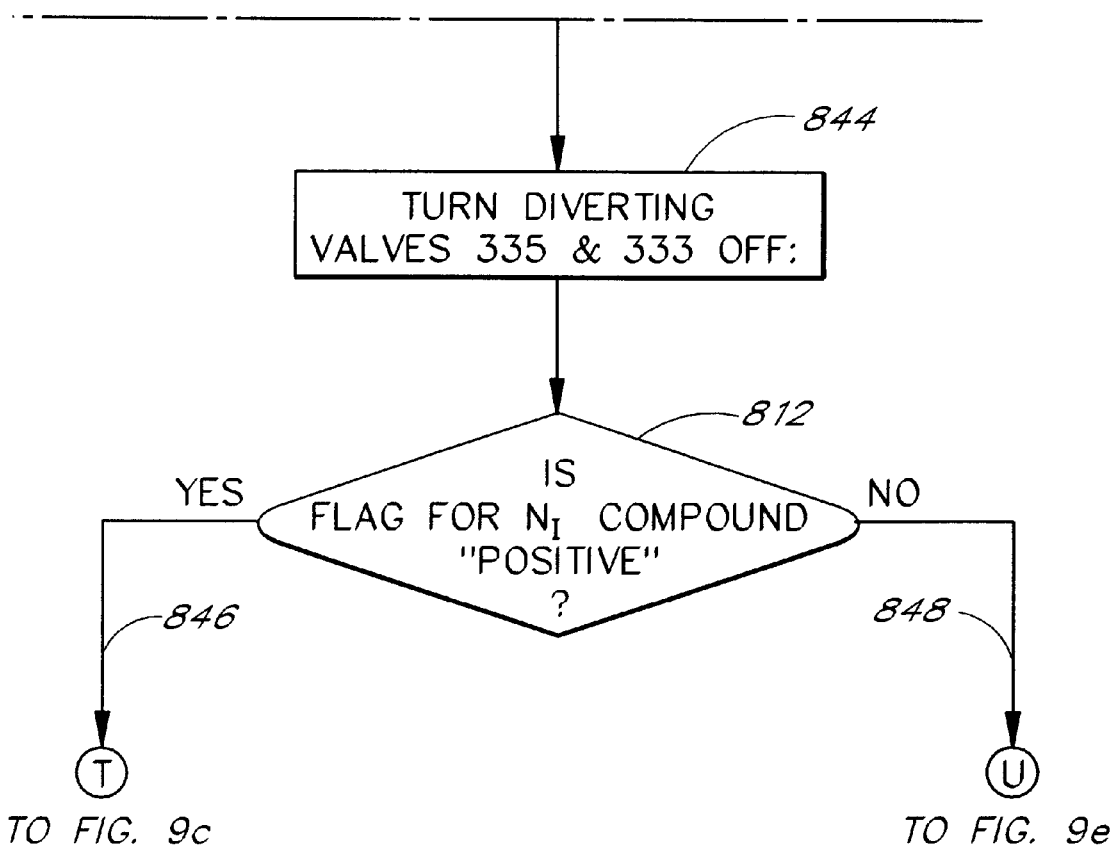
Figure 9C:
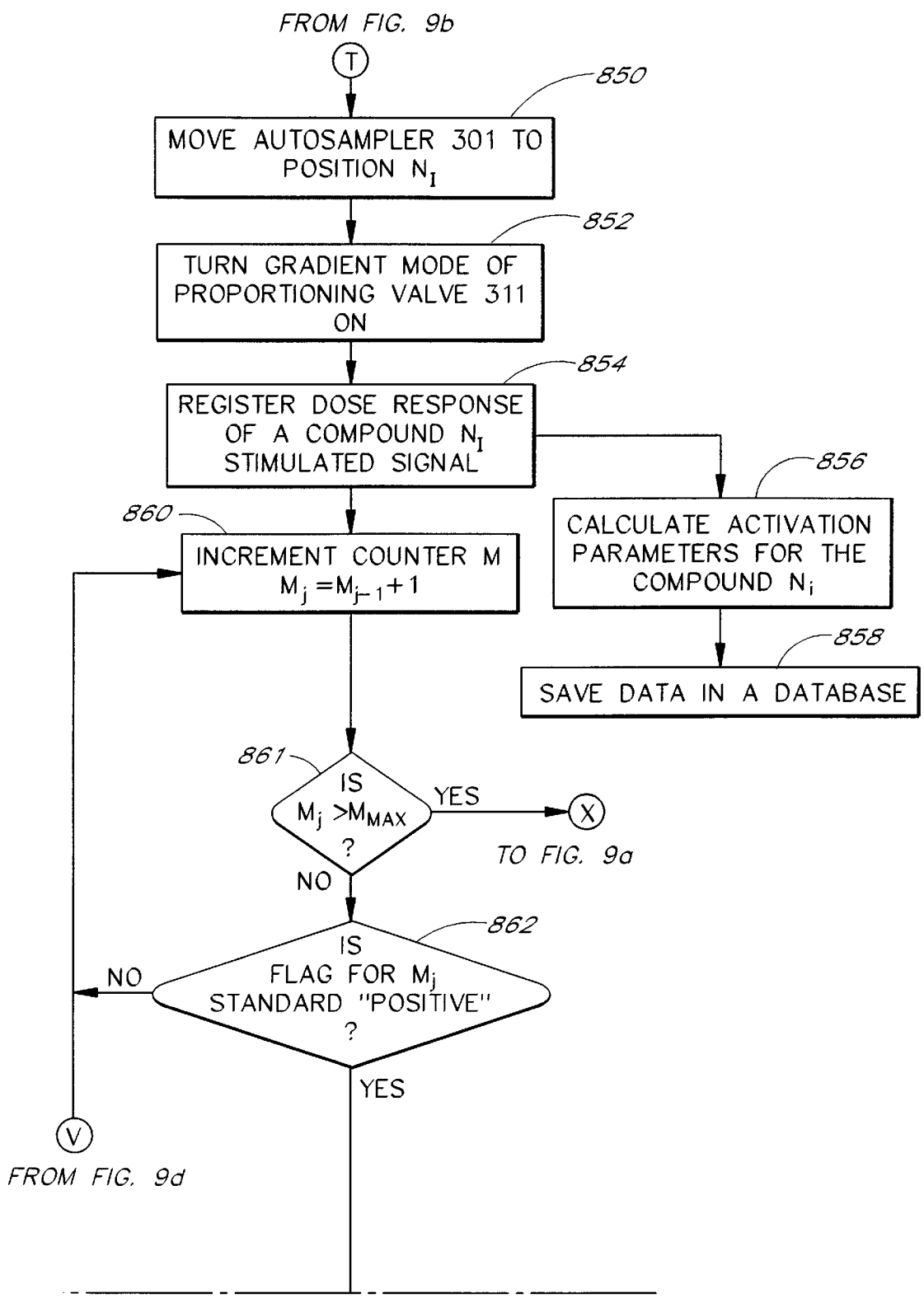
Figure 9D:
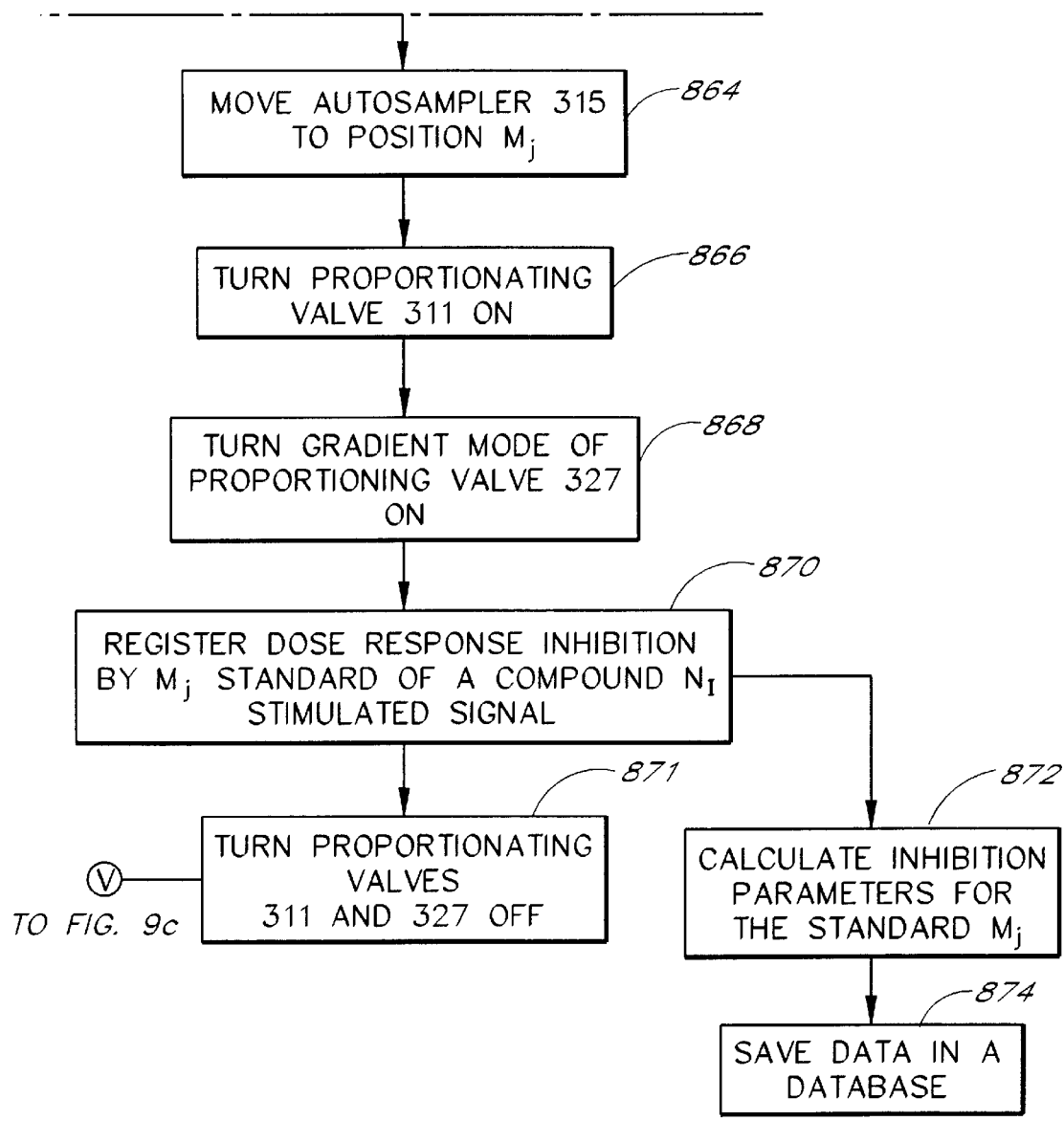
Figure 9E:
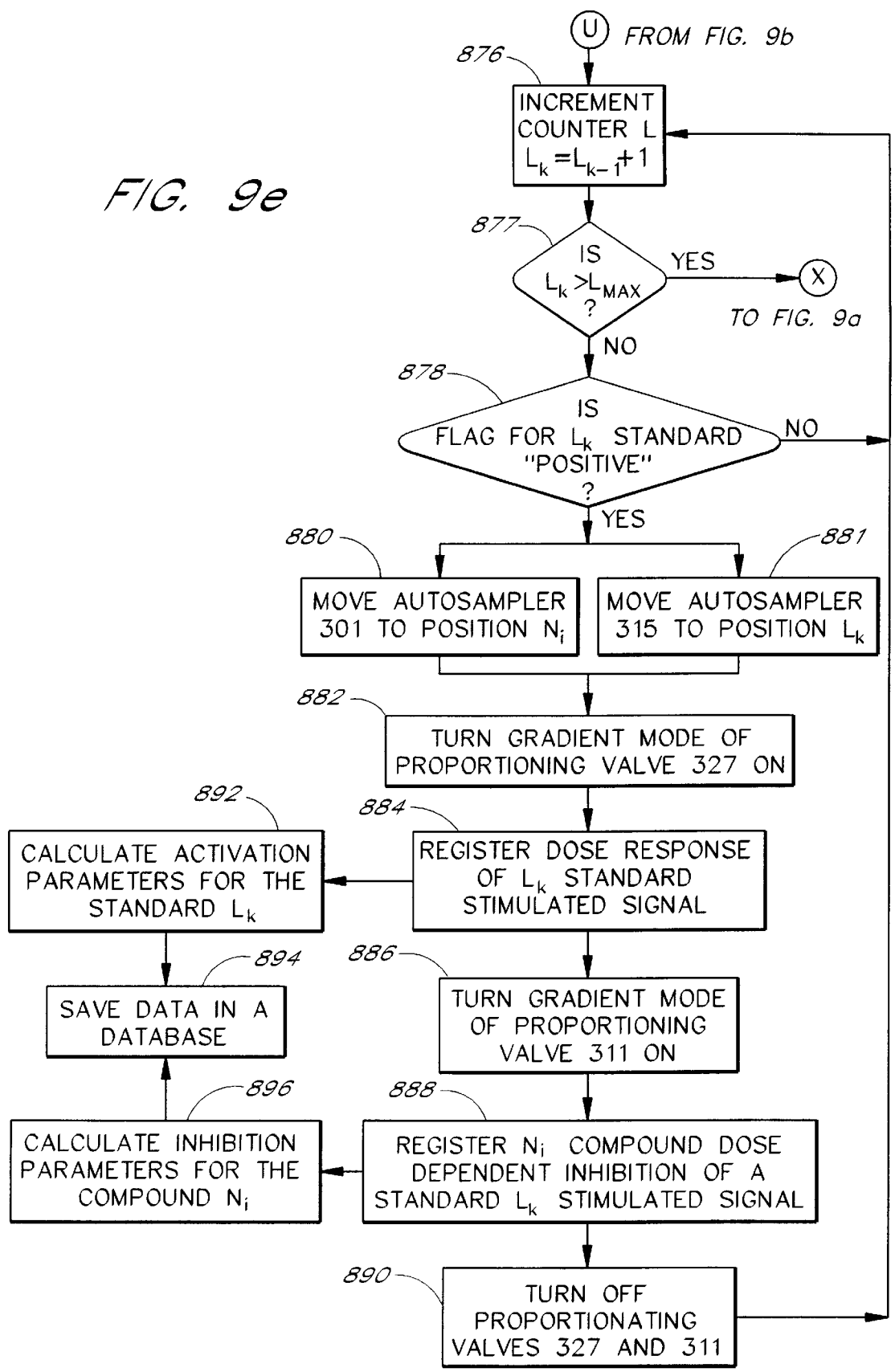

A continuous flow diagram of the presently preferred potencyprofiling mode with the negative pressure fluidics system of FIGS. 4A and 4B is shown in FIGS. 9a–98e.

The potency profiling program begins from a start state 800 and enters state 802 where it sets all incremental counters, L, M, and N, to zero and sets all parameters to their initial values. This initial parameters include, but are not limited to, the internal initialization of hardware and software variables and subroutines. Next, the incremental counter N is started (Step 804), and its numerical content, $N_i$, is compared with the maximum number, $N_{max}$, of standards, entered by the operator before starting the program (Step 806). If $N_i$ exceeds $N_{max}$, the incremental counter N is zeroed (Step 808), and the program stops (Step 810). Otherwise, the program will proceed by turning on pump 357 (Step 816). At this point, in accordance with initial parameters setup in Step 802, the nozzles 307 and 323 of autosamplers 301 and 315 are in zero position, proportioning valves 311 and 327, priming valves 313, 329, 341, and 345, and diverting valves 335, 333, and 347 are turned off. During step 816, the combined flow coming through mixing zone 343, reaction developing lines 353 and detector 355 is composed of one portion of buffer 305 coming from inlet port 309 of proportioning valve 311, one portion of buffer 305, coming from inlet port 325 of proportioning valve 327 and one portion of the cell suspension or particle preparation coming from the diverting valve 347. Next, diverting valve 333 is turned on (Step 820), opening "normally closed" intake port 340 into outlet port 342. During this process, the calibration max solution 337, which determines maximum response, flows through tubing 336 which is connected to outlet tubing 334 of diverting valve 335, through intake port 340 of diverting valve 333, through priming valve 341 and then into mixing zone 343, where it is mixed with cells coming from the cell suspension or particles from the particle preparation, through intake tube 348 and outlet tube 346 of diverting valve 347, and then through priming valve 345 into the mixing zone 343. The cells or particle calibration max mixture will then flow to developing lines 353, and then to detector 355. Next, the maximum signal is measured and registered (Step 824). Diverting valve 335 is then turned on (Step 832) which opens the "normally closed" intake port 338 to outlet port 334 which allows a calibration min solution 339 to flow through diverting valve 333, priming valve 341 and into mixing zone 343 where it is mixed with cells coming from the cell suspension or the particles from the particle preparation, through intake tube 348 and outlet tube 346 of diverting valve 347, and then through priming valve 345, into mixing zone 343. The cells or particle/calibration min. mixture then flows to developing lines 353 and then to detector 335. The minimal response signal is then measured and registered (step 836). Next, both diverting valves 335 and 333 are turned off (Step 844). During step 844, the combined flow coming through mixing zone 343, reaction developing lines 353 and detector 355 is composed of one portion of buffer 305 coming from inlet port 309 of proportioning valve 311, one portion of buffer 305, coming from inlet port 325 of proportioning valve 327 and one portion of the cell suspension or particle preparation coming from the diverting valve 347. This is needed to wash out the remains of calibration solution from the fluidics line. Next, the "flag" value of the compound, $N_i$, is checked (Step 812). If the "flag" value of the $N_i$ compound is "positive", then the system will go to step 850, otherwise it will go to step 876. If the "flag" value of the $N_i$ compound is "positive", autosampler 301 will position nozzle 307 into a reservoir corresponding to the $N_i$ compound, located on rack 303 (Step 850). Next, proportioning valve 311 is operated in a gradient mode (step 852). In the gradient mode, the proportioning valve, 311, combines flows from two intake ports, 307 and 309, in such a way that the proportion of a $N_i$ compound flow and a buffer flow in an outlet port, 312, changes in time to create a discontinuous change of the compound concentration. While the concentration is being changed in time, the fresh portions of the cells or particles, coming into the mixing zone 313 from the cell suspension or particle preparation, at any given time will react with the different concentrations of the $N_i$ compound. The resulting dose response dependence of the signal is registered in Step 854 with the subsequent calculation of the activation parameters for the $N_i$ compound in Step 856 and then saving the data in a database (Step 858).

Next, an incremental counter of the standard antagonists, M, is started (Step 860) and the numerical content, $M_j$, of the counter M is compared with the maximum value, $M_{max}$, entered by the operator (Step 861). If the numerical value $M_j$ does not exceed $M_{max}$, then the 'flag' value of the $M_j$ standard is checked (Step 862). If the "flag" value of the $M_j$ standard is not "positive", the incremental counter, M, is increased by one (Step 860), and the steps following Step 860 will be repeated as described above. If the "flag" value of the $M_j$ standard is "positive", autosampler 315 positions nozzle 323 into the reservoir corresponding to the $M_j$ standard antagonist, located on rack 317 (Step 864). After nozzle 323 is immersed into the standard solution, proportioning valve 311 is turned on (Step 866). When the proportioning valve 311 is turned on, it opens its "normally closed" intake port 307 which is immersed, in Step 850, into a reservoir corresponding to the compound $N_i$, so that the $N_i$ compound flows through the fluidics system and generates a signal when it is mixed with the cells or particles, coming through intake tubing 348 and outlet tubing of diverting valve 347, priming valve 345 to mixing zone 343 and further to developing line 353 and detector 355. Next, proportioning valve 327 is operated in a concentration gradient mode (Step 868). In the gradient mode, proportioning valve 327 combines flows coming from the two intake ports, 323 and 325 into outlet port 328 in such a way that the proportion of a $M_j$ standard antagonist flow and a buffer flow changes in time to create a discontinuous change of the standard antagonist concentration. While the concentration is being changed in time, the fresh portions of the cells or particles flow into mixing zone 343 from the cell suspension or particle preparation and react with the mixture composed of the $N_i$ compound at constant concentration and the standard antagonist $M_j$ at the concentration different at any given time. The resulting dose response inhibition by the $M_j$ standard antagonist of the $N_i$ compound stimulated signal is registered in Step 870, with the subsequent calculation of the inhibition parameters for the $M_j$ standard antagonist in a Step 872 and saving the data in a database (Step 874).

After the curve is registered in Step 870 both proportioning valves 311 and 327 are closed (Step 871) and the program flow returns to Step 860 where incremental counter M is incremented by one and the program returns to Step 861 where $M_j$ is compared to $M_{max}$.

When all of the standard antagonists $M_j$ are counted and those with "positive flags" are measured, the numerical value $M_j$ becomes greater than $M_{max}$, and the decision process in Step 861 returns to Step 804 where the incremental counter N increases its numeric value by one. The value of $N_i$ is then compared to $N_{max}$, the maximum number of compounds to be tested (Step 806). If $N_i$ exceeds $N_{max}$, the incremental counter N is reset to zero (Step 808), and the program stops (Step 810). If multiple cell suspension or particle preparations are to be evaluated, this process can be repeated for each of the cell suspensions or particle preparations in the series of cell suspensions or particle preparations to be tested.

If, in Step 812, the flag value of the $N_i$ compound is determined to be "negative", a incremental counter L which counts the standards, $L_k$, in a set of agonists, located in rack 319, is updated (Step 876). Next, the numerical value $L_k$ is compared with the maximum number, $L_{max}$, of standard agonists entered by an operator (Step 877).

Until the numerical value $L_k$ of the L counter is greater than the $L_{max}$ value, the program will go to Step 878, where the 'flagged' value of the $L_k$ standard is checked. If the flag value is not positive, the program returns to Step 876. If the flag value of the $L_k$ standard is positive, autosampler 301 positions its nozzle 307 into a corresponding reservoir containing the $N_i$ compound located in rack 303 (Step 880), autosampler 315 positions its nozzle 323 into a corresponding reservoir containing the $L_k$ standard agonist, located in rack 319 (Step 881).

Next, the concentration gradient mode of proportioning valve 327 is activated (Step 882) and a dose response stimulation of a signal with the $L_k$ standard agonist is then registered (step 884). In the gradient mode, proportioning valve 327 combines flows coming from the two intake ports, 323 and 325, into outlet port 328 in such a way that the proportion of a $L_k$ standard agonist flow and a buffer flow changes in time to create a concentration gradient of the standard agonist. While the gradient is being created in time, fresh cells or particles flow into mixing zone 343 from the cell suspension or particle preparation through "normally opened" intake tubing 348 and outlet port 346 diverting valve 347, "normally opened" priming valve 345, and discontinuously react with the standard agonist $L_k$ at the discontinuously changing concentration of the standard. Once the dose dependence of the signal stimulation by the $L_k$ standard agonist is registered (Step 884), the activation parameters are calculated (Step 892) and then saved in a database (Step 894).

After the gradient mode of proportioning valve 327 is finished, the valve stays either at the proportion rate reached by the end of the gradient mode or at predetermined proportion rate which establishes the constant concentration of the $L_k$ standard agonist which will be used in further steps. Next, the concentration gradient mode of proportioning valve 311 is activated (Step 886). A dose response inhibition by the $N_i$ compound of the $L_k$ standard agonist stimulated signal is then registered (Step 888) with a subsequent calculation of the inhibition parameters in Step 896. this data is then saved in a database (Step 894). When the registration of the concentration dependence is finished both proportioning valves 311 and 327 are turned off (Step 890) to close their intake ports 307 and 323 and to open "normally opened" intake ports 309 and 325. During this process, the fluidics lines are washed with buffer 305 coming from nozzles 309 and 325 of autosamplers 301 and 315 through outlet ports 312 and 328 of proportioning valves 311 and 327, priming valves 313 and 329, mixing zone 331, "normally opened" intake port 332 and outlet port 342 of diverting valve 333, "normally opened" priming valve 341, mixing zone 343, developing line 353 and detector 355. Next, the program returns to Step 876, at which point the above cycle is repeated until all the standard agonists are counted, and those with a positive flag are measured, and the numerical value $L_k$ of the incremental counter becomes greater than the $L_{max}$ value, at which point, the program will return to Step 804.

When all of the compounds $N_i$ are counted (Step 804) and tested, the $N_i$ number becomes greater than the $N_{max}$ value and the incremental counter N is reset to zero (Step 808) and the program stops (Step 810).

As discussed above, while the methods described in FIGS. 9a–9e include steps for supplying a standard(s) and a calibration solution(s), it will be appreciated that these steps need not be present if the analysis being performed does not require the use of a standard compound(s) or a calibration solution(s).

Cells for use in the apparatus can be selected for the presence of particular known receptors or for their ability to provide predetermined cellular responses to particular stimuli. A large number of such cells are known. For example, to measure the effect of compounds on calcium mobilization induced by different types of receptors, one may wish to use Jurkat T Cells, Platelets, Umbilical Vein, Endothelial Cells, or Chines Hamster Lung Fibroblasts for thrombin receptor; Cerebellar Purkinje Cells, Cortical Astrocytes and Cortical Glial cells for AMPA receptors; Hippocampal Neurons for NMDA Receptor; P-12 cells for Purinergic Receptors; Oligodendrocytes for Platelet-Derived Growth Factor Receptor, Human Neuroblastoma cells and Pituitary Cells for Neuropeptide Y Receptors and protein-tyrosine kinase and protein-tyrosine phosphatase receptors; Human Medulloblastoma cells for Endothelin Receptor; Neutrophils for TNFa Receptor; NG108–15 cells for opioid, bradykainin and ATP; Synovial Fibroblasts for Plasminogen Receptors and so on. If one wishes to measure an intracellular ion concentration, for example, one can preincubate the cells with a dye or other detectable material having sensitivity to concentration of that particular ion. (An actual working example illustrating preparation of cells for detection of calcium ion is set forth in Example 1.)

Alternatively, if one wishes to determine the pattern of natural expression of receptors responsible for $Ca^{2+}$ signaling pathway, then one may use the cells of particular interest and then using a set of agonists known to exert their activity through $Ca^{2+}$ mobilization, to characterize the cells by what type of the receptors are expressed in these particular cells. This set of agonists may consist of acethylcholin, adrenaline, noradrenaline, 5-hydroxitriptamine, DOPA, NMDA, AMPA, Angiotensin II, Bradykinin, Bombesin, Opioid, Endothelin-1 Neuropeptide Y, TNF, PDGF, FGF and so on.

The following examples illustrate specific, non-limiting experiments, or compound profiling operations, in accordance with the present invention.

EXAMPLE 1

TE-671 cells, human medulloblastoma (ATC CCRL 8805), naturally express endothelin subtype A receptor $ET_AR$. This receptor belongs to the family of seven transmembrane-spanning G-protein coupled receptors and is known to activate calcium mobilization in the cell cytoplasm upon binding to its specific agonist endothelin-1, a 21-amino acid peptide. To characterize the affinity of the agonist for the receptor, conventional methods measure the physiological response of the cell in the presence of several concentrations of the agonist or antagonist (Sakamoto, A. et al., 1994, incorporated herein by reference).

Figure 10:
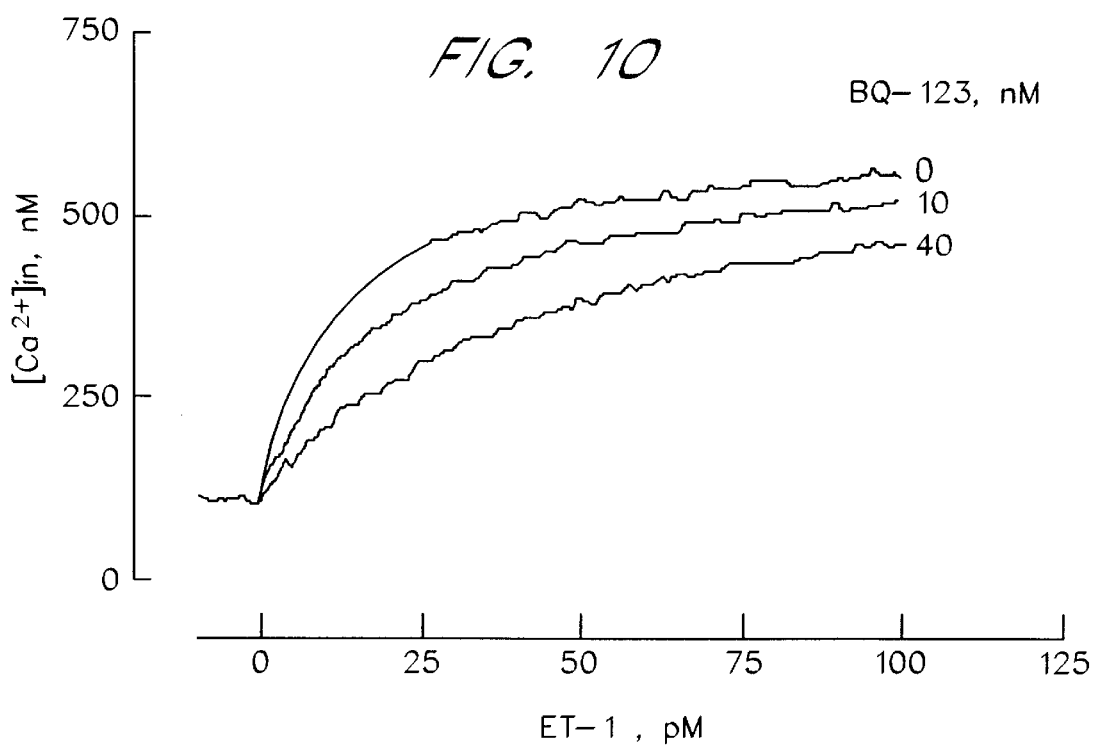
FIG. 10 represents the experimental results of ET-1 dose dependent $Ca^{2+}$ mobilization in the presence of BQ-123.

FIG. 10 illustrates a measurement of the activation of intracellular calcium mobilization ($Ca^{2+}$ measured in nanomolar concentration) as a function of the concentration of endothelin-1 (ET-1, measured in picomolar concentration), using the apparatus and method of the present invention. The apparatus was a negative pressure computer controlled unit as described above. This run was performed in the presence of several concentrations of $ET_AR$ specific competitive antagonist BQ-123 (shown in nanomolar concentration).

TE-671 cells were prepared for use in the cell physiometer of the present invention by growing them in a T75 flask until confluence. The growth media was decanted and the cells were washed twice with Dulbecco's phosphate buffered saline (DPBS) and supplemented with a fresh DPBS containing 2 μM FURA-2AM, which easily penetrates into cell cytoplasm and is hydrolyzed there with nonspecific esterases to form FURA 2, a dye which is sensitive to the ionized form of calcium. After 30 min incubation, the cells were supplemented with the equal volume of fresh DPBS and incubated for further 30 min. The cells, now loaded with the dye, were detached from the flask bottom with 0.05% Trypsin-EDTA solution. The cells were then washed twice with DPBS, containing 0.1% soybean trypsin inhibitor, and resuspended in calcium-free, magnesium-free and phenol red-free Dulbecco's modified Eagle's medium (DMEM).

Briefly, after calibration of the device of FIG. 4A with minimum and maximum standards (339, 337), ET-1 solution, an agonistic test compound, was mixed with DPBS buffer in continuously changing proportion by the proportioning valve 311 and was directed through the proportioning valve 311, mixing zone 331, diverting valve 333, and priming valve 341 into the mixing zone 343, where it was mixed with a suspension of TE-671 cells to provide a final concentration of cells $4 \times 10^5$ cells/ml. At the same time, BQ-123, as a standard antagonist solution, was also directed to the mixing zone 331 at a predetermined concentration prepared by mixing BQ-123 with DPBS in the proportioning valve 327, in a ratio of 1:1 with the ET-1 solution. In mixing zone 343, the mixed flow of BQ-123 at constant concentration, and ET-1 at a continuously changing in time concentration is mixed with cells in a ration of 2:1. This gives three fold final dilution for each component of the flow passing through mixing zone 343 and eventually, detector 355. The proportioning valve 327, was programmed for the first, second and third runs to give final BQ-123 concentration of zero, 10 nM and 40 nM, respectively. The proportioning valve 311 was preprogrammed to give a final concentration of ET-1 in each run from 0 to 100 pM. Changes in intracellular calcium ion concentration in the TE-671 cells passing through the detector 315, were measured in real time as a function of ET-1 concentration using fluorescent dye FURA-2 as described above.

The flow rate and the length of the reaction developing line were chosen so that the time interval from the point of mixing the cells with the compound to the point of signal detection in the flow-through optical cell was 40 seconds. The time required for the complete concentration gradient run to generate the curves in FIG. 10 was five minutes using the present invention. In contrast, in a conventional assay using the phosphatidylinositol turnover rate as an indicator of $ET_AR$ stimulation, it usually takes several hours to get only a few concentration points on the response curve, and it would take an inordinate amount of time to generate a complete curve as shown in FIG. 10.

Figure 11:
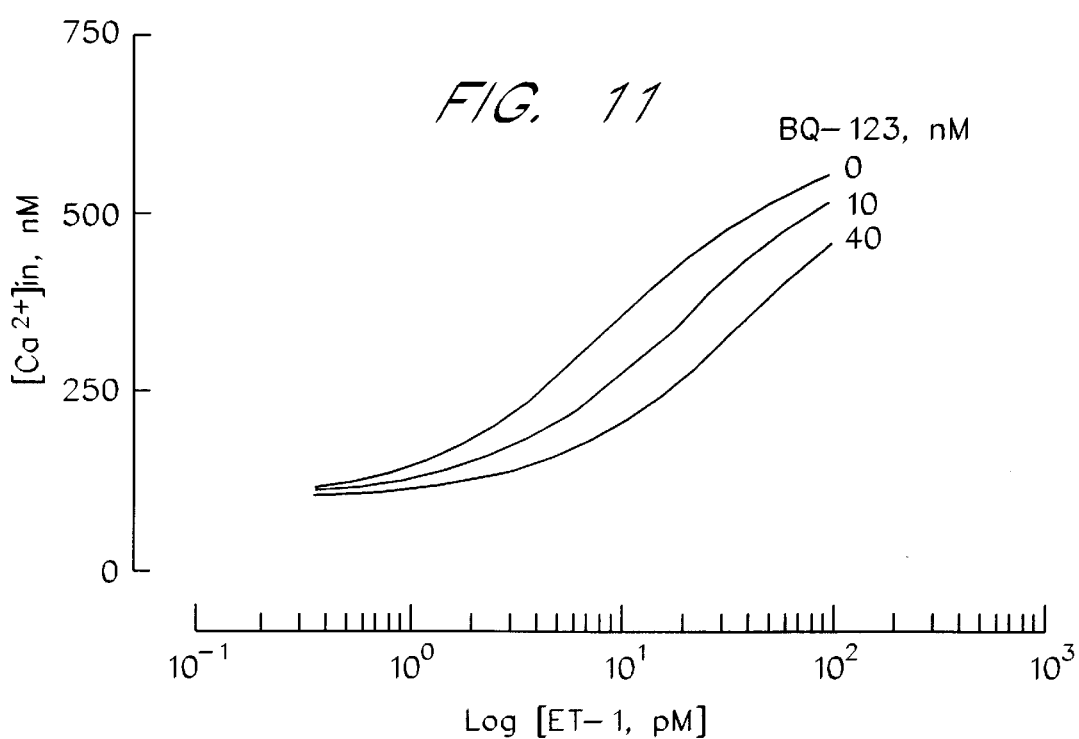
FIG. 11 represents the semi logarithmic transformation of the data of the FIG. 9.

FIG. 11 is a logarithmic transformation of the data in FIG. 10, which is used in the art to calculate maximal cell response in the presence of antagonist as well as $EC_{50}$ value for agonist and $pA_2$ value for antagonist. The $EC_{50}$ value calculated from the activation curve without BQ-123 is equal to 10 pM and one can see that the activation curves in FIG. 11 are parallel shifted to the right in the presence of BQ-123, which is known in the art as characteristic for competitive type of inhibition. The average $pA_2$ value calculated from the two different concentrations of BQ-123 is equal to 7.96. This corresponds to inhibition constant, $K_1$, for BQ-123 of 11 nM. The $EC_{50}$ and $pA_2$ values are in close agreement with the literature data (Masaki Ihara et al., 1992, is incorporated herein by reference).

EXAMPLE 2

Figure 12:
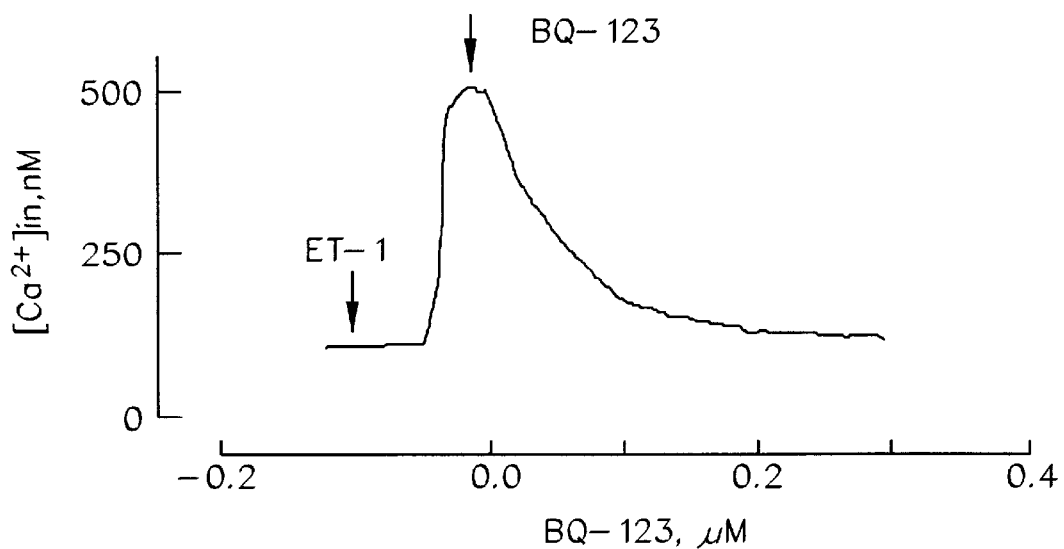
FIG. 12 represents the experimental results of dose dependent inhibition of ET-1 induced $Ca^{2+}$ mobilization in the TE-671 cells with BQ-123.

FIG. 12 illustrates the inhibition of ET-1 induced intracellular calcium mobilization with BQ-123 in TE-671 cells. The same cell physiometer apparatus and cell preparation procedure was used here as in Example 1.

In this experiment, ET-1 was introduced at a constant concentration from the "standard" sipper nozzle of the inventive apparatus and BQ-123 was introduced through the "compound" nozzle of the apparatus. In this example, as in Example 1, the concentration run was five minutes and the reaction time (from mixing to detection) was forty seconds.

Briefly, after calibration of the device of FIG. 4A with minimum and maximum standards (337, 339), ET-1 solution, an agonist standard solution, was directed at a predetermined concentration prepared by proportioning valve 327 by mixing it with DPBS buffer, through priming valve 329, mixing zone 331, diverting valve 333 and priming valve 341 and then into mixing zone 343, where it was mixed with a suspension of TE-671 cells to provide a final concentration of cells of $4 \times 10^5$ cells/ml. At the same time, DPB in volumetric ratio of 1:1 to ET-1 solution was directed through intake port 309 and outlet port 312 of proportioning valve 311, priming valve 313 to mixing zone 331 and further through fluidics system to the detector 355. After the intracellular calcium concentration in the presence of the standard agonist is stabilized, BQ-123, as an antagonistic test compound, was directed from intake port 307 of proportioning valve 311, instead of DPBS, to the mixing zone 331 at continuously changing concentrations prepared by mixing BQ-123 with DPBS in proportioning valve 311, through the system in a volumetric ratio of 1:1 with the ET-1 solution. In mixing zone 343, the mixed flow of ET-1 at constant concentration, and BQ-123 at a continuously changing in time concentration was mixed with cells in a ratio of 2:1. This gives three fold final dilution for each component of the flow passing through mixing zone 343 and, eventually, detector 355. The proportioning valve 327 was preprogrammed to give a final concentration of ET-1 of 40 pM at the detector. The proportioning valve 311 was preprogrammed to give final concentration of BQ-123 from 0 to 300 nM. Changes in intracellular calcium ion concentration in the TE-6712 cells passing through the detector 355, were measured in real time as a function of BQ-123 concentration using fluorescent dye FURA-2 as described above.

EXAMPLE 3

Figure 13:
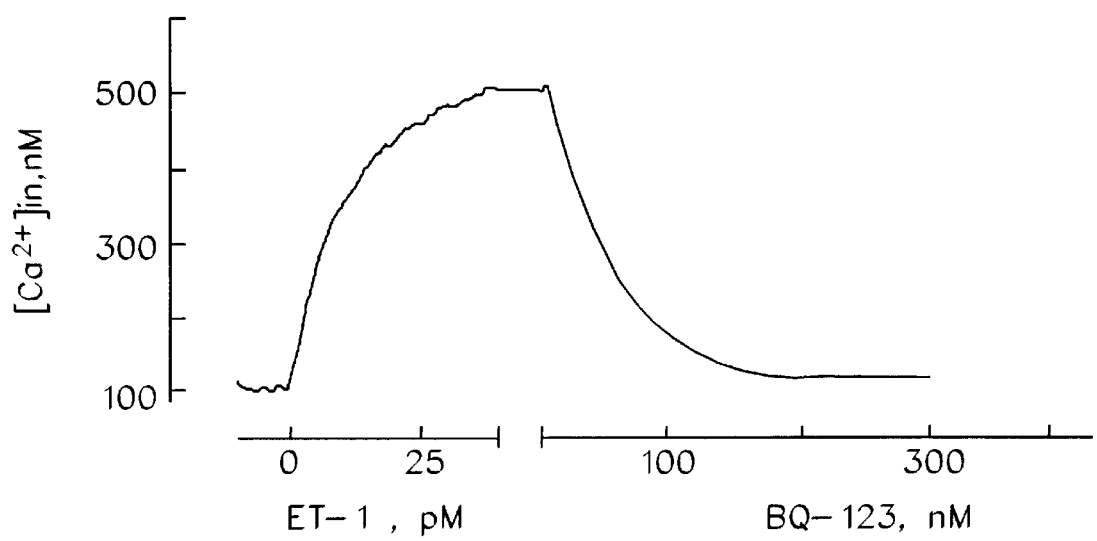
FIG. 13 represents the experimental results of ET-1 dose dependent $Ca^{2+}$ mobilization in TE-671 cells with the subsequent inhibition with the BQ-123

FIG. 13 shows the "null method" experiment design (Lazareno & Birdsall, 1993, incorporated herein by reference). This example uses the same instrument and the same reagents as in Examples 1 and 2.

In this example, a first concentration gradient of ET-1 coming from the "standard" nozzle 323 of the inventive apparatus is prepared with the buffer solution coming from the "compound" nozzle. When the final ET-1 concentration has reached the value of 40 pM, the gradient device 1 keeps the ET-1 concentration constant and gradient device 2 starts raising the concentration of the BQ-123 coming from the "compound" nozzle. One can switch the agonist gradient over to an antagonist at any predetermined concentration of the agonist.

EXAMPLE 4

The devices of the present invention may be used to determine the pattern of cell surface receptors expressed in one or more cell types as follows. Each of the different cell types to be tested is placed in one of a plurality of cell suspension reservoirs, or, if a single cell type is to be examined, an apparatus with a single cell suspension reservoir may be used to hold the cells. The effects of one or more test agents known to influence the activity of particular receptors are measured by combining the cell suspensions with the test agents to form a test mixture, directing the test mixture through a detection zone, and measuring the cellular response using the procedures described above. Preferably, the test agents comprise one or more receptor agonists. However, in some embodiments the test agent may be an antagonist or a mixture of an agonist and an antagonist.

The cellular response may be activation of cellular activity if the test agent is a receptor agonist. Alternatively, if the test agent is an antagonist the cellular response may be inhibition of cellular activity. Likewise, if the test agent is a combination of an agonist and an antagonist the cellular response may be a reduction or absence of the activity normally obtained in response to the agonist due to the presence of the antagonist. If the test agent is a test compound the cellular response would be the response expected to be observed with that agent.

If a cellular response is observed with an agonist, antagonist, agonist/antagonist mixture or test agent known to interact with a particular receptor, the cell type being evaluated possesses that receptor. By examining the effects of several agonists, antagonists, agonist/antagonist mixtures or test compounds on cellular physiology, the spectrum of receptors on the cell type being evaluated may be determined. If multiple cell types are to be tested, this process is repeated for each of the cell types in the series to determine the spectrum of receptors present in each cell type. To facilitate the analysis of multiple cell types, each of the cell types may be placed in one of a plurality of cell suspension reservoirs in the devices described above.

EXAMPLE 5

The devices of the present invention may be used to confirm that a test agent influences the activity of a particular receptor as follows. The test agent may be an agonist, an antagonist, or a mixture of an agonist an antagonist. The test agent may be an agent which is known to influence the activity of the receptor or an agent whose effect on the receptor is unknown. A cell type lacking the receptor serves as a negative control and is placed in one of the cell suspension reservoirs. A cell of the same cell type as the negative control which has been engineered or induced to express the receptor is placed in another cell suspension reservoir. The effects of one or more test agents is assessed in each of these cell types by contacting the cells with the test agent to form a negative control mixture and a test mixture, directing the negative control mixture and the test mixture through a detection zone, and measuring the cellular responses of the negative control cells and the engineered or induced cells. A difference in the response of the engineered or induced cells relative to the response of the negative control cells indicates that the test agent has an effect on the activity of the receptor.

The negative control cell is commonly referred to as the "host cell" and the engineered cell is commonly referred to as the "transfected cell" by those in the industry. To obtain engineered cells, the gene encoding the receptor may be introduced into a cell of the same type as the negative control cell using techniques such as transformation, calcium phosphate mediated transfection, electroporation, viral infection, transposition, or other techniques familiar to those skilled in the art. Expression of the receptor gene may be directed by a variety of vectors familiar to those skilled in the art. Alternatively, the cells may be induced to express the receptor through treatment with chemical agents or bioactive agents such as growth factors, cytokines, cell differentiation factors, or other agents known to those skilled in the art.

EXAMPLE 6

The activity of a particular receptor may also be influenced by the characteristics of the particular cell type in which it is expressed. Thus, the same receptor may exhibit variations in activity between different cell types. The present invention may also be used to assess such cell type dependent differences in receptor activity. Each of the cell types to be assessed is placed in a cell suspension reservoir and the effects of one or more test agents on the activity of one or more receptors on the cells are determined by contacting the cells with one or more test agents to form test mixtures, directing the test mixtures through a detection zone, and measuring the cellular response of the cells as the test mixtures flow through the detection zone. The test agents may be receptor known receptor agonists, known antagonists, mixtures of a known agonist and a known antagonist, or compounds whose activity is unknown as described above. This process is performed for each of the cell types to be tested to determine the nature and magnitude of the cellular response in each cell type. To facilitate the analysis of multiple cell types, each of the cell types may be placed in one of a plurality of cell suspension reservoirs in the devices described above.

Figure 14:
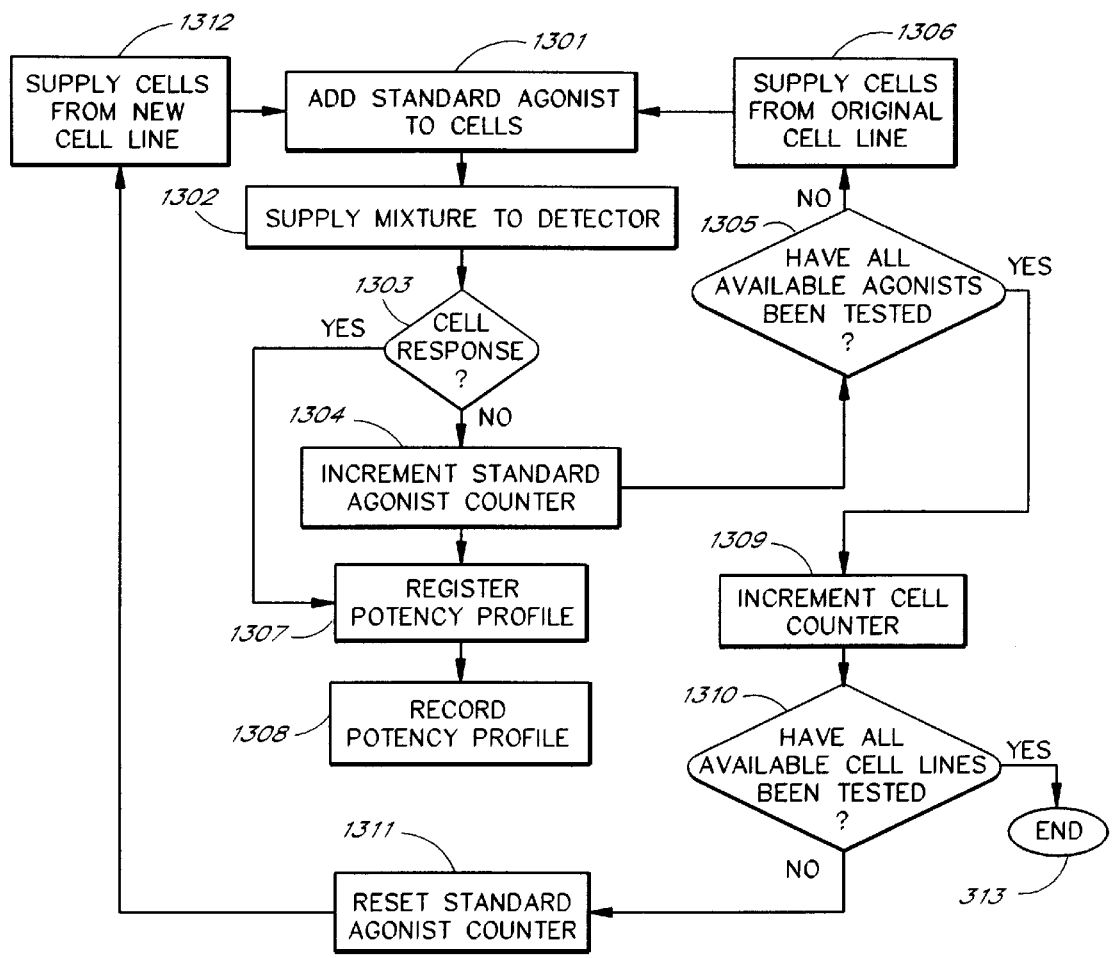
FIG. 14 represents a simplified algorithm for cell mapping mode which may be utilized in a combinatorial screening apparatus of the present invention

FIG. 14 shows an algorithm that may be used in the invention to perform cell mapping and cell receptor "fingerprinting". First, cells are mixed with standard agonist (step 1301) and the mixture is provided to a detector (step 1302). Next, the apparatus determines if this standard agonist, upon contact with the cells, triggers any cell response (step 1303). There are two possibilities: either the standard agonist does not produce any response (NO), or it induces the cell response (YES). Cell response is determined by monitoring the signal from the detector for the particular standard agonist being evaluated. The control system first calibrates to establish a baseline and a maximal response, and any signal from the detector falling between those values is considered to be a positive response.

If the standard agonist causes no cell response, (NO), as measured by the monitoring part of the apparatus, the system increments an agonist counter (step 1309) which indicates that a next standard agonist in a specified set of agonists will be tested with a particular cell line. The system then determines if all available agonists have been tested (step 1305). If all standard agonists have not been tested with a particular cell line, fresh cells from the original cell line are then supplied to the system (step 1306). These new cells are then automatically brought into contact with the next standard agonist from the predetermined set of agonist solutions (step 1301). Each agonist solution in the set contains one or more ingredients that are known to initiate cell response through the stimulation of a known cell receptor, ion pump or ion channel molecules. The apparatus will keep repeating an admixture of different standard agonist substances with the cells until it detects that the cell response is triggered with a particular standard agonist, or until all agonists available to the machine have been tested.

If in step 1303, it is determined that a particular agonist triggers a cell response, the process is switched over to the potency mode of action (step 1306) in which the cellular response at various concentration levels of the standard agonist is recorded. After step 1306 has been completed, the process then records the potency parameters, or profile, representing the level of cellular response produced in a given cell line at various concentration levels of the standard agonist (step 1307). The process then once again determines if all available standard agonists have been tested (step 1304). If all of the available agonists have been tested (YES), the system then determines if all the available cell lines have been tested (step 1308). If the answer to this question is yes the process is complete (step 1312).

If in step 1308 it is determined that not all available cell lines have been tested, a cell counter is incremented (step 1310) which indicates that a next cell line in a specified set of cell lines will be tested. Next, the standard agonist counter is reset (step 1310) which indicates that the new cell line will be tested with all available standard agonists, starting with a first designated agonist in the specified set of standard agonists. Cells from the new cell line are then supplied to the system (step 1311) and subsequently mixed with the specified agonist (step 1301). The above process steps 1301–1311 are then repeated. In one embodiment, the apparatus will keep repeating an admixture of different standard agonist substances with the cells until it detects that all agonists available to the apparatus have been tested with all cell lines available to the apparatus.

Figure 15:
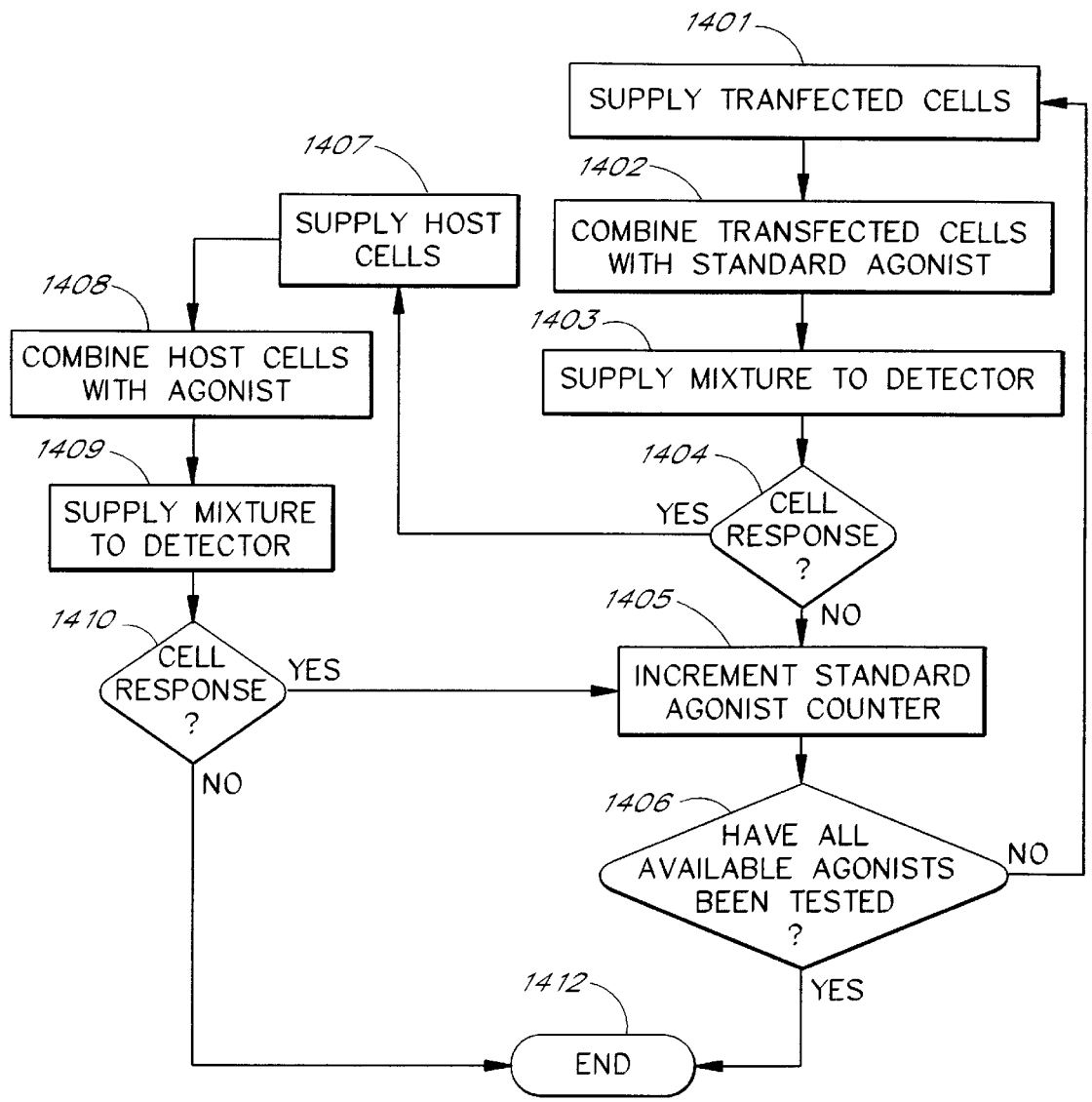
FIG. 15 represents a simplified algorithm for functional characterization of orphaned receptors mode which may be utilized in a combinatorial screening apparatus of the present invention.
Figure 16A:
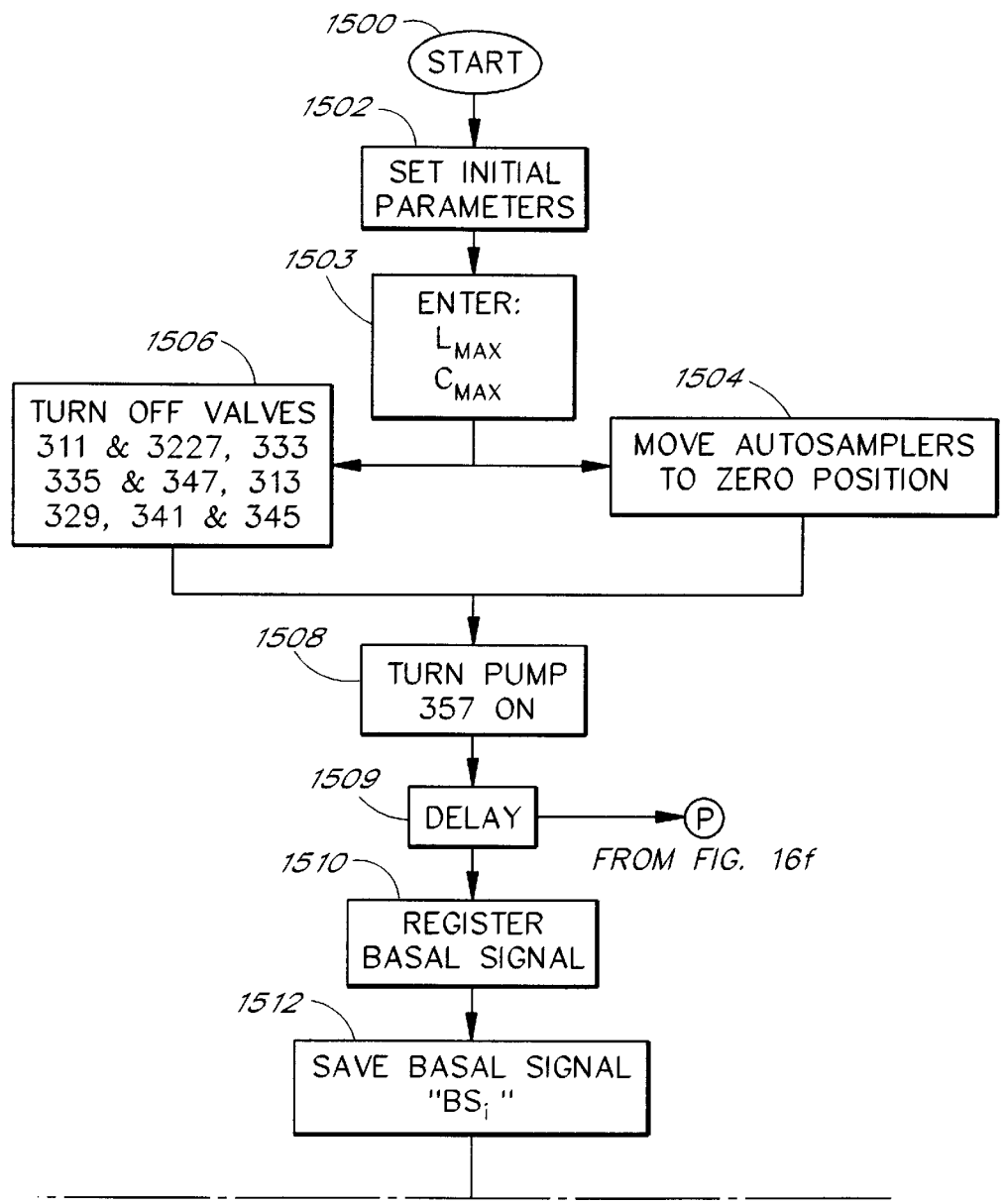
FIG. 16 represents a flow diagram of a preferred cell mapping mode operation which may be implemented by a combinatorial screening apparatus of the present invention.
Figure 16B:
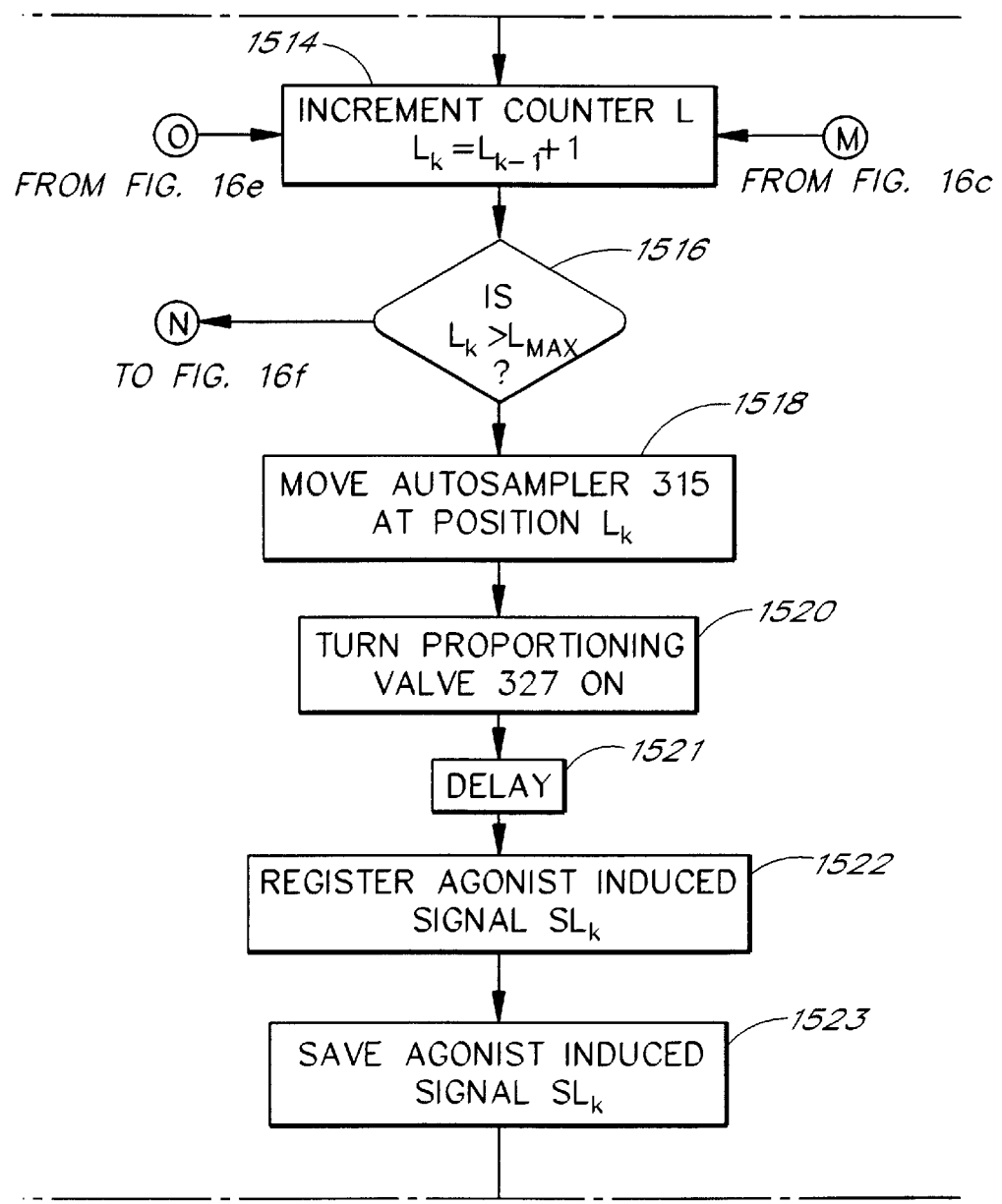
Figure 16C:
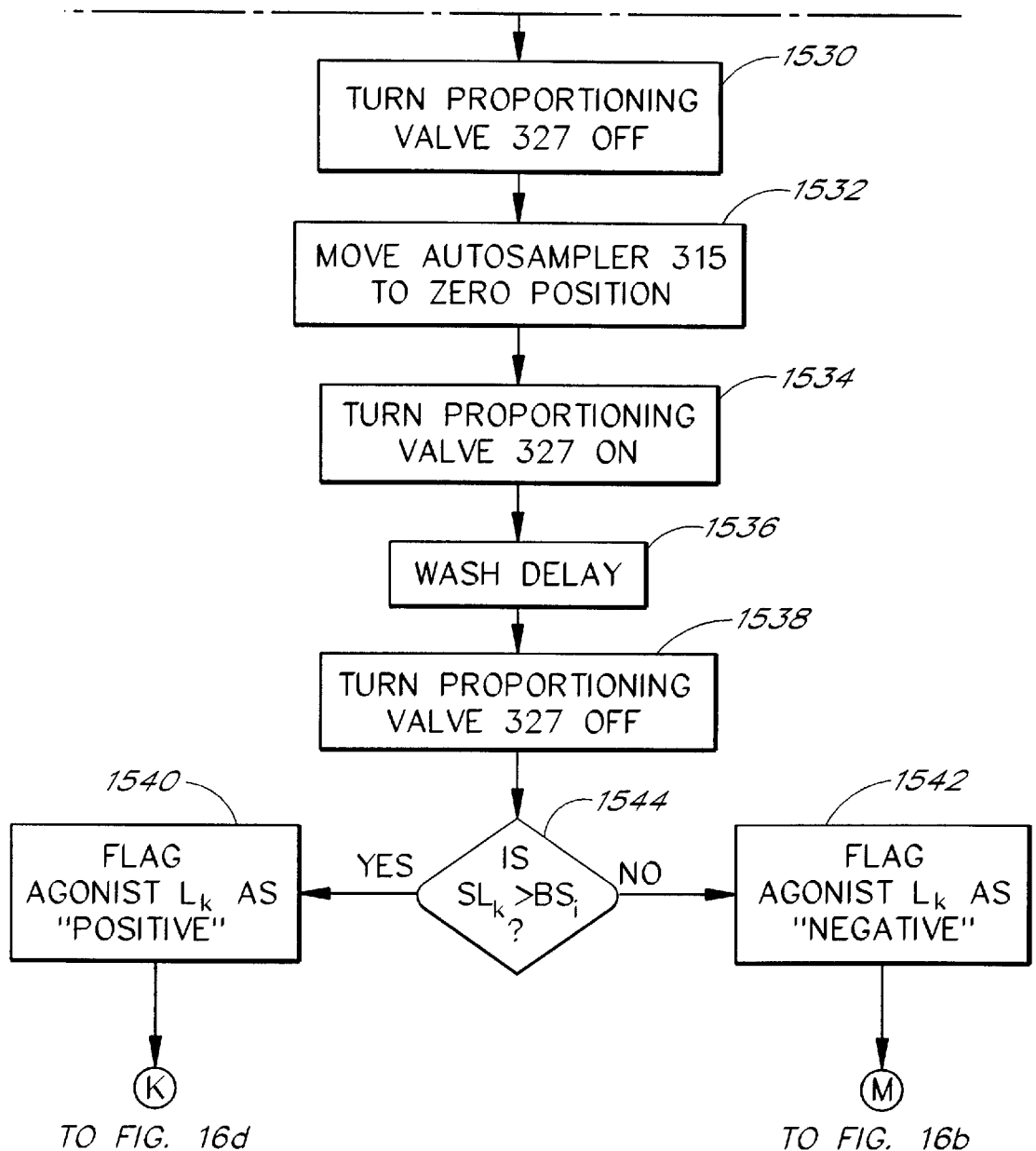
Figure 16D:
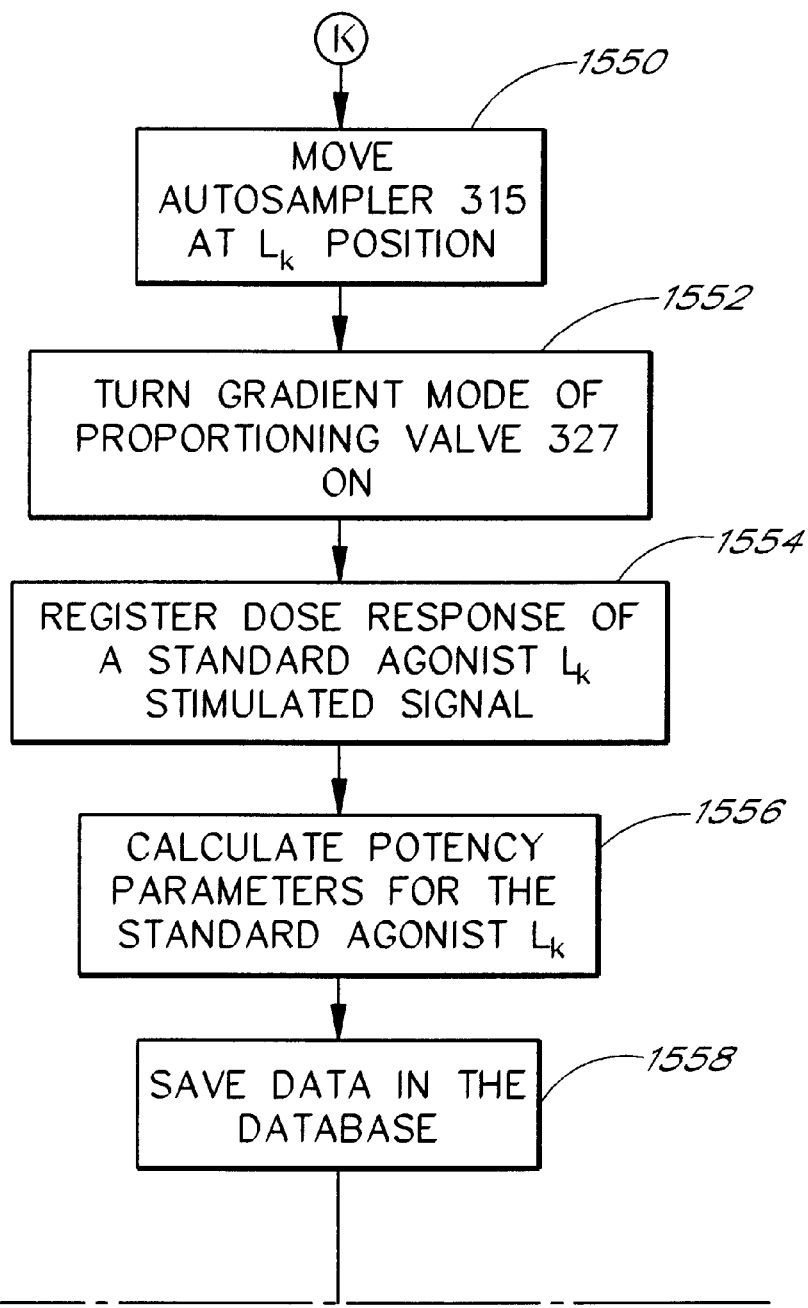
Figure 16E:
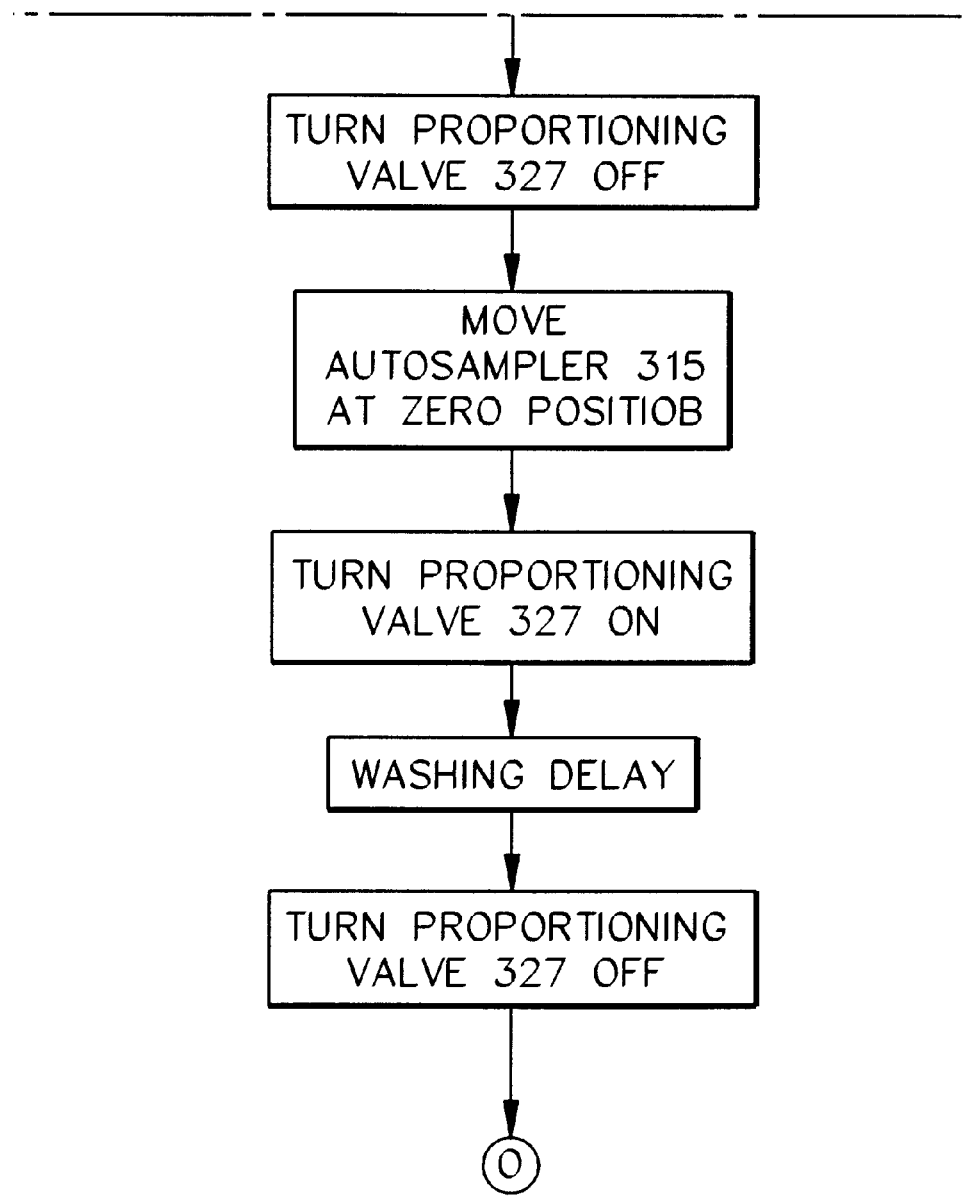
Figure 16F:
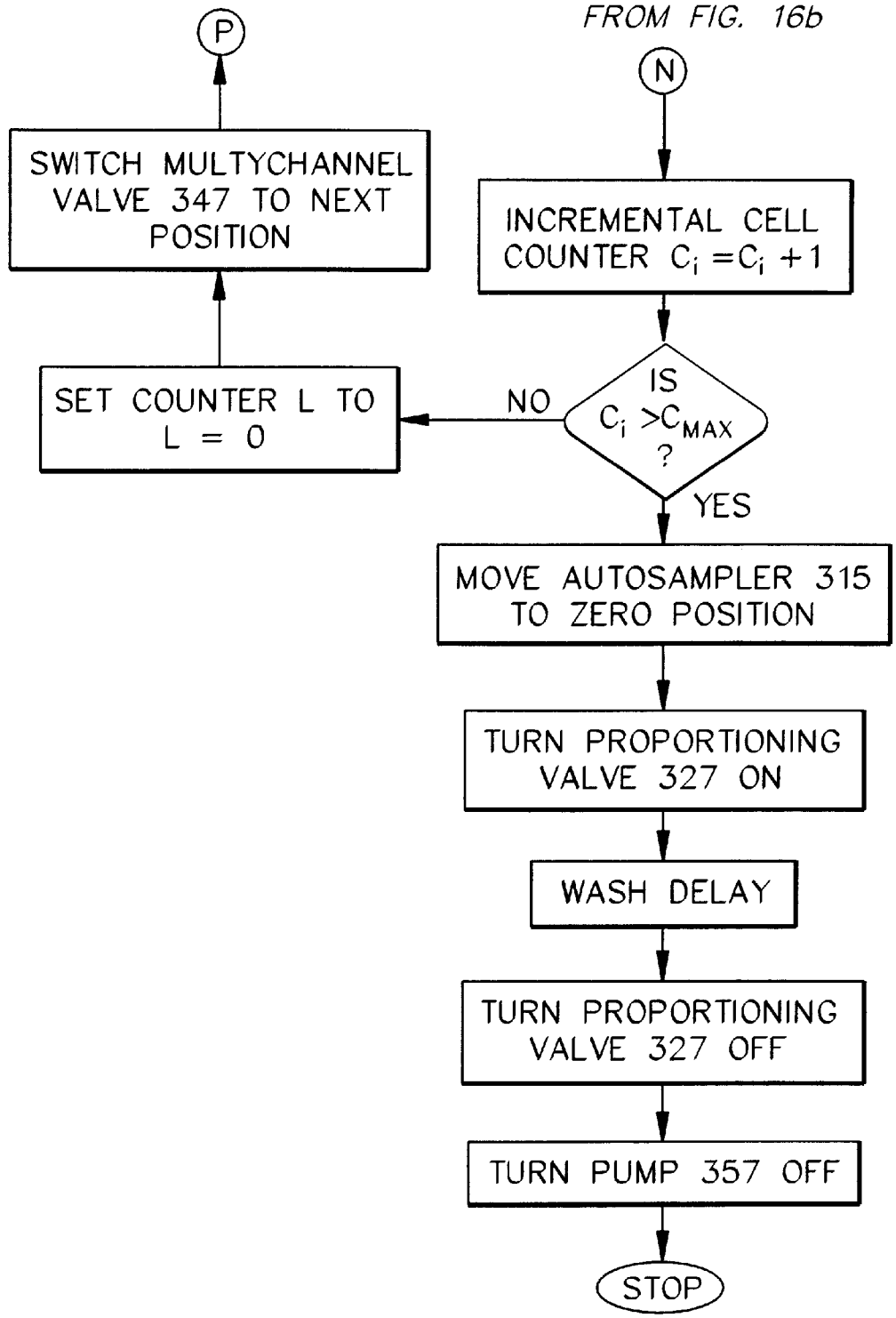
Figure 17B:
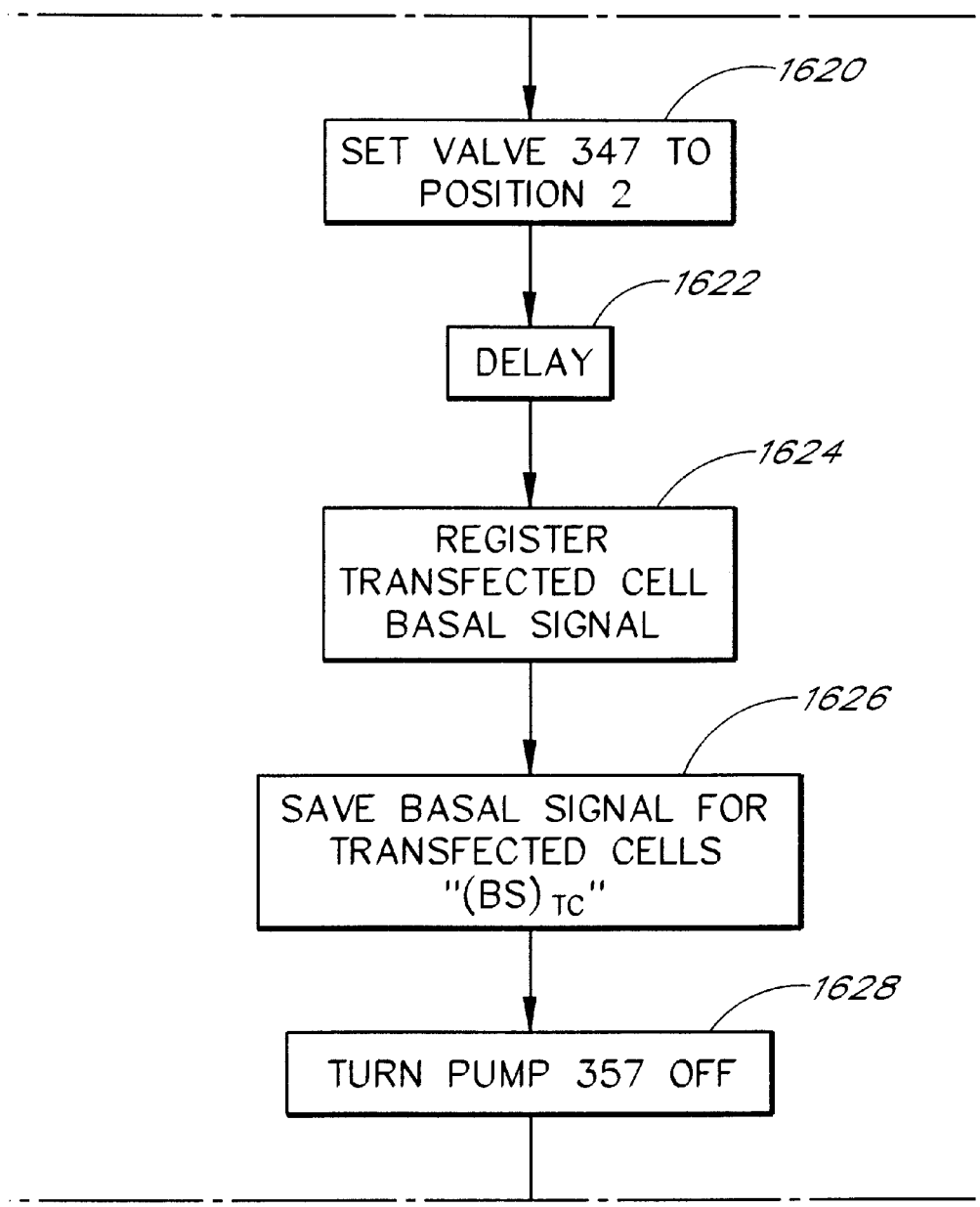
FIG. 17 represents a flow diagram of a preferred orphaned receptor determination mode operation which may be implemented by a combinatorial screening apparatus of the present invention.
Figure 17C:
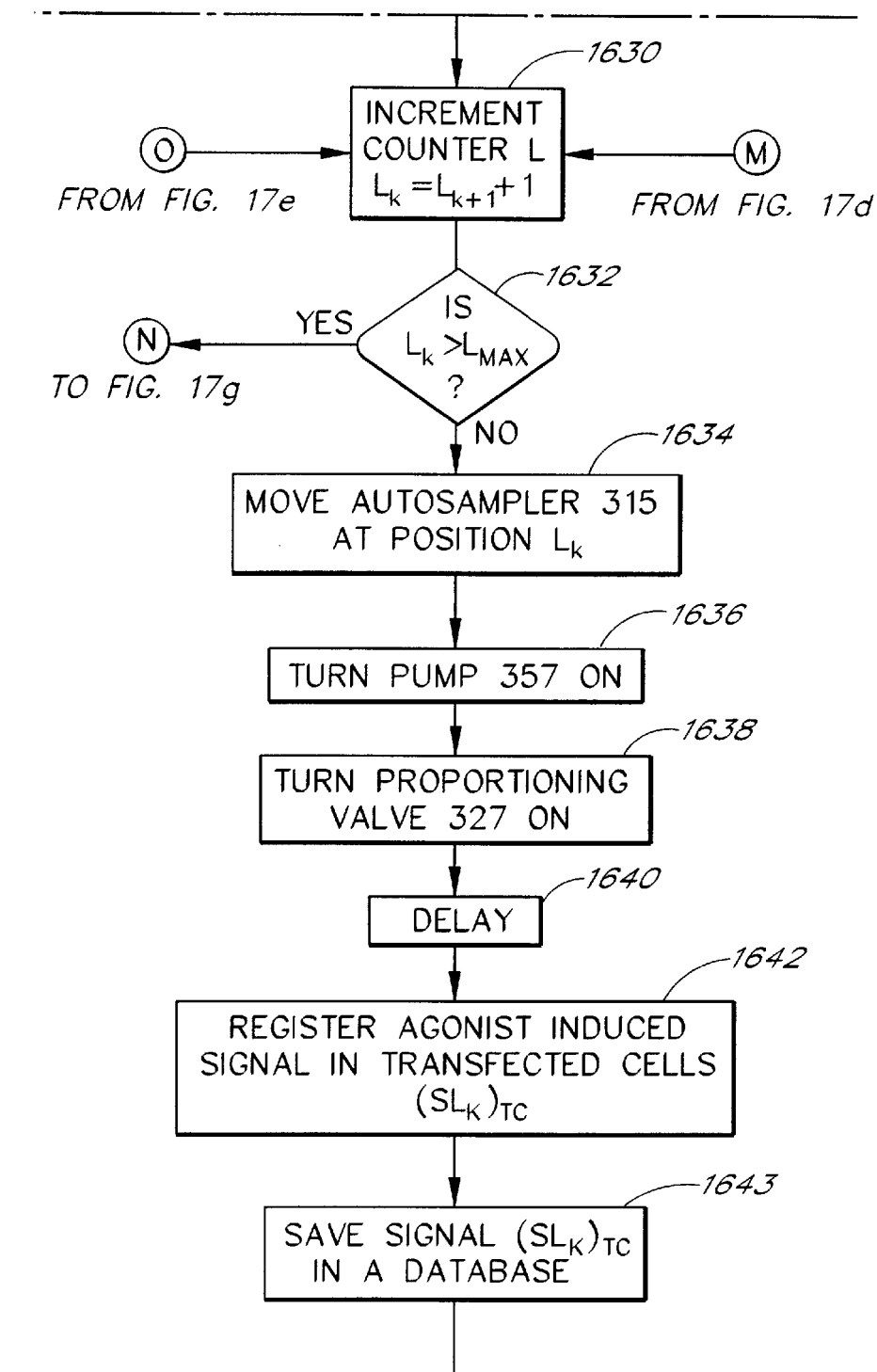
Figure 17D:
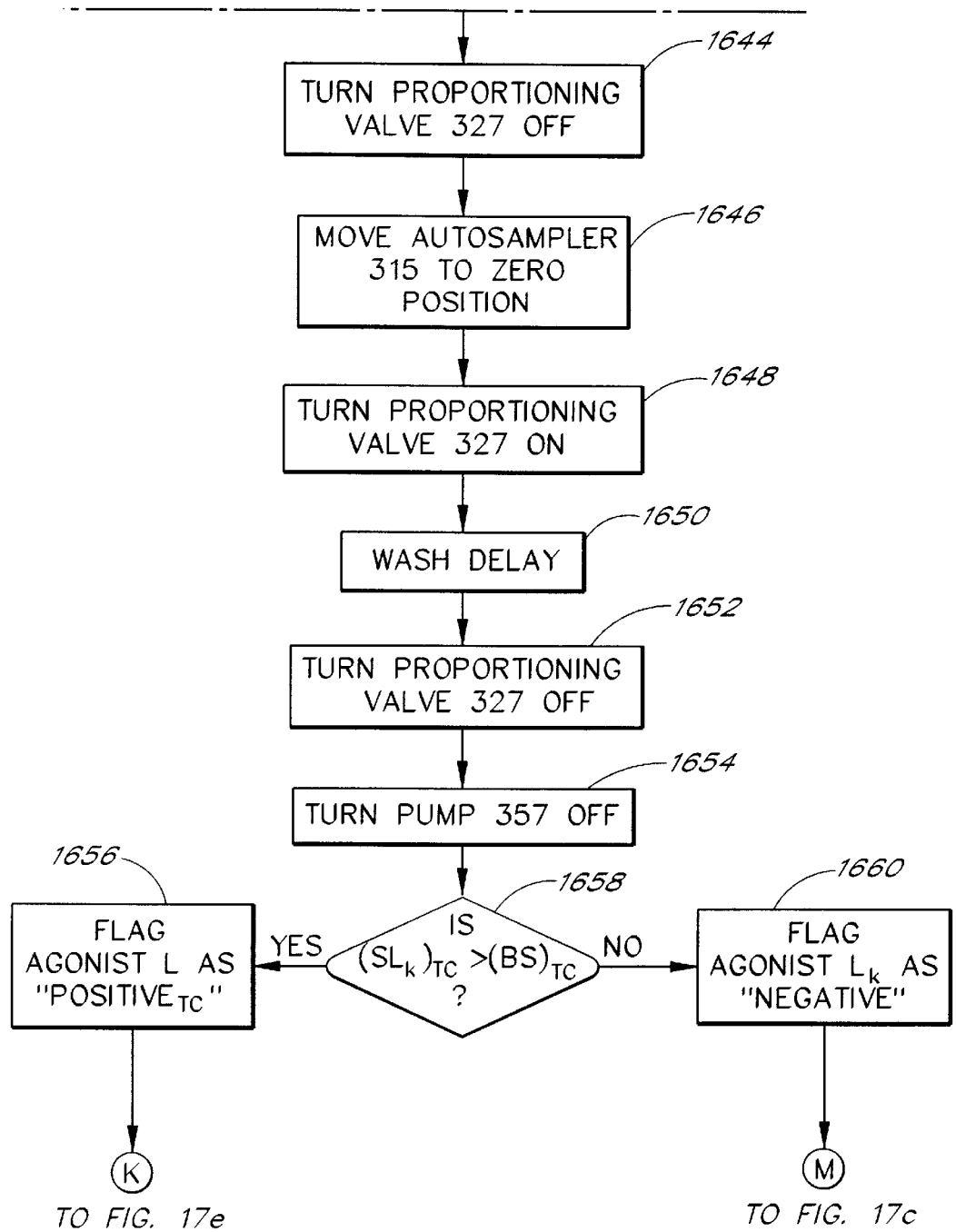
Figure 17E:
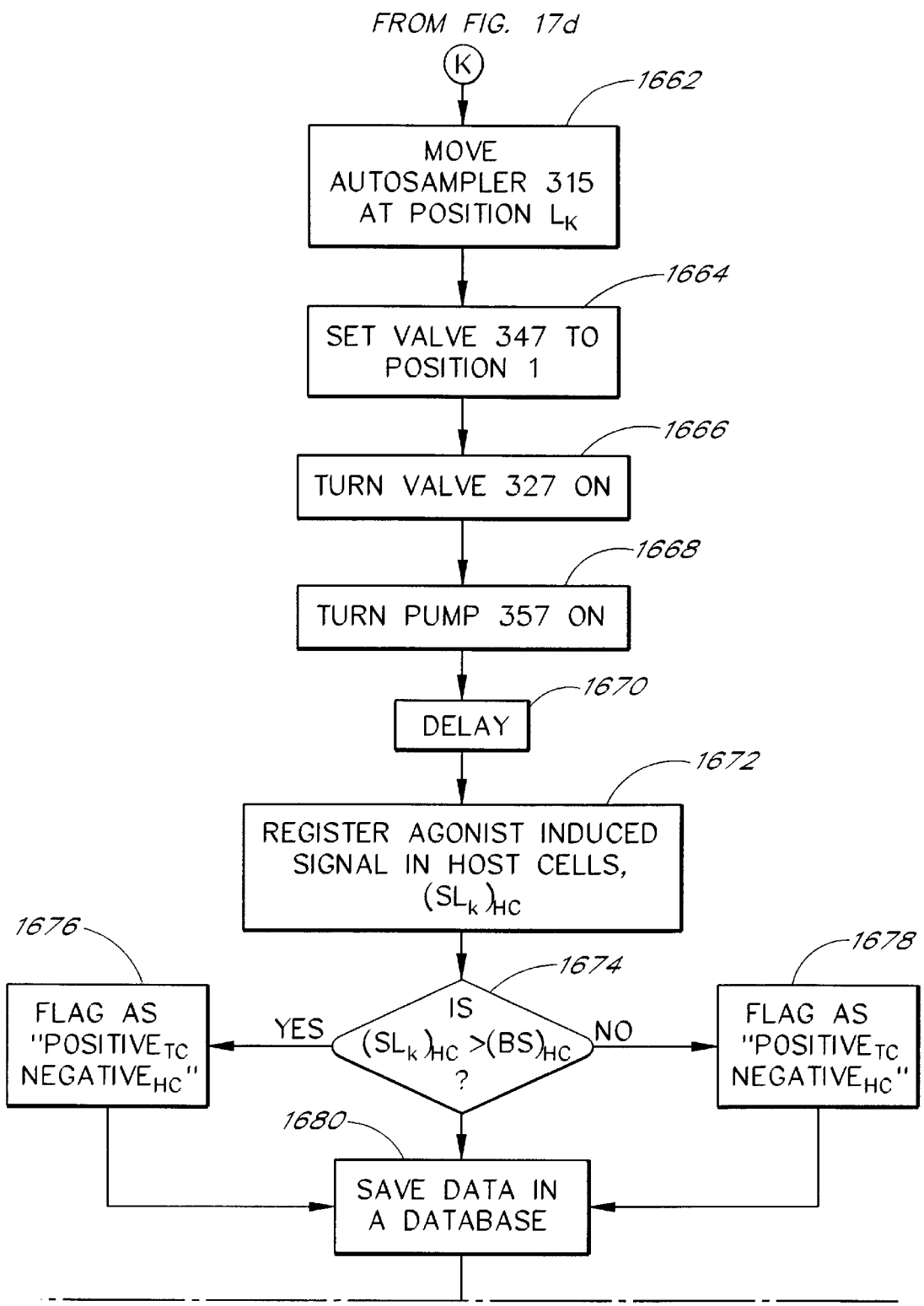
Figure 17F:
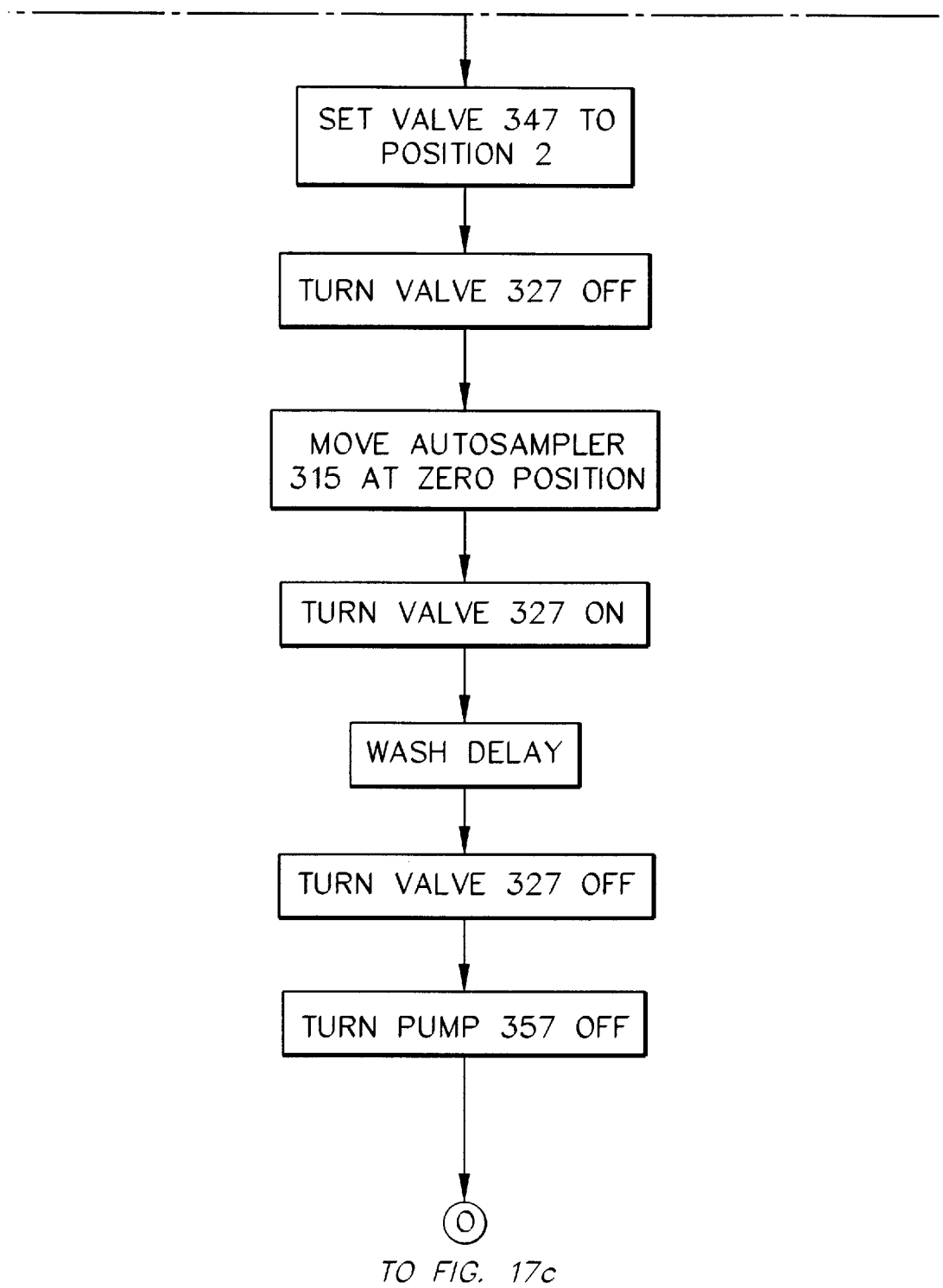
Figure 17G:
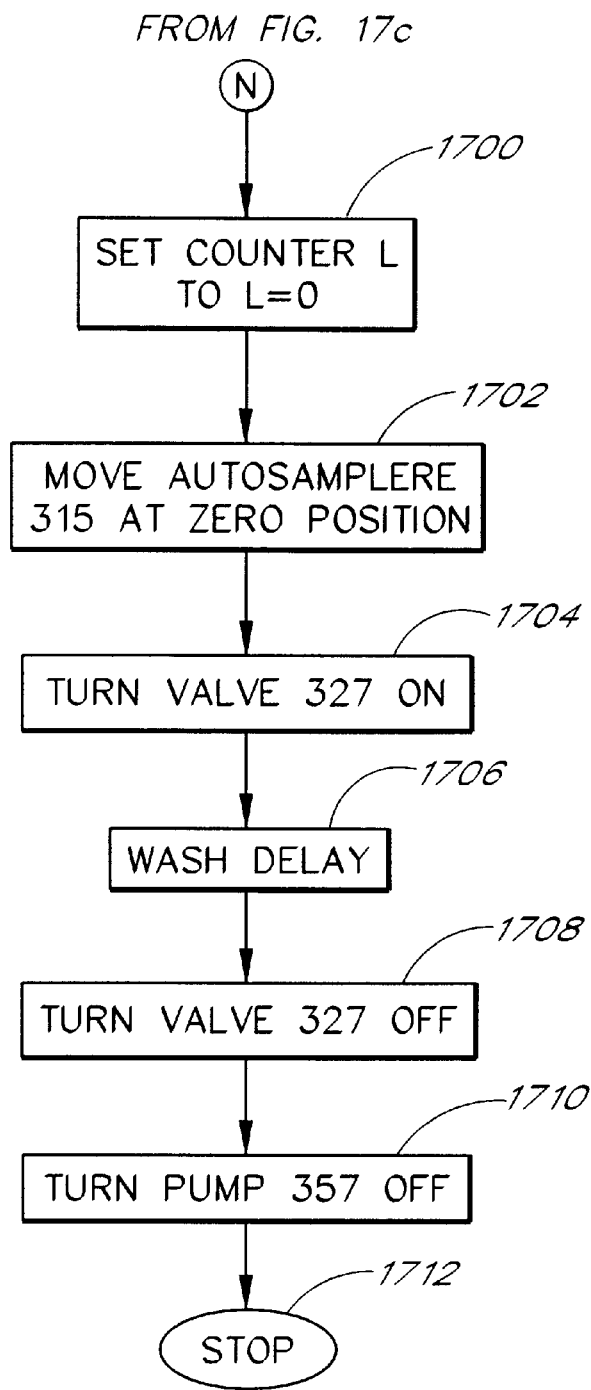

FIG. 15 shows an algorithm that may be used in the invention to perform transfected receptor characterization, particularly, of an orphaned receptor. First, in step 1401, an apparatus supplies cells transfected with a gene which produces a known orphan receptor, and mixes them with a standard agonist (step 1402). The mixture is provided to a detector (step 1403). Next, the apparatus determines if this standard agonist, upon contact with the cells, triggers any cell response (step 1404). There are two possibilities: either the standard agonist does not produce any response (NO), or it induces the cell response (YES). Cell response is determined by monitoring the signal from the detector for the particular standard agonist being evaluated. The control system first calibrates to establish a baseline and a maximal response, and any signal from the detector falling between those values is considered to be a positive response.

If the standard agonist causes no cell response, (NO), as measured by the monitoring part of the apparatus, the system increments a standard agonist counter (step 1405) which indicates that a next standard agonist in a specified set of standard agonists will be tested with the transfected cells. The system then determines whether all available standard agonists have already been tested with the transfected cells (step 1406). If not, the process moves back to step 1401 in which fresh cells from the same transfected cell line are automatically brought into contact with the next standard agonist from the predetermined set of agonist solutions (step 1402). Each standard agonist solution in the set contains one or more ingredients that are known to initiate cell response through the stimulation of a known cell receptor, ion pump or ion channel molecule. The apparatus will keep repeating an admixture of different standard agonist substances with the transfected cells until it detects that the cell response is triggered with a particular standard agonist, or until all agonists available to the machine have been tested.

If in step 1404 it is determined that the contact of the transfected cells with the standard agonist does initiate the cell response, (YES), as measured by the monitoring part of the apparatus, the process then supplies host cells (step 1407) to be mixed with the same standard agonist (step 1408). This mixture is then supplied to the detector (step 1409) for measuring the cellular response produced by the standard agonist on the host cells. Next, the system determines if the standard agonist produces a cellular response in the host cell (step 1410). If a cell response is detected (YES) the system then increments the standard agonist counter (step 1405) after which the system determines if all available agonists have been tested (step 1410). If all available agonists have been tested, the process is complete (step 1412). If all available standard agonists have not been tested, the process moves back to step 1401 where fresh transfected cells are supplied to be mixed with the next standard agonist in the set of standard agonists (step 1402), and the process steps described above are repeated.

If in step 1410, no cell response is produced in the host cell by the standard agonist the process has detected a difference between the host cell and the transfected cell. At this point, the process is complete (step 1412). In one embodiment, the apparatus will keep repeating an admixture of different standard agonist substances with the cells until it detects that a particular agonist stimulates a response in the cells transfected with an orphaned receptor, and do not stimulate a response on host cells or until all standard solutions available to the machine have been tested.

A continuous flow diagram of the presently preferred cell mapping and cell receptor "fingerprinting" mode with the negative pressure fluidics system of FIGS. 4A and 4B is shown on FIGS. 16a–16f. To practice this mode, diverting valve 347 is replaced by a multichannel diverting valve 347 which allows multiple reservoirs, each with a different cell suspension, to be connected separately to the common outlet 346 so that once an experiment with a particular cell line is complete, the valve 347 may switch over to a next cell reservoir.

The screening program starts from a state 1500 and enters state 1502 where it sets all parameters to their initial values. These initial parameters include, but are not limited to, zeroing counters, the internal initialization of software variables and subroutines.

Once the initial parameters are set, the software requests an operator to enter values for a maximum number of standard agonists, $L_{MAX}$, and a maximum number of cell lines, $C_{MAX}$, to be used in the experiment (Step 1503). The autosamplers 301 and 315 (FIGS. 4A and 4B) position the intake nozzles 307 and 323 at the corresponding "zero" positions occupied by a wash buffer reservoir 305 (Step 1504), and turns off proportioning valves 311 and 327, diverting valves 333, 335 and 347, as well as priming valves 313, 329, 341 and 345 (Step 1506). In a turned off state, priming valves 313, 329, 341 and 345, are normally opened, proportioning valves 311 and 327 connect, respectively, their outlets 312 and 328 with corresponding "normally opened" intake ports 309 and 325, diverting valve 335 connects its common outlet 334 with "normally opened" intake port 336, diverting valve 333 connects its common outlet 342 with the "normally opened" intake port 332, and multichannel diverting valve 347 connects its common outlet 346 with the first intake port 348 connected with the reservoir containing first cell suspension under investigation.

After the system has been initialized, pump 357 is started (Step 1508). This will force the wash buffer from the "zero" positioned reservoirs of both autosamplers 301 and 315 to run through nozzles 309 and 325 and outlet ports 312 and 328 of proportioning valves 311 and 327, respectively, priming valves 313 and 329, mixing zone 331, intake port 332 and outlet port 342 of diverting valve 333, priming valve 341, mixing zone 343, a reaction developing line 353, detector 355, pump 357 and then into a drain container 359. In mixing zone 343 this flow is mixed with the cell suspension 349 coming from intake tubing 348 connected with the first cell line, and an outlet port 346 of the multichannel diverting valve 347 through priming valve 345. Thus, the total flow passing mixing zone 343, is a sum of three flows, a first flow coming from the proportioning valve 311, a second flow coming from the valve 327 and a third flow coming from the multichannel diverting valve 347. During this step, both proportioning valves supply wash buffer 305 from the reservoirs located at "zero" position of each autosampler in such a way that the final flowing mixture consists of one part of cell suspension 349 and two parts of wash buffer 305.

After a delay determined in step 1509, which is needed for the flow of the mixture of cell suspension 349 and wash buffer 305 to stabilize, detector 355 registers a basal signal produced by the cells alone (Step 1510). After the basal signal is registered, it is saved as a reference signal, $BS_i$ (Step 1512) and computer 123 (FIGS. 1A and 1B) increments counter L (Step 1514).

The numerical content of the incremental counter L is increased by one each time it is triggered. The numeric value of the counter determines the position of the nozzle of intake port 323 of autosampler 315 that samples the sets of standard agonists 319 to be tested. Next, in step 1516, the numerical content, $L_k$, of the incremental counter L is compared with the previously entered (Step 1503) value of maximal number of the standard agonists to be tested, $L_{max}$.

If $L_k$ does not exceed $L_{max}$, autosampler 315 positions nozzle 323 into the standard agonist reservoir located at the $L_k$ position of a rack of standard agonists 319 (Step 1518). Next, proportioning valve 327 is switched ON to open its "normally closed" intake port 323 to the common output port 328 (Step 1520). During Step 1520, the combined flow in mixing zone 343 and afterwards in detector 355, is composed of one portion of buffer 305 coming through nozzle 309 of proportioning valve 311, one portion of the standard agonist 319 to be tested, coming from nozzle 323 of proportioning valve 327 and one portion of particular cell suspension 349 coming from one of the multitude of the cell reservoirs through the intake tubing 348 to the output port 346 of multichannel diverting valve 347. After a delay provided by Step 1521, which is needed for the mixing process to stabilize, detector 355 registers a standard agonist induced signal, $SL_k$, produced by given cells in the presence of the given standard agonist, $L_k$ (Step 1522). After the $SL_k$ signal is registered, its value is saved as a value, $SL_k$ (Step 1523) and the apparatus proceeds to step 1530 where the proportioning valve 327 is turned OFF, thus connecting normally opened intake port 325 with buffer 305. In step 1532, autosampler 315 moves its nozzle 323 to a zero position occupied with reservoir filled with washing buffer. Proportioning valve 327 is turned ON Step 1534), connecting the normally closed inlet port 323 with outlet port 328. Delay, determined in step 1536, allows for the flow path composed of intake port 323 and outlet port 328 of the proportioning valve 327, priming valve 329, mixing zone 331, intake port 332 and outlet port 342 of the diverting valve 333, priming valve 341, mixing zone 343, reaction developing lines 353 and detector 355 to be washed clean of the remains of the previous compound. After the delay, the proportioning valve 327 is turned OFF in the step 1538, thus bringing the system into original state.

Next, the value of the standard agonist induced signal, $SL_k$, is compared with the value of the reference basal signal, $BS_i$ (Step 1544). If the $SL_k$ signal is greater than the $BS_i$ signal, the computer 123 (FIGS. 1A and 1B) will "flag" the corresponding standard agonist as "positive"(Step 1540), which means that the particular cells express a receptor which is stimulated by the particular agonist. If $SL_k$ is not greater than $BS_i$, computer 123 will "flag" the corresponding standard agonist as "negative"(Step 1542), which means that the particular cells do not contain a receptor which can be stimulated by the particular agonist.

Each time the condition, "$SL_k > BS_i$", is satisfied, the program flow will go through loop K–O initiating the gradient mode of action. In the gradient mode, step 1550 moves autosampler 315 at a position corresponding to the $L_k$ value determined in step 1514. After that, the proportioning valve 327 is turned on to operate in the gradient mode (step 1552). In step 1554, the dose response curve is registered for the standard agonist stimulated signal. Step 1556 calculates a potency parameter that could be determined as some specific concentration of the agonist causing a specific level of a signal. The data are saved in step 1558.

After the data are saved, the proportioning valve 327 is turned OFF (step 1560), autosampler 315 is moved to a zero position (step 1562), proportioning valve 327 is turned ON (step 1564) and, after a washing delay period determined in step 1566, the valve 327 is turned OFF again (step 1568). After step 1568 has been performed, the process goes back, through line O, to the incremental counter L (step 1514).

If in step 1544, the $SL_k$ signal is not larger then $BS_i$, then step 1542 flags the standard agonist as Anegative=, meaning that the particular cells do not have the particular receptor expressed, and the program flow is returned, through line M, to the step 1514.

If in step 1516 (FIG. 16b), $L_k$ exceeds $L_{max}$, indicating that all agonists have been tested, the process moves through line N to step 1570 were a computer 123 increments a cell counter C. The numeric value of the counter is compared (step 1572) with the maximum number of cells entered in step 1503. If the counter value, $C_i$ does not exceed $C_{MAX}$, then controller L is set to zero in step 1574, multichannel diverting valve 347 is switched to the next position, connecting a new cell reservoir with the output 346, and the process returns to step 1509 (FIG. 16a) through line P. If in step 1572 the $C_i$ value is higher then $C_{MAX}$, then the process moves to step 1578, where autosampler 315 is moved to its zero position and, proportioning valve 327 is turned ON (Step 1580). After a washing delay, determined in step 1582, the valve 327 is turned OFF (Step 1584) and pump 357 is turned OFF (Step 1586), and the whole program is stopped in step 1588.

A continuous flow diagram of the presently preferred orphaned receptor detection mode with the negative pressure fluidics system of FIGS. 4A and 4B is shown on FIGS. 17a–17g. To practice this mode, diverting valve 347 is replaced by a multichannel diverting valve 347 which allows for at least two reservoirs 349, containing host cells, native or transfected with an empty vector, and cells transfected with the orphaned receptor of interest, to be connected separately to the common outlet 346.

The program begins from a start state 1600 and enters state 1602 where it sets all parameters to their initial values. These initial parameters include, but are not limited to, the internal initialization of software variables and subroutines. Then the program requests an operator to enter a maximum number of agonists to be tested (Step 1603).

Once the initial parameters are set up, the autosamplers 301 and 315 (FIGS. 4A and 4B) move their intake nozzles 307 and 323 to the corresponding "zero" positions occupied by a wash buffer reservoir 305 (Step 1604). Proportioning valves 311 and 327, diverting valves 333, 335 and 347, and priming valves 313, 329, 341 and 345 are turned OFF (Step 1606). In that turned off state, priming valves 313, 329, 341 and 345, are normally opened, the outlets 312 and 328 of proportioning valves 311 and 327 are connected, respectively, with corresponding "normally opened" intake ports 309 and 325, outlet 334 of diverting valve 335 is connected with "normally opened" intake port 336, common outlet 342 of diverting valve 333 is connected with the "normally opened" intake port 332.

After the system has been initialized, diverting valve 347 is set to connect its common outlet 346 with the reservoir containing host cells, position 1, (Step 1608). The pump 357 is started to pump liquid (Step 1610). This will force the wash buffer from the "zero" positioned reservoirs of both autosamplers 301 and 315 to run through nozzles 309 and 325 and outlet ports 312 and 328 of proportioning valves 311 and 327, respectively, priming valves 313 and 329, mixing zone 331, intake port 332 and outlet port 342 of diverting valve 333, priming valve 341, mixing zone 343, a reaction developing line 353, detector 355, pump 357 and into a drain container 359. In mixing zone 343, this flow is mixed with the host cell suspension coming from intake tubing 348 and an outlet port 346 of the multichannel diverting valve 347 through priming valve 345. Thus, the total flow passing through mixing zone 343 is a sum of three flows, a first flow coming from the proportioning valves 311, a second flow coming from proportioning valve 327 and a third flow coming from the multichannel diverting valve 347. During this step, both proportioning valves supply washing buffer 305 from the reservoirs located at "zero" position of each autosampler in such a way that the final mixture consists of one part of the host cell suspension and two parts of washing buffer.

After a delay determined in step 1612, which is needed for the flow of the mixture of cell suspension and wash buffer to stabilize, detector 355 registers a basal signal produced by the host cells (Step 1614). After the basal signal is registered, it is saved as a reference signal, $(BS)_{HC}$ (Step 1616). In step 1620, multichannel diverting valve 347 is switched over to position 2 to supply the outlet 346 with the suspension of the transfected cells. After a delay determined in step 1622, which is needed for the flow of the mixture of new cell suspension and wash buffer to stabilize, detector 355 registers a second basal signal produced by the transfected cells (Step 1624). After the basal signal is registered, it is saved as a reference signal, $(BS)_{TC}$ (Step 1626) and the pump is turned OFF (Step 1628). The computer 123 (FIGS. 1A and 1B) triggers the incremental counter L (Step 1630).

The numerical content of the incremental counter L is increased by one each time it is triggered, thus determining the position of the nozzle of intake port 323 of autosampler 315 which samples the sets of agonists 319 to be tested. Next, the numerical content, $L_k$, of the incremental counter L is compared with the maximum number of the standard agonists to be tested, $L_{max}$ (Step 1632).

If $L_k$ does not exceed $L_{max}$, autosampler 315 positions nozzle 323 into the agonist reservoir located in the rack 319 at the position determined by the numerical value $L_k$ (Step 1634). The pump 357 is turned ON in step 1636 and proportioning valve 327 is switched ON to open its "normally closed" intake port 323 to the common outlet port 328 (Step 1638) thus allowing the particular agonist flows through the priming valve 329, mixing zone 331 intake port 332 and outlet port 342 of the diverting valve 333, priming valve 341, mixing zone 343, where it is mixed with the suspension of transfected cells coming from outlet port 346 of multichannel diverting valve 347 and priming valve 345. After being mixed with the transfected cells in mixing zone 343, the liquid flow goes through reaction developing lines 353, into detector 355 and further into waste reservoir 359. After a delay provided by Step 1640, which is needed for the mixing process to stabilize, detector 355 registers an agonist induced signal, $(SL_k)_{TC}$, produced by the particular orphaned receptor transfected cells in the presence of the given agonist, $L_k$ (Step 1642). After the signal is registered, its value, $(SL_k)_{TC}$, is saved in step 1643 and the apparatus proceeds to step 1644 where proportioning valve 327 is turned OFF, thus connecting normally opened intake port 325 with buffer 305 to outlet port 328. In step 1646, autosampler 315 moves its nozzle 323 to position zero occupied with reservoir filled with washing buffer. Proportioning valve 327 is turned ON again (Step 1648) connecting inlet 323 with outlet 328. A delay, determined in step 1650, allows for the flow path, composed of intake port 323 and outlet port 328 of the proportioning valve 327, priming valve 329, mixing zone 331, intake port 332 and outlet port 342 of the diverting valve 333, priming valve 341, mixing zone 343, reaction developing lines 353, and detector 355 to be washed out of the remains of the agonist. After the delay (Step 1650), the proportioning valve 327 is turned OFF in step 1652 and the pump 357 is turned OFF in step 1654, thus bringing the system into its original state.

Next, the value of the registered signal for transfected cells, $(SL_k)_{TC}$, is compared with the value of the corresponding reference basal signal, $(BS)_{TC}$ (Step 1658). If the agonist induced signal, $(SL_k)_{TC}$, is not greater than the basal value, $(BS)_{TC}$, the computer 123 (FIGS. 1A and 1B) will "flag" the corresponding agonist, $L_k$ as "negative"(Step 1660), which means that the cell does not contain a receptor which can be stimulated by the particular agonist, and the flow returns through line M back to the incremental counter L (Step 1630). If the $(SL_k)_{TC}$ signal is greater than the $(BS)_{TC}$ signal, the computer 123 will "flag" the corresponding agonist as "POSITIVE$_{TC}$" (Step 1656), which means that the transfected cells do express a receptor which can be stimulated by the particular agonist.

The next task is to determine if the host cells also express this receptor to distinguish it from the orphaned receptor which should be expressed only in transfected cells. To do so, after the standard agonist $L_k$ has been flagged as positive in the step 1656, the program flow enters loop K–O, where, in step 1662, the autosampler 315 moves its nozzle 323 to the position corresponding to the value obtained in counter L, $L_k$. Step 1664 switches diverting valve 347 to position 1, which connects host cell suspension reservoir 349 with mixing zone 343 through common output 346, through intake port 348 of the multichannel diverting valve 347, and through priming valve 345. Steps 1666 and 1668 turn valve 327 and pump 357 ON, respectively, allowing the buffer 305 coming from intake 309 of the autosampler 301, and standard agonist $L_k$, coming from the intake 323 and output port 328 of the proportioning valve 327, to be brought together in mixing zone 331 with the subsequent mixing of this solution with the host cells in the mixing zone 343. After a delay determined by step 1670, which is needed for the stream of the mixture of the cells and agonist to stabilize, detector 355 registers the agonist induced signal in the host cells, $(SL_k)_{HC}$ (Step 1672).

After the signal is registered, it is compared (Step 1674) with the corresponding basal signal, $(BS)_{HC}$, measured in step 1614. Depending on the results of the comparison, the agonist $L_k$ is marked either as "POSITIVE$_{TC}$/POSITIVE$_{HC}$" (Step 1676) or as "POSITIVE$_{TC}$/NEGATIVE$_{HC}$" (Step 1678). In either case, the data are saved in step 1680 for further evaluation by the researcher.

After the data are saved, the multichannel diverting valve 347 is switched over to position 2 in step 1682, the proportioning valve 327 is turned OFF (step 1684), autosampler 315 is moved to the zero position (step 1686), proportioning valve 327 is turned ON (step 1688) and, after a washing delay, determined in step 1690, is turned OFF again (step 1692) and the pump 357 is turned OFF (Step 1694). After the step 1694 has been performed, the flow goes back to the incremental counter L (step 1630) through the line O.

If in step 1632 (FIG. 17c), $L_k$ does exceed $L_{max}$, then the process moves to step 1700 (FIG. 17g) where the counter L is set to zero. Next, the autosampler 315 is moved to the zero position in step 1702, the proportioning valve 327 is turned ON in step 1704 and after a washing delay determined in step 1706, both proportioning valve 327 and pump 357 are turned OFF in steps 1708 and 1710 respectively, after which the program stops in step 1712.

The above devices and procedures may be used to monitor cellular responses to test compounds in living cells. For example, living cells may be used to study signal transduction pathways and global cellular responses using reagents such as fluorescent dyes to generate signals indicative of the activation of the signal transduction pathways or the triggering of the global cellular responses. Preferably, the fluorescent dyes are sensitive to the level or state of biochemical mediators or biophysical parameters that indicate changes in the activation state of the cell. In particular, to measure changes in the concentration of unbound $Ca^{2+}$ ions in the cell, the indicator may be the dye indo I, Other indicators may measure intracellular pH (e.g., SNARF-1), intracellular $K^+$ (e.g., PBFI), intracellular $N^+$ (e.g., SBFI), transmembrane potential (e.g., oxonols and DiBAC dyes), lipid fluidity (e.g., merocyamine 540), lipid oxidation (e.g., cis-paranaric acid) and intracellular oxidation potential and state (e.g., MC-H2CFDA). The preceding indicators are available from Molecular Probes (Eugene, Oreg.) and other vendors.

Example 7 below demonstrates the use of the present devices and methods in which the detector is capable of detecting a plurality of cellular responses simultaneously and/or capable of measuring cellular responses in individual cells, such as devices in which the detector is a flow cytometer, to measure cellular responses to test compounds in living cells.

EXAMPLE 7

Target cells are harvested from the culture vessel using dissociation reagents such as 0.25% Trypsin/1 mM EDTA if necessary, washed in buffered salts solution and counted. As discussed above, the target cells may be obtained from cultures containing a single cell type for from cultures containing a plurality of cell types. If the cultures contain a mixed population of cells, cell type identification reagents will be used as described below.

After harvesting, the cells are loaded or stained with an appropriate cellular response indicator, such as a dye. Loading conditions will vary with the dye used. Conditions to be considered include but are not limited to cell density, temperature, duration and concentration of the dye probe.

A variety of dyes suitable for detecting cellular responses and methods for introducing them into cells are known to those skilled in the art. For example, indo-1, SNARF-1, PBFL, SBFI and MC-H2CFDA are loaded into cells using the membrane permeant, esterase-cleaveable forms at 1–10 $\mu$M and room temperature. Oxonols and DiBAC dyes, merocyanine 540, and cis-paranaric acid are loaded and maintained under equilibrium conditions at 1–50 $\mu$M and room temperature. To extend viability of the cells, loading and staining are performed in Hybridoma Medium (HM Sigma) whenever possible.

After loading with an appropriate indicator dye the cells are washed in HM and resuspended in HM at 2E5 to 2E6 cells/ml. Cells are maintained at room temperature in a vessel with constant stirring prior to mixing with the test compound(s) and analysis.

Cells are drawn into the apparatus and exposed to test compound(s) as described above. For example, the cells may be drawn into the apparatus using negative pressure generated via a peristaltic pump. In some embodiments, the cells may be exposed to mixtures of test compound(s) and standard compound(s) as described above.

In the preferred embodiment having a coupling device, sample slugs comprising cells and test compound(s) or test mixtures are then delivered to the flow cytometer. As discussed above, the coupling device preferably isolates the slugs from the reaction developing lines coming from the mixing chamber and delivers them to the flow cytometer under positive air pressure. Alternatively, cells may also be delivered directly to the flow cytometer without using the coupling devices.

As the loaded cells enter the flow cytometer they are excited by the laser(s). The excitation beam scatter properties and fluorescence emissions are optically selected using steering dichroics and bandpass filters. Fluorescent and/or non-fluorescent optical signals associated with each cell are converted into electronic signals, which are processed and represented graphically.

The response of the cells as indicated by the reporter dye is detected from each cell at the point in time determined by the configuration of the apparatus. The response can be quantitated as the average of the entire population, or as the percentage of cells exceeding a certain fluorescence value. The data are stored in a database for future reference.

Figure 18:
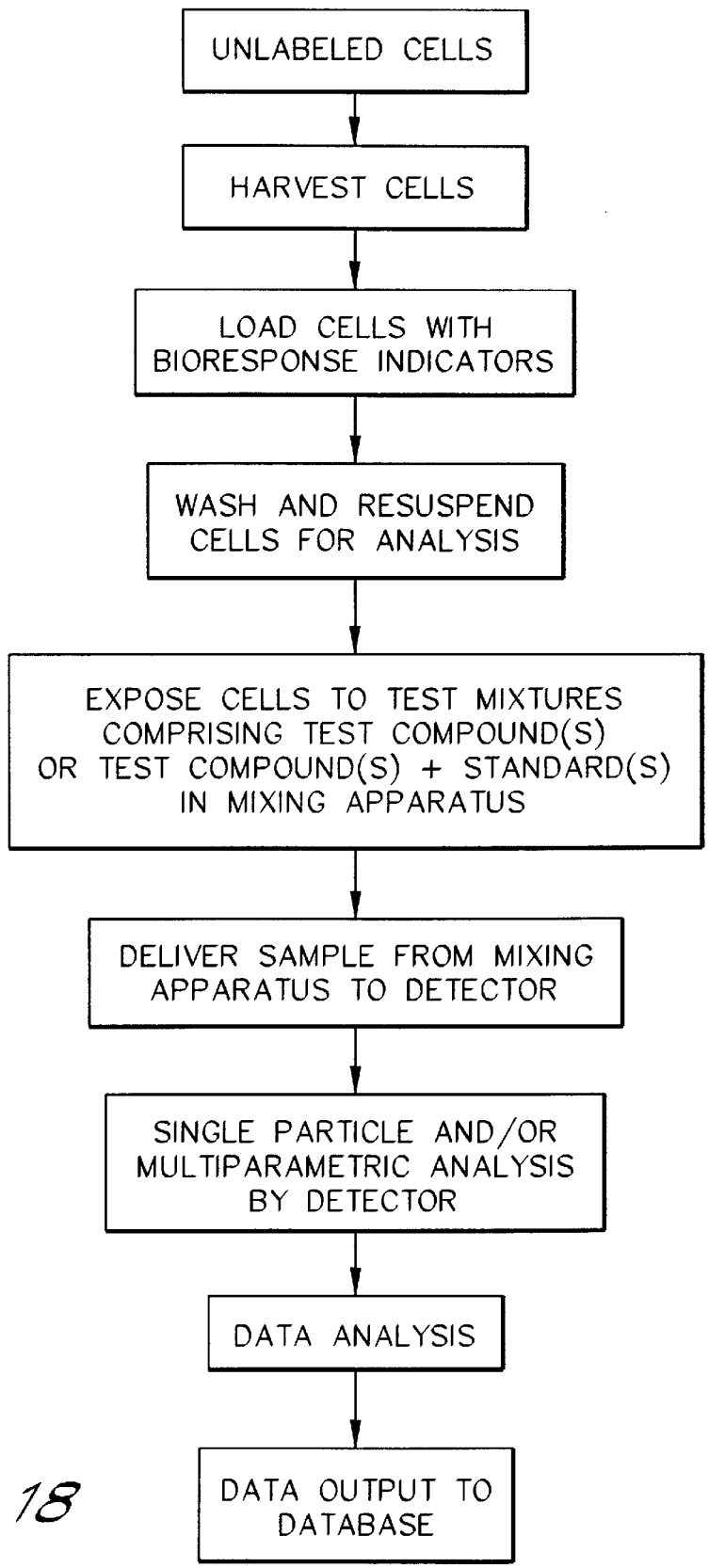
FIG. 18 is a flow diagram of a method for measuring cellular responses.

FIG. 18 illustrates the above procedure.

Embodiments of the present devices and methods in which in which the detector is capable of detecting a plurality of cellular responses simultaneously and/or capable of measuring cellular responses in individual cells, such as devices in which the detector is a flow cytometer, may be used to evaluate cellular responses in cell populations comprising more than one type of cell, to evaluate responses in cell populations obtained from a single cell type or tissue in which only a fraction of the population responds to a stimulus, or to evaluate multiple cellular responses simultaneously.

In analyses in which the cell population contains more than a single cell type, individual cells are tagged with a cell type identification reagent specific for a particular cell type, such as an antibody specific for that cell type. Each cell type identification reagent provides a distinct signal to the detector to enable the determination of which cell type is responding to a test compound.

In addition, the cells are contacted with one or more test compounds or test mixtures comprising one or more test compounds and a standard compound as described above. Alternatively, the cells may be exposed to mixtures of test compound(s) and standard compound(s) as described above. The cells are also contacted with a cellular response indicating reagent, such as those described in Example 7 above, which provides a signal indicative of a particular cellular response.

The cells which have been contacted with the cell type identification reagent, the response indicating reagent, and the test compound(s) or test compound(s)/standard mixture are sent to the detector, which detects signals indicative of the cellular response and the cell type in which the cellular response is occurring. In this way, the cell type or cell types which exhibit the cellular response when exposed to the test compound or compounds may be identified.

Likewise in embodiments in which multiple cellular responses are evaluated simultaneously, the cells are contacted with a plurality of response indicating reagents and a test compound or compounds. Alternatively, the cells may be exposed to mixtures of test compound(s) and standard compound(s) as described above. Each of the response indicating reagents provides a distinct signal to the detector to enable the determination of the cellular response which is occurring. It will be appreciated that the cells may be a single cell type or may comprise a mixed population of cell types as described above. The cells which have been contacted with the test compound or compounds and a plurality of response indicating reagents are sent to the detector, which detects signals indicative of the cellular responses which are occurring. In addition, where a mixed population of cell types is used, the detector detects signals indicative of the cell type or cell types which are exhibiting each response.

Examples 8A and 8B below provide examples of the above methods.

EXAMPLE 8A

If multiple cell types are to be analyzed, the different cell types are labeled with commercially available fluorescent lipid intercalating dyes which enable the different cell types to be distinguished from one another, such as $DiOC_{18}(3)$ or $DiIC_{18}(3)$. Loading procedures vary according to the cell type and dye used, but incubation with 1–5 $\mu$M dye for several hours to overnight is usually sufficient. Other fluorescent dyes may also be used to label the cells. Examples are not limited to, but include, dyes that are trapped within the cytoplasm due to ionic charges (e.g., carboxyfluorescein, Molecular Probes) or dyes that become conjugated to intracellular proteins or organelles (e.g., Mitotracker Red, Molecular Probes). Such dyes are typically loaded into the cells using 1–50 $\mu$M incubation concentrations. Also, fluorochrome conjugated antibodies specific for unique markers on a cell population can be used to identify the populations. Appropriate dyes and staining reagents are selected according to the available excitation spectra in the FCM configuration, and the desired spectral emissions that will enable discrimination of one cell population from another.

Alternatively, the individual cell types may be labeled with antibodies specific for each cell type. In such procedures, the cells are harvested first and then labeled with the antibodies. To label the cells with antibodies, the cells are resuspended at high density in ice-cold staining solution. Staining solution is a buffered salts solution containing a sufficient concentration of antibody to completely saturate all binding sites within 15 minutes on ice. Cells are washed to remove unbound antibody.

The labeled cells are harvested and loaded with the cellular response indicator, such as an indicator dye, of choice as described above. Cells are exposed to one or more test compound(s) or test compound(s)/standard mixtures using the mixing system described above and sent to the flow cytometer as described above.

Upon analysis of the cellular responses by the FCM, electronic gating is performed to discriminate individual cell types and to quantitate the frequency of responding cells within a population.

Figure 19:
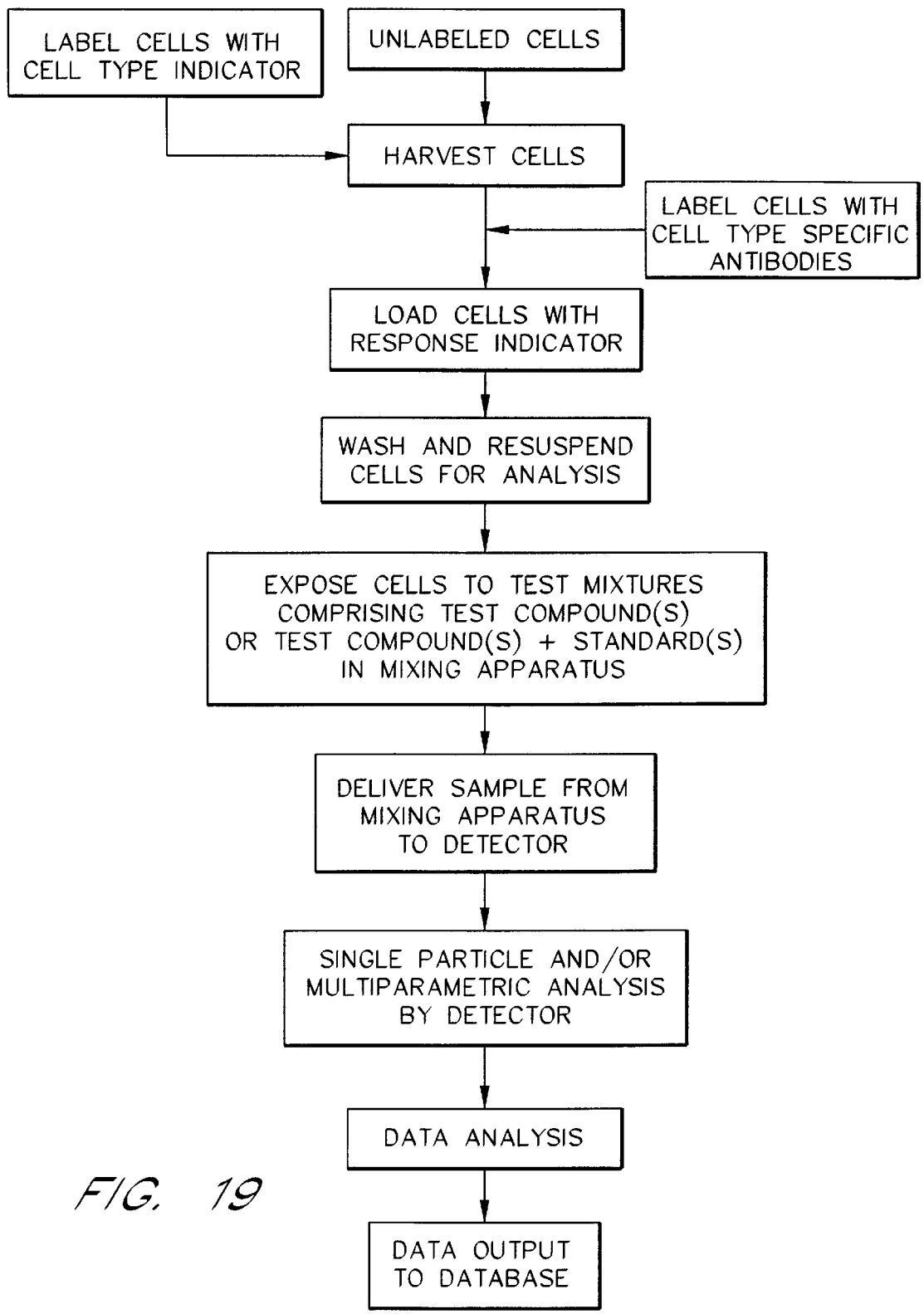
FIG. 19 is a flow diagram of a method for measuring cellular responses in cell populations containing more than one type of cell.

FIG. 19 illustrates the above procedure.

EXAMPLE 8B

Where multiple cellular responses are to be evaluated simultaneously, a cell population is loaded with two or more different cellular response indicators, such as bioresponse reporter dyes. For example, the dyes may be indo-1 for $Ca^{2+}$ responses and SNARF-1 to measure pH. Dyes are loaded and cells are harvested as described above.

Alternatively, is some embodiments, fluorescent ligands may be used to stimulate the cells. In this case the fluorescent ligands are used as normal test agonists or antagonists as described above. This enables the simultaneous analysis and quantification of the cellular bioresponse and ligand binding simultaneously.

Cells are exposed to test compound(s) or test compound(s)/standard mixtures comprising one or more test compounds and a standard and analyzed as described above. The FCM is configured to detect each fluorescent parameter associated with the individual reporter dyes. Upon analysis of the cellular responses by the FCM electronic gating will be performed to determine the distinct bioresponses within the cells and to quantitate the frequency of responding cells within a population.

It will be appreciated that if one desires to simultaneously evaluate a plurality of cellular responses in populations comprising more than one cell type, the procedures described in Examples 8A and 8B may be combined.

Figure 20:
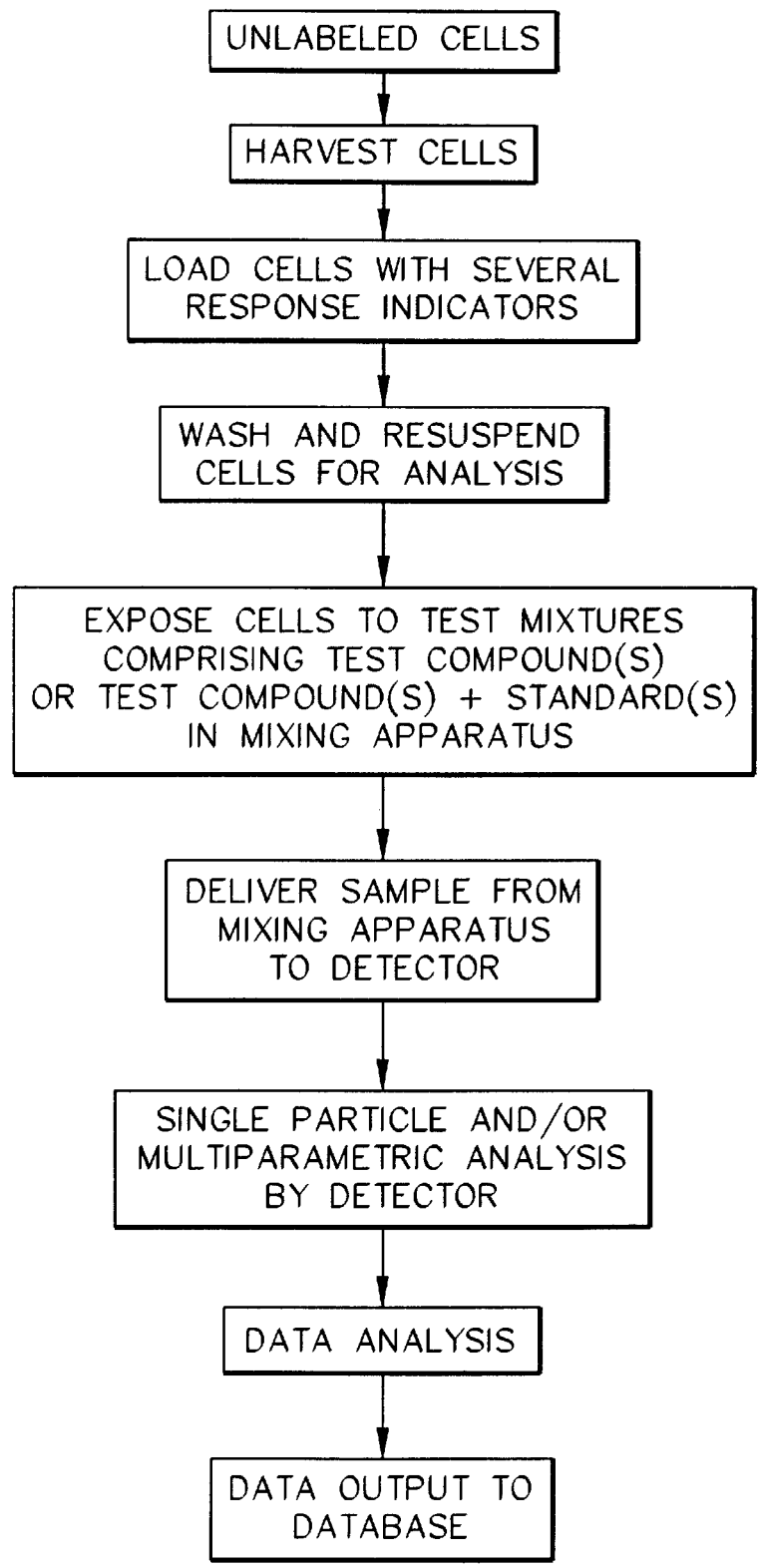
FIG. 20 is a flow diagram of a method for measuring a plurality of cellular responses simultaneously.

FIG. 20 illustrates the above procedure.

The above devices and methods in which the detector is capable of detecting a plurality of cellular responses simultaneously and/or capable of measuring cellular responses in individual cells, such as devices in which the detector is a flow cytometer, may be used to evaluate the effects of test compounds on receptor activity and to correlate the extent of receptor occupancy by the ligand with the functional response triggered by the receptor.

Ligand-specific receptors on cells activate specific second messenger pathways and associated downstream events that result in changes in cell activity or state. Compounds which directly or indirectly block natural ligand binding or that mimic the natural ligand to activate second messenger pathways can be identified. Such compounds have a variety of applications, including use as drugs or therapeutic agents.

As discussed above, the present devices and methods may be used to analyze receptor-mediated cellular responses in mixed cell populations and/or to evaluate multiple receptor-mediated responses simultaneously. In such embodiments, the reagents indicative of cellular responses are reagents which indicate receptor binding or activity. In addition, where mixed cell populations are used, the cells are also contacted with cell type identification reagents.

Example 9 describes the analysis of receptor-mediated responses.

EXAMPLE 9

If populations of different cell types are being evaluated, the cell types are labeled with cell type identification reagents, such as distinct fluorescent dyes or antibodies, as described above to enable discrimination by the FCM.

Labeling may be performed as described in Examples 8A and 8B. Cells are harvested as described in Example 7. If a plurality of cellular responses are being evaluated simultaneously, after harvesting, the cells are loaded with two or more cellular response indicating agents, such as bioresponse indicator dyes, as described in Example 8B. If it is desired to measure a plurality of cellular responses in a population comprising more than one cell type, the procedures of Example 8A and 8B are combined.

After loading the cells are mixed with one or more test compounds or test compound(s)/standard mixtures comprising a test compound(s) and a standard, and analyzed by the FCM as described in Example 7 to determine the effects of the test compound(s) or test compound(s)/standard mixture on receptor activity.

The FCM is configured to detect each fluorescent parameter associated with the individual bioresponse reporter dyes and/or with the each labeled population. Using electronic gating, each bioresponse is determined for each individual cell population simultaneously. Electronic gating is also used to quantitate the frequency of responding cells within a each population simultaneously.

Figure 21:
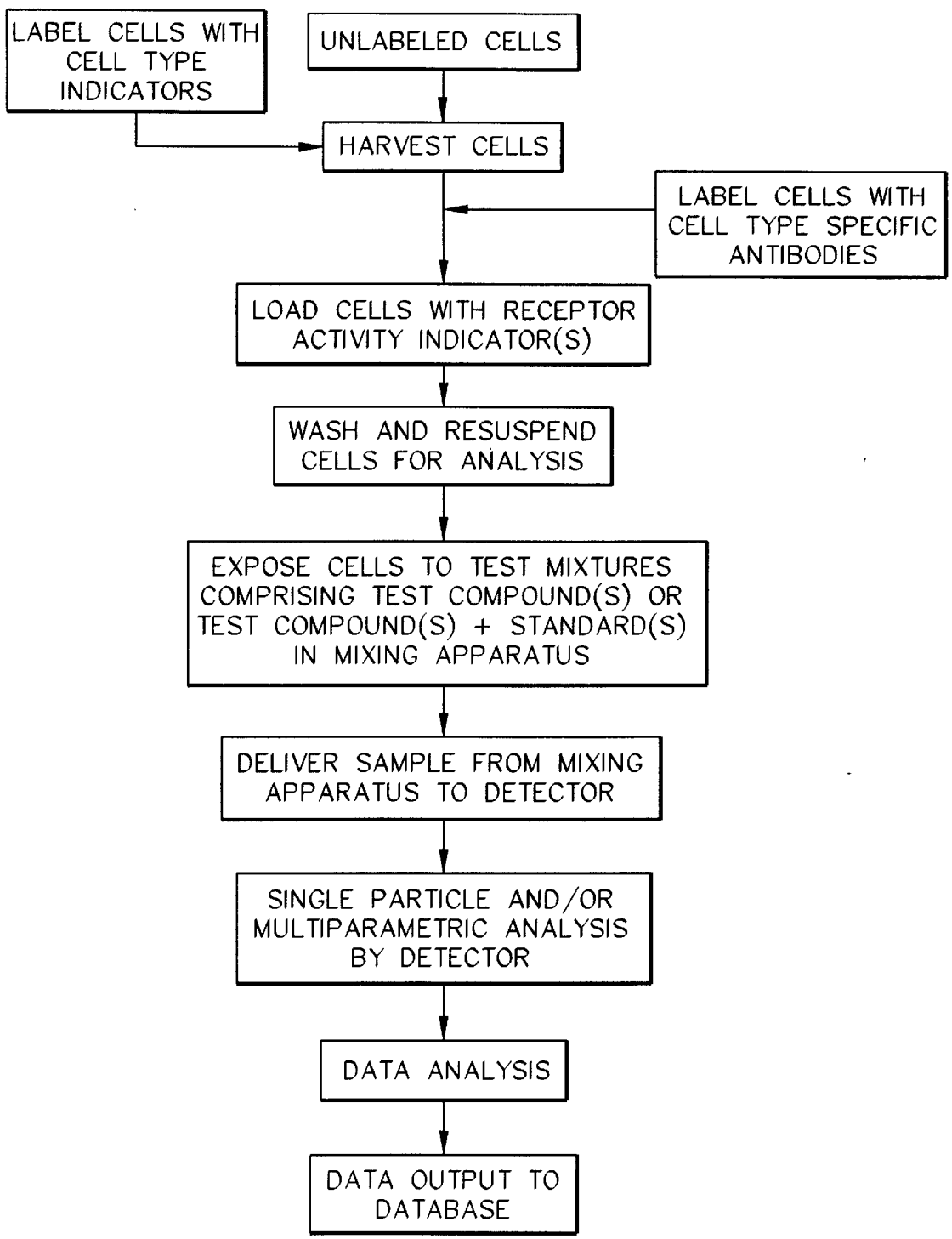
FIG. 21 is a flow diagram of a method for analyzing receptor activity.

FIG. 21 illustrates the above procedure.

The above devices and methods in which the detector is capable of detecting a plurality of cellular responses simultaneously and/or capable of measuring cellular responses in individual cells, such as devices in which the detector is a flow cytometer, may be used to analyze one or more test compounds or test compound(s)/standard mixtures comprising one or more test compounds and a standard for their influence on the activity of ion channels or non-selective pores.

In this embodiment, the reagents indicative of cellular responses are reagents which indicate activation of ion channels or non-selective pores. In addition, where mixed cell populations are used, the cells are also contacted with cell type identification reagents. Different properties of indicator dyes can be exploited to study ion channel and pore function. For example, certain channels are permeant to specific ions, and these ions can alter the fluorescent properties of intracellular dyes. For example, the activation of a $Ca^{2+}$ channel can be visualized directly using a $Ca^{2+}$ sensing dye, or indirectly using techniques based on the ability of $Mn^{2+}$ to pass through the channel and quench fluorescence of a $Ca^{2+}$ indicator dye.

The formation of non-selective pores may be monitored using pore-permeant, fluorescent nucleic acid binding dyes to detect permeability changes. These dyes increase their fluorescence dramatically when bound to nucleic acids, and hence would yield fluorescence: signals only when the opening of pores permitted them to enter the cells.

Thus, the present invention permits multiple channel- and pore-mediated cellular responses to test compounds to be monitored in distinct cell populations in an automated fashion.

Example 10 describes the analysis of ion channels or non-selective pores.

EXAMPLE 10

If populations of different cell types are being evaluated, the cell types are labeled with cell type identification reagents, such as distinct fluorescent dyes or antibodies, as described above to enable discrimination by the FCM.

Labeling may be performed as described in Examples 8A and 8B. Cells are harvested as described in Example 7. If a plurality of cellular responses are being evaluated simultaneously, after harvesting, the cells are loaded with two or more cellular response indicating agents, such as bioresponse indicator dyes, as described in Example 8B. If it is desired to measure a plurality of cellular responses in a population comprising more than one cell type, the procedures of Example 8A and 8B are combined.

Cells are harvested as described in Example 7. The cells are loaded with a $Ca^{2+}$ sensing dye such as indo-1 as described in Example 7. Such cells may be used to evaluate the ability of test compound(s) to block or enhance the influx of $Ca^{2+}$ through $Ca^{2+}$ channels, or to block or enhance the flow through the channel of other competitive channel permeant ions, such as $Mn^{2+}$ that quench dye fluorescence. Other dyes that sense fluxes in other ions such as SBFI for $Na^+$ may also be used to detect flow through a $Na^+$ channel of competitive ions. In situations where the target cellular activity is an activatable, non-selective pore then the cells will not be loaded with a bioresponse indicator, unless more than one bioresponse is to be monitored simultaneously.

Cells are mixed with one or more test compounds or test compound(s)/standard mixtures comprising one or more test compounds and a standard and analyzed by FCM as described in above with the exception that competitive ions such as $Mn^{2+}$ (1–100 $\mu$M final concentration) or nucleic acid binding dyes such as 7-AAD (1–100 $\mu$M) are introduced with the test compounds or test compound(s)/standard mixtures. Sufficient time for the ions or nucleic acid sensing dye is allowed by adjusting the reaction time of the system prior to FCM analysis.

In embodiments in which the test compound(s) is mixed with a standard(s), the standard may be an agonist or antagonist of the channel being evaluated. For example, if the channel being evaluated is an L-type voltage-gated $Ca^{2+}$ channel, the agonist Bay K 8644 or the antagonists Nimodipine, Verapamil, or Diltiazem may be used as standard compounds.

Likewise if the channel being evaluated is an N-type voltage-gated $CA^{2+}$ channel, antagonists such as ω-conotoxin GVIA, ω-conotoxin MVIIC may be used as the standard compounds.

If the channel being evaluated is a voltage-gated $Na^+$ channel, modulators such as batrachotoxin, α-scorpion toxin, class2 β-scorpion toxin or antagonists such as tetrodotoxin, or saxitoxin may be used as standard compounds.

The FCM will be configured to detect the appropriate optical signals in a multiparametric and multicellular format suitable to the labeling and bioresponse indicator dyes utilized.

Figure 22:
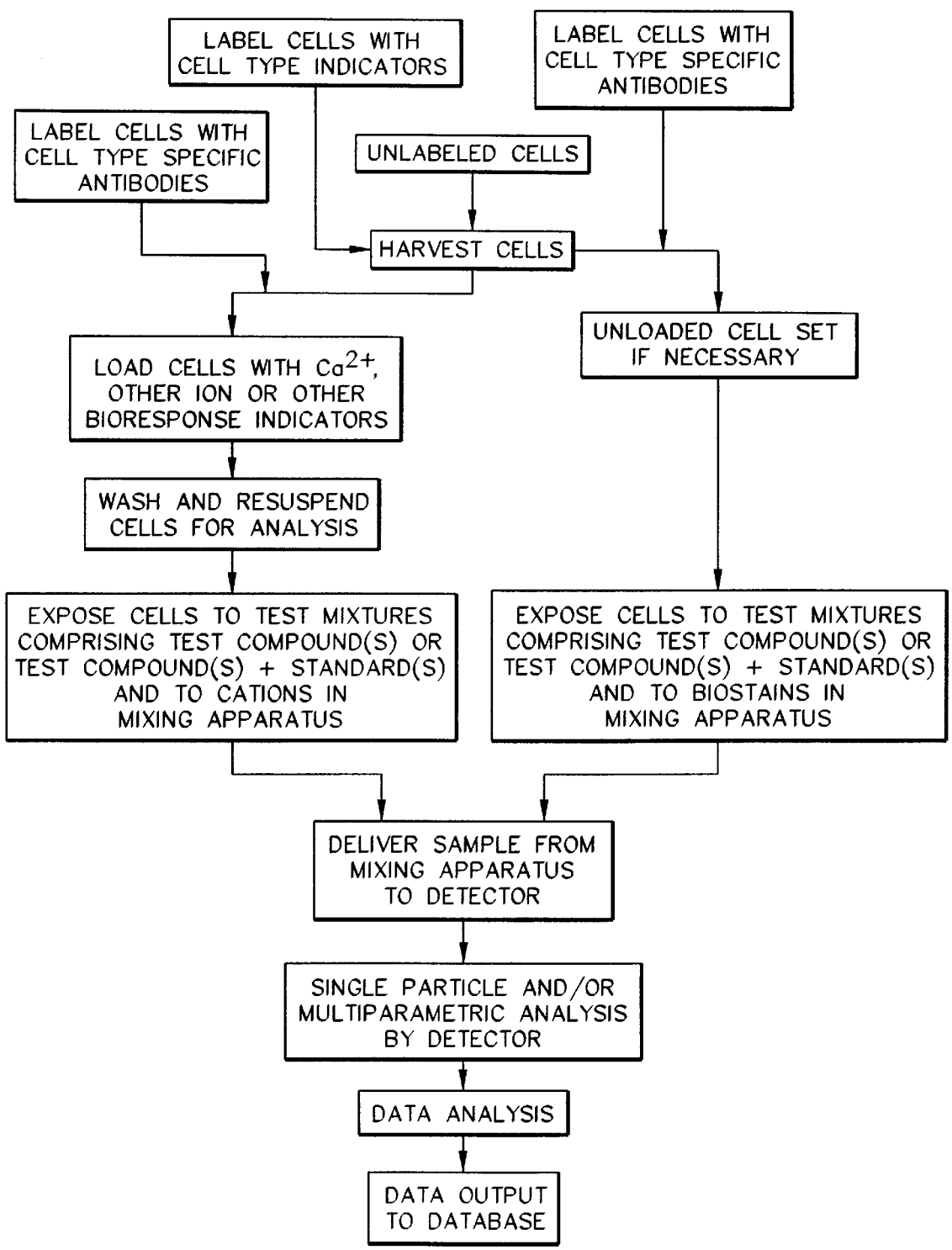
FIG. 22 is a flow diagram of a method for analyzing the activity of ion channels or non-selective pores.

FIG. 22 illustrates the above procedure.

The present devices and methods in which the detector is capable of detecting a plurality of cellular responses simultaneously and/or capable of measuring cellular responses in individual cells, such as devices in which the detector is a flow cytometer, may be used to analyze a test compound or test compounds for their influence on the activity of second messengers at points downstream of a receptor or channel involved in the second messenger pathway. The above devices and methods may be used to evaluate the effects of test compounds on second messengers. As discussed above, the present devices and methods may be used to analyze the effects of a test compound or test compounds on second messengers in mixed cell populations and/or to evaluate multiple second messengers simultaneously. In such embodiments, the reagents indicative of cellular responses are reagents which indicate activity of second messengers either directly or indirectly. In addition, where mixed cell populations are used, the cells are also contacted with cell type identification reagents.

Example 11 describes the analysis of the activity of second messengers.

EXAMPLE 11

Phospholipase C is a 'second messenger' enzyme activated by certain 7-transmembrane receptors and certain single-transmembrane receptors. Upon activation the enzyme catalyzes the formation of inositol trisphosphate ($IP_3$) from membrane lipids. $1P_3$ binds and activates an $IP_3$, receptor on the endoplasmic reticulum (ER) that functions as a $Ca^{2+}$ channel. This results in release of stored $Ca^{2+}$ from the ER. This sudden release of $Ca^{2+}$ can raise intracellular free $Ca^{2+}$ levels from 100 nM to 1 $\mu$M within seconds.

The apparatus of the present invention may be used to study direct activators or inhibitors of phospholipase C, or of the G-protein subunits associated with the receptor that activate the phospholipase C. In such procedures, candidate compounds are introduced to cells containing the desired enzyme using the apparatus of the present invention. The $Ca^{2+}$ mobilization response is monitored with a fluorescent $Ca^{2+}$ indicator such as indol.

Figure 23:
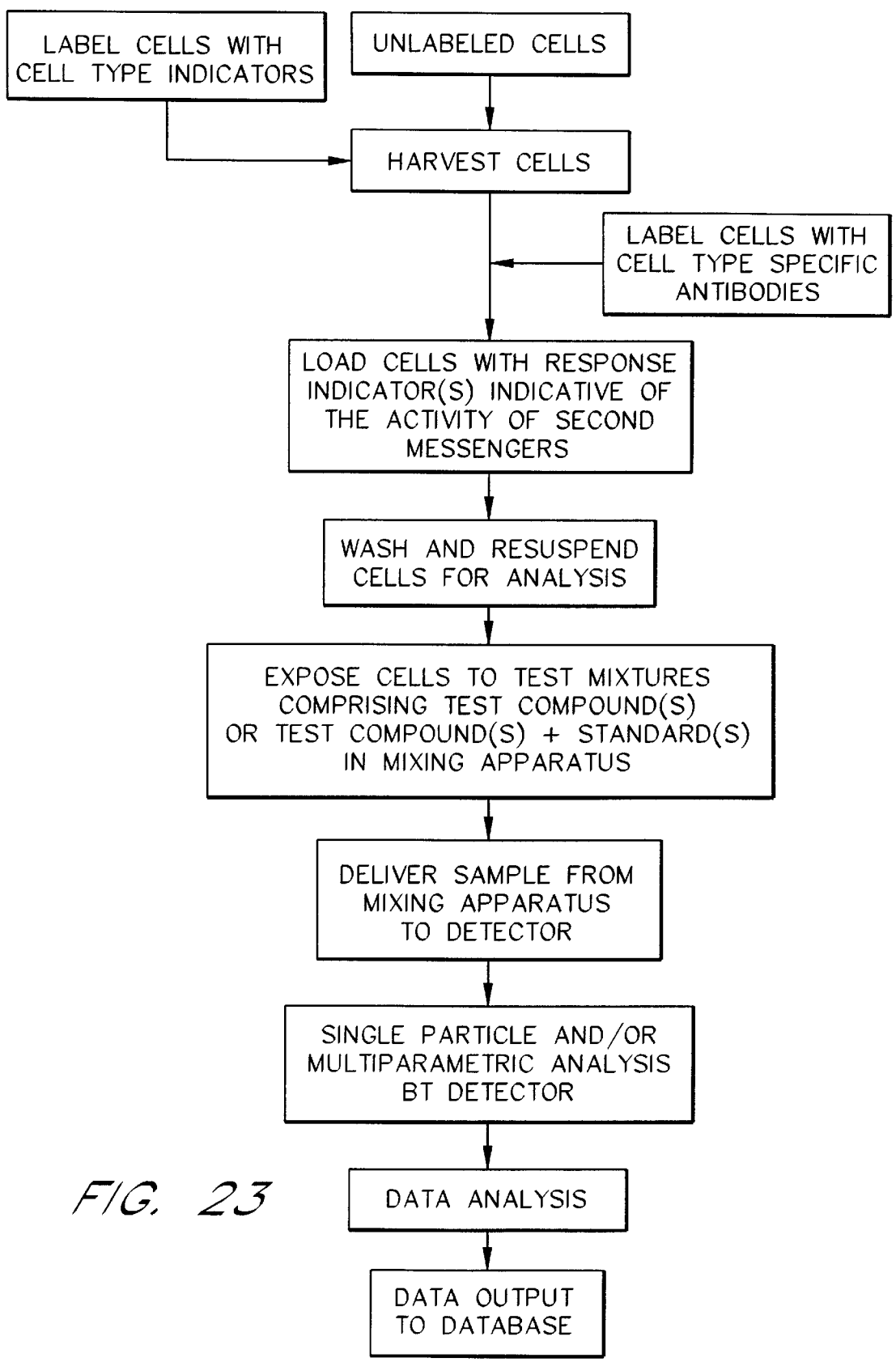
FIG. 23 is a flow diagram of a method for measuring the activity of second messengers.

FIG. 23 illustrates the above procedure.

The present devices and methods in which the detector is capable of detecting a plurality of cellular responses simultaneously and/or capable of measuring cellular responses in individual cells, such as devices in which the detector is a flow cytometer, may be used to analyze a test compound or test compounds for their influence on cellular apoptosis or cellular toxicity. As discussed above, the present devices and methods may be used to analyze the effects of a test compound or test compounds on cellular apoptosis in mixed cell populations and/or to evaluate a plurality of cellular responses including apoptosis simultaneously. In such embodiments, the reagents indicative of cellular responses are reagents which indicate activity of agents involved in cellular apoptosis or cellular toxicity. In addition, where mixed cell populations are used, the cells are also contacted with cell type identification reagents.

Example 12 describes the analysis of the activity of agents involved in cellular apoptosis or cellular toxicity.

EXAMPLE 12

If populations of different cell types are being evaluated, the cell types are labeled with cell type identification reagents, such as distinct fluorescent dyes or antibodies, as described above to enable discrimination by the FCM.

Labeling may be performed as described in Examples 8A and 8B. Cells are harvested as described in Example 7. If a plurality of cellular responses are being evaluated simultaneously, after harvesting, the cells are loaded with two or more cellular response indicating agents, such as bioresponse indicator dyes, as described in Example 8B. If it is desired to measure a plurality of cellular responses in a population comprising more than one cell type, the procedures of Example 8A and 8B are combined.

Certain of the fluorescent biosensors are loaded into the cells prior to exposure to test compounds. Examples include, but are not limited to, JC-1 loaded at 1–10 $\mu$M to measure mitochondrial membrane potential collapse, dihydrofluorescin to measure accumulation of oxygen free radicals and HOE 33342 loaded at 0.1 to 10 $\mu$g/ml to assess chromatin condensation and denaturation.

Cell populations are treated with one or more test compounds or with test compound(s)/standard mixtures comprising one or more test compounds and a standard prior to harvest, and incubated for predetermined optimal time periods. The optimal incubation time will vary depending upon the cell types, but will likely be from 1 to 4 hours under normal culture conditions.

Cells are harvested as described in Example 7.

The cells are preferably input into the apparatus as discrete, pre-treated populations.

After input to the apparatus, the cells are exposed to extra reagents in transit to the FCM. These reagents are additional sensors and detectors of apoptosis. Such reagents may be input through additional input lines in the system. Examples of such reagents include, but are not limited to, FITC conjugated Annexin V which binds phosphatidylserine oriented to the external leaflet of the plasma membrane during apoptosis. Time is allowed through adjustment of the lengths of the reaction developing lines from the coupling device and/or mixing chamber to permit interaction of the additional fluorescent reagents to their targets.

The FCM is configured to detect the appropriate optical signals in a multiparametric and multicellular format suitable to the labeling and bioresponse indicator dyes utilized.

For example, cells are susceptible to the induction of apoptosis by 1 $\mu$M of anti-cancer compounds such as camptothecin or Taxol. Cells are loaded with the response indicator dyes such as indol or Fura Red ($Ca^{2+}$), or JC-1 (mitochondrial potential), all at 1–10 $\mu$M. Next, the loaded cells are aliquoted to multiwell plates and treated with test compounds. The cells are incubated for 1–4 hours to permit early apoptotic events to occur. The cells are then input into the apparatus of the present invention through the autosampler, and exposed to an additional apoptosis detection reagent, such as a fluorochrome-conjugated Annexin V (0.1–100 ug/ml), through a sample input line.

Sufficient time (1–5 minutes) for the Annexin V to bind to phosphatidylserine on the external leaflet of the plasma membrane is provided to the sample mixture. For example, the length of the reaction chamber may be extended to ensure a sufficient amount of time is provided. Samples are then delivered to the detector via the coupling device (PFC).

Figure 24:
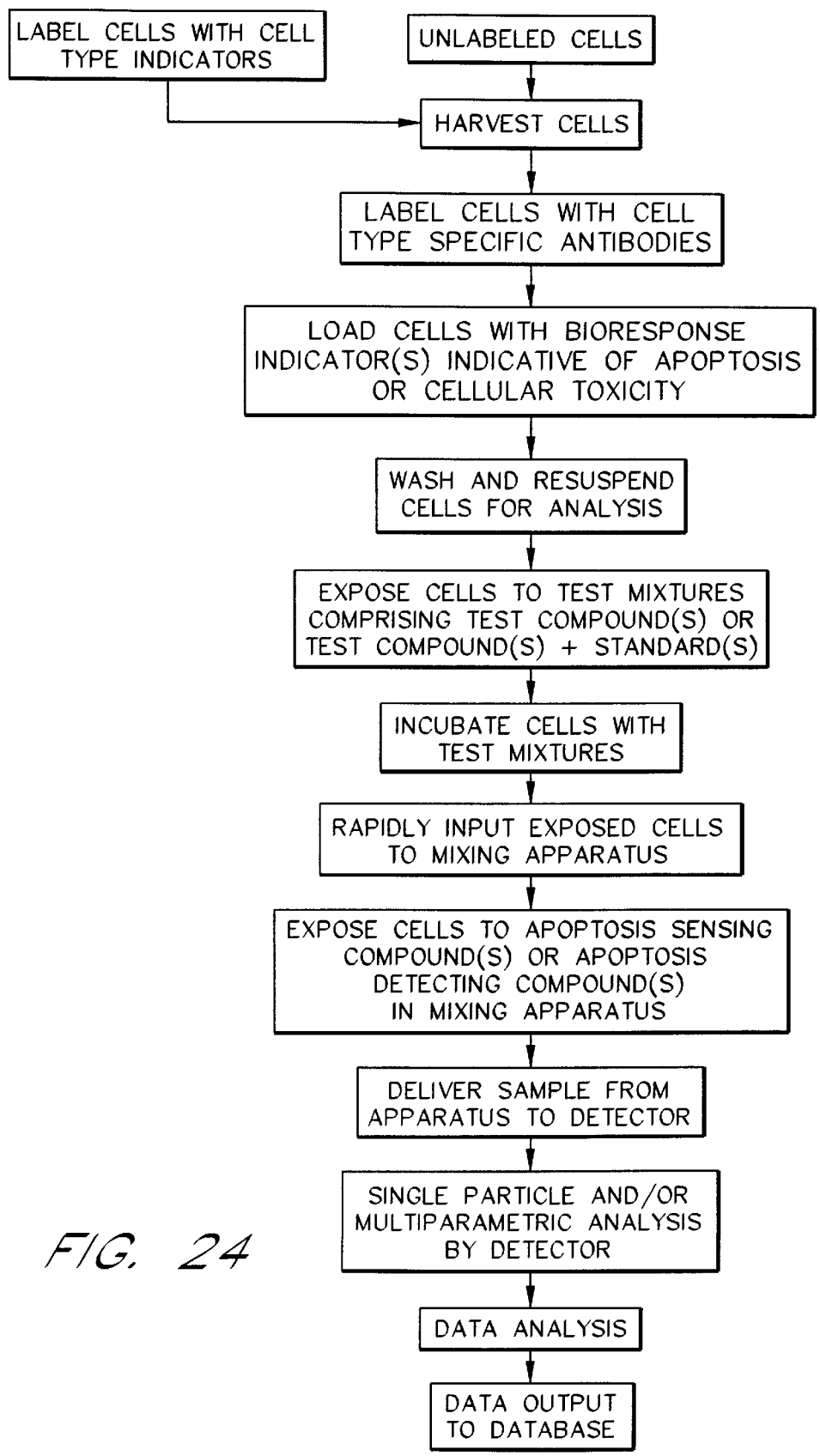
FIG. 24 is a flow diagram of a method for measuring cellular apoptosis or cellular toxicity.

FIG. 24 illustrates the above procedure.

The above devices and methods in which the detector is capable of detecting a plurality of cellular responses simultaneously and/or capable of measuring cellular responses in individual cells, such as devices in which the detector is a flow cytometer, may be used to analyze one or more test compounds or test compound(s)/standard mixtures comprising one or more test compounds and a standard for their influence on the activity of agents involved in cellular necrosis. As discussed above, the present devices and methods may be used to analyze the effects of a test compound or test compounds on agents involved in cellular necrosis in mixed cell populations and/or to evaluate multiple cellular responses simultaneously. In such embodiments, the reagents indicative of cellular responses are reagents which indicate activity of agents involved in cellular necrosis. In addition, where mixed cell populations are used, the cells are also contacted with cell type identification reagents.

Example 13 describes the analysis of the activity of agents involved in cellular necrosis.

EXAMPLE 13

Cells are labeled and treated as described in Example 12, except that the pre-loaded biosensors are appropriate for detecting necrosis rather than apoptosis. An example would be to load the cells with Calcein using Calcein AM at 1–10 $\mu$M. Unlike apoptotic conditions, under necrotic conditions the plasma membrane will become permeant to large molecules like calcein early in the process. Normally well retained green fluorescent calcein will leak out under necrotic conditions and this will be apparent as decreased green fluorescence.

Pre-labeled cells, or naive cells if appropriate, are input to the system through the autosampler port as in Example 12. The cells are exposed to additional fluorescent indicators of membrane permeability, if appropriate, through use of additional input lines as described in Example 12. An example is the red fluorescent, plasma membrane impermeant DNA stain propidium iodide.

The FCM is configured to detect the appropriate optical signals in a multiparametric and multicellular format suitable to the labeling and necrosis indicator dyes utilized.

Figure 25:
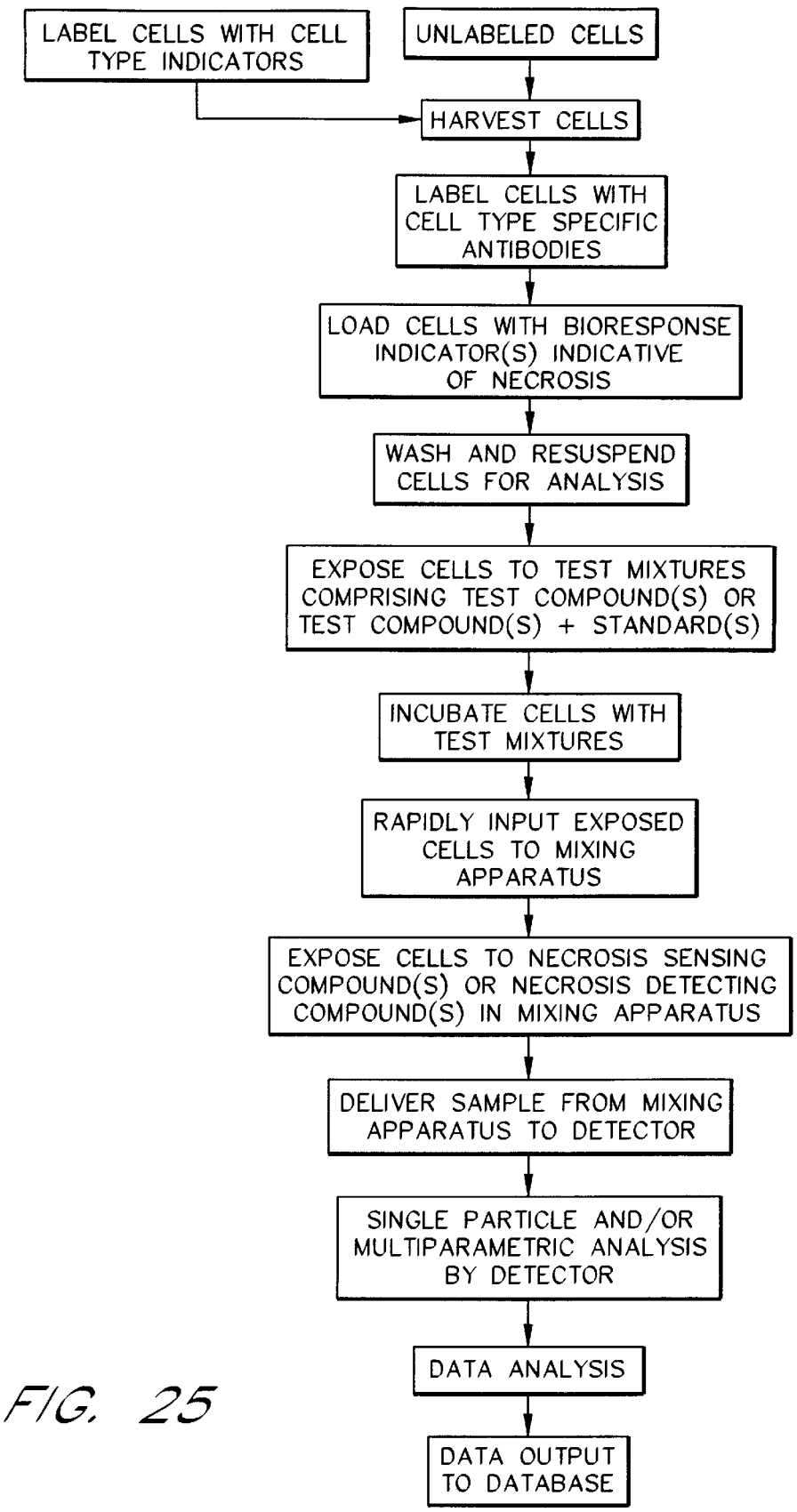
FIG. 25 is a flow diagram of a method for measuring cellular necrosis.

FIG. 25 illustrates the above procedure.

The above devices and methods in which the detector is capable of detecting a plurality of cellular responses simultaneously and/or capable of measuring cellular responses in individual cells, such as devices in which the detector is a flow cytometer, may be used to analyze one or more test compounds or mixtures comprising one or more test compounds and a standard for their effects on both necrosis and apoptosis. As discussed above, the present devices and methods may be used to analyze the effects of a test compound or test compounds on both necrosis and apoptosis in mixed cell populations and/or to evaluate multiple cellular responses simultaneously. In such embodiments, the reagents indicative of cellular responses are reagents which indicate activity of agents involved in cellular necrosis and apoptosis. In addition, where mixed cell populations are used, the cells are also contacted with cell type identification reagents.

Example 14 describes the analysis of the activity of agents involved in cellular necrosis and apoptosis.

EXAMPLE 14

Cells are labeled and treated as described in Examples 12 and 13 to detect both apoptosis and necrosis. Appropriate combinations of labels and response sensing dyes are selected according to the experimental needs to assess both necrotic and apoptotic cells. Pre-stained cells are input to the system through an autosampler port as described above. If appropriate, additional dyes are added to the cell population in transit as described in Examples 12 and 13.

The FCM is configured to detect the appropriate optical signals in a multi parametric and multicellular format suitable to tile labeling and necrosis and apoptosis indicator dyes utilized.

Figure 26:
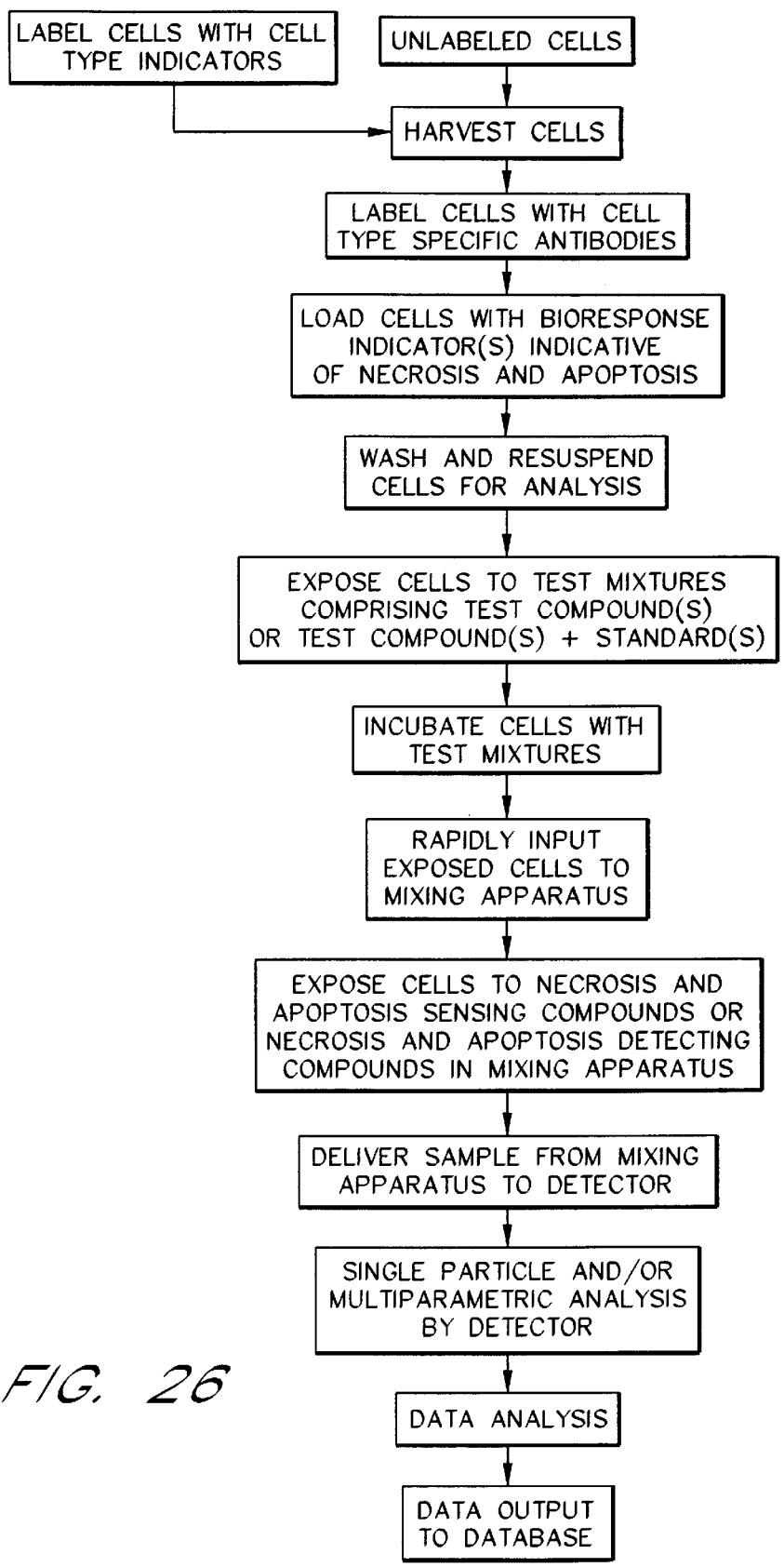
FIG. 26 is a flow diagram of a method for measuring cellular necrosis and cellular apoptosis or cellular toxicity.

FIG. 26 illustrates the above procedure.

The above devices and methods in which the detector is capable of detecting a plurality of cellular responses simultaneously and/or capable of measuring cellular responses in individual cells, such as devices in which the detector is a flow cytometer, may be used to obtain or clone populations of cells having a desired phenotype or cellular response profile. In such embodiments, the flow cytometer is equipped to sort cells exhibiting a desired phenotype. The system may be configured to enable fluorescence activated cell sorting of cells having a desired phenotype or cellular response profile. Preferable, the reagents for detecting one or more cellular responses used in such procedures provide a fluorescent signal indicative of the cellular responses. Additional phenotypic markers, such as fluorescent antibodies which detect the presence of particular cell surface markers may also be used to separate cell is having the desired characteristics. This enables the separation or cloning of cells having the desired phenotype or cellular responses from other cells in the population which do not exhibit the desired characteristics. In this way, a uniform population of cells exhibiting the desired characteristics may be obtained for use in assays. Example 15 below describes such embodiments.

EXAMPLE 15

If populations of different cell types are being evaluated, the cell types are labeled with cell type identification reagents, such as distinct fluorescent dyes or antibodies, as described above to enable discrimination by the FCM.

Labeling may be performed as described in Examples 8A and 8B. Cells are harvested as described in Example 7. If a plurality of cellular responses are being evaluated simultaneously, after harvesting, the cells are loaded with two or more cellular response indicating agents, such as bioresponse indicator dyes, as described in Example 8B. The cellular response indicating reagents may be any of those listed herein. For example, if the cellular response to be detected is calcium influx, the cellular response indicator may be indo-1. If it is desired to measure a plurality of cellular responses in a population comprising more than one cell type, the procedures of Example 8A and 8B are combined.

Cells are mixed with one or more molecules to be evaluated for inducing one or more cellular responses and the mixture is directed through a detector capable of detecting a plurality of cellular responses simultaneously or detecting cellular responses in individual cells as described above. The detector is also configured to sort or clone cells exhibiting the desired characteristics from the population of cells. Sample plugs comprising cells and the one or more test compounds are continuously delivered to the flow cytometer. As the plugs are analyzed by the flow cytometer, cells having the desired characteristics are delivered into a receiving vessel. The delivered cells may be expanded in culture for future storage or use.

Figure 27:
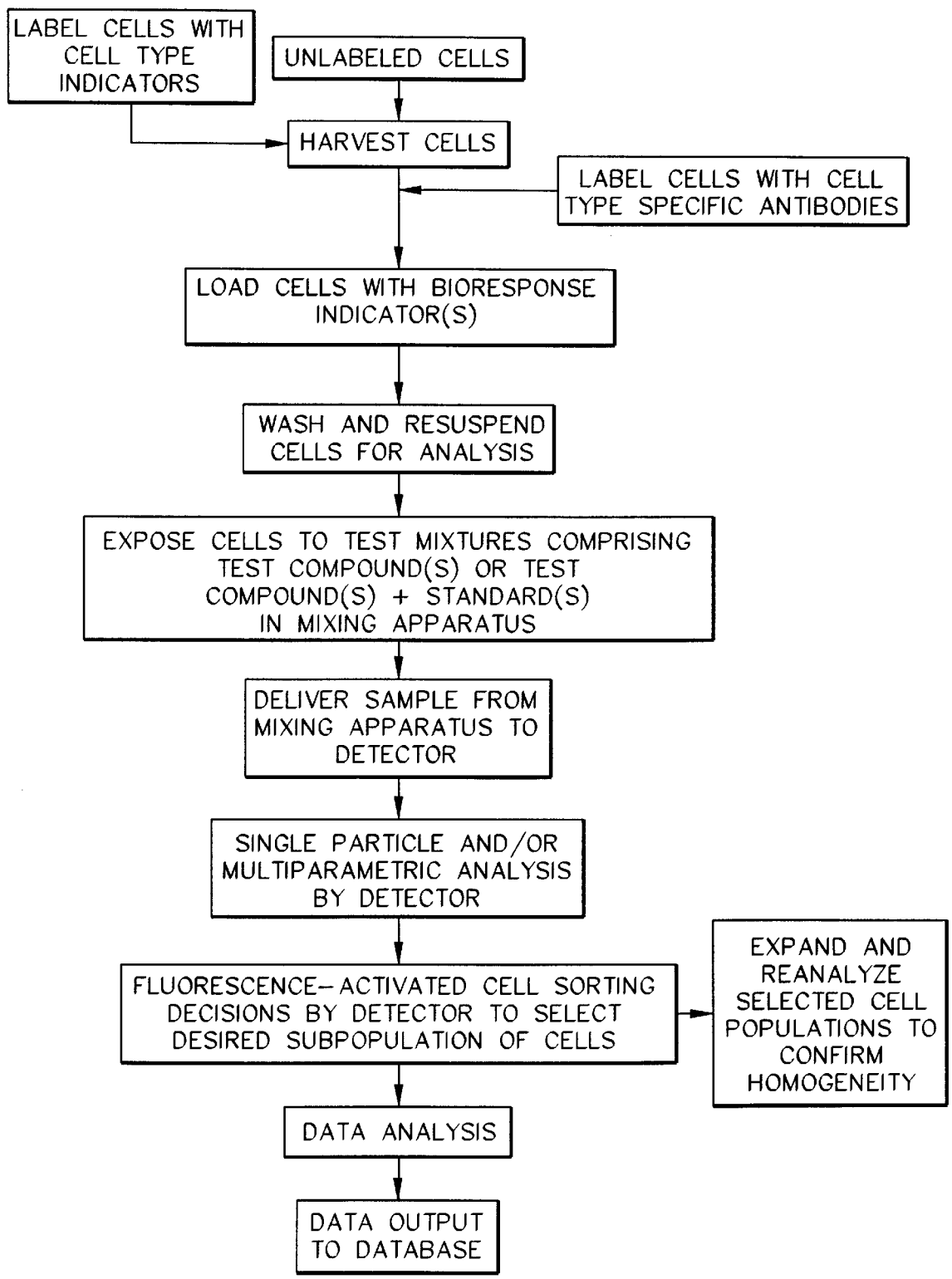
FIG. 27 is a flow diagram of a method for obtaining or cloning populations of cells having a desired phenotype or cellular response profile obtain or clone populations of cells having a desired phenotype or cellular response profile

FIG. 27 illustrates the above procedure.

The above devices and methods in which the detector is capable of evaluating interactions with a plurality of particles simultaneously and/or capable of evaluating interactions with individual particles, such as devices in which the detector is a flow cytometer may be used to perform biochemical analyses to determine whether one or more biochemical molecules are present in a sample. In such embodiments, the sample is contacted with a detection reagent for identifying the presence of a biochemical molecule in a sample. In some embodiments, the presence of several biochemical molecules in the sample is simultaneously evaluated using detection reagents which provide distinct signals for each biochemical molecule being evaluated. In some embodiments, the evaluation of multiple biochemical molecules is accomplished using to beads or particles which provide distinct signals.

For example, the present devices and methods may be used to perform Western analyses to simultaneously evaluate samples for the presence of multiple polypeptides.

Example 16 describes one embodiment of such Western analyses in which multiple polypeptides are simultaneously evaluated for modifications resulting from the activities of signal transduction pathways. However, it will be appreciated that the present devices and methods may be used to conduct Western analyses on any types of polypeptides present in a sample.

EXAMPLE 16

Microsphere populations bearing antibodies specific for a plurality of cellular proteins are prepared by conjugating the antibodies directly to the spheres. Optimal conjugation conditions will vary for each antibody but examples include the use of streptavidin coated microspheres to permit coating with biotinylated antibody. The microspheres may be fluorescent or of different sizes to render each bead population identifiable by FCM. Based on size or fluorescence parameters, several unique and addressable bead and antibody combinations can be constructed. This allows multiple assays to be performed in a single experiment when the populations are analyzed by FCM.

For example, if the polypeptides to be assayed are polypeptides which are modified through the activities of signal transduction pathways, cell populations are treated with test compounds prior to harvest, and incubated for predetermined optimal time periods to allow appropriate downstream signal transduction events to occur. The cells are lysed with a detergent, such as 0.1–1.0% NP-40, to liberate intracellular molecules. Micropsheres bearing specific antibody are added to the lysate to adsorb specific cellular proteins.

Samples of beads are then drawn into the system fluidics from the microtiter plate using an autosampler port. Bead populations are exposed to a second antibody (10 $\mu$M) within the fluidics system by introducing the antibody to the sample slug through a second input system. The second antibody is conjugated with a fluorescent molecule to permit identification by FCM. The second antibody is able to detect modifications of the captured cellular protein on each unique bead population. An example is the use of an anti-phosphotyrosine antibody to detect phosphotyrosine labeled proteins. The length of the reaction developing lines from the coupling device and/or the mixing chamber is sufficient to permit binding of the second antibody to the captured protein (2 to 5 minutes).

The addressable, antibody covered beads with captured cellular protein then enter into the FCM. The FCM is configured with the correct excitation lasers and beam scatter and emissions collecting optics to permit simultaneous analyses of multiple captured cellular proteins. Using multiple unique bead populations, it is possible to simultaneously analyze the modification state of multiple cellular proteins.

Figure 28:
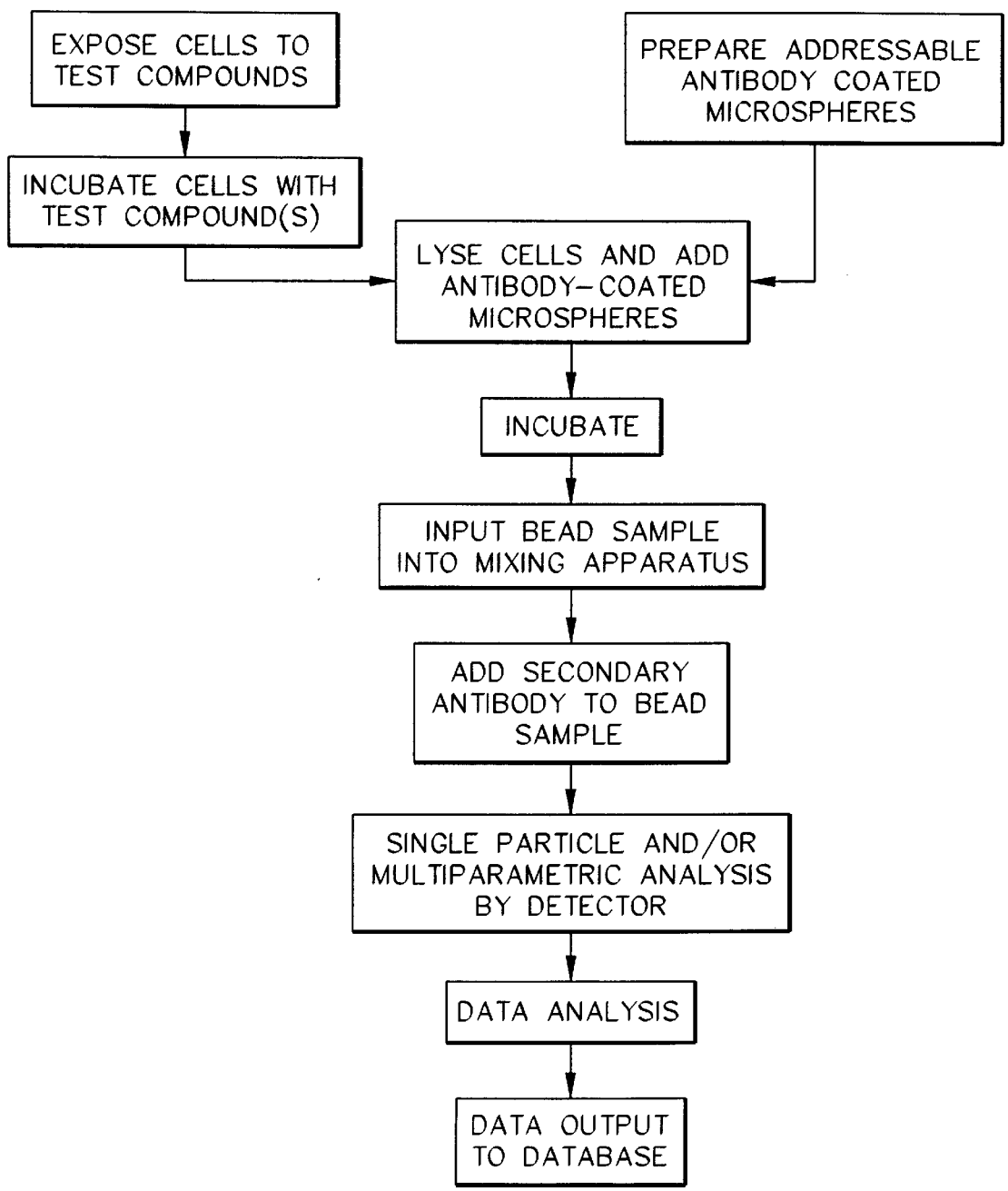
FIG. 28 is a flow diagram of a method for detecting the presence of one or more polypeptides in a sample.

FIG. 28 illustrates the above procedure.

The above devices and methods in which the detector is capable of evaluating interactions with a plurality of particles simultaneously and/or capable of evaluating interactions with individual particles, such as devices in which the detector is a flow cytometer, may be used to perform Northern or Southern analyses to simultaneously evaluate samples for the presence of multiple mRNAs or DNAs.

Example 17 describes one embodiment of such Northern analyses in which Northern analyses are performed on mRNAs which may be induced following treatment with test compounds. However, it will be appreciated that the Northern analyses may be performed to detect the presence of any desired mRNAs in a sample. It will also be appreciated that the method may be performed to detect the presence of any desired DNAs in the sample.

EXAMPLE 17

Microsphere populations bearing oligonucleotide probes complementary for portions of specific cellular mRNA are prepared by conjugating the oligonucleotide directly to the spheres. Optimal conjugation conditions will vary for each oligonucleotide. An example is to use streptavidin coated microspheres to permit coating with biotinylated oligonucleotide probe. The microspheres may be fluorescent or of different sizes to render each bead population identifiable by FCM. Based on size or fluorescence parameters, several unique and addressable bead and oligonucleotide combinations can be constructed. This allows multiple assays to be performed in a single experiment when the populations are analyzed by FCM'.

If the mRNAs to be analyzed may be induced by test compounds, cell populations are treated with test compounds prior to harvest and incubated for predetermined optimal time periods to allow appropriate cellular events to occur that result in synthesis of new mRNA species. Cells are lysed with a reagent such as RNAzol to liberate and preserve intracellular mRNA. Micropsheres bearing specific oligonucleotide probes are added to the lysate to permit hybridization of the oligonucleotide probes on the beads to complementary mRNA.

Oligonucleotide probes containing biotinylated UTP specific for the remaining, unhybridized portions of the mRNA are also added to the hybridization mix. Hybridization between the bead bound probes, the mRNA species and the biotinylated probes will proceed under optimized conditions.

Bead populations are exposed to an anti-biotin antibody (1–5 $\mu$g/ml) within the fluidics system by introducing the antibody to the sample slug through a second input system. The antibody is conjugated with a fluorescent molecule to permit identification by FCM. The length of the reaction developing lines from the coupling device and/or the mixing chamber is sufficient to permit binding of the antibody to the second oligonucleotide probe (2 to 5 minutes). Tile addressable, antibody covered beads with captured mRNA then enter the FCM.

The FCM is configured with the correct excitation lasers and beam scatter and emissions collecting optics to permit simultaneous analyses of multiple captured cellular mRNAs. Using multiple unique bead populations, it will be possible to simultaneously detect multiple mRNA species.

Figure 29:
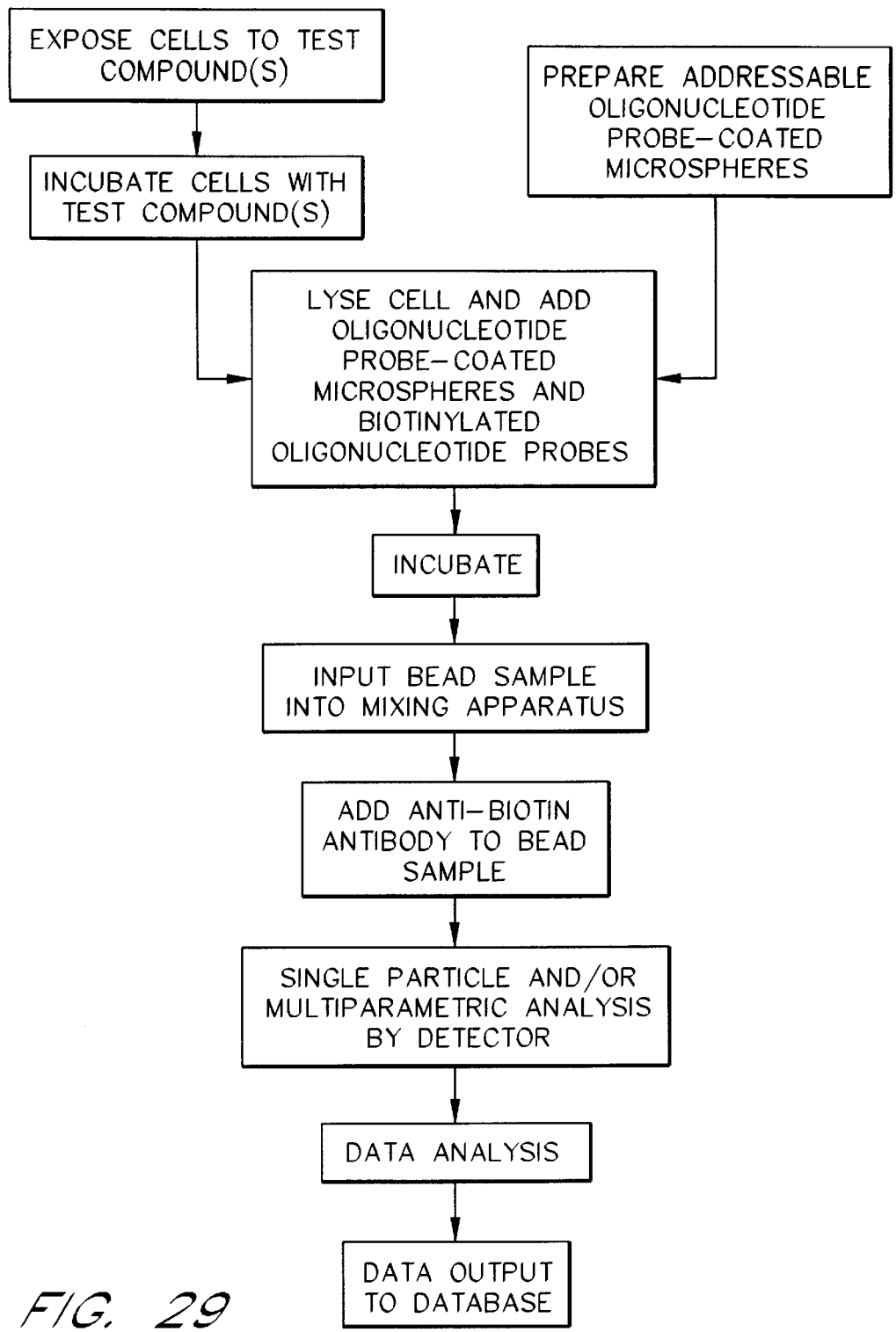
FIG. 29 is a flow diagram of a method for detecting the presence of one or more nucleic acids in a sample.

FIG. 29 illustrates the above procedure.

The above devices and methods in which the detector is capable of evaluating interactions with a plurality of particles simultaneously and/or capable of evaluating interactions with individual particles, such as devices in which the detector is a flow cytometer, may be used to simultaneously evaluate samples for the presence of multiple single nucleotide polymorphisms (SNPs).

Example 18 describes one embodiment of such analyses.

EXAMPLE 18

There are multiple methodologies for determining the identities of polymorphic bases in SNPs in genomic DNA samples. One approach is to prepare a short minisequencing primer that hybridizes to PCR-amplified genomic DNA containing the SNP such that the 3' end of the primer is immediately adjacent to the polymorphic base. DNA polymerase is used to extend the primer by one base to the polymorphic site. If fluorescent bases are used, the identity of the inserted base, which is dictated by the sequence of the amplified DNA, can be identified by the fluorescent signature of the extended primer. Such fluorescent bases are commonly used in high speed DNA sequencing efforts and are commercially available. By constructing the oligonucleotide probes so that they can be affixed to FCM-addressable microspheres, the products of the DNA polymerase reaction can be detected by FCM. Multiple SNPs can be detected in a single sample of DNA by linking primers for each SNP to different addressable beads.

In a preferred embodiment, the extension reaction is performed in microtiter wells using a biotinylated primer and fluorescent dideoxynucleotide triphosphates. Each reaction will target a unique SNP site.

The last step is the addition of a slurry of streptavidin-coated microspheres to adsorb the fluorescent labeled primers. This step is performed by the mixing system.

Extended, labeled primers enter into the system from the microtiter plates using an autosampler port. The primers are mixed with streptavidin coated beads taken from another port. The reaction time is adjusted to permit the beads to adsorb the extended primers while in transit through the tubing from the coupling device or mixing chamber. The FCM is configured to identify the bead populations and the primer-associated fluorescence on each bead set.

Figure 30:
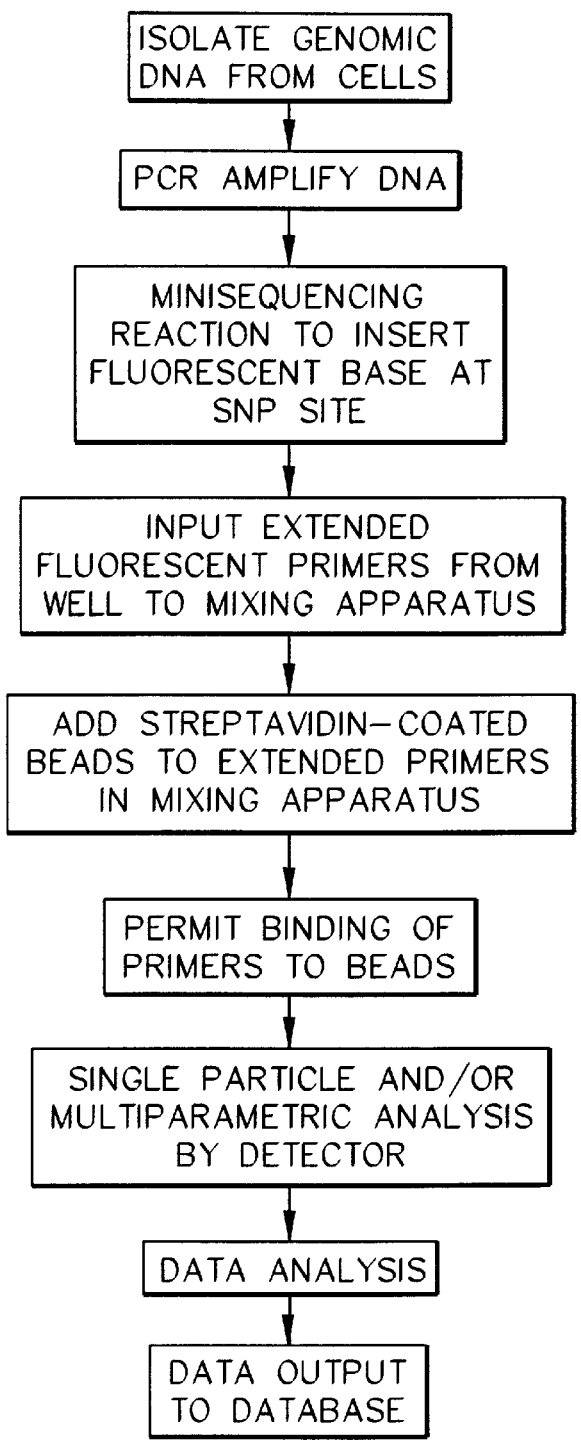
FIG. 30 is a flow diagram of a method for detecting the identities of one or more polymorphic nucleotides in a nucleic acid sample.

FIG. 30 illustrates the above procedure.

The above devices and methods in which the detector is capable of evaluating interactions with a plurality of particles simultaneously and/or capable of evaluating interactions with individual particles, such as devices in which the detector is a flow cytometer, may be used for multiparametric analyses of enzymatic activities.

Example 19 describes such analyses.

EXAMPLE 19

Microsphere populations bearing enzyme substrates are prepared by conjugating the substrates directly to the spheres. Optimal conjugation conditions will vary for each substrate. An example is to use streptavidin coated microspheres to permit coating with biotinylated substrate. The microspheres may be fluorescent or of different sizes to render each bead population identifiable by FCM. Based on size or fluorescence parameters, several unique and addressable bead and substrate combinations can be constructed. This allows multiple assays to be performed in a single experiment when the populations are analyzed by FCM'.

Multiple identifiable bead populations, each bearing a unique substrate, are entered into the mixing system. The beads are mixed with enzyme(s) and candidate enzyme antagonists or agonists. In some embodiments, the beads may be mixed with enzyme(s), candidate antagonists or agonists, and standards. The delay time of the reaction developing lines from the coupling device and/or the mixing chamber is determined according to the reaction kinetics of the enzyme activity towards the substrate and the desired information.

In this example, the ability of the enzyme to cleave fluorescent substrate from the bead in the presence of a compound test compound(s)/standard mixture is detected as a decrease in fluorescence of the bead population. If the test compound(s) or test compound(s)/standard mixture inhibits catalytic activity of the enzyme, then less of the substrate will be cleaved. The fluorescence intensity of the bead population will remain nearly as bright as the control population. If the test compound(s) or mixture increases the catalytic activity of the enzyme then more of the substrate will be cleaved.

The FCM is configured with the correct excitation lasers and beam scatter and emissions collecting optics to permit simultaneous analyses of modifications of multiple enzyme substrates by the test compound(s) or mixtures.

Figure 31:
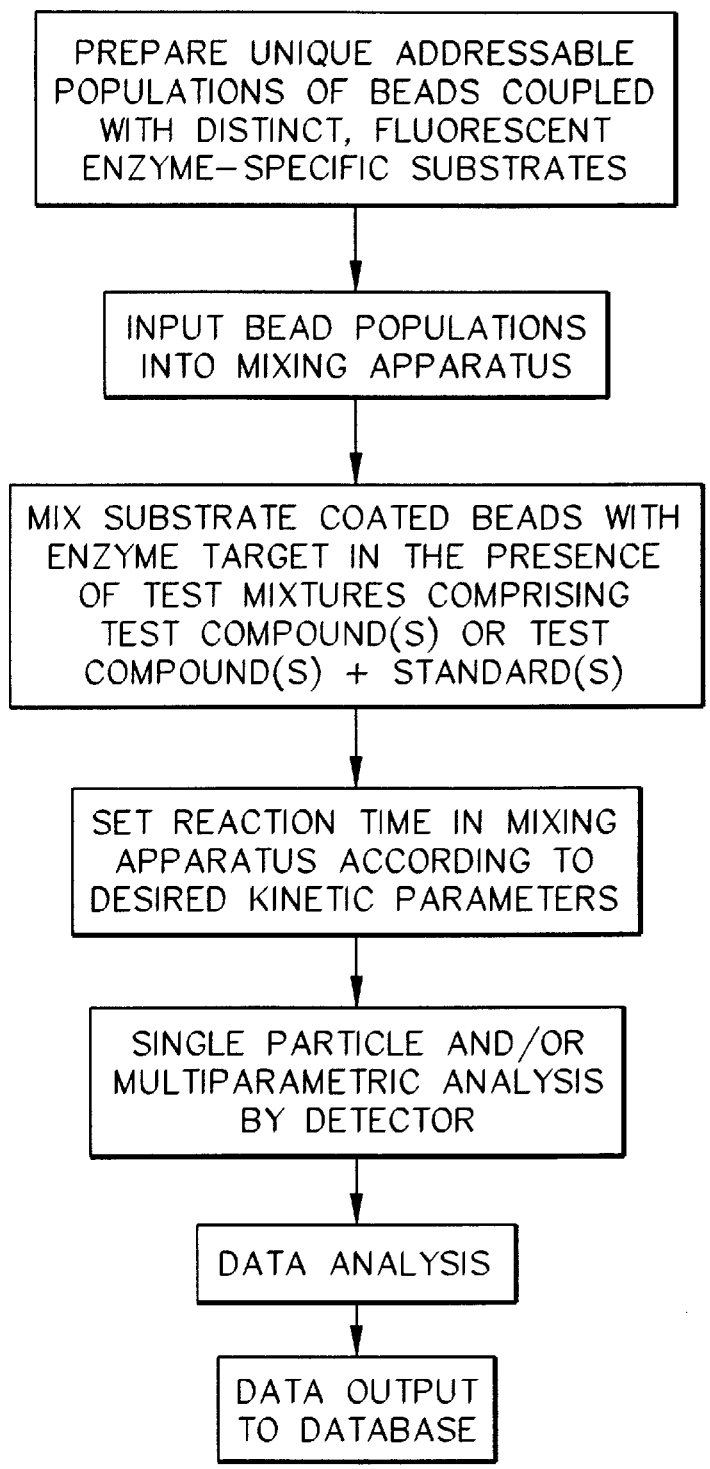
FIG. 31 is a flow diagram of a method for analyzing enzymatice activities.

FIG. 31 illustrates the above procedure.

The above devices and methods in which the detector is capable of evaluating interactions with a plurality of particles simultaneously and/or capable of evaluating interactions with individual particles, such as devices in which the detector is a flow cytometer, may be used for multiparametric analyses of molecular assembly assays.

Example 20 describes such analyses.

EXAMPLE 20

Microsphere populations bearing first molecules to be evaluated for interaction with second molecules are prepared by conjugating the first molecules directly to microspheres. In some embodiments, both the first molecules and the second molecules are polypeptides. For example, the first molecules may be polypeptides involved in signal transduction. Thus, the devices and methods of the present invention may be used to assess the ability of cognate molecules involved in signal transduction to bind with their target molecule in the presence of one or more test compounds.

Optimal conjugation conditions will vary for each molecule. An example is to use streptavidin coated microspheres to permit coating with biotinylated substrate. The microspheres may be fluorescent or of different sizes to render each bead population identifiable by FCM. Based on size or fluorescence parameters, several unique and addressable bead and molecule combinations can be constructed. This allows multiple assays to be performed in a single experiment when the populations are analyzed by FCM.

The beads bearing the first molecule, such as a molecular target are entered into the mixing system and exposed to test mixtures and a fluorescent cognate molecule in fluidics format. In this type of assay, inhibition of the molecular interaction by the test compound(s) will be visible as a reduction in fluorescent signal of the cognate molecule due to reduced binding to the target.

The FCM is configured with the correct excitation lasers and beam scatter and emissions collecting optics to permit simultaneous analyses of binding of cognate molecules to multiple molecular targets, and the effect of the test mixtures.

The purpose of the assay is to assess the ability of cognate signal transduction molecules that bind the target molecule as part of a normal in vivo signaling cascade to bind with the target molecule in the presence of test mixtures, may be used for multiparametric analysis of receptor targets.

Figure 32:
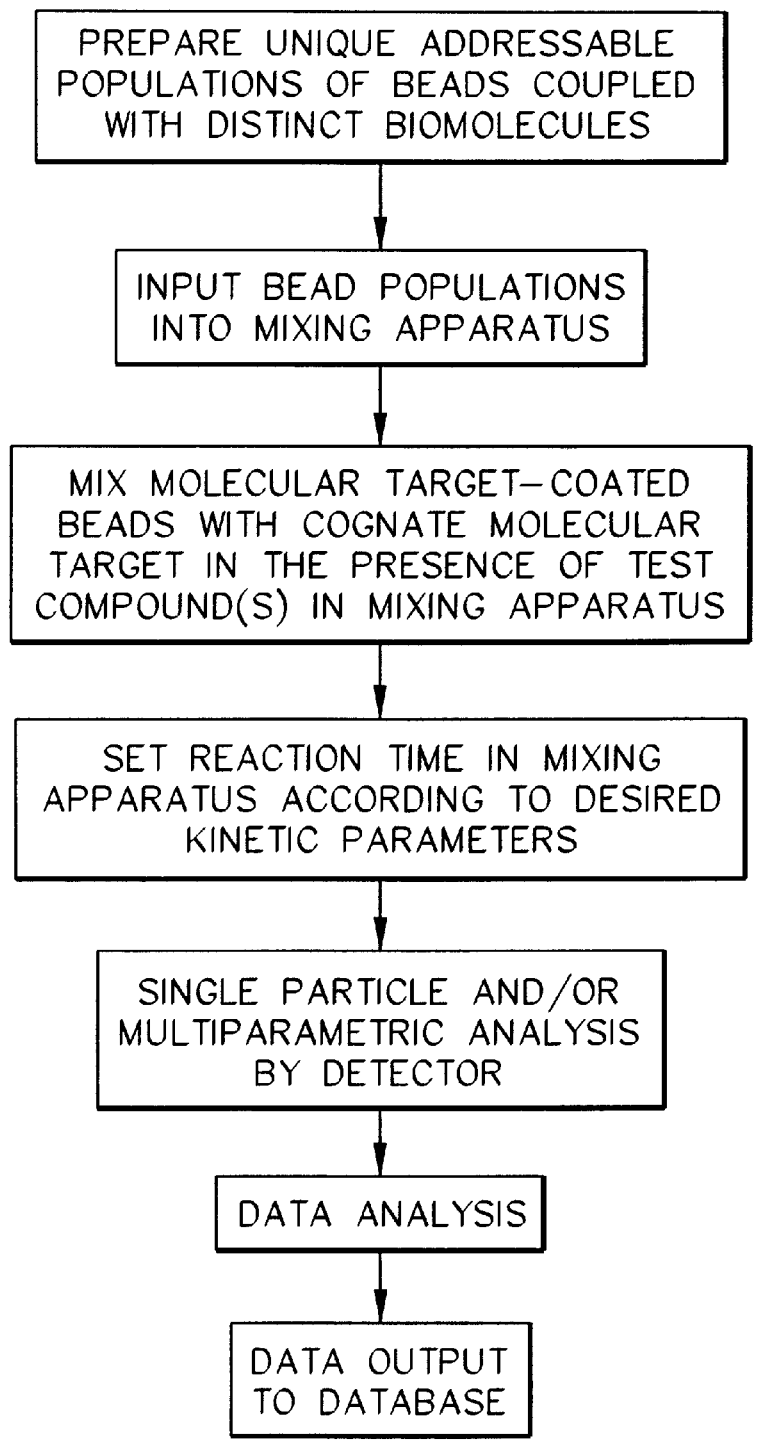
FIG. 32 is a flow diagram of a method for performing molecular assembly assays.

FIG. 32 illustrates the above methods.

The above devices and methods in which the detector is capable of evaluating interactions with a plurality of particles simultaneously and/or capable of evaluating interactions with individual particles, such as devices in which the detector is a flow cytometer, may be used to simultaneously evaluate the interactions of multiple receptors with ligands. Example 21 describes one embodiment of such analyses in which the interactions of multiple membrane spanning receptors with their ligands are simultaneously evaluated. However, it will be appreciated that the present devices and methods may be used to simultaneously evaluate the interactions of any type of molecule with potential binding partners.

EXAMPLE 21

Membrane spanning receptors are isolated from cells using techniques familiar to those skilled in the art. For example membrane spanning receptors may be isolated by performing an immunoprecipitation from detergent solubilized cells using a microsphere-coupled antibody specific for the receptor of interest. Following harvest of the beads with bound receptor, the beads with coupled receptor can be used in the mixing system.

Alternatively the receptor can be engineered to contain a molecular tag such as histidine and expressed in a recombinant form. The tag is then used to isolate the receptor from solubilized cells by mixing the lysate with a slurry of $Ni^+$ coated microspheres. The receptor-coated microspheres can be used in the mixing system.

Beads with attached receptors are entered into the mixing system and mixed with a fluorescent ligand. The effects of test compound(s) on the association of the fluorescent ligand with the receptors are assessed by FCM measurements.

The FCM is configured with the correct excitation lasers and beam scatter and emissions collecting optics to permit simultaneous analyses of binding of ligands to multiple receptors, and the effect of the test compounds.

Figure 33:
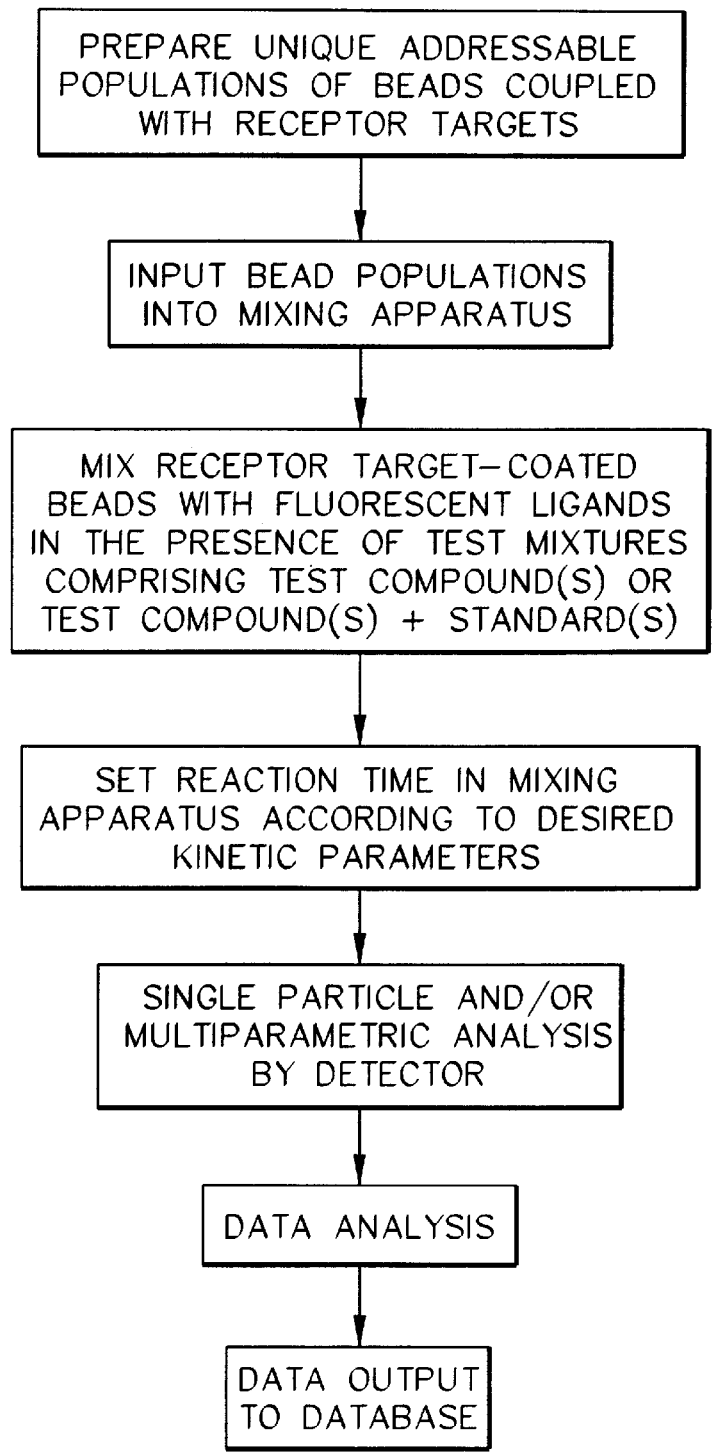
FIG. 33 is a flow diagram of a method for evaluating the interactions of receptors with ligands.

FIG. 33 illustrates the above methods.

Although the invention has been described in detail with reference to certain particular embodiments thereof, it will be understood that any variations and modifications apparent to those of skill in the art will still fall within the spirit and scope of the invention. Other embodiments not specifically described herein may fall within the spirit and scope of the present invention as provided by the following claims.

What is claimed is:

1. A method for identifying compounds which produce a cellular response comprising:
   (a) using an automated and computer controlled apparatus to sequentially combine each of a plurality of cell suspensions with one or more test compounds to sequentially form each of a plurality of test mixtures;
   (b) sequentially directing each of said plurality of test mixtures through a detection zone, the detection zone being capable of detecting a plurality of cellular responses simultaneously; and
   (c) simultaneously measuring a plurality of cellular responses to the one or more test compounds in said suspended cells as each of said plurality of test mixtures are flowing through said detection zone.

2. The method of claim 1, wherein said plurality of cellular responses includes a cellular response selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, activation or inhibition of cellular necrosis, and cellular toxicity.

3. The method of claim 1, wherein said plurality of cellular responses are measured by contacting said cells with one or more response indicating reagents which generate signals indicative of particular cellular responses.

4. The method of claim 3, wherein said signal generated by said response indicating reagents is fluorescence.

5. The method of claim 1, wherein said step of sequentially directing each of said plurality of test mixtures through a detection zone comprises directing each of said plurality of test mixtures through a detection zone which is capable of detecting said cellular responses in individual cells.

6. The method of claim 1, wherein said step of sequentially directing each of said plurality of test mixtures through a detection zone comprises directing each of said plurality of test mixtures through a flow cytometer.

7. The method of claim 1, wherein the step of simultaneously measuring a plurality of cellular responses comprises measuring said plurality of cellular responses in said suspended cells as a slug is flowing through said detection zone.

8. The method of claim 1, wherein each of said plurality of cell suspensions comprises more than one type of cell.

9. A method for identifying compounds which produce a cellular response comprising:
   (a) using an automated and computer controlled apparatus to sequentially combine each of a plurality of cell suspensions with one or more test compounds to form each of a plurality of test mixtures;
   (b) sequentially directing each of said plurality of test mixtures through a detection zone, said detection zone being capable of detecting cellular responses in individual cells; and
   (c) measuring one or more cellular responses to said one or more test compounds in individual suspended cells as each of said plurality of test mixtures are flowing through said detection zone.

10. The method of claim 9, wherein said one or more cellular responses is selected from the group consisting of activation or inhibition of a receptor mediated response, activation or inhibition of an ion channel, activation or inhibition of a non-selective pore, activation or inhibition of a second messenger pathway at a point downstream of a receptor or channel, activation or inhibition of apoptosis, and activation or inhibition of cellular necrosis, and cellular toxicity.

11. The method of claim 9, wherein said one or more cellular responses is measured by contacting said cells with one or more response indicating reagents which generate signals indicative of particular cellular responses.

12. The method of claim 11, wherein said signal generated by said response indicating reagents is fluorescence.

13. The method of claim 9, wherein said step of directing each of said plurality of test mixtures through a detection zone comprises directing each of said plurality of test mixtures through a flow cytometer.

14. The method of claim 9, wherein each of said plurality of cell suspensions comprises more than one type of cell.

15. The method of claim 9, wherein the step of simultaneously measuring a plurality of cellular responses comprises measuring said plurality of cellular responses in said suspended cells as a slug is flowing through said detection zone.

16. A method of determining whether a sample contains one or more molecules comprising:
  using an automated and computer controlled apparatus to sequentially combine one or more agents capable of binding one or more molecules with each of a plurality of samples to form a plurality of test mixtures;
  sequentially directing each of said plurality of test mixtures through a detection zone; and
  determining whether said one or more agents are bound to said one or more molecules as each of said test mixtures are flowing through said detection zone.

17. The method of claim 16, wherein said one or more agents are fixed to a solid support.

18. The method of claim 17, wherein a plurality of agents capable of binding a plurality of molecules are fixed to uniquely identifiable solid supports.

19. The method of claim 18 wherein said determining step comprises detecting a signal from an individual solid support wherein said signal indicates that said agent on said solid support has bound to said molecule.

20. The method of claim 16, wherein said one or more agents are selected from the group consisting of antibodies, nucleic acids, polypeptides, enzymatic substrates, and receptors.

21. The method of claim 16, wherein said one or more molecules are selected from the group consisting of polypeptides, nucleic acids, receptor ligands, enzymatic agonists and enzymatic antagonists.

22. A method of determining whether a sample contains one or more polypeptides comprising:
  attaching one or more antibodies which specifically bind said one or more polypeptides to solid supports;
  using an automated and computer controlled apparatus to sequentially combine said one or more antibodies attached to solid supports with samples to form a plurality of test mixtures;
  sequentially directing each of said plurality of test mixtures through a detection zone; and
  determining whether said one or more antibodies are bound to said one or more polypeptides as each of test mixtures are flowing through said detection zone.

23. The method of claim 22, wherein a plurality of antibodies which specifically bind to a plurality of polypeptides are fixed to uniquely identifiable solid supports.

24. The method of claim 23 wherein said determining step comprises detecting a signal from an individual solid support wherein said signal indicates that said antibodies have bound to said molecules.

25. The method of claim 24, wherein said signal is generated by detectably labeled secondary antibodies which bind said molecules.

26. A method of determining whether a sample contains one or more nulceic acids comprising:
  attaching one or more nucleic acid probes which specifically bind said nucleic acids to solid supports;
  using an automated and computer controlled apparatus to sequentially combine said one or more probes attached to said solid supports with samples to form a plurality test mixtures;
  sequentially directing each of said plurality of test mixtures through a detection zone; and
  determining whether said one or more probes are bound to said one or more nucleic acids as each of said test mixtures are flowing through said detection zone.

27. The method of claim 26, wherein a plurality of nucleic acid probes are fixed to uniquely addressable solid supports.

28. The method of claim 27, wherein said determining step comprises detecting a signal from an individual solid support wherein said signal indicates that said probes have bound to said nucleic acids.

29. The method of claim 28, wherein said signal is generated by detectable nucleic acid probes which bind said nucleic acids.

30. A method of determining whether a sample contains one or more single nucleotide polymorphisms comprising:
  performing an extension reaction on a each of a plurality of nucleic acid samples using one or more nucleic acid primers for each of said plurality of nucleic acid samples, said one or more nucleic acid primers having a 3' end immediately adjacent to the polymorphic base of one or more single nucleotide polymorphisms, thereby incorporating one base into said nucleic acid primers;
  attaching the extended primers to solid supports;
  sequentially directing said solid supports having primers attached thereto for each of said plurality of nucleic acid samples through a detection zone in an apparatus; and
  determining the identities of the bases incorporated in said extension reaction.

31. The method of claim 30, wherein a plurality of primers are fixed to uniquely identifiable solid supports.

32. The method of claim 31, wherein said determining step comprises detecting a signal from an individual solid support wherein said signal is indicative of the identity of the polymorphic base in a SNP.

33. The method of claim 32, wherein said signal is generated by detectably labeled nucleotides incorporated in said extension reaction.

34. The method of claim 1, further comprising the steps of:
  (d) combining a suspension of said cells with one or more standard compounds having a known effect on said cellular response of said cells to form standard mixtures;
  (e) directing the standard mixtures through the detection zone; and
  (f) measuring the cellular response of said cells to said one or more standard compounds.

35. The method of claim 1, wherein one or more standard compounds and said one or more test compounds are simultaneously mixed with each of said cell suspensions, and said measuring step detects whether said one or more test compounds alter a known effect of said one or more standard compounds.

36. The method of claim 35, wherein said one or more standard compounds is an antagonist of said cellular response.

37. The method of claim 35, wherein said one or more standard compounds is an agonist of said cellular response.

38. The method of claim 35, wherein said cell suspensions comprise more than one cell type.

39. The method of claim 35, wherein the step of directing said test mixtures through a detection zone comprises directing said test mixtures through a flow cytometer.

40. A method of obtaining cells having a desired phenotype or cellular response profile comprising the steps of:
  (a) using an automated and computer controlled apparatus to sequentially combine a each of a plurality of cell suspensions with one or more compounds which produce a cellular response to form a plurality of test mixtures;

(b) sequentially directing each of said plurality of test mixtures through a detection zone, said detection zone being capable of detecting a plurality of cellular parameters simultaneously;

(c) simultaneously measuring a plurality of cellular parameters in said suspended cells as each of said plurality of test mixtures are flowing through said detection zone; and (d) delivering cells having a desired phenotype or cellular response profile into a receptacle.

41. A method of obtaining cells having a desired phenotype or cellular response profile comprising the steps of:
(a) using an automated and computer controlled apparatus to sequentially combine a each of a plurality of cell suspensions with one or more compounds which produce a cellular response to form a plurality of test mixtures;
(b) sequentially directing each of said plurality of test mixtures through a detection zone, said detection zone being capable of detecting cellular responses in individual cells;
(c) simultaneously measuring a plurality of cellular parameters in said suspended cells as each of said plurality of test mixtures are flowing through said detection zone; and
(d) delivering cells having a desired phenotype or cellular response profile into a receptacle.

42. An apparatus comprising:
an automated test compound source capable of sequentially providing each of a plurality of test compounds;
an automated test substrate source capable of sequentially providing each of a plurality of test compounds;
a mixing chamber in fluid communication with said test compound source and said test substrate source, wherein said mixing chamber is adapted to combine a test compound received from said test compound source with a test substrate received from said test substrate source to generate a mixture; and
a detector in fluid communication with said mixing chamber, said detector being capable of detecting an interaction between said test compound and said test substrate while said mixture is passing through said detector.

43. The apparatus of claim 42, wherein:
said test compound source comprises one or more sample inputs for sequentially providing each of a plurality of samples, each of said samples comprising one or more test compounds to be evaluated for the ability to produce a cellular response or a solution to be evaluated for the presence of molecules;
said test substrate source comprises one or more cell or particle inputs for sequentially providing a each of a plurality of cell suspensions or particles;
said mixing chamber receives the samples from said test compound source, receives the cell suspensions or particles from the cell or particle input and mixes each sample with the cell suspension or particles; and
said detector is capable of detecting a plurality of signals simultaneously such that said detector can simultaneously measure a plurality of cellular responses in the suspended cells or simultaneously determine whether a plurality of molecules are present in said samples.

44. The apparatus of claim 43 wherein said detector detects a signal from a single cell in said cell suspension or from a single particle.

45. The apparatus of claim 43 wherein said detector is a flow cytometer.

46. The apparatus of claim 43, further comprising a coupler disposed between said mixing zone and said detector.

47. The apparatus of claim 46, wherein said coupler delivers slugs comprising said samples and said cell suspension or particles to said detector.

48. The apparatus of claim 47, wherein said coupler delivers substantially undiluted slugs to said detector.

49. The apparatus of claim 43, wherein said detector delivers cells having a desired phenotype or cellular response to a receptacle.

50. The apparatus of claim 43 wherein said one or more sample inputs comprise an automated robotic sampler capable of sequentially selecting each of a plurality of specified test compounds from a library of test compounds.

51. The apparatus of claim 50 further comprising:
a controller, coupled to said one or more sample inputs, for controlling the operation of the automated robotic sampler; and
a computer, coupled to the controller, for sending command signals to the controller in accordance with a software program implemented by the computer, thereby controlling the selection and retrieval of test compounds by said one or more sample inputs from said test compound library.

52. The apparatus of claim 51 further comprising a gradient pump having an input and an output, coupled to said sample input, for adjusting the concentration level of said test compound transferred to said mixing zone from said sample input, wherein:
said sample input comprises:
a first intake nozzle for receiving each of the said specified test compounds;
a second intake nozzle for receiving a buffer solution; and
wherein said gradient pump is coupled to the first and second intake nozzles and receives specified concentrations of each of the specified test compounds by adjusting the amount of test compound and buffer solution received by the first and second intake nozzles, respectively, wherein the buffer solution is a diluting agent of the test compound.

53. The apparatus of claim 52 further comprising a second pump, coupled to an input of said mixing zone, for pumping said suspension of cells or said particles from said cell or particle input into the mixing zone.

54. The apparatus of claim 53 further comprising a reaction developing line, having an input coupled to an output of said mixing zone and an output in fluid communication with said detector wherein said reaction developing line provides a reaction time delay for a mixture received from the mixing zone.

55. The apparatus of claim 54 further comprising:
a pump, coupled to the output of said detector, for providing negative pressure to the apparatus;
a proportionating valve, coupled to said sample input, for adjusting the concentration level of said test compound transferred to said mixing zone from said one or more sample inputs, wherein said one or more sample inputs further comprise:
a first intake nozzle for receiving each of said specified test compounds;
a second intake nozzle for receiving a buffer solution; and
the proportionating valve receives specified concentrations of each of the specified test compounds by adjusting the amount of test compound and buffer solution received by the first and second intake nozzles, respectively, wherein the buffer solution is a diluting agent of the test compound.

56. The apparatus of claim 43 further comprising a plurality of cell suspension reservoirs.

57. The apparatus of claim 43 further comprising a standard compound sampler, coupled to said mixing zone, for providing one or more standard compounds having a known effect on said cellular response of said suspended cells or a known interaction with said particles, wherein said mixing zone receives said one or more standard compounds from the standard compound sampler and mixes said one or more standard compounds with the suspended cells or particles and said detector measures the cellular response of the suspended cells to said one or more standard compounds or the interaction between said one or more standard compounds and said particles.

58. The apparatus of claim 57 wherein said mixing zone simultaneously mixes said sample and said one or more standard compounds with said suspended cells or said particles and said detector detects said known effect or an alteration of said known effect on the cellular responses of said suspended cells or said known interaction between said standard compound and said particles or an alteration of said known interaction between said standard compound and said particles.

59. The apparatus of claim 58 wherein said standard compound sampler is an automated robotic sampler capable of selecting a specified standard compound from a library of standard compounds.

60. An apparatus comprising:
one or more automated sample inputs for sequentially providing each of a plurality of samples, said each of said samples comprising one or more test compounds to be evaluated for the ability to produce a cellular response or a solution to be evaluated for the presence of molecules;
one or more automated cell or particle inputs for sequentially providing each of a plurality of cell suspensions or particles;
a mixing zone, coupled to said sample input, for receiving the samples, receiving the cell suspension or particles from the cell or particle input and mixing each sample with the cell suspensions or particles; and
a detector which detects one or more signals from a single cell or particle, said detector being coupled to the mixing zone and being capable of measuring one or more cellular responses in the suspended cells or determining whether one or more molecules are present in said samples.

61. The apparatus of claim 60, further comprising a coupler disposed between said mixing zone and said detector.

62. The apparatus of claim 61, wherein said coupler delivers slugs comprising said samples and said cell suspension or particles to said detector.

63. The apparatus of claim 62, wherein said coupler delivers substantially undiluted slugs to said detector.

64. The apparatus of claim 60 further comprising an input system for inputting solutions into said mixing zone.

65. The apparatus of claim 60, wherein said detector delivers cells having a desired phenotype or cellular response to a receptacle.

66. The apparatus of claim 42, wherein said test compound source is capable of providing said test compounds at a single concentration or over a range of concentrations.

67. The apparatus of claim 42, further comprising a known compound source capable of sequentially providing each of a plurality of compounds which produce a known cellular response, said known compound source being in fluid communication with said mixing chamber such that said mixing chamber can combine a test compound, a compound which produces a known cellular response, and a cell suspension.

68. The apparatus of claim 67, wherein said known compound source is capable of providing the compounds which produce a known cellular response at a single concentration or over a range of concentrations.

69. The apparatus of claim 60, wherein said one or more sample inputs is capable of providing said test compounds at a single concentration or over a range of concentrations.

70. The apparatus of claim 60, further comprising a known compound source capable of sequentially providing each of a plurality of compounds which produce a known cellular response, said known compound source being in fluid communication with said mixing zone such that said mixing zone can combine a test compound, a compound which produces a known cellular response, and a cell suspension.

71. The apparatus of claim 70, wherein said known compound source is capable of providing the compounds which produce a known cellular response at a single concentration or over a range of concentrations.

72. The method of claim 1, wherein a range of concentrations of said test compounds is combined with said cell suspensions.

73. The method of claim 1, further comprising combining one or more compounds which produce a known cellular response with said plurality of cell suspensions and said test compounds.

74. The method of claim 73, wherein a range of concentrations of said one or more compounds which produce a known cellular response is combined with said plurality of cell suspensions and said test compounds.

75. The method of claim 9, wherein a range of concentrations of said test compounds is combined with said cell suspensions.

76. The method of claim 9, further comprising combining one or more compounds which produce a known cellular response with said plurality of cell suspensions and said test compounds.

77. The method of claim 76, wherein a range of concentrations of said one or more compounds which produce a known cellular response is combined with said plurality of cell suspensions and said test compounds.

78. The method of claim 1, wherein a range of concentrations of said agents capable of binding said molecules is combined with said samples.

79. The method of claim 40, wherein a range of concentrations of said compounds is combined with said cell suspensions.

80. The method of claim 40, further comprising combining one or more compounds which produce a known cellular response with said plurality of cell suspensions and said compounds.

81. The method of claim 80, wherein a range of concentrations of said one or more compounds which produce a known cellular response is combined with said plurality of cell suspensions and said compounds.

82. The method of claim 41, wherein a range of concentrations of said compounds is combined with said cell suspensions.

83. The method of claim 41, further comprising combining one or more compounds which produce a known cellular response with said plurality of cell suspensions and said compounds.

84. The method of claim 83, wherein a range of concentrations of said one or more compounds which produce a known cellular response is combined with said plurality of cell suspensions and said compounds.

* * * * *

UNITED STATES PATENT AND TRADEMARK OFFICE
CERTIFICATE OF CORRECTION

PATENT NO. : 6,280,967 B1  Page 1 of 1
DATED : August 28, 2001
INVENTOR(S) : John Ransom, Ilya Okun and Alex Okun It is certified that error appears in the above-identified patent and that said Letters Patent is hereby corrected as shown below:

<u>Title page,</u>
Item [54], Title, before the word "OF" please insert -- MEASUREMENTS --.

<u>Column 71,</u>
Line 53, please replace "nulceic" with -- nucleic --.

Signed and Sealed this

Eighth Day of October, 2002

*Attest:*

*Attesting Officer*

JAMES E. ROGAN
*Director of the United States Patent and Trademark Office*